(12) United States Patent
Soldermann et al.

(10) Patent No.: US 9,815,842 B2
(45) Date of Patent: Nov. 14, 2017

(54) PYRAZOLO PYRIMIDINE DERIVATIVES AND THEIR USE AS MALT1 INHIBITORS

(71) Applicants: Carole Pissot Soldermann, Village Neuf (FR); Jean Quancard, Huningue (FR); Achim Schlapbach, Basel (CH); Oliver Simic, Basel (CH); Marina Tintelnot-Blomley, Maulburg (DE); Thomas Zoller, Andolsheim (FR)

(72) Inventors: Carole Pissot Soldermann, Village Neuf (FR); Jean Quancard, Huningue (FR); Achim Schlapbach, Basel (CH); Oliver Simic, Basel (CH); Marina Tintelnot-Blomley, Maulburg (DE); Thomas Zoller, Andolsheim (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/312,321

(22) PCT Filed: May 27, 2015

(86) PCT No.: PCT/IB2015/053975
§ 371 (c)(1),
(2) Date: Nov. 18, 2016

(87) PCT Pub. No.: WO2015/181747
PCT Pub. Date: Dec. 3, 2015

(65) Prior Publication Data
US 2017/0121335 A1    May 4, 2017

(30) Foreign Application Priority Data
May 28, 2014    (EP) .................... 14170408

(51) Int. Cl.
C07D 487/04    (2006.01)
A61K 31/519   (2006.01)
A61K 31/5377  (2006.01)
A61P 35/00    (2006.01)
A61P 29/00    (2006.01)
A61P 9/00     (2006.01)
A61P 35/02    (2006.01)
A61P 35/04    (2006.01)
A61P 19/02    (2006.01)
A61P 11/06    (2006.01)
A61P 11/08    (2006.01)
A61P 9/08     (2006.01)
A61P 11/00    (2006.01)

(52) U.S. Cl.
CPC .......... C07D 487/04 (2013.01); A61K 31/519 (2013.01); A61K 31/5377 (2013.01)

(58) Field of Classification Search
CPC ........................... C07D 487/04; A61K 31/519
USPC ....................................... 544/281; 514/259.3
See application file for complete search history.

(56) References Cited

U.S. PATENT DOCUMENTS

| | | |
|---|---|---|
| 2002/0065296 A1 | 5/2002 | Dumas et al. |
| 2004/0102636 A1 | 5/2004 | Miller et al. |
| 2006/0089362 A1 | 4/2006 | Seno et al. |

FOREIGN PATENT DOCUMENTS

| | | |
|---|---|---|
| EP | 2465928 A1 | 6/2012 |
| WO | 03068228 A1 | 8/2003 |
| WO | 03101993 A1 | 12/2003 |
| WO | 2004022062 A1 | 3/2004 |
| WO | 2009065897 A2 | 5/2009 |
| WO | 2010057833 A1 | 5/2010 |
| WO | 2014100620 A2 | 6/2014 |
| WO | 2014181287 A1 | 11/2014 |

*Primary Examiner* — Susanna Moore
(74) *Attorney, Agent, or Firm* — Daniel E. Raymond; Genomics Institute of the Novartis Research Foundation

(57) ABSTRACT

The present invention describes new pyrazolo-pyrimidine derivatives which are generally interacting with MALT1 proteolytic and/or autoproteolytic activity, and in particular which may inhibit said activity. The present invention further describes the synthesis of said new pyrazolo-pyrimidine derivatives, their use as a medicament, especially by interacting with MALT1 proteolytic and/or autoproteolytic activity.

18 Claims, No Drawings

PYRAZOLO PYRIMIDINE DERIVATIVES AND THEIR USE AS MALT1 INHIBITORS

The present invention describes new pyrazolo-pyrimidine derivatives which are generally interacting with MALT1 proteolytic and/or autoproteolytic activity, and in particular which may inhibit said activity. The present invention further describes the synthesis of said new pyrazolo-pyrimidine derivatives, their use as a medicament, especially by interacting with MALT1 proteolytic and/or autoproteolytic activity.

FIELD OF THE INVENTION

The present invention relates to compounds of formula (I) or pharmaceutically acceptable salts thereof, and to their use in the treatment of a wide range of diseases or disorders, particularly MALT1-related diseases or disorders. This may include, but is not limited to autoimmune disorders and inflammatory diseases, such as rheumatoid arthritis, multiple sclerosis, systemic lupus erythematosus or vasculitic conditions, cancers of hematopoietic origin or solid tumors, including chronic myelogenous leukemia, myeloid leukemia, non-Hodgkin lymphoma and other B cell lymphomas.

BACKGROUND OF THE INVENTION

The essential role of MALT1 (mucosa associated lymphoid tissue lymphoma translocation protein 1) in influencing immune responses is described in numerous publications. For example, Rudi Beyaert et al. (WO 2009/065897) describe certain compounds as inhibitors of MALT1 proteolytic and/or autoproteolytic activity.

Studies in BCL10 and MALT 1 deficient mice seem to suggest their essential role in the signaling cascade from the antigen receptors to the transcription factor NFkB. Moreover chromosomal translocations leading to overexpression of BCL10 and MALT 1, or creating the constitutively active fusion protein API2-MALT1, appear to yield in an uncontrolled and stimulus-independent activation of NFkB. Inhibitors of the proteolytic activity of MALT1 have been described with activity in preclinical lymphoma models (Vincendeau et al. Int. J. Hematol. Oncol. 2013, 2, 409).

Moreover, certain publications appear to suggest the important role of MALT1 and its proteolytic function in signaling cascades triggered by innate cell receptors like Dectin receptors and in signaling cascades triggered by G-protein coupled receptors in many cell types.

Consequently, there appears to be a desire to discover and develop potent MALT1 inhibitors comprising valuable pharmacological properties.

SUMMARY OF THE INVENTION

The present invention describes novel pyrazolo-pyrimidine derivatives according to formula (I) or pharmaceutically acceptable salts thereof as potent inhibitors of MALT1 which may hence be useful in the treatment of a wide range of diseases or disorders, particularly MALT1-related diseases or disorders. This may include, but is not limited to autoimmune disorders and inflammatory diseases, such as rheumatoid arthritis, multiple sclerosis, systemic lupus erythematosus or vasculitic conditions. It may further include allergic diseases, airway diseases, such as asthma and chronic obstructive pulmonary disease (COPD) or conditions caused by delayed or immediate type hypersensitivity and anaphylaxis, acute or chronic transplant rejection or graft versus host disease, cancers of hematopoietic origin or solid tumors, including chronic myelogenous leukemia, myeloid leukemia, non-Hodgkin lymphoma and other B cell lymphomas.

More particularly, in embodiment 1 the present invention provides a compound of formula (I) or a pharmaceutically acceptable salt thereof;

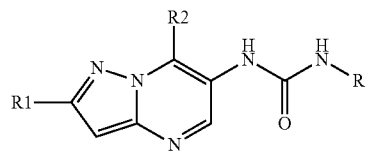

(I)

wherein,

R1 is halogen, cyano, or $C_1$-$C_3$ alkyl optionally substituted by halogen;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy wherein said alkoxy again may optionally be substituted by $C_1$-$C_6$ alkoxy, N,N-di-$C_1$-$C_6$ alkyl amino, Rg or phenyl; $C_3$-$C_6$ cycloalkyl optionally substituted by $C_1$-$C_6$ alkyl, N,N-di-$C_1$-$C_6$ alkyl amino or $C_1$-$C_6$ alkoxy-$C_1$-$C_6$ alkyl, and/or two of said optional substituents together with the atoms to which they are bound may form an annulated or spirocyclic 4-6 membered saturated heterocyclic ring comprising 1-2 O atoms; phenyl optionally substituted by $C_1$-$C_6$ alkoxy; a 5-6 membered heteroaryl ring having 1 to 3 heteroatoms selected from N and O said ring being optionally substituted by $C_1$-$C_6$ alkyl which may be optionally substituted by amino or hydroxy; Rg; or N,N-di-$C_1$-$C_6$ alkyl amino carbonyl; wherein Rg is a 5-6 membered heterocyclic ring having 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is phenyl independently substituted two or more times by Ra, 2-pyridyl independently substituted one or more times by Rb, 3-pyridyl independently substituted one or more times by Rc, or 4-pyridyl independently substituted one or more times by Rd; wherein Ra independently from each other is halogen; cyano; —COO$C_1$-$C_6$ alkyl; $C_1$-$C_6$ alkoxy; $C_1$-$C_6$ alkyl optionally substituted by halogen or a 5-6 membered heterocyclyl ring having 1 to 2 heteroatoms selected from N and O which ring is optionally substituted by $C_1$-$C_6$ alkyl; a 5-6 membered heteroaryl ring having 1 to 3 heteroatoms selected from N and O said ring being optionally substituted by amino, $C_1$-$C_6$ alkyl optionally substituted by amino or hydroxy, or by N-mono- or N,N-di-$C_1$-$C_6$ alkylamino carbonyl; and/or two Ra together with the ring atoms to which they are bound may form a 5 to 6 membered heterocyclic or heteroaromatic ring having 1 to 2 N atoms, any such ring being optionally substituted by $C_1$-$C_6$ alkyl or oxo;

Rb, Rc and Rd independently from each other are halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring having 1 to 3 N atoms said ring being optionally substituted by $C_1$-$C_6$ alkyl optionally substituted by amino or hydroxy, or by mono- or di-N—$C_1$-$C_6$ alkylamino carbonyl; O—Rh; or Rh; wherein Rh is a 5-6 membered heterocyclyl ring having 1 to 4 heteroatoms selected from N, O and S said ring being optionally substituted by $C_1$-$C_6$ alkyl, hydroxyl or oxo.

DETAILED DESCRIPTION OF THE INVENTION

In its broadest embodiment (embodiment 1) the present invention relates to a compound of formula (I) and/or a pharmaceutically acceptable salt thereof as described above in the section Summary of the Invention.

Embodiment 2 relates to a compound of embodiment 1 or a pharmaceutically acceptable salt thereof, wherein R1 is halogen;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 2-pyridyl independently substituted one or more times by Rb, 3-pyridyl independently substituted one or more times by Rc, or 4-pyridyl independently substituted one or more times by Rd; and Rb, Rc and Rd are as defined in embodiment 1.

Embodiment 3 relates to a compound of embodiment 1 or a pharmaceutically acceptable salt thereof, wherein R1 is cyano;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 2-pyridyl independently substituted one or more times by Rb, 3-pyridyl independently substituted one or more times by Rc, or 4-pyridyl independently substituted one or more times by Rd; and Rb, Rc and Rd are as defined in embodiment 1.

Embodiment 4 relates to a compound of embodiment 1 or a pharmaceutically acceptable salt thereof, wherein R1 is $C_1$-$C_3$ alkyl optionally substituted by halogen;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 2-pyridyl independently substituted one or more times by Rb, 3-pyridyl independently substituted one or more times by Rc, or 4-pyridyl independently substituted one or more times by Rd; and Rb, Rc and Rd are as defined in embodiment 1.

Embodiment 5 relates to a compound of embodiment 1 or 2, or a pharmaceutically acceptable salt thereof, wherein R1 is chloro, and the remaining substitutents are as defined therein.

Embodiment 6 relates to a compound of embodiment 2, or a pharmaceutically acceptable salt thereof, wherein R1 is chloro;

R is 2-pyridyl independently substituted one or more times by Rb, and the remaining substitutents are as defined in embodiment 2.

Embodiment 7 relates to a compound of embodiment 2 or a pharmaceutically acceptable salt thereof, wherein R1 is chloro;

R is 3-pyridyl independently substituted one or more times by Rc; and the remaining substitutents are as defined in embodiment 2.

Embodiment 8 relates to a compound of embodiment 2 or a pharmaceutically acceptable salt thereof, wherein R1 is chloro;

R is 4-pyridyl independently substituted one or more times by Rd; and the remaining substitutents are as defined in embodiment 2.

Embodiment 9 relates to a compound of embodiment 4 or a pharmaceutically acceptable salt thereof, wherein R is 4-pyridyl independently substituted one or more times by Rd; and the remaining substitutents are as defined in embodiment 4.

Embodiment 10 relates to a compound of embodiment 1, 5, 6, 7, 8 or 9 or a pharmaceutically acceptable salt thereof, wherein halogen independently of its occurrence is selected from fluoro and chloro.

Embodiment 11 relates to a compound of embodiment 1 or 2 or a pharmaceutically acceptable salt thereof, wherein R1 is fluoro.

Embodiment 12 relates to a compound of embodiment 1, 4 or 9 or a pharmaceutically acceptable salt thereof, wherein R1 is $C_1$-alkyl, optionally substituted by fluoro.

Embodiment 13 relates to a compound of embodiment 1, 4 or 9 or a pharmaceutically acceptable salt thereof, wherein R1 is methyl.

Embodiment 14 relates to a compound of embodiment 5, 6, 7, 8, or 9 or a pharmaceutically acceptable salt thereof, wherein the substituents Rb, Rc and/or Rd independently from each other are halogen; cyano; $C_1$-$C_6$ alkoxy; $C_1$-$C_6$ alkyl optionally substituted by halogen or phenyl; or a 5-6 membered heteroaryl ring containing 1 to 3 N atoms said ring being optionally substituted by $C_1$-$C_6$ alkyl optionally substituted by amino or hydroxy, or by mono- or di-N—$C_1$-$C_6$ alkylamino carbonyl.

Embodiment 15 relates to a compound of embodiment 1 or a pharmaceutically acceptable salt thereof, wherein R1 is halogen, cyano, or $C_1$-$C_3$ alkyl optionally substituted by halogen;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy wherein said alkoxy again may optionally be substituted by $C_1$-$C_6$ alkoxy, N,N-di-$C_1$-$C_6$ alkyl amino, Rg or phenyl; $C_3$-$C_6$ cycloalkyl optionally substituted by $C_1$-$C_6$ alkyl, N,N-di-$C_1$-$C_6$ alkyl amino or $C_1$-$C_6$ alkoxy-$C_1$-$C_6$ alkyl, or two of said optional substituents together with the atoms to which they are bound may form an annulated or spirocyclic 4-6 membered saturated heterocyclic ring comprising 1-2 O atoms; phenyl optionally substituted by $C_1$-$C_6$ alkoxy; a 5-6 membered heteroaryl containing 1 to 3 heteroatoms selected from N and O optionally substituted by $C_1$-$C_6$ alkyl which may optionally be substituted by amino or hydroxy; Rg; or N,N-di-$C_1$-$C_6$ alkyl amino carbonyl;

wherein

Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is phenyl independently substituted two or more times by Ra; wherein

Ra independently from each other is halogen; cyano; —COO$C_1$-$C_6$ alkyl; $C_1$-$C_6$ alkoxy; $C_1$-$C_6$ alkyl optionally substituted by halogen or a 5-6 membered heterocyclic ring containing 1 to 2 N atoms said ring being optionally substituted by $C_1$-$C_6$ alkyl; a 5-6 membered heteroaryl ring containing 1 to 3 N atoms said ring being optionally substituted by amino, $C_1$-$C_6$ alkyl optionally substituted by amino or hydroxy, or by N-mono- or N,N-di-$C_1$-$C_6$ alkylamino carbonyl;

and/or, two Ra together with the ring atoms to which they are bound form a 5 to 6 membered heterocyclic or heteroaromatic ring containing 1 to 2 N atoms, any such ring being optionally substituted by $C_1$-$C_6$ alkyl or oxo.

Embodiment 16 relates to a compound of embodiment 1 or 15, or a pharmaceutically acceptable salt thereof, wherein R1 is halogen;

R is phenyl independently substituted two or more times by Ra; wherein

Ra independently from each other is halogen; cyano; —COO$C_1$-$C_6$ alkyl; $C_1$-$C_6$ alkoxy; $C_1$-$C_6$ alkyl optionally substituted by fluoro or a 5-6 membered heterocyclic ring containing 1 to 2 N atoms which heterocyclyl is optionally substituted by $C_1$-$C_6$ alkyl; a 5-6 membered heteroaryl ring containing 1 to 3 N atoms said ring being optionally substituted by amino, $C_1$-$C_6$ alkyl optionally substituted by amino or hydroxy, or by N-mono- or N,N-di-$C_1$-$C_6$ alkylamino carbonyl, and the remaining substituents are as defined in embodiment 1.

Embodiment 17 relates to a compound of embodiment 15 or 16 or a pharmaceutically acceptable salt thereof, wherein R1 is chloro.

Embodiment 18 relates to a compound of embodiment 15 or 16, or a pharmaceutically acceptable salt thereof, wherein R1 is fluoro.

Embodiment 19 relates to a compound of embodiment 15 or a pharmaceutically acceptable salt thereof, wherein R1 is methyl.

Embodiment 20 relates to a compound of embodiment 15 or a pharmaceutically acceptable salt thereof, wherein R1 is cyano.

Embodiment 21 relates to a compound in particular of embodiment 1 or a pharmaceutically acceptable salt thereof, wherein the compound is selected from (S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea;

(S)-1-(2-chloro-7-(1-methoxyethyl)pyrazolo[1,5-a]pyrimidin-6-yl)-3-(2-(trifluoromethyl)pyridin-4-yl)urea;

(S)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea;

(R)-1-(6-(2H-1,2,3-triazol-2-yl)-5-(trifluoromethyl)pyridin-3-yl)-3-(2-chloro-7-(1-methoxy-2-methylpropyl)pyrazolo[1,5-a]pyrimidin-6-yl)urea;

(R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea;

(S)-1-(7-(1-methoxyethyl)-2-methylpyrazolo[1,5-a]pyrimidin-6-yl)-3-(2-(trifluoromethyl)pyridin-4-yl)urea;

(S)-1-(2-fluoro-7-(1-methoxyethyl)pyrazolo[1,5-a]pyrimidin-6-yl)-3-(2-(trifluoromethyl)pyridin-4-yl)urea;

(S)-1-(2-chloro-7-(1-methoxyethyl)pyrazolo[1,5-a]pyrimidin-6-yl)-3-(5-cyanopyridin-3-yl)urea;

(S)-1-(5-chloro-6-methoxypyridin-3-yl)-3-(2-chloro-7-(1-methoxyethyl)pyrazolo[1,5-a]pyrimidin-6-yl)urea;

(S)-1-(5-chloro-6-(2H-1,2,3-triazol-2-yl)pyridin-3-yl)-3-(2-chloro-7-(1-methoxyethyl)pyrazolo[1,5-a]pyrimidin-6-yl)urea;

(S)-1-(2-chloro-7-(1-methoxyethyl)pyrazolo[1,5-a]pyrimidin-6-yl)-3-(5-methoxy-6-(2H-1,2,3-triazol-2-yl)pyridin-3-yl)urea;

(S)-1-(2-chloro-7-(1-methoxyethyl)pyrazolo[1,5-a]pyrimidin-6-yl)-3-(2-chloropyridin-4-yl)urea;

(S)-methyl 3-chloro-5-(3-(2-chloro-7-(1-methoxyethyl)pyrazolo[1,5-a]pyrimidin-6-yl)ureido)benzoate;

1-(5-chloro-6-(2H-1,2,3-triazol-2-yl)pyridin-3-yl)-3-(2-chloro-7-(2-methoxypropan-2-yl)pyrazolo[1,5-a]pyrimidin-6-yl)urea;

1-(2-chloro-7-(2-methoxypropan-2-yl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(2-chloro-7-(1-methylcyclopropyl)pyrazolo[1,5-a]pyrimidin-6-yl)urea;

1-(2-chloro-7-(1-methylcyclopropyl)pyrazolo[1,5-a]pyrimidin-6-yl)-3-(2-(trifluoromethyl)pyridin-4-yl)urea;

1-(5-chloro-6-methoxypyridin-3-yl)-3-(2-chloro-7-isopropylpyrazolo[1,5-a]pyrimidin-6-yl)urea;

1-(2-chloro-7-isopropylpyrazolo[1,5-a]pyrimidin-6-yl)-3-(3-cyano-4-(3-methyl-1H-1,2,4-triazol-1-yl)phenyl)urea;

1-(3-chloro-4-(2H-1,2,3-triazol-2-yl)phenyl)-3-(2-chloro-7-isopropylpyrazolo[1,5-a]pyrimidin-6-yl)urea;

1-(5-chloro-6-(2H-1,2,3-triazol-2-yl)pyridin-3-yl)-3-(2-chloro-7-isopropylpyrazolo[1,5-a]pyrimidin-6-yl)urea;

1-(5-chloro-6-(4-methyl-2H-1,2,3-triazol-2-yl)pyridin-3-yl)-3-(2-chloro-7-isopropylpyrazolo[1,5-a]pyrimidin-6-yl)urea;

1-(4-(2-aminopyrimidin-4-yl)-3-chlorophenyl)-3-(2-chloro-7-isopropylpyrazolo[1,5-a]pyrimidin-6-yl)urea;

1-(5-chloro-1-methyl-6-oxo-2-(1H-pyrazol-1-yl)-1,6-dihydropyridin-3-yl)-3-(2-chloro-7-isopropylpyrazolo[1,5-a]pyrimidin-6-yl)urea;

1-(5-chloro-6-ethoxypyridin-3-yl)-3-(2-chloro-7-isopropylpyrazolo[1,5-a]pyrimidin-6-yl)urea;

1-(5-bromopyridin-3-yl)-3-(2-chloro-7-isopropylpyrazolo[1,5-a]pyrimidin-6-yl)urea;

1-(2-chloro-7-isopropylpyrazolo[1,5-a]pyrimidin-6-yl)-3-(6-(1,1-dioxidoisothiazolidin-2-yl)-5-(trifluoromethyl)pyridin-3-yl)urea;

1-(3-chloro-4-(3-(hydroxymethyl)-5-methyl-1H-pyrazol-1-yl)phenyl)-3-(2-chloro-7-iso-propylpyrazolo[1,5-a]pyrimidin-6-yl)urea;

1-(5-chloro-6-(1-methyl-1H-pyrazol-5-yl)pyridin-3-yl)-3-(2-chloro-7-isopropylpyrazolo[1,5-a]pyrimidin-6-yl)urea;

1-(2-chloro-7-isopropylpyrazolo[1,5-a]pyrimidin-6-yl)-3-(3,5-dichloro-4-(2H-1,2,3-triazol-2-yl)phenyl)urea;

1-(5-chloro-2-oxoindolin-7-yl)-3-(2-chloro-7-isopropylpyrazolo[1,5-a]pyrimidin-6-yl)urea;

1-(2-chloro-7-isopropylpyrazolo[1,5-a]pyrimidin-6-yl)-3-(1-methyl-2-oxo-5-(trifluoro-methyl)-1,2-dihydropyridin-3-yl)urea;

1-(5-chloro-2-((1-methylpyrrolidin-3-yl)oxy)-6-(2H-1,2,3-triazol-2-yl)pyridin-3-yl)-3-(2-chloro-7-isopropylpyrazolo[1,5-a]pyrimidin-6-yl)urea;

1-(7-(tert-butyl)-2-chloropyrazolo[1,5-a]pyrimidin-6-yl)-3-(5-chloro-6-(2H-1,2,3-triazol-2-yl)pyridin-3-yl)urea;

1-(7-(sec-butyl)-2-chloropyrazolo[1,5-a]pyrimidin-6-yl)-3-(5-chloro-6-(2H-1,2,3-triazol-2-yl)pyridin-3-yl)urea;

1-(2-chloro-7-(2-methyltetrahydrofuran-2-yl)pyrazolo[1,5-a]pyrimidin-6-yl)-3-(2-(trifluoro-methyl)pyridin-4-yl)urea;

(R)-1-(2-chloro-7-(1-methoxy-2-methylpropyl)pyrazolo[1,5-a]pyrimidin-6-yl)-3-(2-(trifluoro-methyl)pyridin-4-yl)urea;

1-(5-chloro-6-(2H-1,2,3-triazol-2-yl)pyridin-3-yl)-3-(2-chloro-7-cyclobutylpyrazolo[1,5-a]-pyrimidin-6-yl)urea;

(S)-1-(5-chloro-6-(2H-1,2,3-triazol-2-yl)pyridin-3-yl)-3-(2-chloro-7-(1-(2-methoxy-ethoxy)-ethyl)pyrazolo[1,5-a]pyrimidin-6-yl)urea;

(S)-1-(5-chloro-6-methoxypyridin-3-yl)-3-(2-chloro-7-(1-(2-methoxyethoxy)-ethyl)-pyrazolo-[1,5-a]pyrimidin-6-yl)urea;

(S)-1-(2-chloro-7-(1-(2-methoxyethoxy)ethyl)pyrazolo[1,5-a]pyrimidin-6-yl)-3-(2-(trifluoromethyl)-pyridin-4-yl)urea;

(R)-1-(5-chloro-6-(2H-1,2,3-triazol-2-yl)pyridin-3-yl)-3-(2-chloro-7-(1-(2-methoxy-ethoxy)-ethyl)pyrazolo[1,5-a]pyrimidin-6-yl)urea;

1-(5-chloro-6-(2H-1,2,3-triazol-2-yl)pyridin-3-yl)-3-(2-chloro-7-(1,4-dioxan-2-yl)-pyrazolo[1,5-a]pyrimidin-6-yl)urea;

(S)-1-(5-chloro-6-(2H-1,2,3-triazol-2-yl)pyridin-3-yl)-3-(2-chloro-7-(1-methoxypropan-2-yl)-pyrazolo[1,5-a]pyrimidin-6-yl)urea;

(R)-1-(5-chloro-6-(2H-1,2,3-triazol-2-yl)pyridin-3-yl)-3-(2-chloro-7-(1-methoxypropan-2-yl)pyrazolo[1,5-a]pyrimidin-6-yl)urea;

(R)-1-(5-chloro-6-(2H-1,2,3-triazol-2-yl)pyridin-3-yl)-3-(2-chloro-7-(1-methoxyethyl)-pyrazolo[1,5-a]pyrimidin-6-yl)urea;

(R)-1-(2-chloro-7-(1-methoxyethyl)pyrazolo[1,5-a]pyrimidin-6-yl)-3-(2-(trifluoromethyl)-pyridin-4-yl)urea;

(R)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea;

1-(5-chloro-6-(2H-1,2,3-triazol-2-yl)pyridin-3-yl)-3-(2-chloro-7-(methoxy(phenyl)methyl)-pyrazolo[1,5-a]pyrimidin-6-yl)urea;

1-(5-chloro-6-(2H-1,2,3-triazol-2-yl)pyridin-3-yl)-3-(2-chloro-7-(1-(methoxymethyl)cyclobutyl)pyrazolo[1,5-a]pyrimidin-6-yl)urea;

1-(2-chloro-7-(1-(methoxymethyl)cyclobutyl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(2-chloro-7-cyclopropylpyrazolo[1,5-a]pyrimidin-6-yl)urea;

1-(5-chloro-6-(2H-1,2,3-triazol-2-yl)pyridin-3-yl)-3-(2-chloro-7-(2-methoxyphenyl)pyrazolo[1,5-a]pyrimidin-6-yl)urea;

1-(6-(2H-1,2,3-triazol-2-yl)-5-(trifluoromethyl)pyridin-3-yl)-3-(2-chloro-7-(tetrahydrofuran-2-yl)pyrazolo[1,5-a]pyrimidin-6-yl)urea;

1-(5-chloro-6-(2H-1,2,3-triazol-2-yl)pyridin-3-yl)-3-(2-chloro-7-(4-methyltetrahydro-2H-pyran-4-yl)pyrazolo[1,5-a]pyrimidin-6-yl)urea;

1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea;

1-(5-chloro-6-(2H-1,2,3-triazol-2-yl)pyridin-3-yl)-3-(2-chloro-7-(tetrahydrofuran-3-yl)pyrazolo[1,5-a]pyrimidin-6-yl)urea;

1-(5-chloro-6-(2H-1,2,3-triazol-2-yl)pyridin-3-yl)-3-(2-chloro-7-(tetrahydro-2H-pyran-4-yl)pyrazolo[1,5-a]pyrimidin-6-yl)urea;

1-(5-chloro-6-(2H-1,2,3-triazol-2-yl)pyridin-3-yl)-3-(2-chloro-7-(methoxymethyl)pyrazolo[1,5-a]pyrimidin-6-yl)urea;

1-(5-chloro-6-(2H-1,2,3-triazol-2-yl)pyridin-3-yl)-3-(2-chloro-7-((tetrahydro-2H-pyran-4-yl)methyl)pyrazolo[1,5-a]pyrimidin-6-yl)urea;

1-(5-chloro-6-(2H-1,2,3-triazol-2-yl)pyridin-3-yl)-3-(2-chloro-7-(isopropoxymethyl)pyrazolo[1,5-a]pyrimidin-6-yl)urea;

1-(5-chloro-6-(2H-1,2,3-triazol-2-yl)pyridin-3-yl)-3-(2-chloro-7-methylpyrazolo[1,5-a]pyrimidin-6-yl)urea;

1-(6-(2H-1,2,3-triazol-2-yl)-5-(trifluoromethyl)pyridin-3-yl)-3-(2-chloro-7-(furan-2-yl)pyrazolo[1,5-a]pyrimidin-6-yl)urea;

1-(5-chloro-6-(2H-1,2,3-triazol-2-yl)pyridin-3-yl)-3-(2-chloro-7-(1,3-dimethoxypropyl)pyrazolo[1,5-a]pyrimidin-6-yl)urea;

(R)-1-(6-(2H-1,2,3-triazol-2-yl)-5-(trifluoromethyl)pyridin-3-yl)-3-(7-(1-(benzyloxy)ethyl)-2-chloropyrazolo[1,5-a]pyrimidin-6-yl)urea;

tert-butyl 2-(2-chloro-6-(3-(5-chloro-6-(2H-1,2,3-triazol-2-yl)pyridin-3-yl)ureido)pyrazolo[1,5-a]pyrimidin-7-yl)morpholine-4-carboxylate;

1-(7-(3-oxabicyclo[3.1.0]hexan-6-yl)-2-chloropyrazolo[1,5-a]pyrimidin-6-yl)-3-(5-chloro-6-methoxypyridin-3-yl)urea;

1-(5-chloro-6-(2H-1,2,3-triazol-2-yl)pyridin-3-yl)-3-(2-chloro-7-(5-oxaspiro[2.4]heptan-1-yl)pyrazolo[1,5-a]pyrimidin-6-yl)urea;

1-(5-chloro-6-methoxypyridin-3-yl)-3-(2-chloro-7-(pyridin-4-yl)pyrazolo[1,5-a]pyrimidin-6-yl)urea;

2-chloro-6-(3-(5-chloro-6-(2H-1,2,3-triazol-2-yl)pyridin-3-yl)ureido)-N,N-dimethyl pyrazolo[1,5-a]pyrimidine-7-carboxamide;

(S)-1-(5-chloro-6-(2H-1,2,3-triazol-2-yl)pyridin-3-yl)-3-(7-(1-methoxyethyl)-2-methylpyrazolo[1,5-a]pyrimidin-6-yl)urea;

1-(5-chloro-6-(2H-1,2,3-triazol-2-yl)pyridin-3-yl)-3-(2-methyl-7-(1-methylcyclopropyl)pyrazolo[1,5-a]pyrimidin-6-yl)urea;

1-(5-chloro-6-methoxypyridin-3-yl)-3-(2-methyl-7-(1-methylcyclopropyl)pyrazolo[1,5-a]pyrimidin-6-yl)urea;

(S)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea;

(S)-1-(2-chloro-7-(1-methoxy-2-methylpropyl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(2-chloro-7-(1-(methoxymethyl)cyclopropyl)pyrazolo[1,5-a]pyrimidin-6-yl)urea;

1-(2-chloro-7-(1-(methoxymethyl)cyclopropyl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(7-(1-(methoxymethyl)cyclopropyl)-2-methylpyrazolo[1,5-a]pyrimidin-6-yl)urea;

1-(7-(1-(methoxymethyl)cyclopropyl)-2-methylpyrazolo[1,5-a]pyrimidin-6-yl)-3-(2-(trifluoromethyl)pyridin-4-yl)urea;

1-(2-chloro-7-(2-(tetrahydro-2H-pyran-4-yl)propan-2-yl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(2-chloro-7-(1,2-dimethoxypropan-2-yl)pyrazolo[1,5-a]pyrimidin-6-yl)urea;

(S)-1-(5-chloro-6-(2H-1,2,3-triazol-2-yl)pyridin-3-yl)-3-(2-chloro-7-(1-(2-(dimethylamino)ethoxy)ethyl)pyrazolo[1,5-a]pyrimidin-6-yl)urea;

1-(5-chloro-6-(2H-1,2,3-triazol-2-yl)pyridin-3-yl)-3-(2-chloro-7-((4-methylmorpholin-3-yl)methyl)pyrazolo[1,5-a]pyrimidin-6-yl)urea;

(S)-1-(5-chloro-6-(2H-1,2,3-triazol-2-yl)pyridin-3-yl)-3-(2-chloro-7-(1-methylpiperidin-2-yl)pyrazolo[1,5-a]pyrimidin-6-yl)urea;

1-(5-chloro-6-(2H-1,2,3-triazol-2-yl)pyridin-3-yl)-3-(2-chloro-7-((S)-1-((R)-2-methoxypropoxy)ethyl)pyrazolo[1,5-a]pyrimidin-6-yl)urea;

1-(5-chloro-6-(2H-1,2,3-triazol-2-yl)pyridin-3-yl)-3-(2-chloro-7-(1-methyl-1H-imidazol-2-yl)pyrazolo[1,5-a]pyrimidin-6-yl)urea;

1-(5-chloro-6-methoxypyridin-3-yl)-3-(2-chloro-7-(5-methyltetrahydrofuran-2-yl)pyrazolo[1,5-a]pyrimidin-6-yl)urea;

1-(5-chloro-6-(2H-1,2,3-triazol-2-yl)pyridin-3-yl)-3-(2-chloro-7-(1-(dimethylamino)cyclopropyl)pyrazolo[1,5-a]pyrimidin-6-yl)urea;

(S)-1-(2-chloro-7-(1-methoxyethyl)pyrazolo[1,5-a]pyrimidin-6-yl)-3-(5-(difluoromethyl)-6-(2H-1,2,3-triazol-2-yl)pyridin-3-yl)urea;

1-(2-chloro-7-(methoxy(tetrahydro-2H-pyran-4-yl)methyl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(2-chloro-7-(2-(methoxymethyl)tetrahydrofuran-2-yl)pyrazolo[1,5-a]pyrimidin-6-yl)urea;

(S)-1-(2-chloro-7-(1-methoxyethyl)pyrazolo[1,5-a]pyrimidin-6-yl)-3-(2-(difluoromethyl)pyridin-4-yl)urea;

(S)-1-(5-chloro-6-(difluoromethoxy)pyridin-3-yl)-3-(2-chloro-7-(1-methoxyethyl)pyrazolo[1,5-a]pyrimidin-6-yl)urea;

(S)-1-(6-(2H-1,2,3-triazol-2-yl)-5-(trifluoromethyl)pyridin-3-yl)-3-(2-fluoro-7-(1-methoxy-ethyl)pyrazolo[1,5-a]pyrimidin-6-yl)urea;

(S)-1-(5-chloro-6-(2H-1,2,3-triazol-2-yl)pyridin-3-yl)-3-(2-fluoro-7-(1-methoxyethyl)pyrazolo[1,5-a]pyrimidin-6-yl)urea;

(S)-1-(5-chloro-6-(2H-1,2,3-triazol-2-yl)pyridin-3-yl)-3-(2-cyano-7-(1-methoxyethyl)pyrazolo[1,5-a]pyrimidin-6-yl)urea;

(S)-1-(5-chloro-6-(difluoromethoxy)pyridin-3-yl)-3-(2-chloro-7-(1-(2-methoxyethoxy)ethyl)pyrazolo[1,5-a]pyrimidin-6-yl)urea;

1-(5-chloro-6-(2H-1,2,3-triazol-2-yl)pyridin-3-yl)-3-(2-chloro-7-((1R,2R)-1,2-dimethoxypropyl)pyrazolo[1,5-a]pyrimidin-6-yl)urea;

(S)-1-(5-chloro-2-(2-(dimethylamino)ethoxy)pyridin-3-yl)-3-(2-chloro-7-(1-methoxyethyl)pyrazolo[1,5-a]pyrimidin-6-yl)urea;

1-(5-chloro-6-(2H-1,2,3-triazol-2-yl)pyridin-3-yl)-3-(2-chloro-7-((S)-1-(((R)-tetrahydrofuran-3-yl)oxy)ethyl)pyrazolo[1,5-a]pyrimidin-6-yl)urea;

1-(5-chloro-6-(2H-1,2,3-triazol-2-yl)pyridin-3-yl)-3-(2-chloro-7-((S)-1-(((S)-tetrahydrofuran-3-yl)oxy)ethyl)pyrazolo[1,5-a]pyrimidin-6-yl)urea;

1-(5-chloro-6-(2H-1,2,3-triazol-2-yl)pyridin-3-yl)-3-(2-chloro-7-((S)-1-(((S)-tetrahydrofuran-3-yl)methoxy)ethyl)pyrazolo[1,5-a]pyrimidin-6-yl)urea;

1-(5-chloro-6-(2H-1,2,3-triazol-2-yl)pyridin-3-yl)-3-(2-chloro-7-((S)-1-(((R)-tetrahydrofuran-3-yl)methoxy)ethyl)pyrazolo[1,5-a]pyrimidin-6-yl)urea;

1-(5-chloro-6-(2H-1,2,3-triazol-2-yl)pyridin-3-yl)-3-(2-methyl-7-(2-methyltetrahydrofuran-2-yl)pyrazolo[1,5-a]pyrimidin-6-yl)urea;

(S)-1-(2-chloro-7-(1-methoxyethyl)pyrazolo[1,5-a]pyrimidin-6-yl)-3-(2-cyanopyridin-4-yl)urea;

1-(2-chloro-7-(2-(methoxymethyl)tetrahydrofuran-2-yl)pyrazolo[1,5-a]pyrimidin-6-yl)-3-(5-(trifluoromethyl)pyridin-3-yl)urea;

1-(6-(2H-1,2,3-triazol-2-yl)-5-(trifluoromethyl)pyridin-3-yl)-3-(2-chloro-7-(1-(dimethylamino)cyclopropyl)pyrazolo[1,5-a]pyrimidin-6-yl)urea;

1-(6-(2H-1,2,3-triazol-2-yl)-5-(trifluoromethyl)pyridin-3-yl)-3-(2-chloro-7-(1,2-dimethoxy-ethyl)pyrazolo[1,5-a]pyrimidin-6-yl)urea;

1-(2-chloro-7-(1,2-dimethoxyethyl)pyrazolo[1,5-a]pyrimidin-6-yl)-3-(2-(trifluoromethyl)pyridin-4-yl)urea;

(S)-1-(6-(2H-1,2,3-triazol-2-yl)-5-(trifluoromethyl)pyridin-3-yl)-3-(2-chloro-7-(1-methoxypropan-2-yl)pyrazolo[1,5-a]pyrimidin-6-yl)urea;

(R)-1-(6-(2H-1,2,3-triazol-2-yl)-5-(trifluoromethyl)pyridin-3-yl)-3-(2-chloro-7-(1-methoxypropan-2-yl)pyrazolo[1,5-a]pyrimidin-6-yl)urea;

1-(5-(2H-1,2,3-triazol-2-yl)-2-(trifluoromethyl)pyridin-4-yl)-3-(2-chloro-7-isopropylpyrazolo[1,5-a]pyrimidin-6-yl)urea;

(R)-1-(6-(2H-1,2,3-triazol-2-yl)-5-(trifluoromethyl)pyridin-3-yl)-3-(2-chloro-7-(1-hydroxyethyl)pyrazolo[1,5-a]pyrimidin-6-yl)urea;

(S)-1-(2-chloro-7-(1-hydroxyethyl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(2-chloro-7-(morpholin-2-yl)pyrazolo[1,5-a]pyrimidin-6-yl)urea;

1-(5-chloro-6-(2H-1,2,3-triazol-2-yl)pyridin-3-yl)-3-(2-chloro-7-(4-methylmorpholin-2-yl)pyrazolo[1,5-a]pyrimidin-6-yl)urea;

1-(4-(4-(aminomethyl)-1H-pyrazol-1-yl)-3-chlorophenyl)-3-(2-chloro-7-isopropylpyrazolo[1,5-a]pyrimidin-6-yl)urea;

1-(6-(4-(aminomethyl)-1H-pyrazol-1-yl)-5-chloropyridin-3-yl)-3-(2-chloro-7-isopropylpyrazolo[1,5-a]pyrimidin-6-yl)urea;

(S)-1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea;

2-(3-(2-chloro-7-isopropylpyrazolo[1,5-a]pyrimidin-6-yl)ureido)-4-(trifluoromethyl)pyridine 1-oxide;

(R)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea;

(S)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea;

1-(5-chloro-6-(2H-1,2,3-triazol-2-yl)pyridin-3-yl)-3-(2-chloro-7-(morpholin-3-yl)pyrazolo[1,5-a]pyrimidin-6-yl)urea;

(S)-1-(5-chloro-6-(2H-1,2,3-triazol-2-yl)pyridin-3-yl)-3-(2-chloro-7-(2-methyl-1-(methylamino)propyl)pyrazolo[1,5-a]pyrimidin-6-yl)urea;

1-(5-chloro-6-(2H-1,2,3-triazol-2-yl)pyridin-3-yl)-3-(2-chloro-7-(4-methylmorpholin-3-yl)pyrazolo[1,5-a]pyrimidin-6-yl)urea;

(R)-1-(5-chloro-6-(2H-1,2,3-triazol-2-yl)pyridin-3-yl)-3-(2-chloro-7-(1,2-dimethoxy ethyl)pyrazolo[1,5-a]pyrimidin-6-yl)urea; and (S)-1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea.

Embodiment 22 relates to a compound of embodiment 1 or a pharmaceutically acceptable salt thereof, wherein R1 is fluoro;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring having 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 2-pyridyl substituted one or more times by Rb; and

Rb independently from each other is halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring having 1 to 3 N atoms said ring being optionally substituted by $C_1$-$C_6$ alkyl optionally substituted by amino or hydroxy, or by mono- or di-N—$C_1$-$C_6$ alkylamino carbonyl; O—Rh; or Rh; wherein Rh is a 5-6 membered heterocyclyl ring having 1 to 4 heteroatoms selected from N, O and S said ring being optionally substituted by $C_1$-$C_6$ alkyl, hydroxyl or oxo.

Embodiment 23 relates to a compound of embodiment 1 or a pharmaceutically acceptable salt thereof, wherein R1 is fluoro;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 3-pyridyl substituted one or more times by Rc; and

Rc independently from each other is halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring having 1 to 3 N atoms said ring being optionally substituted by $C_1$-$C_6$ alkyl optionally substituted by amino or hydroxy, or by mono- or di-N—$C_1$-$C_6$ alkylamino carbonyl; O—Rh; or Rh; wherein Rh is a 5-6 membered heterocyclyl having 1 to 4 heteroatoms selected from N, O and S said ring being optionally substituted by $C_1$-$C_6$ alkyl, hydroxyl or oxo.

Embodiment 24 relates to a compound of embodiment 1 or a pharmaceutically acceptable salt thereof, wherein R1 is fluoro;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 4-pyridyl substituted one or more times by Rd; and

Rd independently from each other is halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring containing 1 to 3 N atoms said ring being optionally substituted by $C_1$-$C_6$ alkyl optionally substituted by amino or hydroxy, or by mono- or di-N—$C_1$-$C_6$ alkylamino carbonyl; O—Rh; or Rh; wherein Rh is a 5-6 membered heterocyclyl containing 1 to 4 heteroatoms selected from N, O and S said ring being optionally substituted by $C_1$-$C_6$ alkyl, hydroxyl or oxo.

Embodiment 25 relates to a pharmaceutical composition comprising a therapeutically effective amount of a compound according to any one of embodiments 1 to 24 and one or more pharmaceutically acceptable carriers.

Embodiment 26 relates to a combination comprising a therapeutically effective amount of a compound according to any one of embodiments 1 to 24 or a pharmaceutically acceptable salt thereof and one or more therapeutically active co-agents.

Embodiment 27 relates to a method of modulating MALT1 activity in a subject, wherein the method comprises administering to the subject a therapeutically effective amount of a compound according to any one of embodiments 1 to 24 or a pharmaceutically acceptable salt thereof.

Embodiment 28 relates to a compound according to any one of embodiments 1 to 24 or a pharmaceutically acceptable salt thereof, for use as a medicament, in particular for use as a medicament acting as a MALT1 inhibitor.

Definitions

As used herein, the term "$C_1$-$C_6$ alkyl" refers to a fully saturated branched or unbranched hydrocarbon moiety having up to 6 carbon atoms. Unless otherwise provided, it refers to hydrocarbon moieties having 1 to 6 carbon atoms, 1 to 4 carbon atoms or 1 to 2 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl and the like.

As used herein, the term "$C_{1-6}$alkylene" refers to divalent fully saturated branched or unbranched hydrocarbon moiety having 1 to 6 carbon atoms. The terms "$C_{1-4}$alkylene", "$C_{1-3}$alkylene" and "$C_{1-2}$alkylene", are to be construed accordingly. Representative examples of $C_{1-6}$alkylene include, but are not limited to, methylene, ethylene, n-propylene, iso-propylene, n-butylene, sec-butylene, iso-butylene, tert-butylene, n-pentylene, isopentylene, neopentylene, and n-hexylene.

As used herein, the term "$C_1$-$C_6$ alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1 to 6 carbon atoms, 1 to 4 carbon atoms or 1 to 2 carbon atoms.

As used herein, the term "$C_1$-$C_6$ alkyl optionally substituted by halogen" refers to $C_1$-$C_6$ alkyl as defined above which may be substituted by one or more halogens. Examples include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "$C_1$-$C_6$ alkyl optionally substituted by hydroxyl" refers to $C_1$-$C_6$ alkyl as defined above which may be substituted by one or more hydroxy. Examples include, but are not limited to, hydroxymethyl, hydroxyethyl, 1,2-dihydroxyethyl, 2,3-dihydroxy-propyl and the like.

As used herein, the term "di $C_{1-6}$ alkylamino" refers to a moiety of the formula —N($R_a$)—$R_a$ where each $R_a$ is a $C_{1-6}$alkyl, which may be the same or different, as defined above. In analogy thereto the term "mono $C_{1-6}$ alkylamino" refers to a moiety of the formula —N(H)—$R_a$ where $R_a$ is a $C_{1-6}$alkyl, which may be the same or different, as defined above.

As used herein, the term "$C_3$-$C_6$cycloalkyl" refers to saturated monocyclic hydrocarbon groups of 3-6 carbon atoms. Cycloalkyl may also be referred to as a carbocyclic ring and vice versa additionally referring to the number of carbon atoms present. Unless otherwise provided, cycloalkyl refers to cyclic hydrocarbon groups having between 3 and 6 ring carbon atoms or between 3 and 4 ring carbon atoms. Exemplary monocyclic hydrocarbon groups include, but are not limited to, cyclopropyl, cyclobutyl, cyclopentyl, and cyclohexyl.

As used herein, the term "halogen" or "halo" refers to fluoro, chloro, bromo, and iodo; and it may in particular refer to chloro; and it may also in particular refer to fluoro.

As used herein, the term "heterocyclyl" refers to a heterocyclic group that is, unless otherwise indicated, saturated or partially saturated and is preferably a monocyclic or a polycyclic ring (in case of a polycyclic ring particularly a bicyclic, tricyclic or spirocyclic ring); and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl excludes heteroaryl. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-4, such as one, or two, or three, or four substituents.

As used herein, the term "heteroaryl" refers to a 5-14 membered monocyclic- or bicyclic- or tricyclic-aromatic ring system, having 1 to 8 heteroatoms. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2, 3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents.

As used herein, the term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl.

A substituted aryl is an aryl group substituted by 1-5 (such as one, or two, or three) substituents independently selected from the group consisting of hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

As used herein, the term a pyridin or a pyridyl optionally substituted by hydroxy e.g. 2-pyridyl, 3-pyridyl, or 4-pyridyl-, refers to a respective hydroxy-pyridin or hydroxy-pyridyl and may include its tautomeric form such as a respective pyridone or pyridon-yl.

As used herein the term pyridin or pyridyl optionally substituted by oxo e.g. 2-pyridyl, 3-pyridyl, or 4-pyridyl-, refers to a respective pyridone or pyridon-yl and may include its tautomeric form such as a respective hydroxy-pyridin or hydroxy-pyridyl, provided said tautomeric form may be obtainable. Pyridin or pyridyl optionally substituted by oxo may further refer to a respective pyridine-N-oxide or pyridyl-N-oxide.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isothionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by MALT1, or (ii) associated with MALT1 activity, or (iii) characterized by activity (normal or abnormal) of MALT1; or (2) reducing or inhibiting the activity of MALT1; or (3) reducing or inhibiting the expression of MALT1; or (4) modifying the protein levels of MALT1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of MALT1; or reducing or inhibiting the expression of MALT1 partially or completely.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiralstationary phase.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (a g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Synthesis of the Compounds of the Present Invention

The synthesis of the compounds of the invention is performed as outlined in Scheme 1:

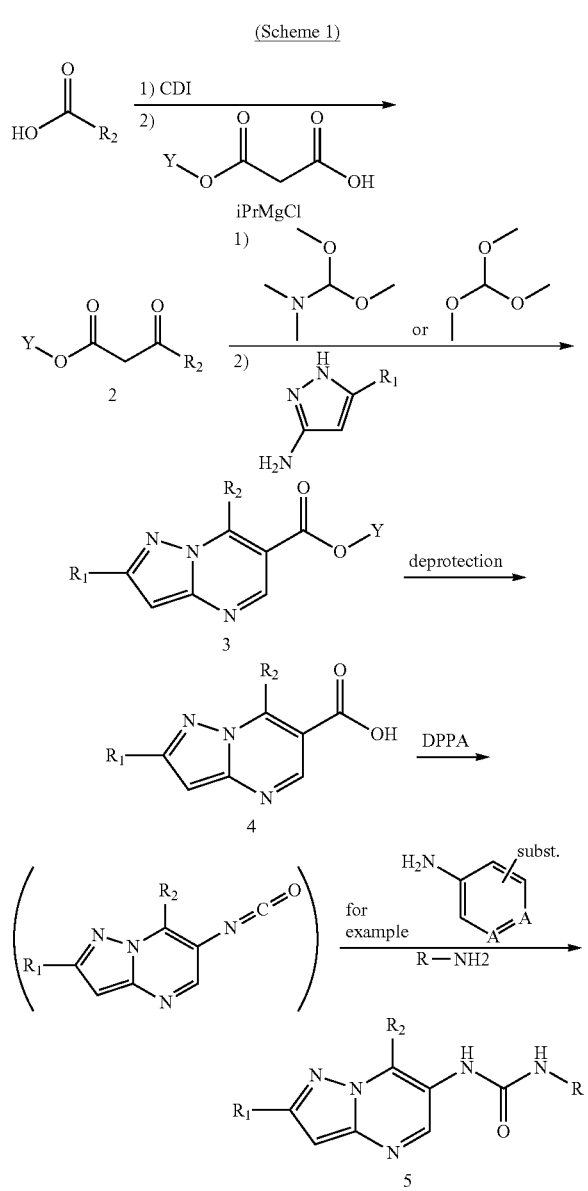

Treatment of an activated acid, e.g. activated as an imidazolid, with the dianion of a malonate mono-ester provides after workup β-ketoester 2. Condensation with a C1 equivalent, e.g. dimethylformamide-dimethylacetal or triethyl orthoformiate, followed by cyclo-condensation with aminopyrazoles in an organic solvent like ethanol at elevated temperature provides the substituted pyrazolo-pyrimidines 3. In case a chiral acid is used in step 1, depending on the substitution pattern, partial racemization may occur during the reaction sequence. In this case the final product may be purified to high enantiomeric purity by chiral chromatography typically as shown for example 119. Deprotecion of the ester provides acid 4. Curtius rearrangement of acid 4 provides an intermediate isocyanate which may be reacted with an appropriate aniline or aminopyridine in a one pot reaction to form the final products.

The synthesis of aminopyrazoles, like 3-amino-5-chloropyrazole can be conducted as follows (Scheme 2):

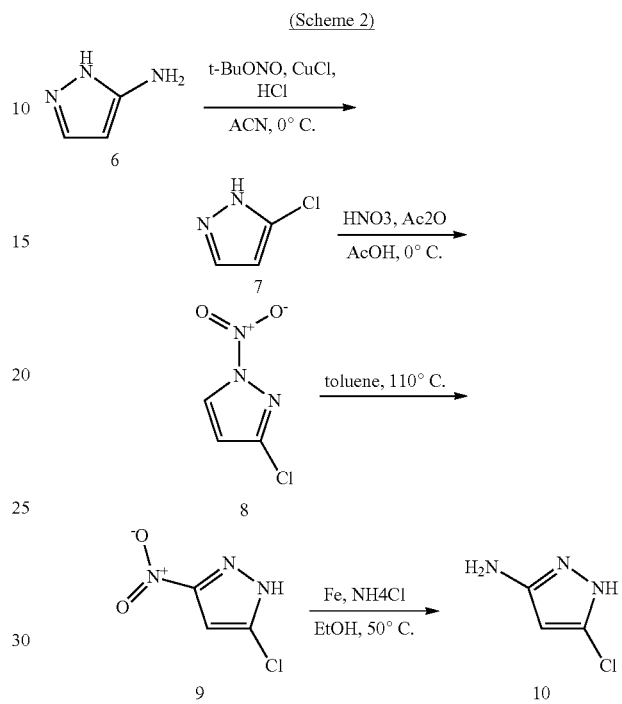

Treatment of aminopyrazole under Sandmeyer conditions provides 3-chloropyrazole. Nitration provides the N-nitropyrazole, which upon heating rearranges to the desired 3-chloro-5-nitropyrazole. Reduction of the nitro group, using iron, tin or tin chloride finally provides the desired 3-amino-5-chloropyrazole 10.

Anilines and aminopyridines used in this invention can be prepared using the following route:

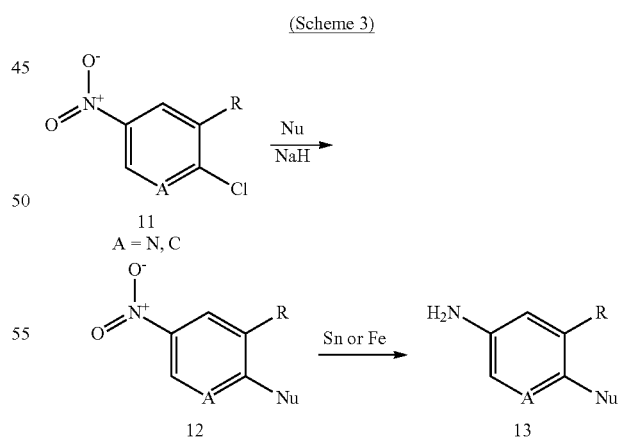

A substituted para-nitro-chlorobenzene or p-nitrochloropyridine is treated with a nucleophile in an inert solvent like DMF, to give the substitution product 12. The nucleophile in this case can be deprotonated alcohols, amines, lactams or heterocycles, e.g. the anion of 1,2,3 triazole. Finally reduction of the nitro substituent using tin or iron in acidic media provides the desired aminophenyl- or aminopyridyl-derivatives 13.

Alternatively, anilines or aminopyridines can be prepared via Curtius rearrangement of suitable aryl acids (Scheme 4):

Pyridones of this invention are generally prepared via alkylation of hydroxypyridines (Scheme 6):

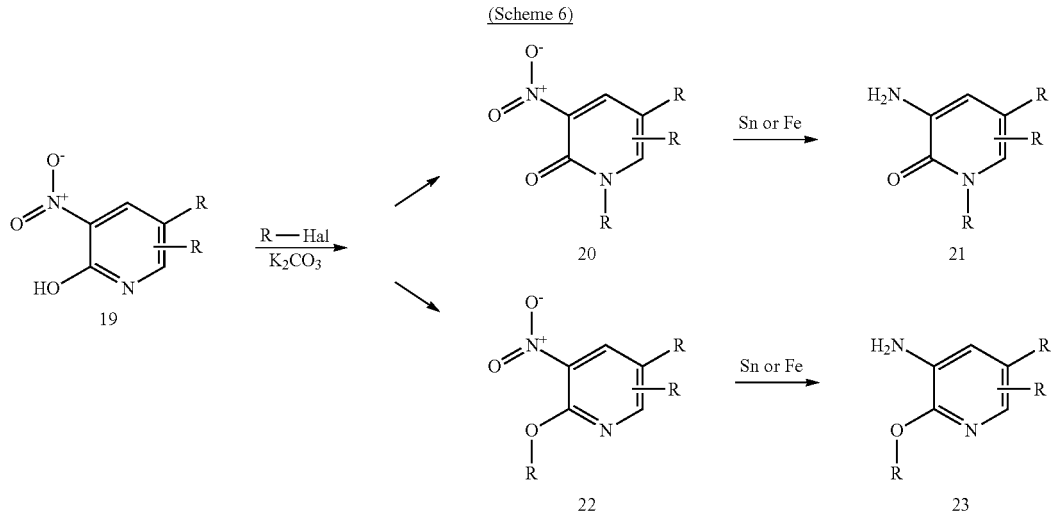

Treatment of a hydroxypyridine 19 with base, e.g. potassium carbonate and an alkylhalide leads to the formation of the pyridone 20 and the alkoxypyridine 22. Depending on the substitution pattern of the reactants selectivity towards one or the other reaction product can be achieved. After separation of the products, each compound can be reduced using standard iron or tin mediated reduction methods to provide the aminopyridones 21, as well as the amino-alkoxypridines 23.

EXPERIMENTAL SECTION

Abbreviations
Ac$_2$O acetic anhydride
AcOEt ethyl acetate
AcOH acetic acid
Boc$_2$O di-tert-butyl dicarbonate
bs broad singulet
BuLi n-Butyllithium
CaCl$_2$ calcium chloride
CCl$_4$ carbon tetrachloride
CDI carbonyldiimidazole
CHCl$_3$ chloroform
CH$_3$CN acetonitrile
CO$_2$ carbon dioxide
Cs$_2$CO$_3$ cesium carbonate
d dublett
DAST diethylamino sulfurtrifluoride
DCE 1,2-dichloroethane
DCM dichloromethane
DMF dimethylformamide
DMSO dimethylsulfoxyde
DPPA diphenyl phosphoryl azide
Et$_2$O diethylether
Et$_3$N triethylamine
EtOH ethanol
h hour
HCl hydrochloric acid
hept. heptett
H$_2$O water
H$_2$SO$_4$ sulfuric acid
HCHO formaldehyde Treatment of acid 14 with diphenyl phosphoryl azide and base in t-butanol provides the t-butoxy-carbonyl-protected amino compound 15, which can be deprotected under acidic conditions using HCl or TFA to give the desired aniline/aminopyridine 16. Certain aminopyridines and anilines can be prepared by palladium-catalyzed coupling of an aryl halide with a boronic acid according to Scheme 5:

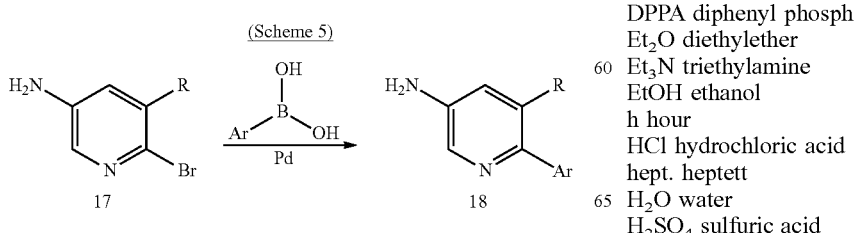

HCOOH formic acid
HNO₃ nitric acid
HPLC High Performance Liquid Chromatography
HV high vacuum
iPrOH isopropanol
IST International Sorbent Technology (supplier)
K₂CO₃ potassium carbonate
KNO₃ potassium nitroperoxous acid
KOH potassium hydroxyde
LDA lithium diisopropylamide
LiAlH₄ lithium aluminium hydride
LiCl lithium chloride
LiOH lithium hydroxide
mCPBA meta-chloroperbenzoic acid
MeI methyl iodide
MeOH methanol
MnO₂ manganese dioxide
m multiplett
M molar
min minute
N normal
NaBH₄ sodium borohydride
NaBH(OAc)₃ sodium triacetoxyborohydride
Na₂CO₃ sodium carbonate
Na₂SO₄ sodium sulfate
NaH sodium hydride
NaHCO₃ sodium bicarbonate
NaIO₄ sodium periodate
NaOH sodium hydroxyde
NH₄Cl ammonium chloride
NMR Nuclear Magnetic Resonance
Pd/C palladium on charcoal
PdCl₂(PPh₃)₂ bis(triphenylphosphine)palladium(II) dichloride
Pd₂(dba)₃ tris(dibenzylideneacetone)dipalladium(0)
Pd(PPh₃)₄ tetrakis(triphenylphospine)palladium(0)
pTsOH para-toluenesulfonic acid
q quadruplet
RT room temperature
Rt retention time
s singulet
SFC supercritical fluid chromatography
t triplet
TBME tert-butylmethyl ether
tBuOH tert-butanol
TBAF tetrabutylammonium fluoride
TFA trifluoroacetic acid
THF tetrahydrofuran
UPLC Ultra Performance Liquid Chromatography
XantPhos 4,5-bis(diphenylphosphino)-9,9-dimethylxanthene Analytical Methods
UPLC Methods
Method B1: Fast 4: Waters UPLC; column: Acquity HSS T3 1.8 µm, 2.1*50 mm, at 60° C., Eluent A: H₂O+0.05% HCOOH+3.75 mM ammonium acetate, B: CH₃CN+0.04% HCOOH, Gradient: 10 to 95% B in 1.5 min, Flow: 1 ml/min.
Method B2: Method LCMS_2_MIN_FINAL_ANALYSIS: Waters UPLC; column: Acquity HSS T3, 1.8 µm, 2.1*50 mm, at 60° C., Eluent A: H₂O+0.05% HCOOH+3.75 mM ammonium acetate, B: CH₃CN+0.04% HCOOH, Gradient: 5% to 98% B in 1.4 min, Flow: 1 ml/min.
Method B3: Method LCMS_2_MIN_MONITORING: Waters UPLC; column: Ascentis Expresse C18 2.1×30 mm, 2.7 µm, at 60° C., Eluent A: H₂O+0.05% TFA, B: CH₃CN+0.04% TFA, Gradient: 2% to 98% B in 1.4 min, Flow: 1 ml/min.
Method B4: Method LCMS_SHORT: Waters UPLC; column: Acquity UPLC BEH C18, 2.1×50 mm, 1.7 µm, at 35° C., Eluent A: H₂O+0.1% TFA, B: CH₃CN+0.1% TFA, Gradient: 5% to 100% B in 1.5 min, Flow: 0.6 ml/min.
Method B5: Method LCMS_2_MIN_POLAR: Waters UPLC; column: Acquity HSS T3, 1.8 µm, 2.1*50 mm, at 50° C., Eluent A: H₂O+0.05% HCOOH+3.75 mM ammonium acetate, B: CH₃CN+0.04% HCOOH, Gradient: 2% to 98% B in 1.4 min, Flow: 1.2 ml/min.
Method B6: Method LCMS_SPECTRA: Waters UPLC; column: Acquity HSS T3, 1.8 µm, 2.1*50 mm, at 50° C., Eluent A: H₂O+0.05% HCOOH+3.75 mM ammonium acetate, B: CH₃CN+0.04% HCOOH, Gradient: 5% to 98% B in 1.4 min, Flow: 1.2 ml/min.
Method B7: Method LCMS_10_MIN: Waters UPLC Acquity; column: Acquity HSS T3, 1.8 µm, 2.1*50 mm, at 60° C., Eluent A: H₂O+0.05% HCOOH+3.75 mM ammonium acetate, B: CH₃CN+0.04% HCOOH, Gradient: 5% to 98% B in 9.4 min, Flow: 1 ml/min.

HPLC Methods
Method C1: HPLC Acid QC: Waters X-Bridge C18, 2.5 µm, 3*50 mm, at 40° C., Eluent A: H₂O+0.1% TFA; B: CH₃CN+0.1% TFA. Gradient 10 to 98% B in 8.6 min hold 1.4 min, Flow: 1.4 ml/min.
Method C2: Fast acid: Waters X-Bridge C18, 2.5 µm, 3*30 mm, at 40° C., Eluent A: water+0.1% TFA; B: CH₃CN+0.1% TFA. Gradient 10 to 98% B in 3 min hold 0.5 min, Flow: 1.4 ml/min.

GC/MS Method
Method D1: Gaschromatograph Finnigan Focus GC (Thermo Electron Corporation) Single Quadrupole Mass Analyzer, EI, column Zebron ZB-5 ms, 15 mm, 0.25 mm i.D., 0.25 µm film thickness, 5% polysilarylene, 95% polydimethylsiloxane.

Preparative Methods
Method A1: HPLC, Waters Sunfire C18 OBD, 5 µm, 30*100 mm, Eluent A: H₂O+0.1% TFA, B: CH₃CN+0.1% TFA.
Method A2: HPLC, Waters X-Bridge C18 OBD, 5 µm, 30*100 mm, Eluent A: H₂O+7.3 mM NH₄OH, B: CH₃CN+7.3 mM NH₄OH.
Method A3: Macherey-Nagel Nucleosil 100-10 C18, 5 µm, 40*250 mm, Eluent A: H₂O+0.1% TFA, B: CH₃CN+0.1% TFA.
Method A4: HPLC, Waters X-Bridge C18 OBD, 10 µm, 19*150 mm, Eluent A: H₂O, B: CH₃CN.
Method A5: Thar SFC 200, elution with CO₂/MeOH with one of the following columns:
Princeton PPU 250×30 mm, 100 Å, 5 µm,
Princeton 4-EP 250×30 mm, 60 Å, 5 µm,
Reprosil diNH₂ 250×30 mm, 100 Å, 5 µm,
Princeton Silica 250×30 mm, 60 Å, 5 µm,
Waters Atlantis Hilic Silica 250×30 mm, 5 µm.

Part A: Synthesis of Aminopyrazoles

A1: 5-chloro-1H-pyrazol-3-amine

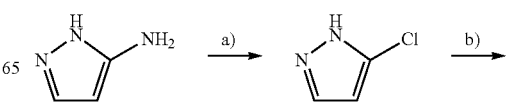

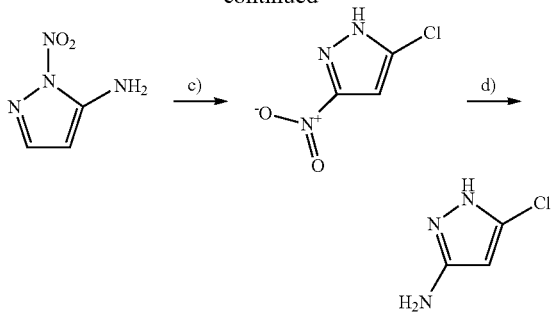

a) 5-chloro-1H-pyrazole

To a solution of 1H-pyrazol-5-amine (23.6 g, 284 mmol) in CH$_3$CN (1 L) under a nitrogen atmosphere were added HCl (140 ml, 1420 mmol, 32%) and copper chloride (56.3 g, 568 mmol) at 0° C. Isopentyl nitrite (80 ml, 568 mmol) was added at 0° C. and the mixture was stirred at 0° C. for 2 days. Isopentyl nitrite (20 ml, 0.5 eq) was added and the mixture was stirred at RT for another 5.5 days. The reaction mixture was slowly poured into ammonium hydroxide (1 L, 25%) and extracted with AcOEt. The organic phase was separated and the aqueous phase was extracted with AcOEt. The combined organic layers were washed with brine, dried over Na$_2$SO$_4$ and concentrated. The crude product was purified by silica gel column chromatography (hexane/TBME from 1:0 to 4:6) to afford 5-chloro-1H-pyrazole. M/z=103/105 [M+H]+, Rt=0.48 min (UPLC Method B2), $^1$H NMR (600 MHz, DMSO-d$_6$): δ ppm: 13.00 (bs, 1H), 7.79 (t, 1H), 6.29 (t, 1H), isoamyl alcohol: 4.28 (t, 1H), 3.41 (q, 2H), 1.30 (q, 2H), 0.85 (d, 6H).

b) 5-chloro-1-nitro-1H-pyrazole

To a solution of 5-chloro-1H-pyrazole (3.88 g, 35.2 mmol) in AcOH (5.10 ml, 89 mmol) was added at 0° C. dropwise 90% aqueous HNO$_3$ (5.10 ml, 35.2 mmol) and the reaction mixture was stirred at 0° C. for 2 h. Ac$_2$O (12.92 ml, 137 mmol) was then added dropwise. The mixture was stirred at RT for 4 h. The mixture was poured into ice-water and AcOEt and Na$_2$CO$_3$ (33.6 g, 317 mmol) were added. The organic phase was separated and the aqueous phase was extracted with AcOEt. The combined organic layers were washed with aqueous saturated NaHCO$_3$ and brine, dried over Na$_2$SO$_4$ and concentrated to afford 5-chloro-1-nitro-1H-pyrazole. M/z=146/148 [M–H]–, Rt=0.71 min (UPLC Method B2), $^1$H NMR (400 MHz, DMSO-d$_6$): δ ppm: 8.91 (d, 1H), 6.90 (d, 1H).

c) 5-chloro-3-nitro-1H-pyrazole

In an autoclave, 5-chloro-1-nitro-1H-pyrazole (5.44 g, 35.0 mmol) was dissolved in dry anisole (70 ml) and the reactor was sealed. The mixture was heated at 140° C. for 16 h. The mixture was cooled down, filtered and the filtrate was evaporated to dryness. To the residue was added hexane and the suspension was sonicated and triturated. The precipitate was filtered and rinsed with hexane to afford 5-chloro-3-nitro-1H-pyrazole. M/z=146/148 [M–H]–, Rt=0.60 min (UPLC Method B2), $^1$H NMR (400 MHz, DMSO-d$_6$): δ ppm: 7.29 (s, 1H).

d) 5-chloro-1H-pyrazol-3-amine

To a solution of 5-chloro-3-nitro-1H-pyrazole (4.345 g, 29.2 mmol) in MeOH (389 ml) was added carefully at RT 32% aqueous HCl (57.3 ml, 583 mmol). After cooling to 0° C., SnCl$_2$ (27.6 g, 146 mmol) was added portionwise and the reaction mixture was stirred at RT overnight. The solvent was evaporated to dryness, the residue was diluted with ethyl acetate and 30% aq. NaOH solution was added until the pH became basic. After cooling to 0° C. overnight, the salts were filtered off through a pad of celite and the cake was rinsed with AcOEt and water. The organic phase was separated and the aqueous phase was extracted with AcOEt. The combined organic layers were washed with brine, dried over Na$_2$SO$_4$, filtered and concentrated under vacuum to dryness to afford 5-chloro-1H-pyrazol-3-amine. M/z=118/120 [M+H]+, Rt=0.36 min (UPLC Method B2), $^1$H NMR (600 MHz, DMSO-d$_6$): δ ppm: 11.54 (s, 1H), 5.25 (s, 2H), 5.20 (s, 1H).

Part B: Synthesis of Carboxylic Acid Compounds

B1: (R)-2-methoxy-3-methylbutanoic acid

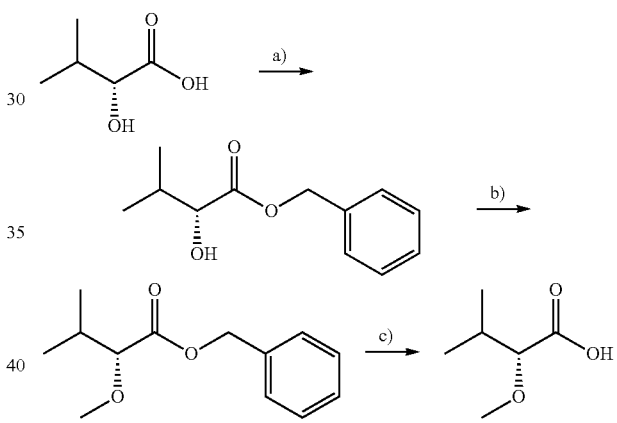

a) (R)-benzyl 2-hydroxy-3-methylbutanoate

To D-alpha-hydroxyisovaleric acid (5 g, 42.3 mmol) in DMF (50 ml) were added benzylbromide (6.00 ml, 50.8 mmol) and DBU (6.38 ml, 42.3 mmol) and the reaction mixture was stirred for 64 h at RT. The solvent was evaporated and the residue was taken up in AcOEt/water. The organic phase was dried over Na$_2$SO$_4$, filtered and evaporated. The crude product was purified by flash column chromatography on silica gel (cyclohexane/AcOEt: 1/0 to 9/1) to afford (R)-benzyl 2-hydroxy-3-methylbutanoate. M/z=209 [M+H]+, Rt=0.95 min (UPLC Method B2), $^1$H NMR (400 MHz, DMSO-d$_6$) δ ppm: 7.46-7.29 (m, 5H), 5.35 (d, 1H), 5.14 (d, 2H), 3.87 (dd, 1H), 2.00-1.90 (m, 1H), 0.88 (d, 3H), 0.82 (d, 3H).

b) (R)-benzyl 2-methoxy-3-methylbutanoate

To (R)-benzyl 2-hydroxy-3-methylbutanoate (7.8 g, 37.5 mmol) in THF (150 ml) at –20° C. was added NaH (1.80 g, 44.9 mmol, 60% oil dispersion) and the mixture was warmed to RT over 30 min. After cooling to 0° C., dimethylsulfate (4.26 ml, 44.9 mmol) was added and the reaction mixture was stirred at RT for 117 h. The mixture was quenched with Et₃N, acidified with 1N HCl, the aqueous phase was extracted with TBME and the organic phase washed with brine, dried over Na₂SO₄, filtered and evaporated. The residue was purified by flash column chromatography on silica gel (cyclohexane/AcOEt: 1/0 to 9/1) to afford (R)-benzyl 2-methoxy-3-methylbutanoate.

M/z=223 [M+H]+, Rt=1.15 min (UPLC Method B2), ¹H NMR (400 MHz, DMSO-d₆) δ 7.47-7.30 (m, 5H), 5.26-5.10 (m, 2H), 3.63 (d, 1H), 3.27 (s, 3H), 2.05-1.90 (m, 1H), 0.88 (d, 3H), 0.84 (d, 3H).

c) (R)-2-methoxy-3-methylbutanoic acid

To (R)-benzyl 2-methoxy-3-methylbutanoate (3.4 g, 15.30 mmol) in AcOEt (100 ml) was added Pd/C (0.81 g, 10% Pd). The mixture was purged with H₂-gas and the suspension was stirred for 3 h at RT. The reaction mixture was filtered, washed with AcOEt and the solvent was evaporated to afford (R)-2-methoxy-3-methylbutanoic acid. M/z=133 [M+H]+, Rt=0.54 min (UPLC Method B2), ¹H NMR (400 MHz, DMSO-d₆) δ ppm: 12.63 (s, 1H), 3.45 (d, 1H), 3.27 (s, 3H), 2.00-1.90 (m, 1H), 0.91 (d, 3H), 0.87 (d, 3H).

B2: (S)-2-methoxy-3-methylbutanoic acid

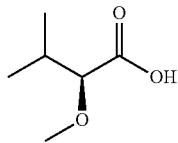

(S)-2-methoxy-3-methylbutanoic acid was prepared analogously as described in procedure B1 using L-alpha-hydroxyisovaleric acid instead of D-alpha-hydroxyisovaleric acid. ¹H NMR (400 MHz, DMSO-d₆) δ ppm: 12.6 (s, 1H), 3.46 (d, 1H), 3.27 (s, 3H), 1.95 (dtd, 1H), 0.91 (d, 3H), 0.87 (d, 3H).

B3: (S)-2-(2-methoxyethoxy)propanoic acid

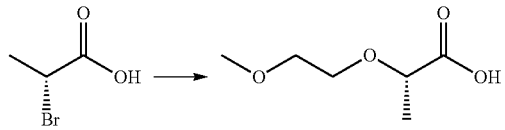

To a suspension of NaH (3.19 g, 80 mmol, 60% oil dispersion) in DMF (60 ml) at 0° C. was added 2-methoxyethanol (2.75 ml, 34.8 mmol). After 30 min, (R)-2-bromopropanoic acid (1.5 ml, 16.6 mmol) was added and the reaction mixture was stirred for 1 h at RT. The mixture was quenched with water, concentrated and extracted with AcOEt. The organic phase was dried over Na₂SO₄, filtered and concentrated to afford (S)-2-(2-methoxyethoxy)propanoic acid. ¹H NMR (400 MHz, DMSO-d₆) δ ppm: 12.56 (bs, 1H), 3.92 (q, 1H), 3.66-3.57 (m, 1H), 3.50-3.40 (m, 4H), 3.24 (s, 3H), 1.26 (d, 3H).

In analogy the following acids were prepared:

| Name | Structure | Analytical data |
| --- | --- | --- |
| B4: (R)-2-(2-methoxyethoxy)propanoic acid | 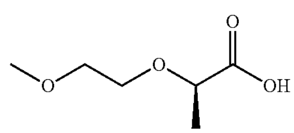 | ¹H NMR (400 MHz, DMSO-d₆) δ ppm: 12.60 (bs, 1H), 3.91 (q, 1H), 3.65-3.57 (m, 1H), 3.49-3.39 (m, 3H), 3.24 (s, 3H), 1.25 (d, 3H). |
| B5: (S)-2-(2-(dimethylamino)ethoxy)propanoic acid | 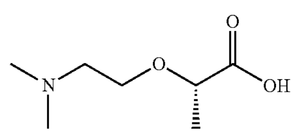 | ¹H NMR (400 MHz, DMSO-d₆) δ ppm: 3.79-3.70 (m, 2H), 3.59-3.52 (m, 1H), 3.00-2.81 (m, 2H), 2.57 (s, 6H), 1.21 (d, 3H). |
| B6: (S)-2-((R)-2-methoxypropoxy)propanoic acid | 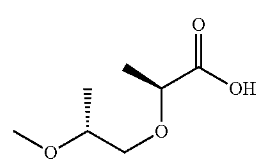 | ¹H NMR (400 MHz, DMSO-d₆) δ ppm: 3.92 (q, 1H), 3.51-3.38 (m, 2H), 3.30-3.25 (m, 1H), 3.24 (s, 3H), 1.26 (d, 3H), 1.05 d, 3H). |
| B7: (S)-2-(((R)-tetrahydrofuran-3-yl)oxy)propanoic acid | 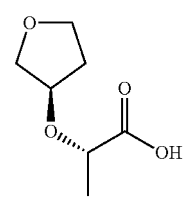 | ¹H NMR (400 MHz, DMSO-d₆) δ ppm: 12.59 (bs, 1H), 4.18 (m, 1H), 4.00 (m, 1H), 3.75-3.59 (m, 4H), 1.87 (m, 1H), 1.69 (dd, 1H), 1.25 (d, 3H). |

-continued

| Name | Structure | Analytical data |
|---|---|---|
| B8: (S)-2-(((S)-tetrahydrofuran-3-yl)oxy)propanoic acid | 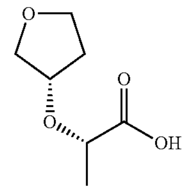 | $^1$H NMR (400 MHz, DMSO-$d_6$) δ ppm: 12.60 (bs, 1H), 4.22 (m, 1H), 3.96 (m, 1H), 3.76-3.57 (m, 4H), 1.86 (m, 1H), 1.69 (m, 1H), 1.24 (d, 3H). |
| B9: (S)-2-(((S)-tetrahydrofuran-3-yl)methoxy)propanoic acid | 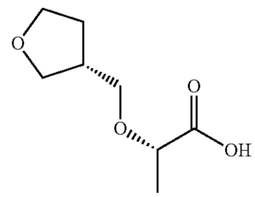 | $^1$H NMR (400 MHz, DMSO-$d_6$) δ ppm: 12.48 (bs, 1H), 3.93 (m, 2H), 3.70 (q, 1H), 3.60 (m, 1H), 3.44 (m, 1H), 1.88-1.73 (m, 4H), 1.53 (m, 1H), 1.25 (d, 3H). |
| B10: (S)-2-(((R))tetrahydrofuran-3-yl)methoxy)propanoic acid | | $^1$H NMR (400 MHz, DMSO-$d_6$) δ ppm: 12.50 (bs, 1H), 3.96-3.87 (m, 2H), 3.71 (q, 1H), 3.59 (q, 1H), 3.47 (m, 1H), 1.85-1.75 (m, 4H), 1.59 (m, 1H), 1.25 (d, 3H). |

B11: 2,3-dimethoxypropanoic acid

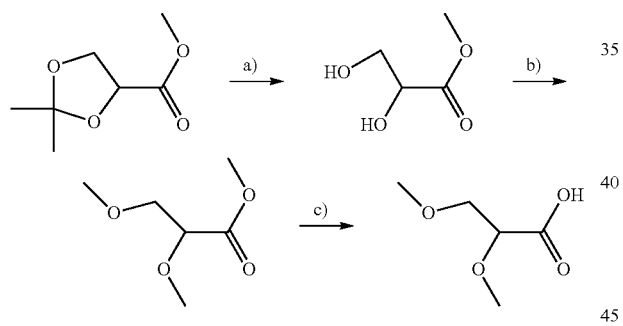

a) methyl 2,3-dihydroxypropanoate

A solution of methyl 2,2-dimethyl-1,3-dioxolane-4-carboxylate (3 ml, 20.7 mmol) and 1N HCl (25.9 ml, 25.9 mmol) in MeOH (40 ml) at RT was stirred for 20 h. The reaction mixture was extracted with AcOEt, the aqueous phase was extracted with 2-methyltetrahydrofuran, the combined organic phases were dried over Na$_2$SO$_4$, filtered and concentrated to afford methyl 2,3-dihydroxypropanoate. $^1$H NMR (400 MHz, DMSO-$d_6$) δ ppm: 5.38 (d, 1H), 4.82 (t, 1H), 4.08-4.03 (m, 1H), 3.62 (s, 3H), 3.57-3.52 (m, 2H).

b) methyl 2,3-dimethoxypropanoate

A solution of methyl 2,3-dihydroxypropanoate (500 mg, 4.16 mmol), methyl iodide (5.21 ml, 83 mmol) and silver oxide (9.65 g, 41.6 mmol) in DCM (10 ml) was stirred overnight at RT. Water was added and the mixture was extracted with AcOEt, dried over Na$_2$SO$_4$, filtered and concentrated. The residue was purified by flash column chromatography on silica gel (cyclohexane/AcOEt 1/0 to 0/1) to afford methyl 2,3-dimethoxypropanoate. $^1$H NMR (400 MHz, DMSO-$d_6$) δ ppm: 4.02 (dd, 1H), 3.67 (d, 3H), 3.60-3.51 (m, 2H), 3.30 (s, 3H), 3.24 (s, 3H).

c) 2,3-dimethoxypropanoic acid

To a solution of methyl 2,3-dimethoxypropanoate (190 mg, 1.28 mmol) in THF (3 ml) was added NaOH (0.96 ml, 1.92 mmol). The reaction mixture was stirred overnight at RT. 1N HCl was added to adjust the pH to 2-3. The mixture was extracted with AcOEt, dried over Na$_2$SO$_4$, filtered and concentrated to afford 2,3-dimethoxypropanoic acid. $^1$H NMR (400 MHz, DMSO-$d_6$) δ ppm: 12.74 (bs, 1H), 3.89 (dd, 1H), 3.58-3.50 (m, 2H), 3.29 (s, 3H), 3.24 (s, 3H).

B12: 2,4-dimethoxybutanoic acid

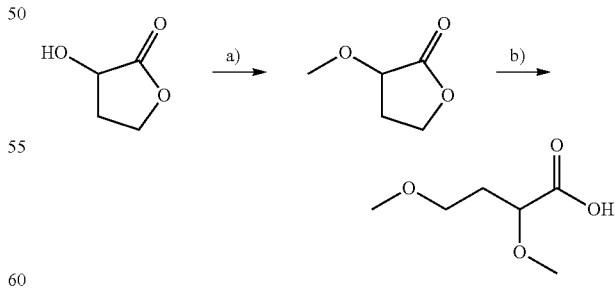

a) 3-methoxydihydrofuran-2(3H)-one

A solution of alpha-hydroxy-butyrolactone (1.33 g, 13.03 mmol), methyl iodide (8.15 ml, 130 mmol) and silver oxide (9.7 g, 41.9 mmol) in dry CHCl$_3$ (43.4 ml) was stirred at 63°

C. for 3 h in absence of light. The reaction mixture was cooled and filtered over a celite pad and the filtrate was concentrated to afford 3-methoxydihydrofuran-2(3H)-one. $^1$H NMR (400 MHz, DMSO-$d_6$) δ ppm: 4.31 (tdd, 1H), 4.24-4.14 (m, 2H), 3.41 (d, 3H), 2.55-2.45 (m, 1H), 2.12-2.01 (m, 1H).

b) 2,4-dimethoxybutanoic acid $H_2SO_4$ (0.022 ml, 0.413 mmol) was added to a stirred solution of 3-methoxydihydrofuran-2(3H)-one (1.6 g, 13.78 mmol) and trimethylorthoformate (2.92 g, 27.6 mmol) in MeOH (10 ml). The mixture was stirred at 50° C. overnight. After cooling to RT, the reaction mixture was evaporated. The residue was dissolved in THF (28.3 ml), 2M aqueous LiOH (8.50 ml, 17.0 mmol) was added and the reaction mixture was stirred at RT for 48 h. Water and AcOEt were added. The separated aqueous phase was acidified with 1N HCl to pH=1, extracted with AcOEt and the organic phase was dried over a phase separator cartridge (IST) and evaporated to afford 2,4-dimethoxybutanoic acid. $^1$H NMR (400 MHz, DMSO-$d_6$) δ ppm: 3.74 (dd, 1H), 3.45-3.30 (m, 2H), 3.25 (s, 3H), 3.21 (s, 3H), 1.94-1.83 (m, 1H), 1.81-1.69 (m, 1H).

B13: 5-methyltetrahydrofuran-2-carboxylic acid

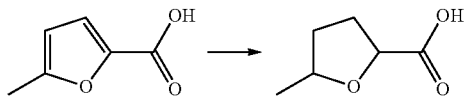

To 5-methyl-2-furoic acid (2.15 g, 16.54 mmol) in AcOEt (150 ml) was added Pd/C (0.880 g). The suspension was stirred for 4 h at RT under $H_2$ atmosphere. The reaction mixture was filtered, washed with AcOEt and the filtrate was evaporated to afford 5-methyltetrahydrofuran-2-carboxylic acid. $^1$H NMR (400 MHz, DMSO-$d_6$) δ ppm: 12.50 (s, 1H), 4.26 (dd, 1H), 4.01 (dp, 1H), 2.19-2.11 (m, 1H), 2.02-1.91 (m, 2H), 1.46-1.35 (m, 1H), 1.20 (d, 3H).

B14: 2-methoxy-2-(tetrahydro-2H-pyran-4-yl)acetic acid

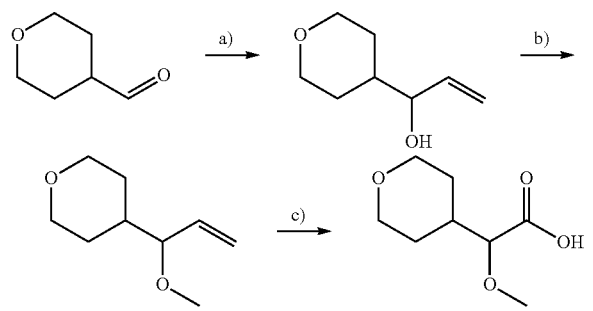

a) 1-(tetrahydro-2H-pyran-4-yl)prop-2-en-1-ol

To a solution of tetrahydro-2H-pyran-4-carbaldehyde (5.0 g, 43.8 mmol) in THF (146 ml) at -78° C. was added dropwise 1N vinylmagnesium bromide in THF (52.6 ml, 52.6 mmol). The reaction mixture was stirred at -78° C. for 3 h and quenched with saturated aqueous $NH_4Cl$. The mixture was extracted with AcOEt, the organic layer was dried over a phase separator cartridge (IST) and evaporated. The residue was purified by flash chromatography on silica gel (cyclohexane/AcOEt 1/0 to 1/1) to afford 1-(tetrahydro-2H-pyran-4-yl)prop-2-en-1-ol. $^1$H NMR (400 MHz, DMSO-$d_6$) δ ppm: 5.86-5.77 (m, 1H), 5.19-5.03 (m, 2H), 4.75 (d, 1H), 3.90-3.80 (m, 2H), 3.69 (tdt, 1H), 3.23 (ddd, 2H), 1.63 (ddq, 1H), 1.55-1.42 (m, 2H), 1.32-1.21 (m, 2H).

b) 4-(1-methoxyallyl)tetrahydro-2H-pyran

To 1-(tetrahydro-2H-pyran-4-yl)prop-2-en-1-ol (4.93 g, 34.7 mmol) in THF (217 ml) at -78° C. was added NaH (2.77 g, 69.3 mmol) over 30 min and the mixture was stirred at RT for 30 min. After cooling to 0° C., dimethyl sulfate (6.63 ml, 69.3 mmol) was added and the reaction mixture was stirred at RT overnight. $Et_3N$ (9.66 ml, 69.3 mmol) was added, the mixture was acidified with 4N HCl and extracted with $Et_2O$. The organic phase was dried over a phase separator cartridge (IST) and evaporated. The residue was purified by flash chromatography on silica gel (cyclohexane/AcOEt 1/0 to 7/3) to afford 4-(1-methoxyallyl)tetrahydro-2H-pyran. $^1$H NMR (400 MHz, DMSO-$d_6$) δ ppm: 5.63 (ddd, 1H), 5.33-5.16 (m, 2H), 3.90-3.78 (m, 2H), 3.39-3.21 (m, 3H), 3.17 (s, 3H), 1.70-1.57 (m, 2H), 1.44 (dt, 1H), 1.29-1.12 (m, 2H).

c) 2-methoxy-2-(tetrahydro-2H-pyran-4-yl)acetic acid

To 4-(1-methoxyallyl)tetrahydro-2H-pyran (1 g, 6.40 mmol) in $CCl_4$ (12.8 ml), $CH_3CN$ (12.8 ml), water (17.1 ml) were added $NaIO_4$ (5.20 g, 24.32 mmol) and ruthenium trichloride (0.027 g, 0.13 mmol). The suspension was stirred at RT for 2 h. The solid was removed by filtration, rinsed with $CHCl_3$, the filtrate was extracted with $CHCl_3$, the organic phase was dried over a phase separator cartridge (IST) and evaporated. The residue was diluted in DCM, filtered through a pad of celite and evaporated to afford 2-methoxy-2-(tetrahydro-2H-pyran-4-yl)acetic acid. $^1$H NMR (400 MHz, DMSO-$d_6$) δ ppm: 12.70 (s, 1H), 3.88-3.80 (m, 2H), 3.52 (d, 1H), 3.28-3.20 (m, 2H), 3.17 (s, 3H), 1.92-1.82 (m, 1H), 1.41 (dddd, 4H).

B15: 1-(dimethylamino)cyclopropanecarboxylic acid

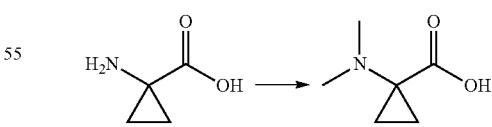

To 1-aminocyclopropanecarboxylic acid (5.2 g, 48.9 mmol) were added 37% formaldehyde in $H_2O$ (10 ml, 134 mmol) and dropwise formic acid (13 ml, 332 mmol). After 2 h of stirring at reflux and cooling to RT, 37% aq. HCl (5 ml, 58.6 mmol) was added and the mixture was concentrated. The residue was treated with MeOH (3 ml) and $Et_2O$ (20 ml), the suspension was filtered and the solid was dried under vacuum to afford 1-(dimethylamino)cyclopropanecarboxylic acid. $^1$H NMR (400 MHz, DMSO-d$_6$) δ ppm: 2.92 (s, 6H), 1.70 (t, 2H), 1.45 (t, 2H).

B16: 2-(methoxymethyl)tetrahydrofuran-2-carboxylic acid

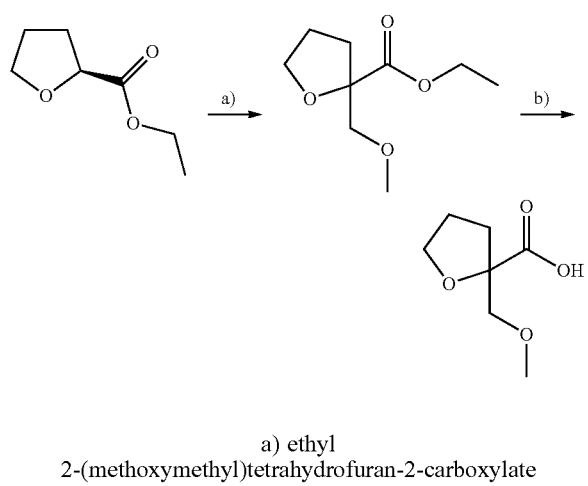

a) ethyl 2-(methoxymethyl)tetrahydrofuran-2-carboxylate

To a solution of diisopropylamine (5.93 ml, 41.6 mmol) in THF (173 ml) at −78° C. was added dropwise 10 M BuLi in Hexane (4.16 ml, 41.6 mmol). The solution was stirred at −78° C. for 2 h. To this freshly prepared solution of LDA at −78° C. was added dropwise a solution of (S)-ethyl tetrahydrofuran-2-carboxylate (5.0 g, 34.7 mmol) in THF (173 ml). The reaction mixture was stirred at −78° C. for 1.5 h. Then, chloro(methoxy)methane (2.90 ml, 38.1 mmol) was added dropwise, reaction mixture was allowed to warm up to RT and stirred for 24 h. The mixture was quenched with saturated aqueous NH$_4$Cl and extracted twice with AcOEt. The organic layer was dried over a phase separator cartridge (IST) and evaporated. The crude material was purified by flash chromatography on silica gel (cyclohexane/AcOEt 1/0 to 1/3) to afford ethyl 2-(methoxymethyl)tetrahydrofuran-2-carboxylate. $^1$H NMR (400 MHz, DMSO-d$_6$) δ ppm: 4.08 (m, 2H), 3.80 (m, 2H), 3.59 (d, 1H), 3.40 (d, 1H), 3.25 (s, 3H), 1.82 (m, 4H), 1.18 (m, 3H).

b) 2-(methoxymethyl)tetrahydrofuran-2-carboxylic acid

To a solution of ethyl 2-(methoxymethyl)tetrahydrofuran-2-carboxylate (3.72 g, 19.8 mmol) in THF (49.4 ml)/MeOH (24.7 ml)/water (24.7 ml) was added LiOH monohydrate (0.91 g, 21.7 mmol). The reaction mixture was stirred at RT for 2.5 h. The mixture was evaporated, the residue taken-up in AcOEt and acidified with 1M aqueous HCl. Phases were separated and the aqueous layer was extracted with AcOEt. The combined organic layers were dried over a phase separator cartridge (IST) and evaporated to afford 2-(methoxymethyl)tetrahydrofuran-2-carboxylic acid. $^1$H NMR (400 MHz, DMSO-d$_6$) δ ppm: 12.40 (bs, 1H), 3.83-3.76 (m, 2H), 3.58 (d, 1H), 3.38 (d, 1H), 3.25 (s, 3H), 1.87-1.76 (m, 4H).

Part C: Synthesis of Beta-ketoesters

C1: (S)-tert-butyl 4-methoxy-3-oxopentanoate

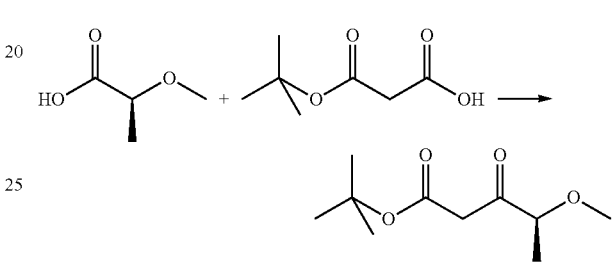

To a solution of (S)-2-methoxypropanoic acid (10.0 g, 96 mmol) in THF (200 ml) at 0° C. was added CDI (17.13 g, 106 mmol) and the reaction mixture was stirred at RT for 3 h. In a separate flask, to a solution of 3-(tert-butoxy)-3-oxopropanoic acid (22.2 ml, 144 mmol) in THF (200 ml) at 0° C. was added dropwise 2M isopropylmagnesium chloride in THF (139 ml, 279 mmol) and the reaction mixture was stirred for 3 h at 20° C. Then, this solution was added dropwise to the acyl imidazole solution at 0° C. and the resulting mixture was stirred for 1 h at RT. The reaction mixture was quenched with 10% aqueous citric acid (25 ml), extracted with AcOEt, washed with aqueous saturated NaHCO$_3$, dried over Na$_2$SO$_4$, filtered and concentrated. The residue was purified by flash column chromatography on silica gel (cyclohexane/AcOEt: 100/0 to 70/30) to afford (S)-tert-butyl 4-methoxy-3-oxopentanoate. M/z=203 [M+H]+, Rt=0.91 min (UPLC Method B1), $^1$H NMR (400 MHz, DMSO-d$_6$) δ ppm: 3.85 (q, 1H), 3.54-3.46 (m, 2H), 3.27 (s, 3H), 1.40 (s, 9H), 1.19 (d, 3H).

In analogy the following ketoesters were prepared:

| Name | Structure | Analytical data |
|---|---|---|
| C2: tert-butyl 4-methoxy-4-methyl-3-oxopentanoate | 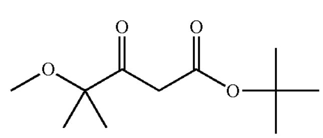 | $^1$H NMR (400 MHz, DMSO-d$_6$) δ ppm: 3.54 (s, 2H), 3.13 (s, 3H), 1.39 (s, 9H), 1.21 (s, 6H). |
| C3: tert-butyl 3-(1-methylcyclopropyl)-3-oxopropanoate | 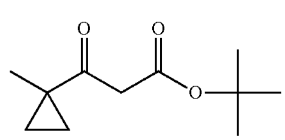 | $^1$H NMR (400 MHz, DMSO-d$_6$) δ ppm: 3.42 (s, 2H), 1.41 (s, 9H), 1.26 (s, 3H), 1.18 (d, J = 3.4 Hz, 2H), 0.81 (d, 2H). |

-continued

| Name | Structure | Analytical data |
|---|---|---|
| C4: tert-butyl 4,4-dimethyl-3-oxopropanoate | 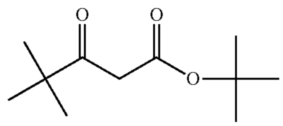 | $^1$H NMR (400 MHz, DMSO-d$_6$) δ ppm: 3.57 (s, 2H), 1.42 (s, 9H), 1.10 (s, 9H). |
| C5: Ethyl 4-methyl-3-oxohexanoate | 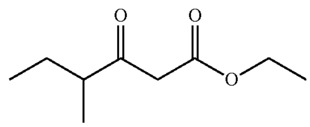 | $^1$H NMR (400 MHz, DMSO-d$_6$) δ ppm: 4.08 (q, 3H), 3.62 (s, 1H), 2.60-2.51 (s, 1H), 1.65-1.55 (m, 1H), 1.38-1.28 (m, 1H), 1.17 (t, 3H), 1.00 (d, 3H), 0.80 (t, 3H). |
| C6: tert-butyl 3-(2-methyltetrahydrofuran-2-yl)-3-oxopropanoate | 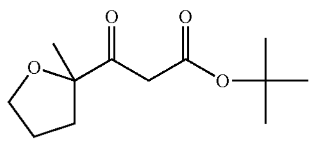 [SMILES: CC(C)(C)OC(=O)CC(=O)C1(C)CCCO1] | $^1$H NMR (400 MHz, DMSO-d$_6$) δ ppm: 3.89 (q, 1H), 3.78 (q, 1H), 3.52 (d, 2H), 2.17-1.64 (m, 4H), 1.41 (s, 9H), 1.24 (s, 3H). |
| C7: (S)-tert-butyl 4-(2-methoxyethoxy)-2-oxopentanoate | 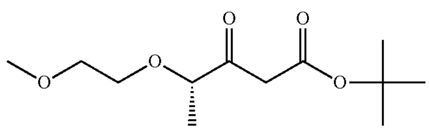 [SMILES: COCCO[C@@H](C)C(=O)CC(=O)OC(C)(C)C] | $^1$H NMR (400 MHz, DMSO-d$_6$) δ ppm: 3.97 (q, 1H), 3.59-3.50 (m, 4H), 3.48-3.41 (m, 2H), 3.25 (s, 3H), 1.40 (s, 9H), 1.20 (d, 3H). |
| C8: (R)-tert-butyl 4-(2-methoxyethoxy)-2-oxopenatoate | 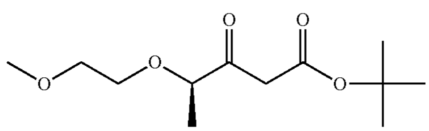 [SMILES: COCCO[C@H](C)C(=O)CC(=O)OC(C)(C)C] | $^1$H NMR (400 MHz, DMSO-d$_6$) δ ppm: 3.97 (q, 1H), 3.59-3.50 (m, 4H), 3.48-3.41 (m, 2H), 3.25 (s, 3H), 1.40 (s, 9H), 1.20 (d, 3H). |
| C9: tert-butyl 3-(1,4-dioxan-2-yl)-3-oxopropanoate | 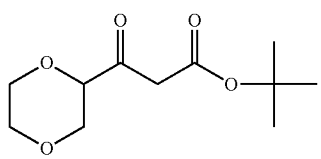 [SMILES: CC(C)(C)OC(=O)CC(=O)C1COCCO1] | $^1$H NMR (400 MHz, DMSO-d$_6$) δ ppm: 4.19 (dd, 1H), 3.91-3.79 (m, 2H), 3.72-3.62 (m, 2H), 3.53 (d, 2H), 3.51-3.42 (m, 2H), 1.42 (s, 9H). |
| C10: tert-butyl 5-methoxy-4-methyl-3-oxopentanoate | 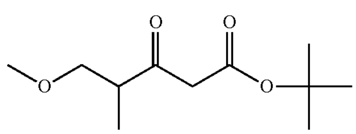 | $^1$H NMR (400 MHz, DMSO-d$_6$) δ ppm: 3.56-3.45 (m, 2H), 3.46-3.35 (m, 2H), 3.21 (s, 3H), 2.92-2.83 (m, 1H), 1.40 (s, 9H), 0.98 (d, 3H). |
| C11: (R)-tert-butyl 4-methoxy-3-oxopentanoate | 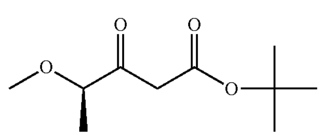 | $^1$H NMR (400 MHz, DMSO-d$_6$) δ ppm: 3.85 (q, 1H), 3.55-3.45 (m, 2H), 3.27 (s, 3H), 1.40 (s, 9H), 1.19 (d, 3H). |
| C12: tert-butyl 4-methoxy-3-oxo-4-phenylbutanoate | 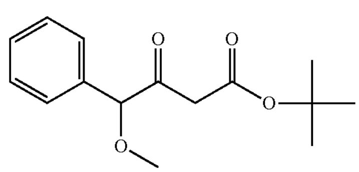 [SMILES: COC(C(=O)CC(=O)OC(C)(C)C)c1ccccc1] | Rt = 1.12 min (UPLC Method B2), $^1$H NMR (400 MHz, DMSO-d$_6$) δ ppm: 7.47-7.31 (m, 5H), 4.89 (s, 1H), 3.50 (s, 2H), 3.29 (s, 3H), 1.37 (s, 9H). |
| C13: tert-butyl 3-(1-(methoxymethyl)cyclobutyl)-3-oxopropanoate | 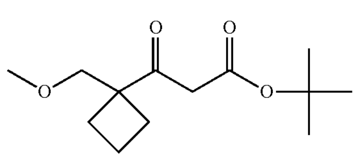 [SMILES: COCC1(C(=O)CC(=O)OC(C)(C)C)CCC1] | $^1$H NMR (400 MHz, DMSO-d$_6$) δ ppm: 3.64 (s, 2H), 3.44 (s, 2H), 3.26 (s, 3H), 2.33-2.20 (m, 2H), 1.96-1.78 (m, 3H), 1.75-1.60 (m, 1H), 1.42 (m, 9H). |

-continued

| Name | Structure | Analytical data |
|---|---|---|
| C14: tert-butyl 3-(2-methoxyphenyl)-3-oxopropanoate | 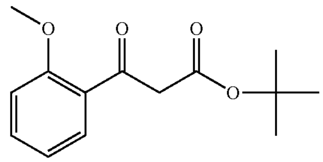 [SMILES: COc1ccccc1C(=O)CC(=O)OC(C)(C)C] | $^1$H NMR (400 MHz, DMSO-d$_6$) δ ppm: 7.70 (d, 1H), 7.60 (ddd, 1H), 7.20 (dd, 1H), 7.12-7.01 (m, 1H), 3.89 (s, 3H), 3.84 (s, 2H), 1.36 (s, 9H). |
| C15: tert-butyl 3-(4-methyltetrahydro-2H-pyran-4-yl)-3-oxopropanoate | 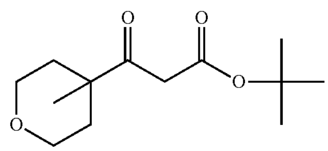 | $^1$H NMR (400 MHz, DMSO-d$_6$) δ ppm: 3.67-3.60 (m, 2H), 3.58 (s, 2H), 3.42 (ddd, 2H), 1.93-1.81 (m, 2H), 1.46-1.41 (m, 2H), 1.41 (s, 9H), 1.14 (s, 3H). |
| C16: tert-butyl 4,5-dimethoxy-3-oxopentanoate | 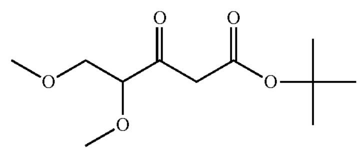 [SMILES: COCC(OC)C(=O)CC(=O)OC(C)(C)C] | $^1$H NMR (400 MHz, DMSO-d$_6$) δ ppm: 3.94 (t, 1H), 3.58 (d, 2H) 3.52-3.42 (m, 2H), 3.34 (s, 3H), 3.23 (s, 3H), 1.40 (s, 9H). |
| C17: tert-butyl 3-oxo-3-(tetrahydrofuran-3-yl)propanoate | 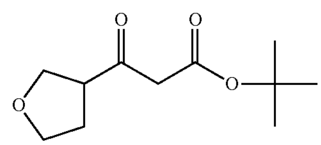 | $^1$H NMR (400 MHz, DMSO-d$_6$) δ ppm: 3.79 (s, 1H), 3.77 (s, 1H), 3.72 (td, 1H), 3.64 (dt, 1H), 3.57 (s, 2H), 3.39-3.30 (m, 1H), 2.11-1.89 (m, 2H), 1.42 (s, 9H). |
| C18: tert-butyl 3-oxo-4-(tetrahydro-2H-pyran-4-yl)butanoate | 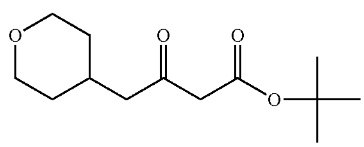 [SMILES: CC(C)(C)OC(=O)CC(=O)CC1CCOCC1] | $^1$H NMR (400 MHz, DMSO-d$_6$) δ ppm: 3.84-3.74 (m, 2H), 3.45 (s, 2H), 3.29 (td, 2H), 2.46 (d, 2H), 1.96 (dddt, 1H), 1.52 (ddd, 2H), 1.41 (s, 9H), 1.25-1.08 (m, 2H). |
| C19: tert-butyl 4-isopropoxy-3-oxobutanoate | 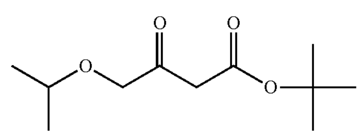 | $^1$H NMR (400 MHz, DMSO-d$_6$) δ ppm: 4.12 (s, 2H), 3.59 (p, 1H), 3.44 (s, 2H), 1.42 (s, 9H), 1.11 (d, 6H). |
| C20: tert-butyl 4,6-dimethoxy-3-oxohexanoate | 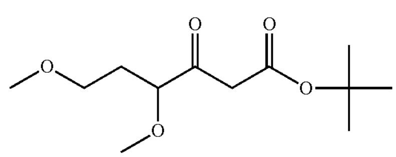 [SMILES: COCCC(OC)C(=O)CC(=O)OC(C)(C)C] | $^1$H NMR (400 MHz, DMSO-d$_6$) δ ppm: 3.82-3.75 (m, 1H), 3.48 (s, 2H), 3.37-3.20 (m, 2H), 3.28 (s, 3H), 3.18 (s, 3H), 1.93-1.70 (m, 2H), 1.40 (s, 9H). |
| C20: (R)-tert-butyl 4-(benzyloxy)-3-oxopentanoate | 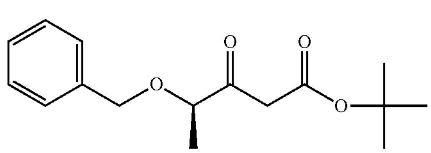 [SMILES: C[C@@H](OCc1ccccc1)C(=O)CC(=O)OC(C)(C)C] | $^1$H NMR (400 MHz, DMSO-d$_6$) δ ppm: 7.40-7.26 (m, 5H), 4.55-4.49 (m, 2H), 4.07 (q, 1H), 3.56-3.49 (m, 2H), 1.36 (s, 9H), 1.26 (d, 3H). |
| C21: tert-butyl 2-(3-ethoxy-3-oxopropanoyl)morpholine-4-carboxylate | 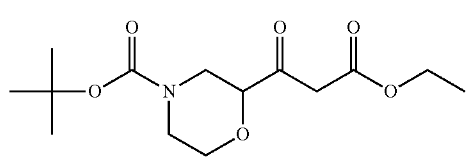 [SMILES: CCOC(=O)CC(=O)C1CN(C(=O)OC(C)(C)C)CCO1] | $^1$H NMR (400 MHz, DMSO-d$_6$) δ ppm: 4.21-4.11 (m, 1H), 4.10 (q, 2H), 4.03 (dd, 1H), 3.95-3.83 (m, 2H), 3.71-3.60 (m, 3H), 3.53-3.43 (m, 1H), 3.03-2.78 (m, 1H), 1.40 (s, 9H), 1.18 (t, 3H). |
| C22: tert-butyl 3-(3-oxobicyclo[3.1.0]hexan-6-yl)-3-oxopropanoate | 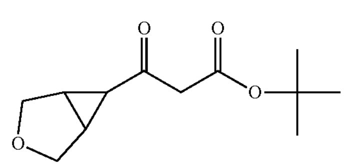 [SMILES: CC(C)(C)OC(=O)CC(=O)C1C2COCC21] | $^1$H NMR (400 MHz, DMSO-d$_6$) δ ppm: 3.81 (d, 2H), 3.68-3.61 (m, 2H), 3.56 (s, 2H), 2.19-2.14 (m, 2H), 1.96 (t, 1H), 1.42 (s, 9H). |

| Name | Structure | Analytical data |
|---|---|---|
| C23: tert-butyl 3-oxo-3-(5-oxaspiro[2.4]heptan-1-yl)propanoate | 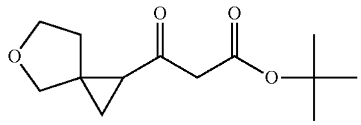 [SMILES: CC(C)(C)OC(=O)CC(=O)C1CC12CCOC2] | $^1$H NMR (400 MHz, DMSO-d$_6$) δ ppm: 3.82-3.73 (m, 2H), 3.65-3.44 (m, 4H), 2.44-2.30 (m, 1H), 2.00-1.72 (m, 2H), 1.41 (2s, 9H), 1.36-1.29 (m, 1H), 1.27-1.22 (m, 1H). |
| C24: tert-butyl 4-(dimethylamino)-3,4-dioxobutanoate | 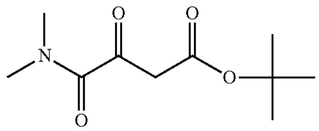 | M/z = 216 [M + H]+, Rt = 0.82 min (UPLC Method B2). |
| C25: (S)-tert-butyl 4-methoxy-5-methyl-3-oxohexanoate | 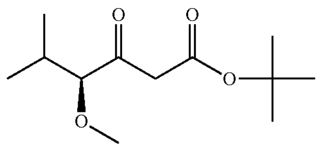 [SMILES: CO[C@H](C(=O)CC(=O)OC(C)(C)C)C(C)C] | $^1$H NMR (400 MHz, DMSO-d$_6$) δ ppm: 3.49 (d, 2H), 3.46-3.42 (m, 1H), 3.29 (s, 3H), 2.00 (pd, 1H), 1.41 (s, 9H), 0.88 (d, 3H), 0.84 (d, 3H). |
| C26: tert-butyl 3-(1-(methoxymethyl)cyclopropyl)-3-oxopeopanoate | 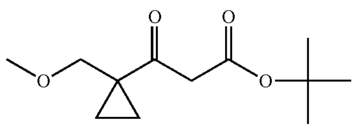 [SMILES: COCC1(C(=O)CC(=O)OC(C)(C)C)CC1] | $^1$H NMR (400 MHz, DMSO-d$_6$) δ ppm: 3.60 (s, 2H), 3.51 (s, 2H), 3.26 (s, 3H), 1.41 (s, 9H), 1.16 (q, 2H), 0.92 (q, 2H). |
| C27: tert-butyl 4-methyl-3-oxo-4-(tetrahydro-2H-pyran-4-yl)pentanoate | 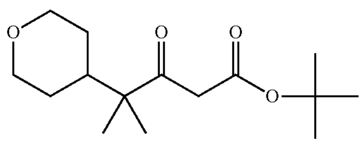 [SMILES: CC(C)(C)OC(=O)CC(=O)C(C)(C)C1CCOCC1] | $^1$H NMR (400 MHz, DMSO-d$_6$) δ ppm: 3.87 (ddd, 2H), 3.55 (s, 2H), 3.32-3.23 (m, 2H), 1.86 (tt, 1H), 1.39 (s, 9H), 1.37-1.30 (m, 2H), 1.30-1.19 (m, 2H), 1.00 (s, 6H). |
| C28: tert-butyl 4,5-dimethoxy-4-methyl-3-oxopentanoate | 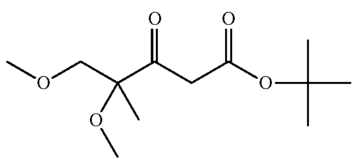 [SMILES: COCC(C)(OC)C(=O)CC(=O)OC(C)(C)C] | $^1$H NMR (400 MHz, DMSO-d$_6$) δ ppm: 3.62-3.51 (m, 2H), 3.42-3.37 (m, 2H), 3.24 (s, 3H), 3.21 (s, 3H), 1.41 (s, 9H), 1.18 (s, 3H). |
| C29: (S)-tert-butyl 4-(2-(dimethylamino)ethoxy)-3-oxopentanoate | 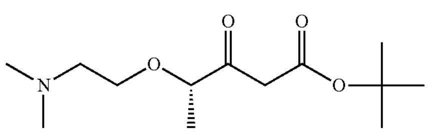 [SMILES: C[C@H](OCCN(C)C)C(=O)CC(=O)OC(C)(C)C] | $^1$H NMR (400 MHz, DMSO-d$_6$) δ ppm: 3.95 (q, 1H), 3.60-3.19 (m, 4H), 2.42 (td, 2H), 2.16 (s, 6H), 1.40 (s, 9H), 1.19 (d, 3H). |
| C30: tert-butyl 3-(4-(tert-butoxy)-2,4-dioxobutyl)morpholine-4-carboxylate | 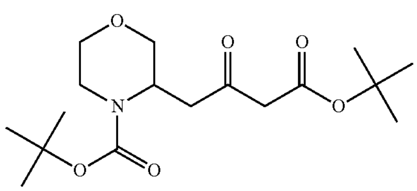 [SMILES: CC(C)(C)OC(=O)CC(=O)CC1COCCN1C(=O)OC(C)(C)C] | $^1$H NMR (400 MHz, DMSO-d$_6$) δ ppm: 4.03 (dq, 1H), 3.57 (dd, 1H), 3.36 (dd, 2H), 3.33 (s, 1H), 3.29 (s, 1H), 3.27-3.23 (m, 1H), 3.08 (dd, 1H), 2.89 (dd, 1H), 2.78 (s, 1H), 2.51-2.36 (m, 1H), 1.19 (d, 18H). |
| C31: tert-butyl 2-(3-(tert-butoxy)-3-oxopropanoyl)piperidine-1-carboxylate | 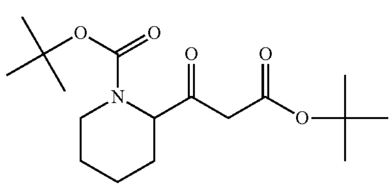 [SMILES: CC(C)(C)OC(=O)CC(=O)C1CCCCN1C(=O)OC(C)(C)C] | $^1$H NMR (400 MHz, DMSO-d$_6$) δ ppm: 4.51-4.39 (m, 1H), 3.62-3.50 (m, 1H), 3.42 (d, 1H), 3.27 (d, 2H), 2.56 (dt, 1H), 1.88 (d, 1H), 1.33 (d, 3H), 1.12 (s, 18H), 1.00-0.82 (m, 2H). |
| C32: (S)-tert-butyl 4-((R)-2-methoxypropoxy)-3-oxopentanoate | 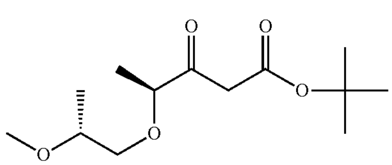 [SMILES: CO[C@H](C)CO[C@@H](C)C(=O)CC(=O)OC(C)(C)C] | $^1$H NMR (400 MHz, DMSO-d$_6$) δ ppm: 3.96 (dq, 1H), 3.60-3.47 (m, 2H), 3.46-3.38 (m, 3H), 3.26 (d, 3H), 1.41 (d, 9H), 1.21 (dd, 3H), 1.07 (dd, 3H). |

| Name | Structure | Analytical data |
|---|---|---|
| C33: tert-butyl 3-(1-methyl-1H-imidazol-2-yl)-3-oxopropanoate | 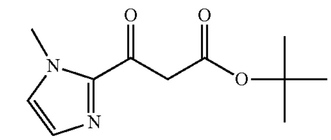 [SMILES: Cn1ccnc1C(=O)CC(=O)OC(C)(C)C] | $^1$H NMR (400 MHz, DMSO-d$_6$) δ ppm: 7.55 (d, 1H), 7.15 (d, 1H), 3.95 (s, 2H), 3.93 (s, 3H), 1.41 (s, 9H). |
| C34: tert-butyl 3-(5-methyltetrahydrofuran-2-yl)-3-oxopropanoate | 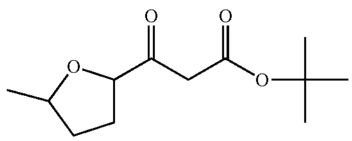 [SMILES: CC1CCC(C(=O)CC(=O)OC(C)(C)C)O1] | $^1$H NMR (400 MHz, DMSO-d$_6$) δ ppm: 4.32-4.26 (m, 1H), 4.04 (dp, 1H), 3.52 (d, 2H), 2.14 (dddt, 1H), 2.02-1.90 (m, 3H), 1.42 (d, 9H), 1.21 (dd, 3H). |
| C35: tert-butyl 4-methoxy-3-oxo-4-(tetrahydro-2H-pyran-4-yl)butanoate | 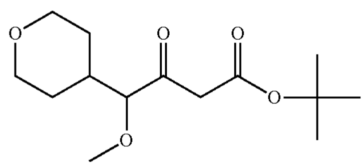 [SMILES: COC(C(=O)CC(=O)OC(C)(C)C)C1CCOCC1] | $^1$H NMR (400 MHz, DMSO-d$_6$) δ ppm: 3.84 (dt, 2H), 3.59-3.47 (m, 2H), 3.29 (s, 2H), 3.28-3.20 (m, 4H), 1.98-1.89 (m, 1H), 1.41 (s, 9H), 1.38 (dd, 4H). |
| C36: tert-butyl 3-(1-(dimethylamino)cyclopropyl)-3-oxopropanoate | 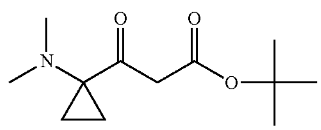 [SMILES: CN(C)C1(C(=O)CC(=O)OC(C)(C)C)CC1] | $^1$H NMR (400 MHz, DMSO-d6) δ 3.28 (s, 2H), 2.36 (s, 6H), 1.41 (s, 9H), 1.29-1.14 (m, 2H), 1.10-1.00 (m, 2H); M/z = 228 [M + H]+, Rt = 0.61 min (UPLC Method B2). |
| C37: tert-butyl 3-(2-(methoxymethyl)tetrahydrofuran-2-yl)-3-oxopropanoate | 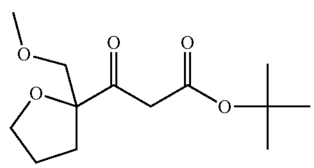 [SMILES: COCC1(C(=O)CC(=O)OC(C)(C)C)CCCO1] | $^1$H NMR (400 MHz, DMSO-d$_6$) δ ppm: 3.85-3.77 (m, 2H), 3.62-3.44 (m, 2H), 3.40-3.36 (m, 2H), 3.22 (s, 3H), 1.83-1.76 (m, 3H), 1.40 (s, 9H), 1.20 (m, 1H). |
| C38: (S)-tert-butyl 3-oxo-4-(((R)-tetrahydrofuran-3-yl)oxy)pentanoate | 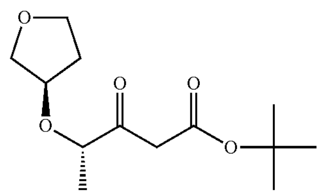 [SMILES: C[C@H](O[C@@H]1CCOC1)C(=O)CC(=O)OC(C)(C)C] | $^1$H NMR (400 MHz, DMSO-d$_6$) δ ppm: 4.21 (m, 1H), 4.05 (m, 1H), 3.77-3.63 (m, 4H), 3.51 (m, 2H), 1.96-1.83 (m, 2H), 1.40 (s, 9H), 1.21 (d, 3H). |
| C39: (S)-tert-butyl 3-oxo-4-(((S)-tetrahydrofuran-3-yl)oxy)pentanoate | 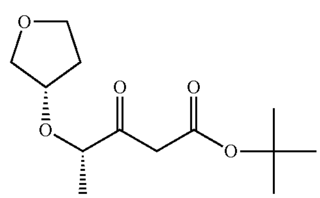 [SMILES: C[C@H](O[C@H]1CCOC1)C(=O)CC(=O)OC(C)(C)C] | $^1$H NMR (400 MHz, DMSO-d$_6$) δ ppm: 4.21 (m, 1H), 4.04 (m, 1H), 3.76-3.63 (m, 4H), 3.51 (m, 2H), 1.92 (m, 2H), 1.40 (s, 9H), 1.20 (d, 3H). |
| C40: (S)-tert-butyl 3-oxo-4-(((S)-tetrahydrofuran-3-yl)methoxy)pentanoate | 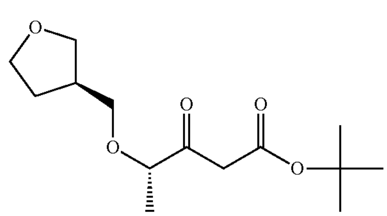 [SMILES: C[C@H](OC[C@H]1CCOC1)C(=O)CC(=O)OC(C)(C)C] | $^1$H NMR (400 MHz, DMSO-d$_6$) δ ppm: 4.00-3.90 (m, 2H), 3.72 (q, 1H), 3.62 (q, 1H), 3.52 (m, 2H), 3.40 (d, 1H), 1.89 (m, 1H), 1.80 (m, 2H), 1.55 (m, 1H), 1.40 (s, 9H), 1.20 (d, 3H). |
| C41: (S)-tert-butyl 3-oxo-4-(((R)-tetrahydrofuran-3-yl)methoxy)pentanoate | 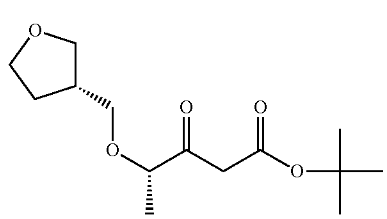 [SMILES: C[C@H](OC[C@@H]1CCOC1)C(=O)CC(=O)OC(C)(C)C] | $^1$H NMR (400 MHz, DMSO-d$_6$) δ ppm: 4.02-3.92 (m, 2H), 3.73 (m, 1H), 3.63 (m, 1H), 3.55 (d, 1H), 3.42 (m, 2H), 1.92-1.76 (m, 3H), 1.57 (m, 1H), 1.41 (s, 9H), 1.40 (m, 1H), 1.21 (s, 3H). |

| Name | Structure | Analytical data |
|---|---|---|
| C42(S): (S)-tert-butyl 4-(benzyl-oxy)-3-oxopentanoate | 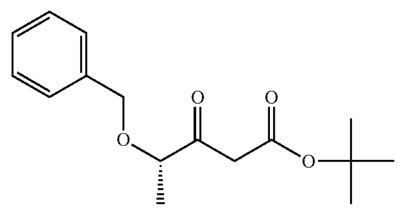 [SMILES: C[C@H](OCc1ccccc1)C(=O)CC(=O)OC(C)(C)C] | $^1$H NMR (400 MHz, DMSO-d$_6$) δ ppm: 7.40-7.27 (m, 5H), 4.55-4.49 (m, 2H), 4.07 (q, 1H), 3.62-3.50 (m, 2H), 1.37 (s, 9H), 1.26 (d, 3H). |

C43: (S)-tert-butyl 4-((tert-butoxycarbonyl)(methyl)amino)-3-oxopentanoate

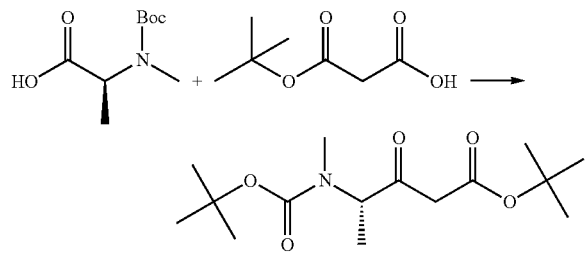

To a solution of Boc-N-Me-L-alanine (5.0 g, 24.6 mmol) in THF (100 ml) at 0° C. was added CDI (4.39 g, 27.1 mmol) and the reaction mixture was stirred at RT for 3 h. In a separate flask, 2M isopropylmagnesium chloride in THF (35.7 ml, 71.3 mmol) was added dropwise to a solution of 3-(tert-butoxy)-3-oxopropanoic acid (5.68 ml, 36.9 mmol) in THF (100 ml) at 0° C., the reaction mixture was stirred at RT for 3 h. Then, this solution was added dropwise to the acyl imidazole solution at 0° C. and the resulting mixture was allowed to warm up to RT and stirred overnight. The mixture was quenched by addition of 10% aqueous citric acid (100 ml) and the aqueous layer was extracted twice with AcOEt. The combined organic layers were washed with saturated aqueous NaHCO$_3$, dried over Na$_2$SO$_4$, filtered and evaporated. The crude material was purified by flash column chromatography on silica gel (cyclohexane/AcOEt 1/0 to 7/3) to afford (S)-tert-butyl 4-((tert-butoxycarbonyl)(methyl)amino)-3-oxopentanoate. M/z=302 [M+H]+, Rt=1.23 min (UPLC Method B1), $^1$H NMR (400 MHz, DMSO-d$_6$) δ ppm: 4.41-4.32 and 4.18-4.10 (m, 1H) 3.53-3.28 (m, 2H), 2.80 and 2.74 (2s, 3H), 1.40 and 1.34 (2s, 18H), 1.24-1.17 (m, 3H).

C44: (R)-tert-butyl 4-methoxy-5-methyl-3-oxohexanoate

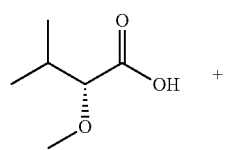

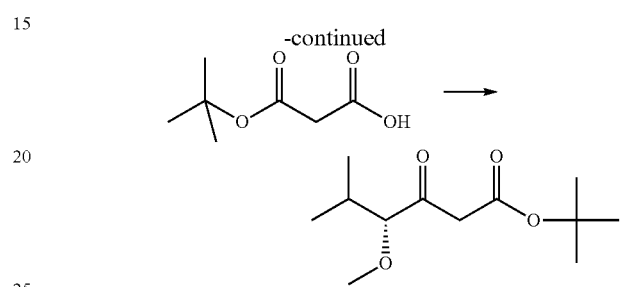

To a solution of (R)-2-methoxy-3-methylbutanoic acid (2.0 g, 15.1 mmol) in THF (50 ml) at 0° C. under argon was added CDI (2.78 g, 16.65 mmol) and the reaction mixture was stirred at RT for 24 h. In a separate flask, 2M isopropylmagnesium chloride in THF (25.0 ml, 49.9 mmol) was added dropwise to a solution of 3-(tert-butoxy)-3-oxopropanoic acid (3.68 ml, 22.7 mmol) in THF (50 ml) at 0° C., and the reaction mixture was stirred at RT for 1 h. Then, this solution was added dropwise to the acyl imidazole solution at 0° C., the resulting mixture was allowed to warm up to RT and was stirred overnight. The reaction was quenched by addition of 10% aqueous citric acid (200 ml) and water. The aqueous layer was extracted twice with AcOEt. The combined organic layers were washed with saturated aqueous NaHCO$_3$, water and brine, dried over Na$_2$SO$_4$, filtered and evaporated. The crude material was purified by flash column chromatography on silica gel (cyclohexane/AcOEt 1/0 to 98/2) to afford (R)-tert-butyl 4-methoxy-5-methyl-3-oxohexanoate. $^1$H NMR (400 MHz, DMSO-d$_6$) δ ppm: 3.48 (d, 2H), 3.43 (d, 1H), 3.28 (s, 3H), 2.01-1.96 (m, 1H), 1.41 (s, 9H), 0.88 (d, 3H), 0.83 (d, 3H).

C45: (S)-tert-butyl 3-(3-(tert-butoxy)-3-oxopropanoyl)morpholine-4-carboxylate

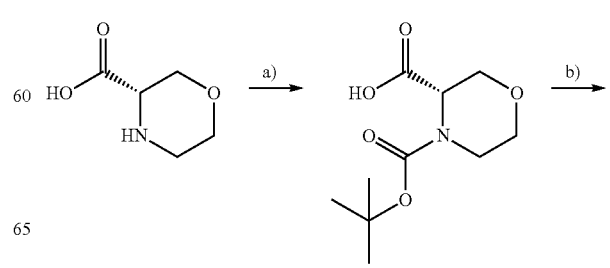

-continued

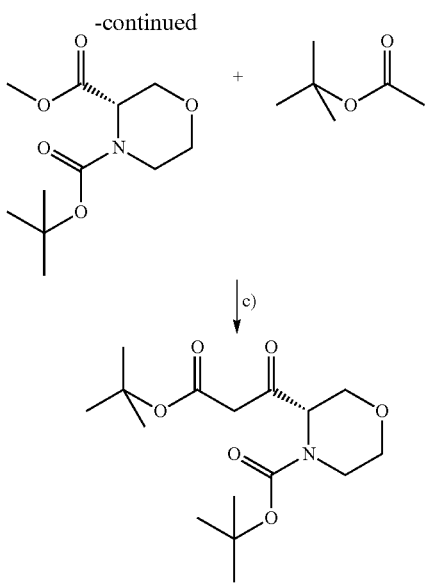

a)
(S)-4-(tert-butoxycarbonyl)morpholine-3-carboxylic acid

A mixture of (S)-morpholine-3-carboxylic acid (1.0 g, 7.63 mmol) and Boc$_2$O (1.77 ml, 7.63 mmol) in 10% NaHCO$_3$ solution in water (10 ml, 7.63 mmol) and 1,4-dioxane (10 ml) was stirred at RT for 16 h. Water and AcOEt were added to mixture and phases were separated. The aqueous layer was acidified to pH 3-4 with 1M aqueous citric acid (12 ml) and extracted 3 times with AcOEt. The organic layer was washed with brine, dried over a phase separator cartridge (IST), the solvent was evaporated and the residue dried under vacuum to afford (S)-4-(tert-butoxycarbonyl)morpholine-3-carboxylic acid. M/z=232 [M+H]+, Rt=0.70 min (UPLC Method B2), $^1$H NMR (400 MHz, DMSO-d$_6$) δ ppm: 12.94 (bs, 1H), 4.32 (dd, 1H), 4.15 (dd, 1H), 3.79 (ddd, 1H), 3.58-3.51 (m, 2H), 3.39-2.97 (m, 2H), 1.38 (d, 9H).

b) (S)-4-tert-butyl 3-methyl morpholine-3,4-dicarboxylate

To a mixture of (S)-4-(tert-butoxycarbonyl)morpholine-3-carboxylic acid (1.31 g, 5.66 mmol) in MeOH (10 ml) at 0° C. was added dropwise 2M trimethylsilyl-diazomethane in hexanes (8.0 ml, 16.0 mmol). The reaction mixture was allowed to warm-up to RT and stirred for 2 h. Water was added to the mixture and the aqueous layer was extracted twice with AcOEt. The organic layer was washed with saturated aqueous NaHCO$_3$, water, brine, dried over a phase separator cartridge (IST) and concentrated. The crude product was purified by flash column chromatography on silica gel (cyclohexane/AcOEt 1/0 to 7/3) to afford (S)-4-tert-butyl 3-methyl morpholine-3,4-dicarboxylate. M/z=246 [M+H]+, Rt=0.89 min (UPLC Method B2).

c) (S)-tert-butyl 3-(3-(tert-butoxy)-3-oxopropanoyl)morpholine-4-carboxylate

At −78° C. under argon, a solution of tert-butyl acetate (2.32 ml, 17.1 mmol) in dry THF (10 ml) was added dropwise to a mixture of 2M LDA in THF/heptane/ethylbenzene (7.49 ml, 15.0 mmol) and dry THF (10 ml). After 1 h stirring at −78° C., a solution of (S)-4-tert-butyl 3-methyl morpholine-3,4-dicarboxylate (1.05 g, 4.28 mmol) in dry THF (10 ml) was added dropwise to the reaction mixture. The resulting reaction mixture was stirred at −78° C. for 3 h. The mixture was poured into 1M aqueous HCl and extracted with AcOEt. The organic layer was washed with saturated aqueous NaHCO$_3$, dried over a phase separator cartridge (IST) and the solvent was evaporated. The crude material was purified by flash column chromatography on silica gel (cyclohexane/AcOEt 1/0 to 4/1) to afford (S)-tert-butyl 3-(3-(tert-butoxy)-3-oxopropanoyl)morpholine-4-carboxylate. M/z=330 [M+H]+, Rt=1.11 min (UPLC Method B2), $^1$H NMR (400 MHz, DMSO-d$_6$) δ ppm: 4.56 (m, 1H), 4.33 (m, 1H), 3.81-3.50 (m, 5H), 3.38-3.34 (m, 1H), 2.99 (m, 1H), 1.41-1.34 (m, 18H).

C46: (4S,5R)-tert-butyl 4,5-dimethoxy-3-oxohexanoate

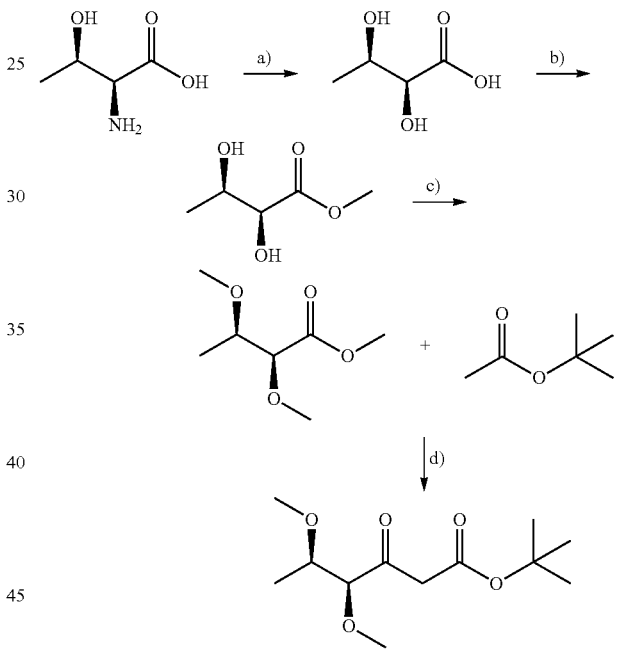

a) (2S,3R)-2,3-dihydroxybutanoic acid

To a solution of L-threonine (2.2 g, 18.5 mmol) in 0.5M aqueous H$_2$SO$_4$ (40 ml, 20 mmol) was added dropwise at 0° C. a solution of sodium nitrite (4.14 g, 60 mmol) in water (15 ml). The reaction mixture was allowed to warm-up to RT and stirred overnight. The mixture was concentrated and the residue was taken up in EtOH, filtered and the filtrate was concentrated. The residue was taken-up in water, frozen and lyophilized to afford (2S,3R)-2,3-dihydroxybutanoic acid. $^1$H NMR (400 MHz, D$_2$O) δ ppm: 4.01 (m, 1H), 3.79 (m, 1H), 1.20 (d, 3H).

b) (2S,3R)-methyl 2,3-dihydroxybutanoate

To a mixture of (2S,3R)-2,3-dihydroxybutanoic acid (1.90 g, 15.8 mmol) in MeOH (35 ml) at 0° C. was added dropwise SOCl$_2$ (2.89 ml, 39.5 mmol). The reaction mixture was allowed to warm-up to RT and stirred for 2 h. The mixture was concentrated and the residue was purified by flash column chromatography on silica gel (cyclohexane/AcOEt 1/0 to 1/1) to afford (2S,3R)-methyl 2,3-dihydroxybutanoate. M/z=135 [M+H]+, $^1$H NMR (400 MHz, CDCl$_3$) δ ppm: 4.09 (m, 1H), 4.03 (m, 1H), 3.83 (s, 3H), 1.31 (d, 3H).

c) (2S,3R)-methyl 2,3-dimethoxybutanoate

A solution of (2S,3R)-methyl 2,3-dihydroxybutanoate (1.70 g, 12.7 mmol), methyl iodide (15.85 ml, 253 mmol) and silver oxide (17.6 g, 76 mmol) in DCM (100 ml) was stirred at RT for 6 days in the dark. The mixture was filtered and concentrated and the crude product was purified by flash column chromatography on silica gel (cyclohexane/AcOEt 1/0 to 1/1) to afford (2S,3R)-methyl 2,3-dimethoxybutanoate. $^1$H NMR (400 MHz, DMSO-d$_6$) δ ppm: 3.85 (m, 1H), 3.66 (s, 3H), 3.61 (m, 1H), 3.29 (s, 3H), 3.21 (s, 3H), 1.07 (d, 3H).

d) (4S,5R)-tert-butyl 4,5-dimethoxy-3-oxohexanoate

At −78° C., a solution of tert-butyl acetate (0.33 ml, 2.47 mmol) in dry THF (0.9 ml) was added dropwise to a mixture of dry THF (0.9 ml) and 2M LDA in THF/heptane/ethylbenzene (1.08 ml, 2.16 mmol). After 1 h stirring at −78° C., the solution was cannulated dropwise to a solution of (2S,3R)-methyl 2,3-dimethoxybutanoate (100 mg, 0.62 mmol) in dry THF (0.9 ml). The resulting mixture was stirred at −78° C. for 2 h. The reaction mixture was poured into 1M aqueous HCl and extracted with AcOEt, dried over a phase separator cartridge (IST) and evaporated. The crude material was purified by flash column chromatography on silica gel (cyclohexane/AcOEt 1/0 to 9/1) to afford (4S,5R)-tert-butyl 4,5-dimethoxy-3-oxohexanoate. M/z=247 [M+H]+, $^1$H NMR (400 MHz, DMSO-d$_6$) δ ppm: 3.78 (m, 1H), 3.64 (m, 1H), 3.48 (s, 2H), 3.21 (s, 3H), 1.40 (s, 9H), 1.06 (d, 3H), one CH3 obscured by water.

C47: (S)-tert-butyl 4-((tert-butoxycarbonyl)(methyl)amino)-5-methyl-3-oxohexanoate

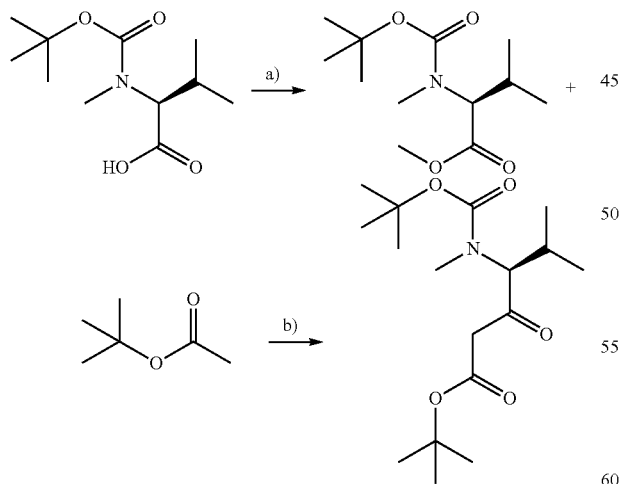

a) (S)-methyl 2-((tert-butoxycarbonyl)(methyl)amino)-3-methylbutanoate

To a mixture of N-Me-Boc-Val-OH (2.0 g, 8.65 mmol) in MeOH (29 ml) at 0° C. was added dropwise 2M trimethylsilyldiazomethane in hexanes (8.65 ml, 17.3 mmol). The reaction mixture was allowed to warm-up to RT and was stirred overnight. Water was added to the mixture and the aqueous layer was extracted twice with AcOEt. The organic layer was washed with saturated aqueous NaHCO$_3$, water, brine, dried over a phase separator cartridge (IST) and concentrated. The crude material was purified by flash column chromatography on silica gel (cyclohexane/AcOEt 1/0 to 4/1) to afford (S)-methyl 2-((tert-butoxycarbonyl)(methyl)amino)-3-methylbutanoate. M/z=246 [M+H]+, Rt=1.15 min (UPLC Method B2).

b) (S)-tert-butyl 4-((tert-butoxycarbonyl)(methyl)amino)-5-methyl-3-oxohexanoate At −78° C. under argon, a solution of tert-butyl acetate (2.20 ml, 16.3 mmol) in dry THF (10 ml) was added dropwise to a mixture of 2M LDA in THF/heptane/ethylbenzene (7.13 ml, 14.3 mmol) and dry THF (10 ml). After 1 h stirring at −78° C., a solution of (S)-methyl 2-((tert-butoxycarbonyl)(methyl)amino)-3-methylbutanoate (1.0 g, 4.1 mmol) in dry THF (10 ml) was added dropwise to the reaction mixture. The resulting reaction mixture was stirred at −78° C. for 2 h. The mixture was poured into 1M aqueous HCl and extracted with AcOEt. The organic layer was washed with saturated aqueous NaHCO$_3$, dried over a phase separator cartridge (IST) and the solvent was evaporated. The crude product was purified by flash column chromatography on silica gel (cyclohexane/AcOEt 1/0 to 9/1) to afford (S)-tert-butyl 4-((tert-butoxycarbonyl)(methyl)amino)-5-methyl-3-oxohexanoate. M/z=330 [M+H]+, Rt=1.34 min (UPLC Method B2), $^1$H NMR (400 MHz, DMSO-d$_6$) δ ppm: 4.29-3.95 (d, 1H), 3.52-3.37 (m, 2H), 2.68+2.61 (s, 3H), 2.14 (m, 1H), 1.42-1.39 (m, 18H), 0.87 (dd, 3H), 0.77 (dd, 3H).

Part D: Synthesis of C-substituted pyrazolo[1,5-a]pyrimidine-6-carboxylates

D1: (S)-2-chloro-7-(1-methoxyethyl)pyrazolo[1,5-a]pyrimidine-6-carboxylic acid

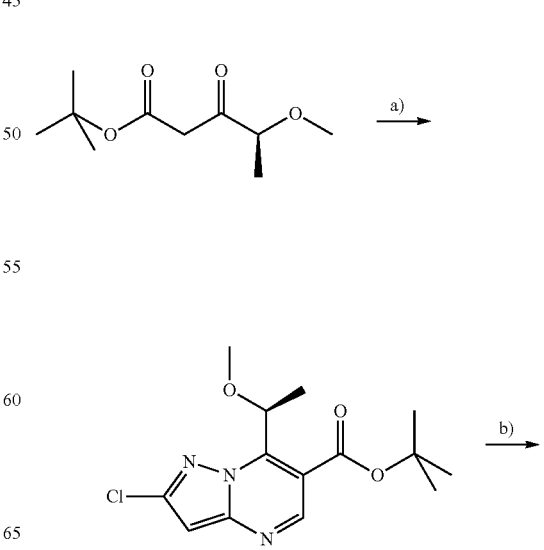

-continued

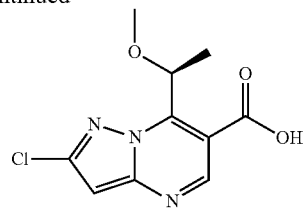

a) (S)-tert-butyl 2-chloro-7-(1-methoxyethyl)pyrazolo[1,5-a]pyrimidine-6-carboxylate A mixture of 1,1-dimethoxy-N,N-dimethylmethanamine (12.4 ml, 94 mmol) and (S)-tert-butyl 4-methoxy-3-oxopentanoate (18.9 g, 94 mmol) was stirred at 120° C. for 1.5 h. Then, a solution of 5-chloro-1H-pyrazol-3-amine (11.0 g, 94 mmol) in EtOH (100 ml) was added and the resulting mixture was stirred 1 h at 85° C. The reaction mixture was concentrated and the residue was purified by flash column chromatography on silica gel (cyclohexane/AcOEt: 100/0 to 70/30) to afford (S)-tert-butyl 2-chloro-7-(1-methoxyethyl) pyrazolo[1,5-a]pyrimidine-6-carboxylate. M/z=312-314 [M+H]+, Rt=1.31 min (UPLC Method B1), $^1$H NMR (400 MHz, DMSO-d$_6$) δ ppm: 8.65 (s, 1H), 7.03 (s, 1H), 5.26 (q, 1H), 3.22 (s, 3H), 1.62 (d, 3H), 1.55 (s, 9H).

b) (S)-2-chloro-7-(1-methoxyethyl)pyrazolo[1,5-a]pyrimidine-6-carboxylic acid

To a solution of (S)-tert-butyl 2-chloro-7-(1-methoxyethyl)pyrazolo[1,5-a]pyrimidine-6-carboxylate (15.0 g, 48.1 mmol) in DCM (75 ml) at RT was added TFA (74 ml). The reaction mixture was stirred overnight and concentrated. Et$_2$O was added to the residue and the suspension was evaporated to dryness to afford (S)-2-chloro-7-(1-methoxyethyl)pyrazolo[1,5-a]pyrimidine-6-carboxylic acid. M/z=256-258 [M+H]+, Rt=0.57 min (UPLC Method B1), $^1$H NMR (400 MHz, DMSO-d$_6$) δ ppm: 8.72 (s, 1H), 7.03 (s, 1H), 5.40 (q, 1H), 3.20 (s, 3H), 1.64 (d, 3H).

D2: 2-chloro-7-(2-methoxypropan-2-yl)pyrazolo[1,5-a]pyrimidine-6-carboxylic acid

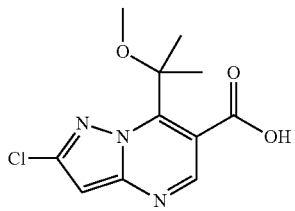 [SMILES: COC(C)(C)c1c(C(=O)O)cnc2cc(Cl)nn12]

2-chloro-7-(2-methoxypropan-2-yl)pyrazolo[1,5-a]pyrimidine-6-carboxylic acid was prepared analogously as described for compound D1 using tert-butyl 4-methoxy-4-methyl-3-oxopentanoate instead of (S)-tert-butyl 4-methoxy-3-oxopentanoate. M/z=270-272 [M+H]+, Rt=0.77 min (UPLC Method B1), $^1$H NMR (400 MHz, DMSO-d$_6$) δ ppm: 8.55 (s, 1H), 6.99 (s, 1H), 3.21 (s, 3H), 1.80 (s, 6H).

D3: 2-chloro-7-(1-methylcyclopropyl)pyrazolo[1,5-a]pyrimidine-6-carboxylic acid

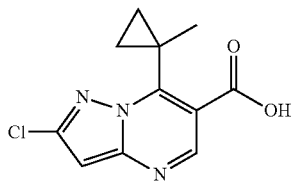 [SMILES: CC1(c2c(C(=O)O)cnc3cc(Cl)nn23)CC1]

2-chloro-7-(1-methylcyclopropyl)pyrazolo[1,5-a]pyrimidine-6-carboxylic acid was prepared analogously as described for D1 using tert-butyl 3-(1-methylcyclopropyl)-3-oxopropanoate instead of (S)-tert-butyl 4-methoxy-3-oxopentanoate. Step a) was performed at 80° C. for 41 h. M/z=252 [M+H]+, Rt=0.75 min (UPLC Method B2), $^1$H NMR (400 MHz, DMSO-d$_6$) δ ppm: 13.7 (s, 1H), 8.77 (s, 1H), 7.00 (s, 1H), 1.53 (s, 3H), 1.10 (t, 2H), 0.91 (t, 2H).

In analogy the following compounds were prepared:

| Name | Structure | Analytical data |
| --- | --- | --- |
| D4: 7-(tert-butyl)-2-chloropyrazolo[1,5-a]pyrimidine-6-carboxylic acid | 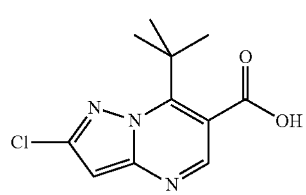 [SMILES: CC(C)(C)c1c(C(=O)O)cnc2cc(Cl)nn12] | M/z = 254-256 [M + H]+, Rt = 0.75 min (UPLC Method B2). |
| D5: 2-chloro-7-(2-methyltetrahydrofuran-2-yl)pyrazolo[1,5-a]pyrimidine-6-carboxylic acid | 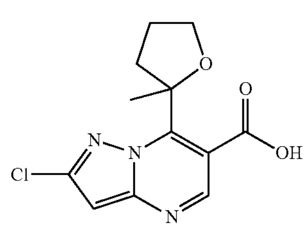 [SMILES: CC1(c2c(C(=O)O)cnc3cc(Cl)nn23)CCCO1] | M/z = 282-284 [M + H]+, Rt = 0.78 min (UPLC Method B2). $^1$H NMR (400 MHz, DMSO-d$_6$) δ ppm: 13.1 (s, 1H), 8.57 (s, 1H), 7.00 (s, 1H), 3.91 (q, 1H), 3.70 (q, 1H), 2.45-2.26 (m, 2H), 1.98-1.88 (m, 1H), 1.85-1.77 (m, 1H), 1.74 (s, 3H). |

-continued

| Name | Structure | Analytical data |
|------|-----------|-----------------|
| D6: (S)-2-chloro-7-(1-(2-methoxyethoxy)ethyl)pyrazolo[1,5-a]pyrimidine-6-carboxylic acid | 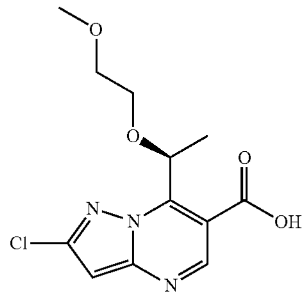 [SMILES: COCCO[C@@H](C)c1c(C(=O)O)cnc2cc(Cl)nn12] | M/z = 300-302 [M + H]+, Rt = 0.63 min (UPLC Method B1). |
| D7: (R)-2-chloro-7-(1-(2-methoxyethoxy)ethyl)pyrazolo[1,5-a]pyrimidine-6-carboxylic acid | 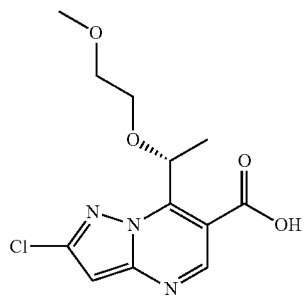 [SMILES: COCCO[C@H](C)c1c(C(=O)O)cnc2cc(Cl)nn12] | M/z = 300-302 [M + H]+, Rt = 0.63 min (UPLC Method B1). |
| D8: 2-chloro-7-(1,4-dioxan-2-yl)pyrazolo[1,5-a]pyrimidine-6-carboxylic acid | 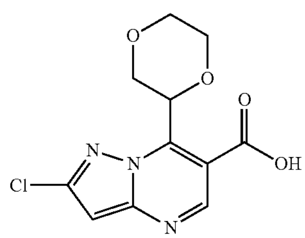 [SMILES: O=C(O)c1cnc2cc(Cl)nn2c1C1COCCO1] | M/z = 284-286 [M + H]+, Rt = 0.57 min (UPLC Method B2). |
| D9: 2-chloro-7-(1-methoxypropan-2-yl)pyrazolo[1,5-a]pyrimidine-6-carboxylic acid | 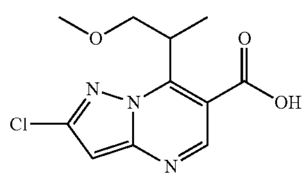 [SMILES: COCC(C)c1c(C(=O)O)cnc2cc(Cl)nn12] | M/z = 270-272 [M + H]+, Rt = 0.79 min (UPLC Method B2). |
| D10: (R)-2-chloro-7-(1-methoxyethyl)pyrazolo[1,5-a]pyrimidine-6-carboxylic acid | 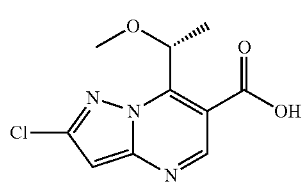 [SMILES: CO[C@H](C)c1c(C(=O)O)cnc2cc(Cl)nn12] | M/z = 256-258 [M + H]+, Rt = 0.63 min (UPLC Method B2). $^1$H NMR (400 MHz, DMSO-$d_6$) δ ppm: 8.72 (s, 1H), 7.03 (s, 1H), 5.40 (q, 1H), 3.20 (s, 3H), 1.64 (d, 3H). |
| D11: 2-chloro-7-(methoxy(phenyl)methyl)pyrazolo[1,5-a]pyrimidine-6-carboxylic acid | 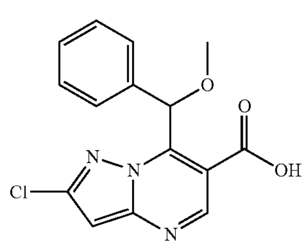 [SMILES: COC(c1ccccc1)c1c(C(=O)O)cnc2cc(Cl)nn12] | M/z = 318-320 [M + H]+, Rt = 0.82 min (UPLC Method B2). |

-continued

| Name | Structure | Analytical data |
|---|---|---|
| D12: 2-chloro-7-(1-(methoxymethyl)cyclobutyl)pyrazolo[1,5-a]pyrimidine-6-carboxylic acid | 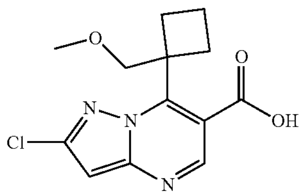 [SMILES: COCC1(c2c(C(=O)O)cnc3cc(Cl)nn23)CCC1] | M/z = 296-298 [M + H]+, Rt = 0.92 min (UPLC Method B2). $^1$H NMR (400 MHz, DMSO-$d_6$) δ ppm: 13.70 (s, 1H), 8.659 (s, 1H), 6.96 (s, 1H), 3.95 (s, 2H), 3.34 (s, 3H), 2.65-2.55 (m, 2H), 2.37-2.22 (m, 1H), 2.10-1.92 (m, 1H), 1.89-1.79 (m, 1H), 1.65-1.55 (m, 1H). |
| D13: 2-chloro-7-(2-methoxyphenyl)pyrazolo[1,5-a]pyrimidine-6-carboxylic acid | 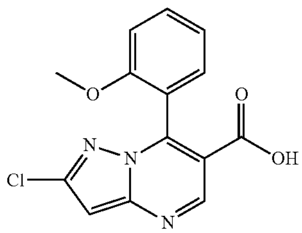 [SMILES: COc1ccccc1-c1c(C(=O)O)cnc2cc(Cl)nn12] | M/z = 304-306 [M + H]+, Rt = 0.80 min (UPLC Method B2). |
| D14: 2-chloro-7-(4-methyltetrahydro-2H-pyran-4-yl)pyrazolo[1,5-a]pyrimidine-6-carboxylic acid | 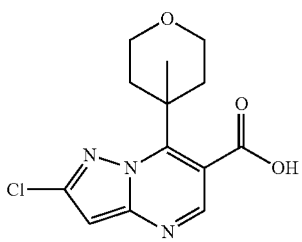 | M/z = 296-298 [M + H]+, Rt = 0.63 min (UPLC Method B2). |
| D15: 2-chloro-7-(1,2-dimethoxyethyl)pyrazolo[1,5-a]pyrimidine-6-carboxylic acid | 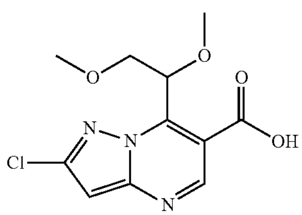 [SMILES: COCC(OC)c1c(C(=O)O)cnc2cc(Cl)nn12] | M/z = 286-288 [M + H]+, Rt = 0.57 min (UPLC Method B1), $^1$H NMR (400 MHz, DMSO-$d_6$) δ ppm: 8.77 (s, 1H), 7.04 (s, 1H), 5.65 (dd, 1H), 4.01 (dd, 1H), 3.79 (dd, 1H), 3.31 (s, 3H), 3.25 (s, 3H). |
| D16: 2-chloro-7-(tetrahydrofuran-3-yl)pyrazolo[1,5-a]pyrimidine-6-carboxylic acid | | M/z = 268-270 [M + H]+, Rt = 0.64 min (UPLC Method B2). |
| D17: 2-chloro-7-((tetrahydro-2H-pyran-4-yl)methyl)pyrazolo[1,5-a]pyrimidine-6-carboxylic acid | 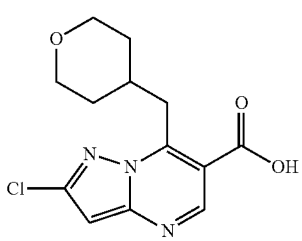 [SMILES: O=C(O)c1cnc2cc(Cl)nn2c1CC1CCOCC1] | M/z = 296-298 [M + H]+, Rt = 0.76 min (UPLC Method B2). |
| D18: 2-chloro-7-(isopropoxymethyl)pyrazolo[1,5-a]pyrimidine-6-carboxylic acid | 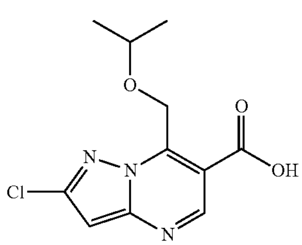 [SMILES: CC(C)OCc1c(C(=O)O)cnc2cc(Cl)nn12] | M/z = 270-272 [M + H]+, Rt = 0.76 min (UPLC Method B2). |

-continued

| Name | Structure | Analytical data |
|---|---|---|
| D19: 2-chloro-7-(1,3-dimethoxypropyl)pyrazolo[1,5-a]pyrimidine-6-carboxylic acid | 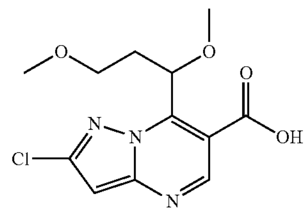 [SMILES: COCCC(OC)c1c(C(=O)O)cnc2cc(Cl)nn12] | M/z = 300-302 [M + H]+, Rt = 0.67 min (UPLC Method B2). |
| D20: (R)-7-(1-(benzyloxy)ethyl)-2-chloropyrazolo[1,5-a]pyrimidine-6-carboxylic acid | 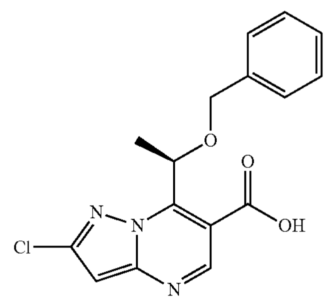 [SMILES: C[C@@H](OCc1ccccc1)c1c(C(=O)O)cnc2cc(Cl)nn12] | M/z = 332-334 [M + H]+, Rt = 0.94 min (UPLC Method B1). |
| D21: 7-(3-oxabicyclo[3.1.0]hexan-6-yl)-2-chloropyrazolo[1,5-a]pyrimidine-6-carboxylic acid | 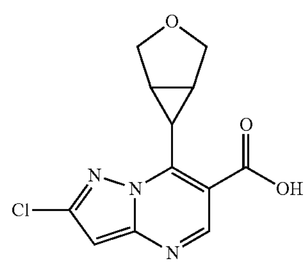 [SMILES: O=C(O)c1cnc2cc(Cl)nn2c1C1C2COCC21] | M/z = 280-282 [M + H]+, Rt = 0.67 min (UPLC Method B2). |
| D22: 2-chloro-7-(5-oxaspiro[2.4]heptan-1-yl)pyrazolo[1,5-a]pyrimidine-6-carboxylic acid | 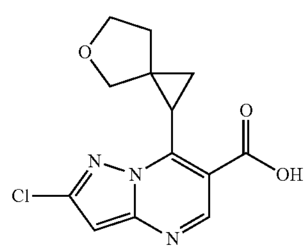 [SMILES: O=C(O)c1cnc2cc(Cl)nn2c1C1CC12CCOC2] | M/z = 294-296 [M + H]+, Rt = 0.65 min (UPLC Method B2). |
| D23: 2-chloro-7-(dimethylcarbamoyl)pyrazolo[1,5-a]pyrimidine-6-carboxylic acid | 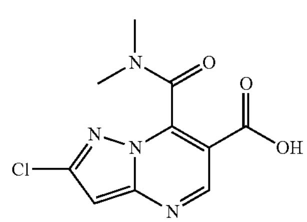 [SMILES: CN(C)C(=O)c1c(C(=O)O)cnc2cc(Cl)nn12] | M/z = 269-271 [M + H]+, Rt = 0.49 min (UPLC Method B2). |
| D24: (S)-7-(1-methoxyethyl)-2-methylpyrazolo[1,5-a]pyrimidine-6-carboxylic acid | 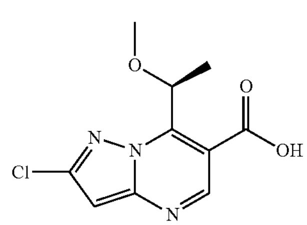 | M/z = 236 [M + H]+, Rt = 0.50 min (UPLC Method B1). |

-continued

| Name | Structure | Analytical data |
|---|---|---|
| D25: 2-methyl-7-(1-methylcyclopropyl)pyrazolo[1,5-a]pyrimidine-6-carboxylic acid | 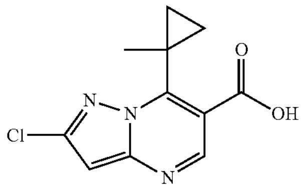 | M/z = 232 [M + H]+, Rt = 0.65 min (UPLC Method B2). |
| D26: (S)-2-chloro-7-(1-methoxy-2-methylpropyl)pyrazolo[1,5-a]pyrimidine-6-carboxylic acid | 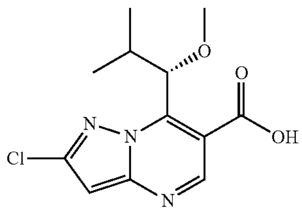 [SMILES: CO[C@H](c1c(C(=O)O)cnc2cc(Cl)nn12)C(C)C] | M/z = 284-286 [M + H]+, Rt = 0.81 min (UPLC Method B2). |
| D27: 2-chloro-7-(1-(methoxymethyl)cyclopropyl)pyrazolo[1,5-a]pyrimidine-6-carboxylic acid | 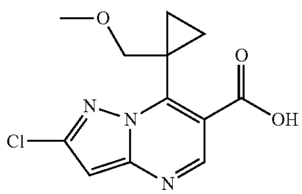 [SMILES: COCC1(c2c(C(=O)O)cnc3cc(Cl)nn23)CC1] | M/z = 282-284 [M + H]+, Rt = 0.76 min (UPLC Method B2). |
| D28: 7-(1-(methoxymethyl)cyclopropyl)-2-ethylpyrazolo[1,5-a]pyrimidine-6-carboxylic acid | 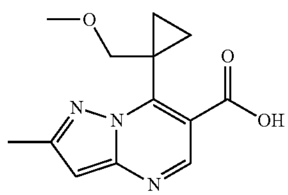 [SMILES: COCC1(c2c(C(=O)O)cnc3cc(C)nn23)CC1] | M/z = 262 [M + H]+, Rt = 0.68 min (UPLC Method B2). |
| D29: 2-chloro-7-(2-(tetrahydro-2H-pyran-4-yl)propan-2-yl)pyrazolo[1,5-a]pyrimidine-6-carboxylic acid | 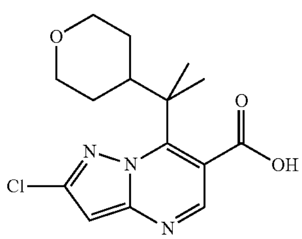 [SMILES: CC(C)(c1c(C(=O)O)cnc2cc(Cl)nn12)C1CCOCC1] | M/z = 324-326 [M + H]+, Rt = 0.75 min (UPLC Method B2). |
| D30: 2-chloro-7-(1,2-dimethoxy propan-2-yl)pyrazolo[1,5-a]pyrimidine-6-carboxylic acid | 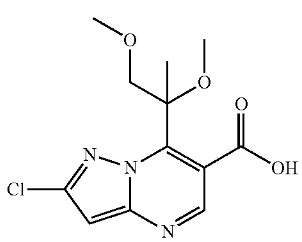 [SMILES: COCC(C)(OC)c1c(C(=O)O)cnc2cc(Cl)nn12] | M/z = 300-302 [M + H]+, Rt = 0.77 min (UPLC Method B2). |
| D31: 2-chloro-7-(1-(2-(dimethylamino)ethoxy)ethyl)pyrazolo[1,5-a]pyrimidine-6-carboxylic acid | | M/z = 313-315 [M + H]+, Rt = 0.40 min (UPLC Method B1). |

-continued

| Name | Structure | Analytical data |
|---|---|---|
| D32: 2-chloro-7-((S)-1-((R)-2-methoxypropoxy)ethyl)pyrazolo[1,5-a]pyrimidine-6-carboxylic acid | 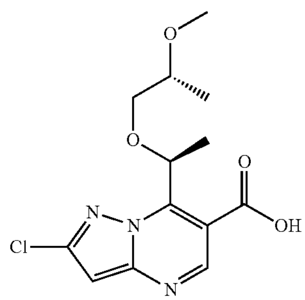 [SMILES: CO[C@H](C)CO[C@@H](C)c1c(C(=O)O)cnc2cc(Cl)nn12] | M/z = 314-316 [M + H]+, Rt = 0.76 min (UPLC Method B2). |
| D33: 2-chloro-7-(1-methyl-1H-imidazol-2-yl)pyrazolo[1,5-a]pyrimidine-6-carboxylic acid | 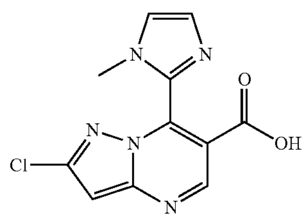 [SMILES: Cn1ccnc1-c1c(C(=O)O)cnc2cc(Cl)nn12] | M/z = 278-280 [M + H]+, Rt = 0.44 min (UPLC Method B2). |
| D34: 2-chloro-7-(5-methyl-tetrahydrofuran-2-yl)pyrazolo[1,5-a]pyrimidine-6-carboxylic acid | 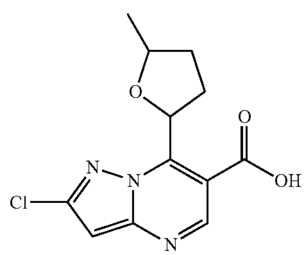 [SMILES: CC1CCC(c2c(C(=O)O)cnc3cc(Cl)nn23)O1] | M/z = 282-284 [M + H]+, Rt = 0.76-0.77 min (UPLC Method B2), 2:1 trans/cis mixture as determined by $^1$H NMR. |
| D35: 2-chloro-7-(methoxy-(tetrahydro-2H-pyran-4-yl)methyl)pyrazolo[1,5-a]pyrimidine-6-carboxylic acid | 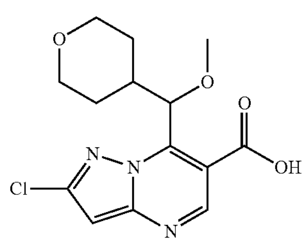 [SMILES: COC(c1c(C(=O)O)cnc2cc(Cl)nn12)C1CCOCC1] | M/z = 326-328 [M + H]+, Rt = 0.66 min (UPLC Method B2). |
| D36: 2-chloro-7-(1-(dimethyl-amino)cyclopropyl)pyrazolo[1,5-a]pyrimidine-6-carboxylic acid | 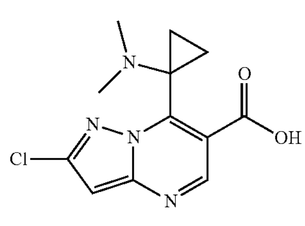 [SMILES: CN(C)C1(c2c(C(=O)O)cnc3cc(Cl)nn23)CC1] | M/z = 281-283 [M + H]+, Rt = 0.46 min (UPLC Method B2). |
| D37: 2-chloro-7-(2-(methoxy-methyl)tetrahydrofuran-2-yl)pyrazolo[1,5-a]pyrimidine-6-carboxylic acid | 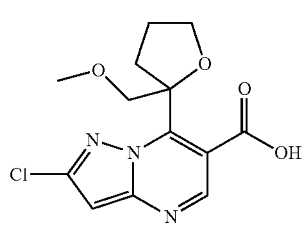 [SMILES: COCC1(c2c(C(=O)O)cnc3cc(Cl)nn23)CCCO1] | M/z = 312-314 [M + H]+, Rt = 0.77 min (UPLC Method B2). |

| Name | Structure | Analytical data |
|---|---|---|
| D38: (S)-2-cyano-7-(1-methoxyethyl)pyrazolo[1,5-a]pyrimidine-6-carboxylic acid | 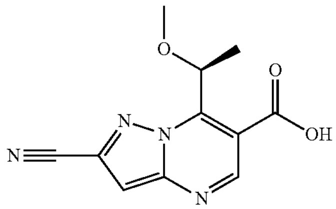 [SMILES: CO[C@@H](C)c1c(C(=O)O)cnc2cc(C#N)nn12] | M/z = 247 [M + H]+, Rt = 0.52 min (UPLC Method B1). |
| D39: 2-chloro-7-((1R,2R)-1,2-dimethoxypropyl)pyrazolo[1,5-a]pyrimidine-6-carboxylic acid | 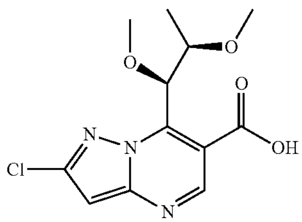 [SMILES: CO[C@H](c1c(C(=O)O)cnc2cc(Cl)nn12)[C@@H](C)OC] | M/z = 300-302 [M + H]+, Rt = 0.70 min (UPLC Method B2). |
| D40: 2-chloro-7-((S)-1-(((R)-tetrahydrofuran-3-yl)oxy)ethyl)pyrazolo[1,5-a]pyrimidine-6-carboxylic acid | 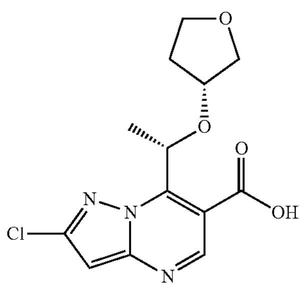 [SMILES: C[C@H](O[C@@H]1CCOC1)c1c(C(=O)O)cnc2cc(Cl)nn12] | M/z = 312-314 [M + H]+, Rt = 0.67 min (UPLC Method B1). |
| D41: 2-chloro-7-((S)-1-(((S)-tetrahydrofuran-3-yl)oxy)ethyl)pyrazolo[1,5-a]pyrimidine-6-carboxylic acid | 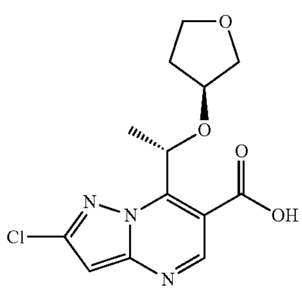 [SMILES: C[C@H](O[C@H]1CCOC1)c1c(C(=O)O)cnc2cc(Cl)nn12] | M/z = 312-314 [M + H]+, Rt = 0.65 min (UPLC Method B1). |
| D42: 2-chloro-7-((S)-1-(((S)-tetrahydrofuran-3-yl)methoxy)ethyl)pyrazolo[1,5-a]pyrimidine-6-carboxylic acid | 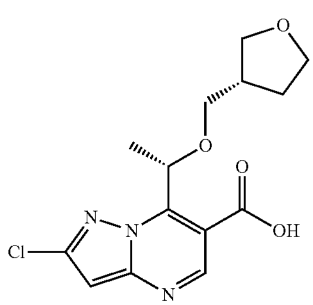 [SMILES: C[C@H](OC[C@H]1CCOC1)c1c(C(=O)O)cnc2cc(Cl)nn12] | M/z = 326-328 [M + H]+, Rt = 0.76 min (UPLC Method B1). |

-continued

| Name | Structure | Analytical data |
|---|---|---|
| D43: 2-chloro-7-((S)-1-(((R)-tetrahydrofuran-3-yl)methoxy)ethyl)pyrazolo[1,5-a]pyrimidine-6-carboxylic acid | 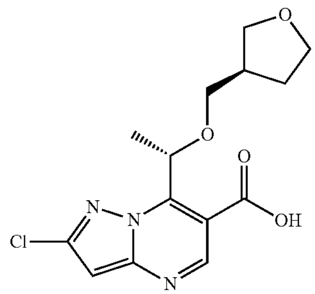 [SMILES: C[C@H](OC[C@@H]1CCOC1)c1c(C(=O)O)cnc2cc(Cl)nn12] | M/z = 326-328 [M + H]+, Rt = 0.77 min (UPLC Method B1). |
| D44: 2-methyl-7-(2-methyl-tetrahydrofuran-2-yl)pyrazolo[1,5-a]pyrimidine-6-carboxylic acid | 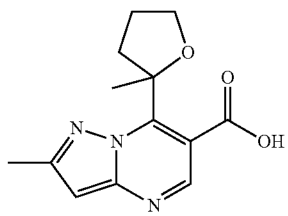 [SMILES: Cc1cc2ncc(C(=O)O)c(C3(C)CCCO3)n2n1] | M/z = 262 [M + H]+, Rt = 0.71 min (UPLC Method B2). ¹H NMR (400 MHz, DMSO-d₆) δ ppm: 12.96 (bs, 1H), 8.38 (s, 1H), 6.59 (s, 1H), 3.88 (q, 1H), 3.70 (q, 1H), 2.56 (m, 1H), 2.46 (s, 3H), 2.37 (m, 1H), 1.91 (m, 1H), 1.75 (s, 3H), 1.70 (m, 1H). |
| D45: (S)-7-(1-(benzyloxy)ethyl)-2-chloropyrazolo[1,5-a]pyrimidine-6-carboxylic acid | 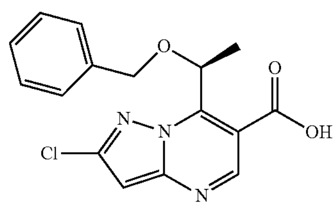 [SMILES: C[C@H](OCc1ccccc1)c1c(C(=O)O)cnc2cc(Cl)nn12] | M/z = 332-334 [M + H]+, Rt = 0.96 min (UPLC Method B1). |

D46: (S)-2-chloro-7-(1-methoxyethyl)pyrazolo[1,5-a]pyrimidine-6-carboxylic acid

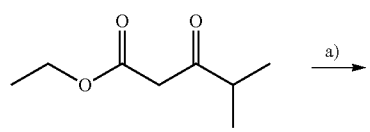

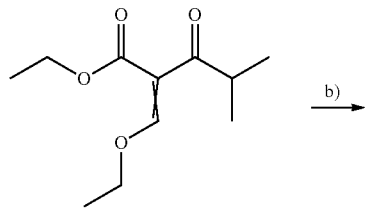

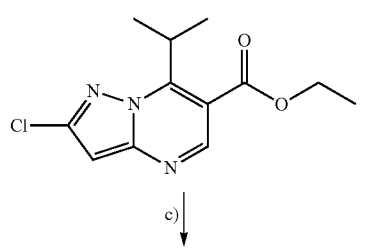

-continued

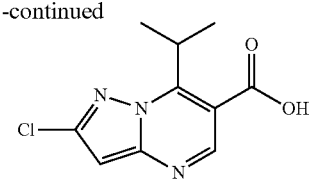

a) ethyl 2-(ethoxymethylene)-4-methyl-3-oxopentanoate

Ethyl isobutyrylacetate (9.0 g, 56.9 mmol), triethyl orthoformate (18.9 ml, 114 mmol) and Ac₂O (10.7 ml, 114 mmol) were stirred at 135° C. overnight. The solution was concentrated (16 mbar/60° C.) to afford ethyl 2-(ethoxymethylene)-4-methyl-3-oxopentanoate as a cis/trans mixture M/z=215 [M+H]+, Rt=0.93 and 0.99 min (UPLC Method B2), ¹H NMR (400 MHz, DMSO-d₆) 7.84 and 7.66 (2s, 1H), 4.27-4.06 (m, 4H), 3.12-3.05 (m, 1H), 1.27-1.15 (m, 6H), 1.03-0.98 (m, 6H).

b) (ethyl 2-chloro-7-isopropylpyrazolo[1,5-a]pyrimidine-6-carboxylate

Ethyl 2-(ethoxymethylene)-4-methyl-3-oxopentanoate (11.8 g, 55.1 mmol) and 5-chloro-1H-pyrazol-3-amine (6.15 g, 52.3 mmol) in EtOH (130 ml) were stirred at 80° C. overnight. Water was added to the reaction mixture and the aqueous phase was extracted with AcOEt. The organic phase was washed with aqueous saturated NaHCO₃, water and brine, dried over Na₂SO₄, filtered and concentrated. The crude product was purified by flash column chromatography on silica gel (cyclohexane/AcOEt: 1/0 to 9/1) to afford (ethyl 2-chloro-7-isopropylpyrazolo[1,5-a]pyrimidine-6-carboxylate. M/z=268-270 [M+H]+, Rt=1.27 min (UPLC Method B2), $^1$H NMR (400 MHz, DMSO-d$_6$) δ 8.80 (s, 1H), 7.00 (s, 1H), 4.40-4.33 (m, 1H), 4.37 (q, 2H), 1.31 (d, 6H), 1.36 (t, 3H).

c) 2-chloro-7-isopropylpyrazolo[1,5-a]pyrimidine-6-carboxylic acid

Ethyl 2-chloro-7-isopropylpyrazolo[1,5-a]pyrimidine-6-carboxylate (10.5 g, 39.3 mmol) was dissolved in EtOH (100 ml) and 2N NaOH (39.3 ml, 79 mmol) was added. The reaction mixture was stirred at 60° C. for 3 h. EtOH was evaporated, AcOEt was added and the mixture was acidified with 1M aqueous HCl to give a white suspension. The solid was filtered, washed with water and dried under vacuum. The resulting residue was treated with AcOEt and extracted with aqueous saturated NaHCO$_3$. The aqueous phase was separated, acidified to pH=2 and the precipitate filtered and washed with cold AcOEt to afford 2-chloro-7-isopropylpyrazolo[1,5-a]pyrimidine-6-carboxylic acid. M/z=240-242 [M+H]+, Rt=0.83 min (UPLC Method B2), $^1$H NMR (400 MHz, DMSO-d$_6$) δ ppm: 8.83 (s, 1H), 6.98 (s, 1H), 4.58-4.47 (m, 1H), 1.51 (d, 6H).

In analogy the following compounds were prepared:

| Name | Structure | Analytical data |
|---|---|---|
| D47: 7-(sec-butyl)-2-chloropyrazolo[1,5-a]pyrimidine-6-carboxylic acid | 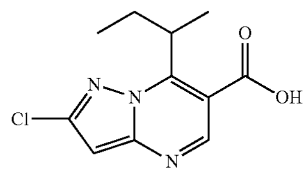 [SMILES: CCC(C)c1c(C(=O)O)cnc2cc(Cl)nn12] | M/z = 252-254 [M − H]−, Rt = 0.94 min (UPLC Method B2). |
| D48: 2-chloro-7-cyclobutyl-pyrazolo[1,5-a]pyrimidine-6-carboxylic acid | 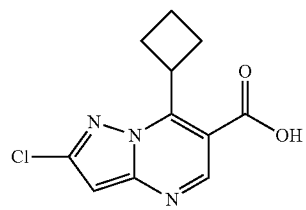 [SMILES: O=C(O)c1cnc2cc(Cl)nn2c1C1CCC1] | [a], M/z = 252-254 [M − H]−, Rt = 0.81 min (UPLC Method B2). |
| D49: 2-chloro-7-chloropropylpyrazolo[1,5-a]pyrimidine-6-carboxylic acid | 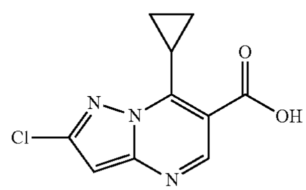 [SMILES: O=C(O)c1cnc2cc(Cl)nn2c1C1CC1] | [a], M/z = 238-240 [M + H]+, Rt = 0.69 min (UPLC Method B2). |
| D50: 2-chloro-7-(tetrahydro-furan-2-yl)pyrazolo[1,5-a]pyrimidine-6-carboxylic acid | 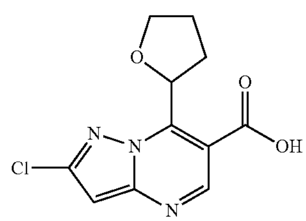 [SMILES: O=C(O)c1cnc2cc(Cl)nn2c1C1CCCO1] | [a], M/z = 268-270 [M + H]+, Rt = 0.67 min (UPLC Method B2). |
| D51: 2-chloro-7-(tetrahydro-2H-pyran-4-yl)pyrazolo[1,5-a]pyrimidine-6-carboxylic acid | 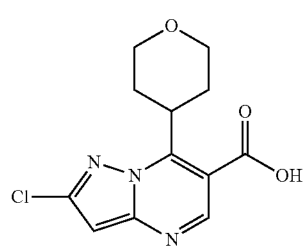 [SMILES: O=C(O)c1cnc2cc(Cl)nn2c1C1CCOCC1] | [a], M/z = 282-284 [M + H]+, Rt = 0.69 min (UPLC Method B2). |
| AD52: 2-chloro-7-(methoxy-methyl)pyrazolo[1,5-a]pyrimidine-6-carboxylic acid | 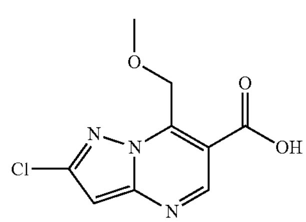 [SMILES: COCc1c(C(=O)O)cnc2cc(Cl)nn12] | [a], M/z = 242-244 [M + H]+, Rt = 0.56 min (UPLC Method B2). |

| Name | Structure | Analytical data |
|---|---|---|
| D53: 2-chloro-7-methyl-pyrazolo[1,5-a]pyrimidine-6-carboxylic acid | 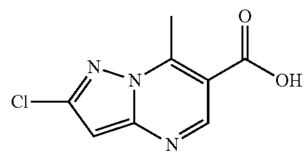 | M/z = 210-212 [M − H]−, Rt = 0.65 min (UPLC Method B2). |
| D54: 2-chloro-7-(furan-2-yl)pyrazolo[1,5-a]pyrimidine-6-carboxylic acid | 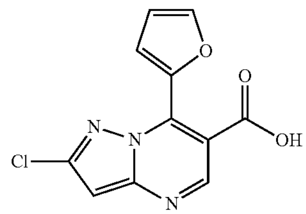 [SMILES: O=C(O)c1cnc2cc(Cl)nn2c1-c1ccco1] | [a], M/z = 264-266 [M + H]+, Rt = 0.68 min (UPLC Method B2). |
| D55: 7-(4-(tert-butoxy-carbonyl)morpholin-2-yl)-2-chloropyrazolo[1,5-a]pyrimidine-6-carboxylic acid | 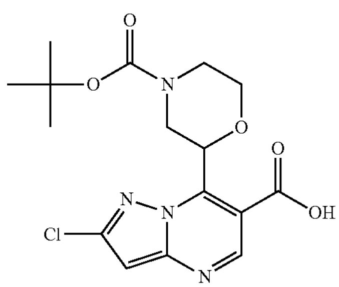 [SMILES: CC(C)(C)OC(=O)N1CCOC(c2c(C(=O)O)cnc3cc(Cl)nn23)C1] | [a], M/z = 383-385 [M + H]+, Rt = 0.91 min (UPLC Method B2). |
| D56: 2-chloro-7-(pyridin-4-yl)pyrazolo[1,5-a]pyrimidine-6-carboxylic acid | 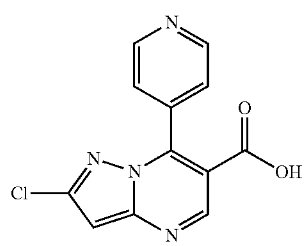 [SMILES: O=C(O)c1cnc2cc(Cl)nn2c1-c1ccncc1] | M/z = 273-275 [M + H]+, Rt = 0.49 min (UPLC Method B2). |

[a] Step c) was performed with LiOH monohydrate in THF/water at 40° C.

D57: 2-chloro-7-((4-methylmorpholin-3-yl)methyl)pyrazolo[1,5-a]pyrimidine-6-carboxylic acid

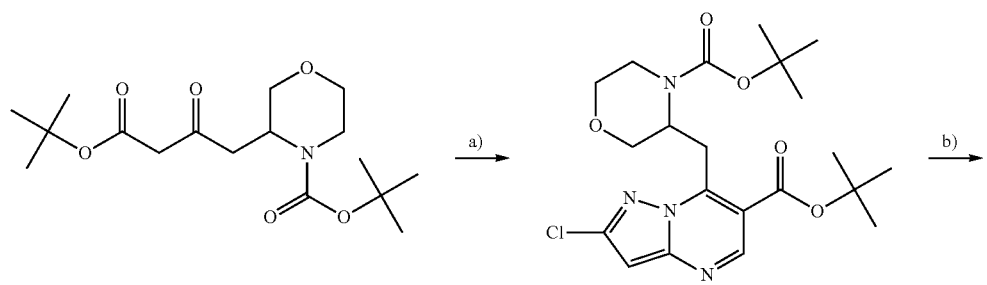

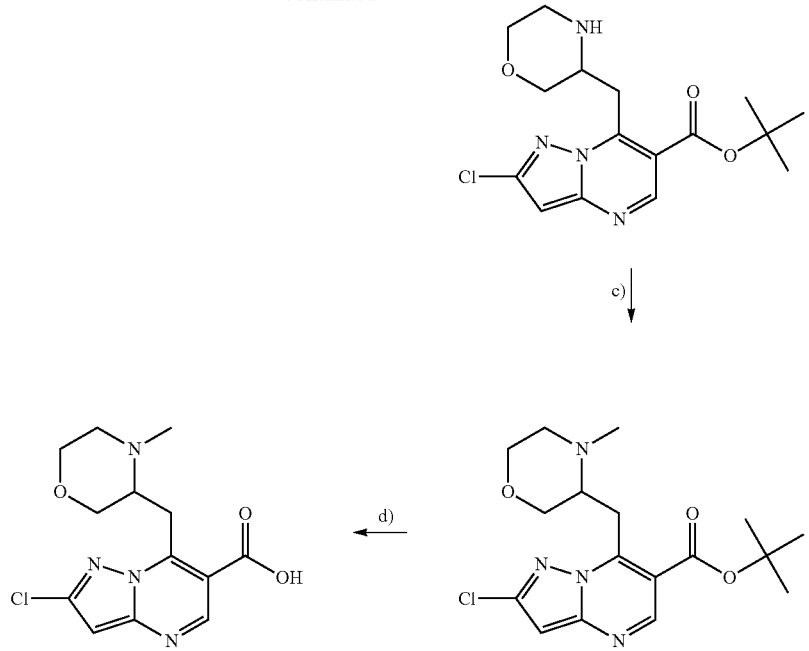

a) tert-butyl 3-((6-(tert-butoxycarbonyl)-2-chloropyrazolo[1,5-a]pyrimidin-7-yl)methyl)morpholine-4-carboxylate tert-butyl 3-((6-(tert-butoxycarbonyl)-2-chloropyrazolo[1,5-a]pyrimidin-7-yl)methyl)morpholine-4-carboxylate was prepared analogously as described for compound D1 step a) using tert-butyl 3-(4-(tert-butoxy)-2,4-dioxobutyl)morpholine-4-carboxylate instead of (S)-tert-butyl 4-methoxy-3-oxopentanoate. M/z=453-455 [M+H]+, Rt=1.36 min (UPLC Method B2).

b) tert-butyl 2-chloro-7-(morpholin-3-ylmethyl)pyrazolo[1,5-a]pyrimidine-6-carboxylate tert-butyl 3-((6-(tert-butoxycarbonyl)-2-chloropyrazolo[1,5-a]pyrimidin-7-yl)methyl)morpholine-4-carboxylate (100 mg, 0.22 mmol) in 4N HCl in 1,4-dioxane (1.0 ml, 4.0 mmol) was stirred at RT for 2 h. The solvent was evaporated to afford tert-butyl 2-chloro-7-(morpholin-3-ylmethyl)pyrazolo[1,5-a]pyrimidine-6-carboxylate. M/z=353-355 [M+H]+, Rt=0.72 min (UPLC Method B2).

c) tert-butyl 2-chloro-7-((4-methylmorpholin-3-yl)methyl)pyrazolo[1,5-a]pyrimidine-6-carboxylate To tert-butyl 2-chloro-7-(morpholin-3-ylmethyl)pyrazolo[1,5-a]pyrimidine-6-carboxylate (70 mg, 0.18 mmol) in MeOH (4.5 ml) were added 37% aq. formaldehyde (40 μl, 0.54 mmol) and AcOH (15 μl, 0.27 mmol). After 30 min at RT, NaBH(OAc)₃ (57 mg, 0.27 mmol) was added and the reaction mixture was stirred at RT for 4 h. Then 37% aq. formaldehyde (40 μl, 0.54 mmol) was added and after 30 min of stirring, NaBH(OAc)₃ (57 mg, 0.27 mmol) was added. The mixture was stirred for additional 1 h. The solvent was removed, the residue was treated with saturated aqueous NaHCO₃ and extracted with AcOEt. The organic phase was dried over an IST cartridge to afford after removal of the solvent tert-butyl 2-chloro-7-((4-methylmorpholin-3-yl)methyl)pyrazolo[1,5-a]pyrimidine-6-carboxylate. M/z=367-369 [M+H]+, Rt=0.78 min (UPLC Method B2).

d) 2-chloro-7-((4-methylmorpholin-3-yl)methyl)pyrazolo[1,5-a]pyrimidine-6-carboxylic acid 2-chloro-7-((4-methylmorpholin-3-yl)methyl)pyrazolo[1,5-a]pyrimidine-6-carboxylic acid was prepared analogously as described for compound D1 step b) using tert-butyl 2-chloro-7-((4-methylmorpholin-3-yl)methyl)pyrazolo[1,5-a]pyrimidine-6-carboxylate instead of (S)-tert-butyl 2-chloro-7-(1-methoxyethyl)pyrazolo[1,5-a]pyrimidine-6-carboxylate. M/z=311-313 [M+H]+, Rt=0.43 min (UPLC Method B2).

D58: (S)-2-chloro-7-(1-methylpiperidin-2-yl)pyrazolo[1,5-a]pyrimidine-6-carboxylic acid

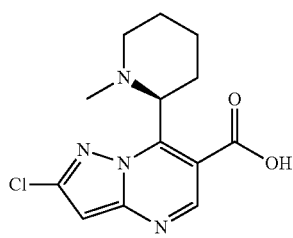 [SMILES: CN1CCCC[C@H]1c1c(C(=O)O)cnc2cc(Cl)nn12]

(S)-2-chloro-7-(1-methylpiperidin-2-yl)pyrazolo[1,5-a]pyrimidine-6-carboxylic acid was prepared analogously as described for compound D57 using (S)-tert-butyl 2-(3-(tert-butoxy)-3-oxopropanoyl)piperidine-1-carboxylate instead of tert-butyl 3-(4-(tert-butoxy)-2,4-dioxobutyl)morpholine-4-carboxylate. Step a) was performed at 80° C. overnight. M/z=295-297 [M+H]+, Rt=0.57 min (UPLC Method B2).

D59: (S)-7-(1-((tert-butoxycarbonyl)(methyl)amino)ethyl)-2-chloropyrazolo[1,5-a]pyrimidine-6-carboxylic acid

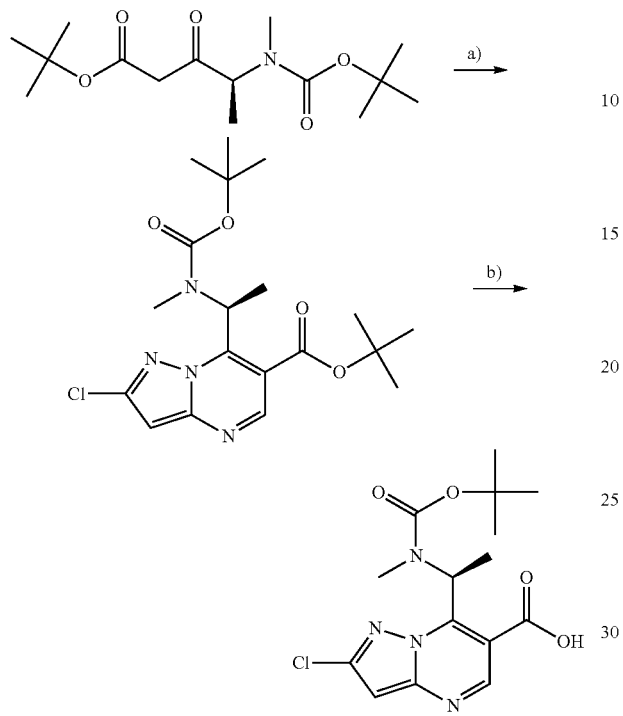

a) (S)-tert-butyl 7-(1-((tert-butoxycarbonyl)(methyl)amino)ethyl)-2-chloropyrazolo[1,5-a]pyrimidine-6-carboxylate A mixture of 1,1-dimethoxy-N,N-dimethylmethanamine (2.77 ml, 20.8 mmol) and (S)-tert-butyl 4-((tert-butoxycarbonyl)(methyl)amino)-3-oxopentanoate (6.28 g, 20.8 mmol) was stirred at 120° C. for 1 h. Then, a solution of 5-chloro-1H-pyrazol-3-amine (2.45 g, 20.8 mmol) in EtOH (25 ml) was added and the reaction mixture was stirred at 80° C. for 2 h. The mixture was concentrated and crude material was purified by flash column chromatography on silica gel (cyclohexane/AcOEt 1/0 to 7/3) to afford (S)-tert-butyl 7-(1-((tert-butoxycarbonyl)(methyl)amino)ethyl)-2-chloropyrazolo[1,5-a]pyrimidine-6-carboxylate. M/z=411-413 [M+H]+, Rt=1.53 min (UPLC Method B1), $^1$H NMR (400 MHz, DMSO-d$_6$) δ ppm: 8.72 (s, 1H), 7.03 (s, 1H), 5.77 (m, 1H), 2.94 (s, 3H), 1.67 (d, 3H), 1.55 (s, 9H), 1.40-0.83 (m, 9H).

b) (S)-7-(1-((tert-butoxycarbonyl)(methyl)amino)ethyl)-2-chloropyrazolo[1,5-a]pyrimidine-6-carboxylic acid A mixture of (S)-tert-butyl 7-(1-((tert-butoxycarbonyl)(methyl)amino)ethyl)-2-chloropyrazolo[1,5-a]pyrimidine-6-carboxylate (680 mg, 1.66 mmol) and TFA (2.55 ml, 33 mmol) was stirred overnight. The mixture was concentrated, DCM was added and the mixture was concentrated again. The residue was dissolved in THF (10 ml) and 2N aqueous Na$_2$CO$_3$ (10 ml) was added followed by di-tert-butyl dicarbonate (0.429 mg, 1.97 mmol) and the reaction mixture was stirred for 48 h. The mixture was concentrated, acidified with 1N aqueous citric acid (to pH 4-5) and extracted with AcOEt. The organic phase was dried over Na$_2$SO$_4$, filtered and concentrated. The residue was purified by flash column chromatography on silica gel (cyclohexane/AcOEt 1/0 to 0/1) to afford (S)-7-(1-((tert-butoxycarbonyl)(methyl)amino)ethyl)-2-chloropyrazolo[1,5-a]pyrimidine-6-carboxylic acid. M/z=355-357 [M+H]+, Rt=1.00 min (UPLC Method B1). $^1$H NMR (400 MHz, DMSO-d$_6$) δ ppm: 8.80 (s, 1H), 7.02 (s, 1H), 6.05-5.94 (m, 1H), 2.99 (s, 3H), 1.67 (d, 3H), 1.26+0.88 (2s, 9H)

D60: (R)-2-chloro-7-(1-methoxy-2-methylpropyl)pyrazolo[1,5-a]pyrimidine-6-carboxylic acid

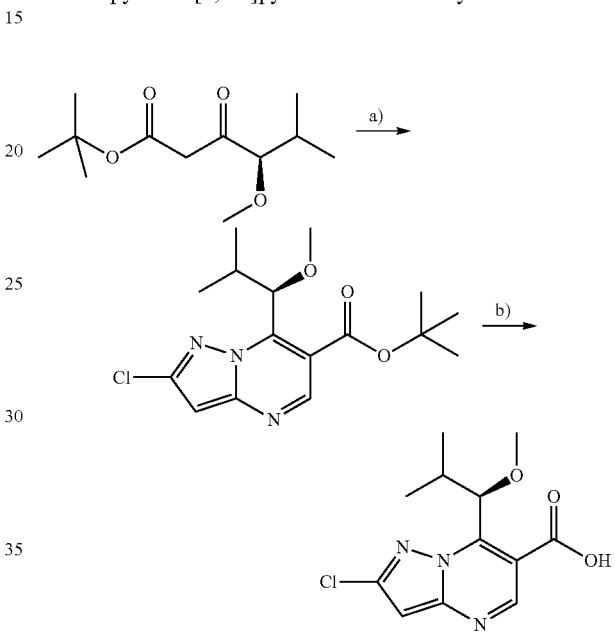

a) (R)-tert-butyl 2-chloro-7-(1-methoxy-2-methylpropyl)pyrazolo[1,5-a]pyrimidine-6-carboxylate A mixture of 1,1-dimethoxy-N,N-dimethylmethanamine (1.19 ml, 8.51 mmol) and (R)-tert-butyl 4-methoxy-5-methyl-3-oxohexanoate (1.96 g, 8.51 mmol) was stirred at 120° C. for 20 h. The mixture was evaporated and dried under vacuum. Then, a solution of 5-chloro-1H-pyrazol-3-amine (500 mg, 4.25 mmol) in EtOH (35 ml) was added to the intermediate obtained previously and the reaction mixture was stirred at 80° C. for 45 h. Mixture was concentrated and the residue was taken-up in AcOEt/water. Phases were separated and the organic layer was washed with saturated aqueous NaHCO$_3$, water and brine, dried over Na$_2$SO$_4$, filtered and evaporated. The crude material was purified by flash column chromatography on silica gel (cyclohexane/AcOEt 1/0 to 9/1) to afford (R)-tert-butyl 2-chloro-7-(1-methoxy-2-methylpropyl)pyrazolo[1,5-a]pyrimidine-6-carboxylate. M/z=340-342 [M+H]+, Rt=1.40 min (UPLC Method B2).

b) (R)-2-chloro-7-(1-methoxy-2-methylpropyl)pyrazolo[1,5-a]pyrimidine-6-carboxylic acid To a solution of (R)-tert-butyl 2-chloro-7-(1-methoxy-2-methylpropyl)pyrazolo[1,5-a]pyrimidine-6-carboxylate (1.2 g, 2.97 mmol) in DCM (10 ml) was added TFA (9.1 ml, 119 mmol). The reaction mixture was stirred at RT for 1 h. The mixture was evaporated and the residue was taken-up in toluene, evaporated and dried under vacuum to afford (R)-2-chloro-7-(1-methoxy-2-methylpropyl)pyrazolo[1,5-a]pyrimidine-6-carboxylic acid. M/z=284-286 [M+H]+, Rt=0.81 min (UPLC Method B2), ¹H NMR (400 MHz, DMSO-d₆) δ ppm: 13.81 (s, 1H), 8.79 (s, 1H), 7.03 (s, 1H), 5.10 (d, 1H), 3.17 (s, 3H), 2.76 (m, 1H), 1.10 (d, 3H), 0.68 (d, 3H).

D61: (S)-7-(1-methoxyethyl)-2-methylpyrazolo[1,5-a]pyrimidine-6-carboxylic acid

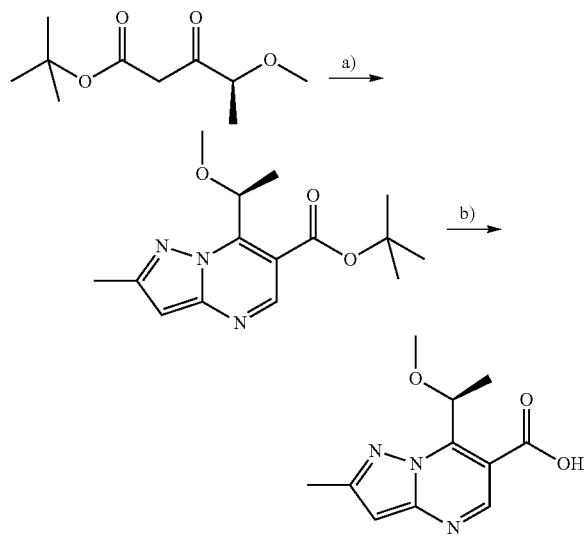

a) (S)-tert-butyl 7-(1-methoxyethyl)-2-methylpyrazolo[1,5-a]pyrimidine-6-carboxylate A mixture of 1,1-dimethoxy-N,N-dimethylmethanamine (0.66 ml, 4.94 mmol) and (S)-tert-butyl 4-methoxy-3-oxopentanoate (1.0 g, 4.94 mmol) was stirred at 120° C. for 1 h. Then, a solution of 5-methyl-1H-pyrazol-3-amine (0.48 g, 4.94 mmol) in EtOH (5 ml) was added and the reaction mixture was stirred at 80° C. for 1.5 h. The mixture was concentrated and the crude product was purified by flash column chromatography on silica gel (cyclohexane/AcOEt 1/0 to 8/2) to afford (S)-tert-butyl 7-(1-methoxyethyl)-2-methylpyrazolo[1,5-a]pyrimidine-6-carboxylate. M/z=292 [M+H]+, Rt=1.19 min (UPLC Method B1).

b) (S)-7-(1-methoxyethyl)-2-methylpyrazolo[1,5-a]pyrimidine-6-carboxylic acid

To a solution of (S)-tert-butyl 7-(1-methoxyethyl)-2-methylpyrazolo[1,5-a]pyrimidine-6-carboxylate (1.07 g, 3.67 mmol) in DCM (5 ml) was added TFA (5.66 ml, 73.5 mmol). The reaction mixture was stirred at RT for 2 days. Mixture was evaporated and residue was taken-up in Et₂O, solid was filtered, washed with Et₂O and dried under HV to afford (S)-7-(1-methoxyethyl)-2-methylpyrazolo[1,5-a]pyrimidine-6-carboxylic acid. The filtrate was concentrated and basified with saturated aqueous NaHCO₃ and extracted with AcOEt. The organic layer was dried over Na₂SO₄, filtered and evaporated to afford another batch of (S)-7-(1-methoxyethyl)-2-methylpyrazolo[1,5-a]pyrimidine-6-carboxylic acid. M/z=236 [M+H]+, Rt=0.50 min (UPLC Method B1), ¹H NMR (400 MHz, DMSO-d₆) δ ppm: 13.47 (bs, 1H), 8.58 (s, 1H), 6.65 (s, 1H), 5.46 (q, 1H), 3.19 (s, 3H), 2.47 (s, 3H), 1.65 (d, 3H).

D62: (S)-2-fluoro-7-(1-methoxyethyl)pyrazolo[1,5-a]pyrimidine-6-carboxylic acid

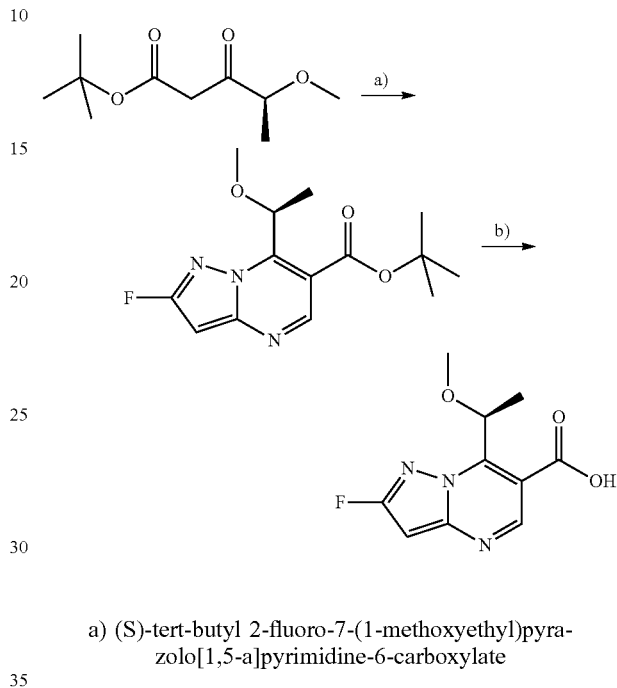

a) (S)-tert-butyl 2-fluoro-7-(1-methoxyethyl)pyrazolo[1,5-a]pyrimidine-6-carboxylate A mixture of 1,1-dimethoxy-N,N-dimethylmethanamine (1.31 ml, 9.89 mmol) and (S)-tert-butyl 4-methoxy-3-oxopentanoate (0.40 g, 1.98 mmol) was stirred at 120° C. for 1 h. Then, a solution of 5-fluoro-1H-pyrazol-3-amine (0.30 mg, 2.97 mmol) in EtOH (6.6 ml) was added and the reaction mixture was stirred overnight at 80° C. Mixture was diluted with water and extracted twice with AcOEt. The organic layer was washed saturated aqueous NaHCO₃, water and brine, dried over a phase separator cartridge (IST) and evaporated. The crude material was purified by flash column chromatography on silica gel (cyclohexane/AcOEt 1/0 to 9/1) to afford (S)-tert-butyl 2-fluoro-7-(1-methoxyethyl)pyrazolo[1,5-a]pyrimidine-6-carboxylate. M/z=296 [M+H]+, Rt=1.21 min (UPLC Method B2), ¹H NMR (400 MHz, DMSO-d₆) δ ppm: 8.65 (s, 1H), 6.67 (d, 1H), 5.20 (q, 1H), 3.21 (s, 3H), 1.61 (d, 3H), 1.55 (s, 9H).

b) (S)-2-fluoro-7-(1-methoxyethyl)pyrazolo[1,5-a]pyrimidine-6-carboxylic acid

To a solution of (S)-tert-butyl 2-fluoro-7-(1-methoxyethyl)pyrazolo[1,5-a]pyrimidine-6-carboxylate (0.67 g, 2.25 mmol) in DCM (5 ml) was added TFA (3.47 ml, 45.0 mmol). The reaction mixture was stirred overnight at RT. Mixture was evaporated and taken-up in toluene and co-evaporated. The residue was taken-up in Et₂O, the solid was filtered, washed with Et₂O and dried under HV to afford (S)-2-fluoro-7-(1-methoxyethyl)pyrazolo[1,5-a]pyrimidine-6-carboxylic acid. M/z=240 [M+H]+, Rt=0.57 min (UPLC Method B2), ¹H NMR (400 MHz, DMSO-d₆) δ ppm: 13.63 (bs, 1H), 8.73 (s, 1H), 6.67 (d, 1H), 5.37 (q, 1H), 3.19 (s, 3H), 1.63 (d, 3H).

D63: 2-Chloro-7-(1-methoxy-2-methylpropyl)pyrazolo[1,5-a]pyrimidine-6-carboxylic acid

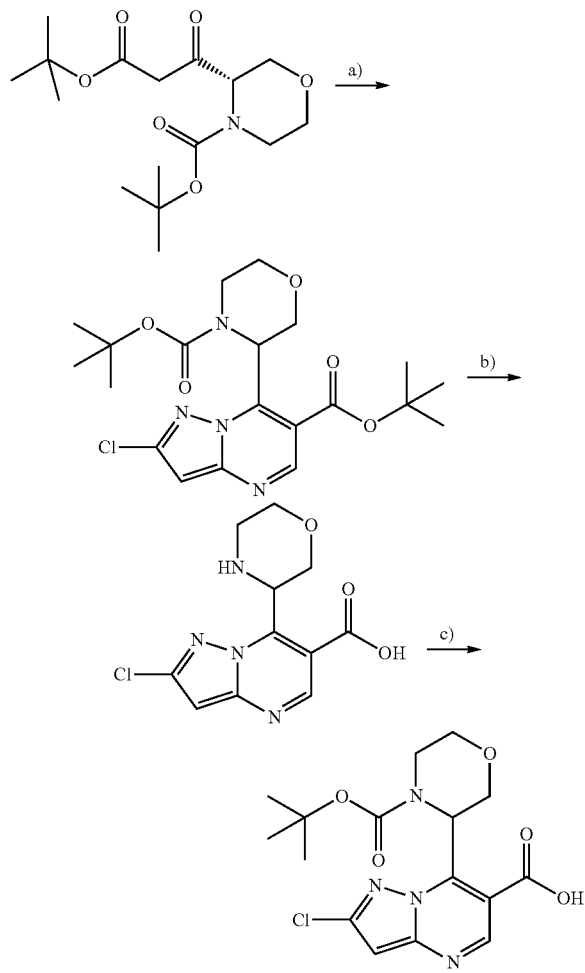

a) tert-butyl 3-(6-(tert-butoxycarbonyl)-2-chloropyrazolo[1,5-a]pyrimidin-7-yl)morpholine-4-carboxylate A mixture of 1,1-dimethoxy-N,N-dimethylmethanamine (1.21 ml, 9.11 mmol) and (S)-tert-butyl 3-(3-(tert-butoxy)-3-oxopropanoyl)morpholine-4-carboxylate (600 mg, 1.822 mmol) was stirred at 120° C. for 1 h. Then, a solution of 5-chloro-1H-pyrazol-3-amine (321 mg, 2.73 mmol) in EtOH (6.1 ml) was added and the reaction mixture was stirred overnight at 80° C. and then at 100° C. for 5 h. Mixture was evaporated and residue was dissolved again in tBuOH (6.1 ml) and reaction mixture was stirred at 120° C. for 2 days. 5-chloro-1H-pyrazol-3-amine (321 mg, 2.73 mmol) was then added to reaction mixture which was stirred at 120° C. for 2 h. Mixture was diluted with water and extracted twice with AcOEt. The organic layer was washed saturated aqueous $NaHCO_3$, water and brine, dried over a phase separator cartridge (IST) and evaporated. The crude material was purified by flash column chromatography on silica gel (cyclohexane/AcOEt 1/0 to 4/1) to afford tert-butyl 3-(6-(tert-butoxycarbonyl)-2-chloropyrazolo[1,5-a]pyrimidin-7-yl)morpholine-4-carboxylate. Chiral analysis showed essentially complete racemisation of the stereocenter, which might have occurred in the previous step, already. M/z=439-441 [M+H]+, Rt=1.36 min (UPLC Method B2), $^1$H NMR (400 MHz, DMSO-$d_6$) δ ppm: 8.75 (s, 1H), 7.05 (s, 1H), 5.75 (m, 1H), 4.12 (t, 1H), 3.99 (m, 2H), 3.86 (m, 1H), 3.69 (m, 1H), 3.49 (m, 1H), 1.55 (s, 9H), 0.88 (bs, 9H).

b) 2-chloro-7-(morpholin-3-yl)pyrazolo[1,5-a]pyrimidine-6-carboxylic acid

To a solution of tert-butyl 3-(6-(tert-butoxycarbonyl)-2-chloropyrazolo[1,5-a]pyrimidin-7-yl)morpholine-4-carboxylate (275 mg, 0.63 mmol) in 1,4-dioxane (3 ml) was added 4M HCl in 1,4-dioxane (1.57 ml, 6.27 mmol) and reaction mixture was stirred at RT for 2 h. The mixture was evaporated and the residue was dissolved again in DCM (3 ml). TFA (0.96 ml, 12.5 mmol) was added and the reaction mixture was stirred overnight at RT. The mixture was evaporated and taken-up in toluene and co-evaporated. The residue was taken-up in $Et_2O$, solid was filtered, washed with $Et_2O$ and dried on HV to afford 2-chloro-7-(morpholin-3-yl)pyrazolo[1,5-a]pyrimidine-6-carboxylic acid. M/z=283-285 [M+H]+, Rt=0.48 min (UPLC Method B2), $^1$H NMR (400 MHz, DMSO-$d_6$) δ ppm: 9.05 (s, 1H), 7.11 (s, 1H), 5.74 (m, 1H), 4.14-4.05 (m, 4H), 3.79 (m, 2H).

c) 7-(4-(tert-butoxycarbonyl)morpholin-3-yl)-2-chloropyrazolo[1,5-a]pyrimidine-6-carboxylic acid To a solution of 2-chloro-7-(morpholin-3-yl)pyrazolo[1,5-a]pyrimidine-6-carboxylic acid (200 mg, 0.71 mmol) in THF (2 ml)/2N aqueous $Na_2CO_3$ (2 ml) at RT was added $Boc_2O$ (0.2 ml, 0.85 mmol). The reaction mixture was stirred at RT for 2 days. The mixture was filtered, the filtrate was concentrated, and the residue was frozen and lyophilized to afford 7-(4-(tert-butoxycarbonyl)morpholin-3-yl)-2-chloropyrazolo[1,5-a]pyrimidine-6-carboxylic acid. M/z=383-385 [M+H]+, Rt=0.88 min (UPLC Method B2), $^1$H NMR (400 MHz, DMSO-$d_6$) δ ppm: 8.82 (s, 1H), 6.75 (s, 1H), 6.50 (m, 1H), 4.10-3.97 (m, 2H), 3.91-3.85 (m, 3H), 3.50-3.44 (m, 1H), 0.83 (bs, 9H).

D64: (S)-7-(1-((tert-butoxycarbonyl)(methyl)amino)-2-methylpropyl)-2-chloropyrazolo[1,5-a]pyrimidine-6-carboxylic acid

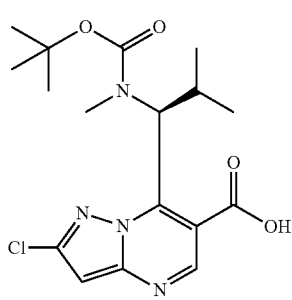 [SMILES: CC(C)[C@@H](c1c(C(=O)O)cnc2cc(Cl)nn12)N(C)C(=O)OC(C)(C)C]

(S)-7-(1-((tert-butoxycarbonyl)(methyl)amino)-2-methylpropyl)-2-chloropyrazolo[1,5-a]pyrimidine-6-carboxylic acid was prepared in analogy to D63 using (S)-tert-butyl 4-((tert-butoxycarbonyl)(methyl)amino)-5-methyl-3-oxo-hexanoate instead of (S)-tert-butyl 3-(3-(tert-butoxy)-3-oxopropanoyl)morpholine-4-carboxylate in step a). M/z=383-385 [M+H]+, Rt=1.20 min (UPLC Method B2), $^1$H NMR (400 MHz, DMSO-d$_6$) δ ppm: 8.57 (s, 1H), 6.74 (s, 1H), 6.12 (m, 1H), 3.08 (m, 1H), 2.90 (s, 3H), 1.32 (s, 9H), 0.98 (d, 3H), 0.77 (d, 3H).

Part E: Synthesis of Anilines, Amino-pyridines and Pyridones

E1: 6-(2H-1,2,3-triazol-2-yl)-5-(trifluoromethyl)pyridin-3-amine

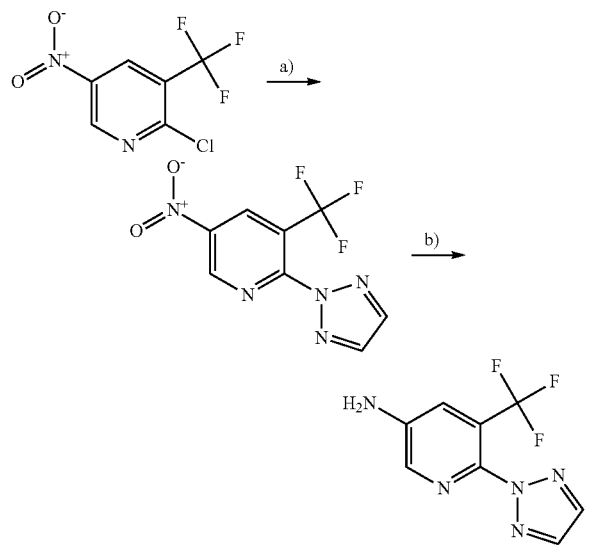

a) 5-nitro-2-(2H-1,2,3-triazol-2-yl)-3-(trifluoromethyl)pyridine

To a solution of 2-chloro-5-nitro-3-(trifluoromethyl)pyridine (1.0 g, 4.41 mmol) and K$_2$CO$_3$ (1.22 g, 8.83 mmol) in THF (5 ml) was added 2H-1,2,3-triazole (0.31 ml, 5.30 mmol). The reaction mixture was stirred for 1 h at RT. Water was added and the mixture was extracted with AcOEt. The organic layer was washed with brine, dried over Na$_2$SO$_4$, filtered and concentrated under vacuum. The residue was purified by flash column chromatography on silica gel (cyclohexane/AcOEt: 100/0 to 50/50) to afford 5-nitro-2-(2H-1,2,3-triazol-2-yl)-3-(trifluoromethyl)pyridine. M/z=260 [M+H]+, Rt=0.88 min (UPLC Method B1), $^1$H NMR (400 MHz, DMSO-d$_6$) δ ppm: 9.69 (d, 1H), 9.17 (d, 1H), 8.37 (s, 2H).

b) 6-(2H-1,2,3-triazol-2-yl)-5-(trifluoromethyl)pyridin-3-amine

To a solution of 5-nitro-2-(2H-1,2,3-triazol-2-yl)-3-(trifluoromethyl)pyridine (770 mg, 2.97 mmol) in 1.25M HCl in MeOH (48 ml, 59 mmol) at RT was added portionwise tin(II) chloride (2.82 g, 14.9 mmol). The reaction was stirred at RT for 2 h. 4N aqueous NaOH was added and the solution was extracted with DCM. The organic layer was dried over anhydrous Na$_2$SO$_4$, filtered and concentrated under vacuum. The crude product was purified by flash column chromatography on silica gel (cyclohexane/AcOEt: 100/0 to 0/100) to afford 6-(2H-1,2,3-triazol-2-yl)-5-(trifluoromethyl)pyridin-3-amine. M/z=230 [M+H]+, Rt=0.64 min (UPLC Method B1), $^1$H NMR (400 MHz, DMSO-d$_6$) δ ppm: 8.08 (d, 1H), 8.05 (s, 2H), 7.43 (d, 1H), 6.39 (s, 2H).

E2: 5-methoxy-6-(2H-1,2,3-triazol-2-yl)pyridin-3-amine

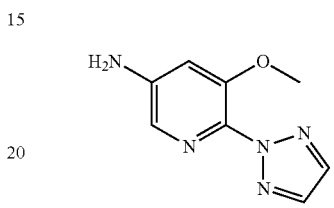

5-methoxy-6-(2H-1,2,3-triazol-2-yl)pyridin-3-amine was prepared analogously as described for E1 using 2-chloro-3-methoxy-5-nitropyridine instead of 2-chloro-5-nitro-3-(trifluoromethyl)pyridine. Step a) was performed overnight. M/z=192 [M+H]+, Rt=0.35 min (UPLC Method B1).

E3: 5-chloro-6-(4-methyl-2H-1,2,3-triazol-2-yl)pyridin-3-amine

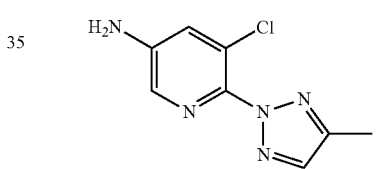

5-chloro-6-(4-methyl-2H-1,2,3-triazol-2-yl)pyridin-3-amine was prepared analogously as described for E1 using 4-methyl-2H-1,2,3-triazole instead of 2H-1,2,3-triazole. Step a) was performed overnight and step b) was performed with 1.25 N HCl in EtOH overnight. M/z=210 [M+H]+, Rt=0.65 min (UPLC Method B2).

E4: 5-(difluoromethyl)-6-(2H-1,2,3-triazol-2-yl)pyridin-3-amine

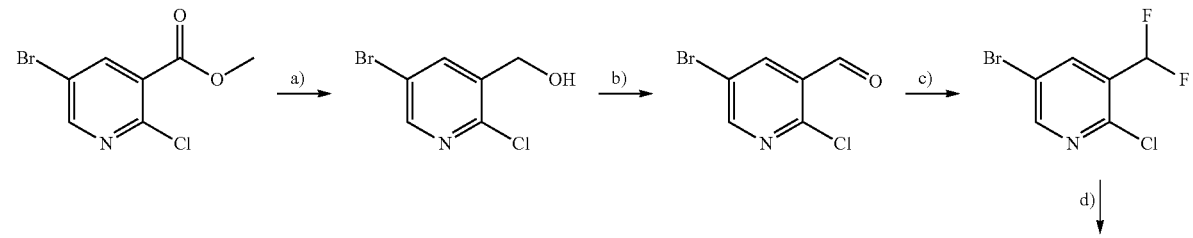

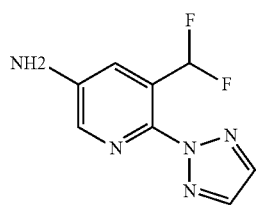 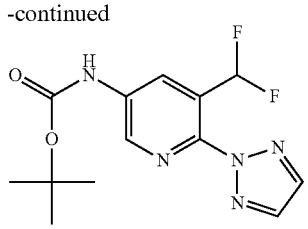 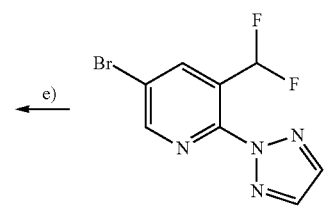

a) (5-bromo-2-chloropyridin-3-yl)methanol

To methyl 5-bromo-2-chloronicotinate (5.92 g, 23.6 mmol) in DCM (70 ml) under $N_2$ atmosphere at RT were added anhydrous $CaCl_2$ (10.5 g, 94 mmol) then at 0° C. portionwise $NaBH_4$ (3.57 g, 94 mmol). The reaction mixture was stirred at RT overnight. THF (70.0 ml) was added and the mixture was stirred at 60° C. for 24 h. 1,4-dioxane (70 ml) was added and the mixture was stirred at 90° C. for 28 h After cooling to 0° C., the reaction mixture was quenched carefully with water and stirred at RT overnight. Lithium salts were collected by filtration through a pad of celite and washed with THF. The filtrate was diluted with water and AcOEt, the organic phase was separated and the aqueous phase was extracted with AcOEt. The combined organic phases were washed with brine, dried over $Na_2SO_4$, filtered and evaporated to dryness to afford (5-bromo-2-chloropyridin-3-yl)methanol. M/z=222/224/226 [M+H]+, Rt=0.70 min (UPLC Method B2). $^1$H NMR (400 MHz, DMSO $d_6$) δ ppm: 8.47 (m, 1H), 8.08-8.07 (m, 1H), 5.69 (t, 1H), 4.53 (d, 2H)

b) 5-bromo-2-chloronicotinaldehyde

To (5-bromo-2-chloropyridin-3-yl)methanol (5.24 g, 22.1 mmol) in DCM (250 ml) under $N_2$ atmosphere was added $MnO_2$ (19.2 g, 22.1 mmol). After 2 h of stirring at RT, $MnO_2$ (3.85 g, 44.2 mmol) was added, the reaction mixture was stirred for 3 h at RT. Then $MnO_2$ (1.92 g, 22.1 mmol) was added and the mixture was stirred at RT for 4 h. $MnO_2$ was collected by filtration through a pad of celite, washed with DCM and the filtrate was evaporated. The residue was purified by flash column chromatography on silica gel (hexane/TBME 1/0 to 3/7) to afford 5-bromo-2-chloronicotinaldehyde. Rt=1.02 min (UPLC Method B2), $^1$H NMR (400 MHz, DMSO-$d_6$) δ ppm: 10.19 (s, 1H), 8.85 (d, 1H), 8.39 (d, 1H).

c) 5-bromo-2-chloro-3-(difluoromethyl)pyridine

To 5-bromo-2-chloronicotinaldehyde (2.96 g, 12.8 mmol) in DCM (75 ml) under $N_2$ atmosphere were added EtOH (0.075 ml, 1.27 mmol) and dropwise over 5 min DAST (3.74 ml, 25.5 mmol) at RT. The reaction mixture was stirred at RT for 2 h. After cooling to 0° C., the reaction mixture was quenched with aqueous saturated $NaHCO_3$, the organic phase was separated and the aqueous phase was extracted with DCM. The combined organic phases were washed with water, brine and dried over $Na_2SO_4$, filtered and evaporated to dryness to afford 5-bromo-2-chloro-3-(difluoromethyl)pyridine. Rt=1.02 min (UPLC Method B2), $^1$H NMR (400 MHz, DMSO-$d_6$) δ ppm: 8.78 (d, 1H), 8.40 (d, 1H), 7.13 (t, 1H), $^{19}$F NMR (400 MHz, DMSO d6): δ ppm: −117.02/−116.88 (d, 2F).

d) 5-bromo-3-(difluoromethyl)-2-(2H-1,2,3-triazol-2-yl)pyridine

To 5-bromo-2-chloro-3-(difluoromethyl)pyridine (1.30 g, 5.0 mmol) and $K_2CO_3$ (1.38 g, 10.0 mmol) in DMF (5 ml) under argon was added 1H-1,2,3-triazole (0.38 ml, 6.48 mmol). The reaction mixture was stirred at 90° C. overnight. The suspension was filtered and the filtrated was concentrated. The residue was diluted with ice-cold water, extracted with AcOEt, the organic phase was washed with brine, dried over $Na_2SO_4$, filtered and evaporated. The residue was purified by flash column chromatography on silica gel (hexane/TBME 1/0 to 1/1) to afford a mixture of 5-bromo-3-(difluoromethyl)-2-(2H-1,2,3-triazol-2-yl)pyridine and 5-bromo-3-(difluoromethyl)-2-(1H-1,2,3-triazol-1-yl)pyridine. M/z=275/277 [M+H]+, Rt=0.92-0.93 min (UPLC Method B2).

e) tert-butyl (5-(difluoromethyl)-6-(2H-1,2,3-triazol-2-yl)pyridin-3-yl)carbamate To a mixture of 5-bromo-3-(difluoromethyl)-2-(2H-1,2,3-triazol-2-yl)pyridine and 5-bromo-3-(difluoromethyl)-2-(1H-1,2,3-triazol-1-yl)pyridine (1.09 g, 3.96 mmol) were added tert-butylcarbamate (0.93 mg, 7.93 mmol), Xantphos (206 mg, 0.36 mmol), $Cs_2CO_3$ (2.58 g, 7.93 mmol) and $Pd_2dba_3$ (109 mg, 0.12 mmol). The mixture was purged with argon and 1,4-dioxane (50 ml) was added. The reaction mixture was stirred at 90° C. overnight. The suspension was filtered, the filtrated was diluted with DCM and water and the organic phase was washed with brine, dried over $Na_2SO_4$, filtered and evaporated. The crude product was purified by flash column chromatography on silica gel (hexane/TBME 1/0 to 1/1) to afford tert-butyl (5-(difluoromethyl)-6-(2H-1,2,3-triazol-2-yl)pyridin-3-yl)carbamate. M/z=312/313 [M+H]+, Rt=1.02 min (UPLC Method B2). $^1$H NMR (400 MHz, DMSO $d_6$) δ ppm: 10.16 (s, 1H), 8.73 (d, 1H), 8.47 (d, 1H), 8.19 (s, 2H), 7.26 (t, 1H), 1.52 (s, 9H).

f) 5-(difluoromethyl)-6-(2H-1,2,3-triazol-2-yl)pyridin-3-amine

To tert-butyl (5-(difluoromethyl)-6-(2H-1,2,3-triazol-2-yl)pyridin-3-yl)carbamate (0.68 g, 2.13 mmol) was added 4N HCl in 1,4-dioxane (5.3 ml, 21.3 mmol) and the reaction mixture was stirred at RT for 1.5 days. The solvent was evaporated, the residue was taken with DCM, washed with aqueous saturated $NaHCO_3$, brine and dried over $Na_2SO_4$, filtered and concentrated to dryness to afford 5-(difluoromethyl)-6-(2H-1,2,3-triazol-2-yl)pyridin-3-amine. M/z=212/213 [M+H]+, Rt=0.55 min (UPLC Method B2). $^1$H NMR (400 MHz, DMSO $d_6$) δ ppm: 8.08 (d, 2H), 7.99 (s, 1H), 7.34 (d, 1H), 6.97 (t, 1H), 6.14 (bs, 2H), $^{19}$F NMR (400 MHz, DMSO d6): δ ppm: −113.89/−114.03 (d, 2F).

E5: 5-chloro-6-ethoxypyridin-3-amine

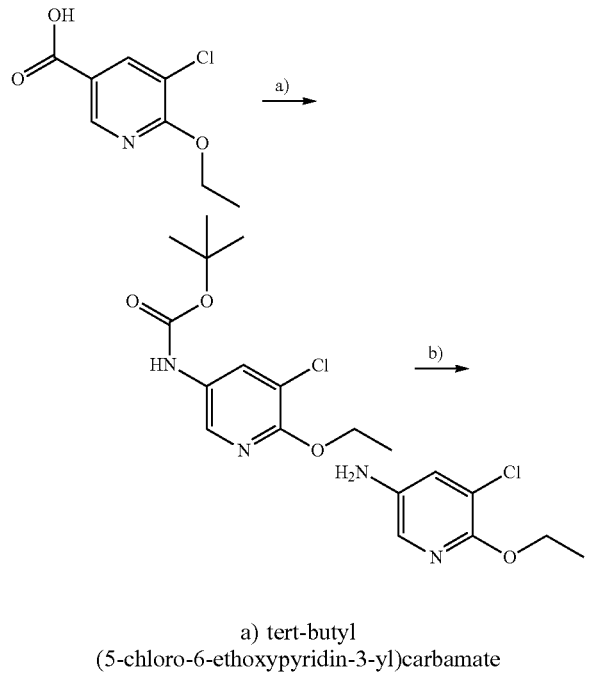

a) tert-butyl (5-chloro-6-ethoxypyridin-3-yl)carbamate

To 5-chloro-6-ethoxynicotinic acid (0.40 mg, 1.98 mmol) in tBuOH (10 ml) were added DPPA (0.51 ml, 2.38 mmol) and Et₃N (0.55 ml, 3.97 mmol). The reaction mixture was stirred at RT for 2 h, then at 100° C. for 4 h. After cooling to RT, AcOEt was added, the organic phase was washed with aqueous saturated NaHCO₃, dried over Na₂SO₄, filtered and concentrated. The residue was purified by silica gel column (cyclohexane/AcOEt 100/0 to 80/20) to afford tert-butyl (5-chloro-6-ethoxypyridin-3-yl)carbamate. M/z=273-275 [M+H]+, Rt=1.27 min (UPLC Method B1).

b) 5-chloro-6-ethoxypyridin-3-amine

To tert-butyl (5-chloro-6-ethoxypyridin-3-yl)carbamate (0.42 g, 1.0 mmol) in MeOH (5 ml) was added 4N HCl in 1,4-dioxane (1.27 ml, 5.1 mmol) and the reaction mixture was stirred for 5 h at RT. The solvent was evaporated. Et₂O was added to the residue, the solid was filtered and rinsed with Et₂O to afford 5-chloro-6-ethoxypyridin-3-amine. M/z=173-175 [M+H]+, Rt=0.75 min (UPLC Method B1).

E6: 6-methoxy-5-(trifluoromethyl)pyridin-3-amine

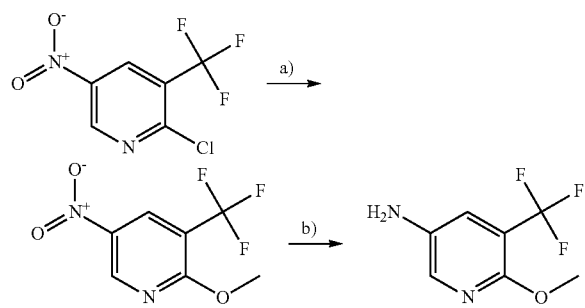

a) 2-methoxy-5-nitro-3-(trifluoromethyl)pyridine

To 2-chloro-5-nitro-3-(trifluoromethyl)pyridine (2.0 g, 8.83 mmol) in THF (5 ml) at 0° C. was added sodium methoxide (1.80 ml, 9.71 mmol). The reaction mixture was stirred 1 h at RT. The mixture was evaporated, dissolved in water and cooled at 0° C. The precipitate was filtered, washed with cold water and dried under HV to afford 2-methoxy-5-nitro-3-(trifluoromethyl)pyridine. M/z=223 [M+H]+, Rt=1.11 min (UPLC Method B3).

b) 6-methoxy-5-(trifluoromethyl)pyridin-3-amine

To 2-methoxy-5-nitro-3-(trifluoromethyl)pyridine (1.84 g, 8.28 mmol) in AcOH (30 ml) was added iron powder (4.63 g, 83 mmol) at RT and the reaction mixture was stirred at RT overnight. Celite was added and the solvent was evaporated to dryness. The residue was taken in DCM and aqueous saturated NaHCO₃, sonicated and filtered through a pad of Celite. The cake was washed with DCM and the binary system was separated. The aqueous phase was extracted with DCM, the combined organic phases were washed with water, dried over Na₂SO₄, filtered and concentrated under vacuum to dryness to afford 6-methoxy-5-(trifluoromethyl)pyridin-3-amine. M/z=193 [M+H]+, Rt=0.76 min (UPLC Method B3), ¹H NMR (400 MHz, DMSO-d₆) δ ppm: 7.75 (m, 1H), 7.33 (d, 1H), 5.17 (s, 2H), 3.82 (s, 3H).

E7: 2-(5-amino-3-(trifluoromethyl)pyridin-2-yl)isothiazolidine 1,1-dioxide

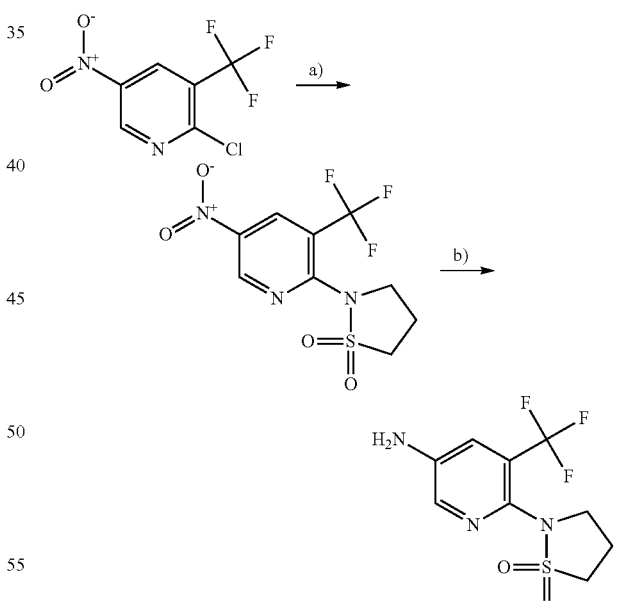

a) 2-(5-nitro-3-(trifluoromethyl)pyridin-2-yl)isothiazolidine 1,1-dioxide

To 2-chloro-5-nitro-3-trifluoromethylpyridine (0.56 g, 2.48 mmol) and isothiazolidine 1,1-dioxide (0.60 g, 4.96 mmol) in 1,4-dioxane (12 ml) were added Cs₂CO₃ (0.81 g, 2.48 mmol) and argon was bubbled though the mixture for 10 min. Then Xantphos (287 mg, 0.50 mmol) and Pd₂(dba)₃

(114 mg, 0.124 mmol) were added. The reaction mixture was stirred for 40 min at 140° C. in a microwave oven. The mixture was filtered through a pad of Celite and the solvent was evaporated. The crude product was purified by flash column chromatography on silica gel (cyclohexane/AcOEt 100/0 to 50/50) to afford 2-(5-nitro-3-(trifluoromethyl)pyridin-2-yl)isothiazolidine 1,1-dioxide. M/z=312 [M+H]+, Rt=0.87 min (UPLC Method B2).

b) 2-(5-amino-3-(trifluoromethyl)pyridin-2-yl)isothiazolidine 1,1-dioxide

To 2-(5-nitro-3-(trifluoromethyl)pyridin-2-yl)isothiazolidine 1,1-dioxide (0.34 g, 1.09 mmol) in 1.25N HCl in EtOH (17.5 ml, 21.9 mmol) at RT was added portionwise tin(II) chloride (1.04 g, 5.46 mmol). The reaction mixture was stirred at RT for 1 h. The mixture was concentrated, diluted with DCM, treated with 1N NaOH, extracted with DCM, dried over $Na_2SO_4$, filtered and concentrated. The residue was purified by flash column chromatography on silica gel (DCM/MeOH 1/0 to 9/1) to afford 2-(5-amino-3-(trifluoromethyl)pyridin-2-yl)isothiazolidine 1,1-dioxide. M/z=282 [M+H]+, Rt=0.65 min (UPLC Method B2), $^1$H NMR (400 MHz, DMSO-$d_6$) δ ppm: 8.03 (d, 1H), 7.26 (d, 1H), 6.02 (bs, 2H), 3.68 (t, 2H), 3.20 (t, 2H), 2.44 (m, 2H).

E8: 3-amino-1-methyl-5-(trifluoromethyl)pyridin-2(1H)-one

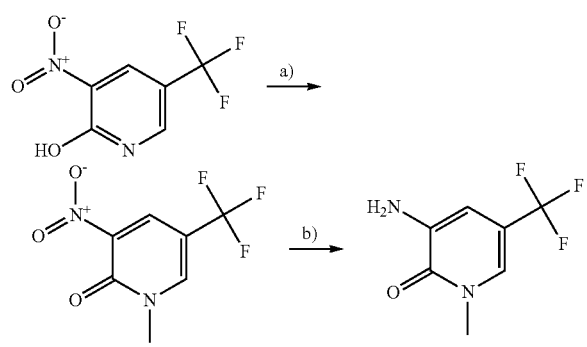

a) 1-methyl-3-nitro-5-(trifluoromethyl)pyridin-2(1H)-one

To 3-nitro-5-(trifluoromethyl)-pyridin-2-ol (1.97 g, 9.46 mmol) and $K_2CO_3$ (2.62 g, 18.9 mmol) in dry DMF (30 ml) at 0° C. was added dropwise iodomethane (0.89 ml, 14.2 mmol) and the reaction mixture was stirred at RT for 1.5 h. The mixture was poured onto ice/water and extracted with AcOEt. The combined organic phases were washed with brine, dried over $Na_2SO_4$, filtered and concentrated under vacuum to afford 1-methyl-3-nitro-5-(trifluoromethyl)pyridin-2(1H)-one. M/z=223 [M+H]+, Rt=0.68 min (UPLC Method B2), $^1$H NMR (400 MHz, DMSO-$d_6$) δ ppm: 8.89 (m, 1H), 8.68 (m, 1H), 3.61 (s, 3H).

b) 3-amino-1-methyl-5-(trifluoromethyl)pyridin-2(1H)-one

To 1-methyl-3-nitro-5-(trifluoromethyl)pyridin-2(1H)-one (1.41 g, 6.33 mmol) in EtOH (30 ml) were added 7M aqueous $NH_4Cl$ (9.0 ml, 63 mmol) and iron powder (1.06 g, 19.0 mmol). The reaction mixture was heating at reflux under vigorous stirring for 1 h. After cooling to RT, the mixture was filtered through a pad of celite, rinsed with hot EtOH and the filtrate was evaporated to dryness. $Et_2O$ was added to the residue, the mixture was triturated with sonication and filtered. The filtrate was evaporated to dryness to afford 3-amino-1-methyl-5-(trifluoromethyl)pyridin-2(1H)-one. M/z=193 [M+H]+, Rt=0.64 min (UPLC Method B2), $^1$H NMR (400 MHz, DMSO-$d_6$) δ ppm: 7.54 (m, 1H), 6.50 (m, 1H), 5.55 (bs, 2H), 3.49 (s, 3H).

E9: 3-amino-5-chloro-1-methylpyridin-2(1H)-one

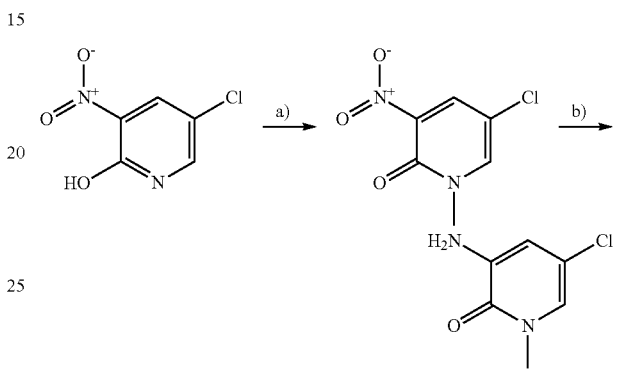

a) 5-chloro-1-methyl-3-nitropyridin-2(1H)-one

To 5-chloro-2-hydroxy-3-nitropyridine (15.0 g, 86 mmol) in DMF (200 ml) at 0° C. was added NaH (4.13 g, 103 mmol) in portions and the reaction mixture was stirred at 0° C. for 1 h. Iodomethane (8.06 ml, 129 mmol) was added and the mixture was stirred at RT for 4 h. The mixture was concentrated, water was added and the mixture was extracted with AcOEt. The organic phase was washed with brine, dried over $Na_2SO_4$ and evaporated to dryness to afford 5-chloro-1-methyl-3-nitropyridin-2(1H)-one. M/z=189-191 [M+H]+, Rt=0.55 min (UPLC Method B4).

b) 3-amino-5-chloro-1-methylpyridin-2(1H)-one

To 5-chloro-1-methyl-3-nitropyridin-2(1H)-one (14.6 g, 78 mmol) in MeOH (300 ml) was added Raney-Nickel in EtOH (4 g). The reaction mixture was stirred at RT for 8 h under $H_2$ atmosphere. The mixture was filtered through Celite and evaporated to dryness to afford 3-amino-5-chloro-1-methylpyridin-2(1H)-one. M/z=159-161 [M+H]+, Rt=0.51 min (UPLC Method B4).

E10: 5-amino-3-chloro-1-methyl-6-(1H-pyrazol-1-yl)pyridin-2(1H)-one

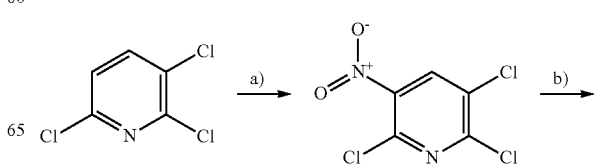

-continued

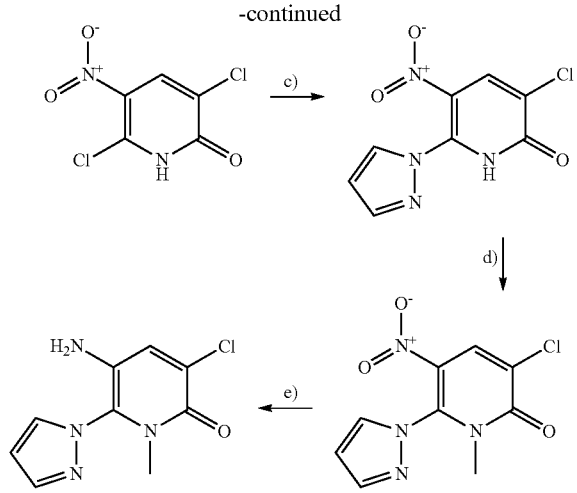

a) 2,3,6-trichloro-5-nitropyridine

To fuming HNO₃ (136 ml) were added H₂SO₄ (111 ml) and 2,3,6-trichloropyridine (24.2 g, 133 mmol) at 0° C. The reaction mixture was allowed to warm to RT, then stirred at 100° C. overnight. After cooling to 0° C., the mixture was poured onto ice-water. The unsoluble material was collected by filtration to afford 2,3,6-trichloro-5-nitropyridine. Rt=1.07 min (UPLC Method B2), $^1$H NMR (400 MHz, DMSO-d₆) δ ppm: 9.06 (s, 1H).

b) 3,6-dichloro-5-nitropyridin-2(1H)-one

To 2,3,6-trichloro-5-nitropyridine (7.00 g, 30.8 mmol) in dry tBuOH (80 ml) was added KOH (5.18 g, 92 mmol) and the reaction mixture was stirred at RT over the weekend. The solvent was evaporated and the residual solid was partitioned between AcOEt and 2N aqueous HCl. The resulting suspension was sonicated and filtered. The organic phase was separated, the aqueous phase was extracted with AcOEt and the combined organic phase was washed with brine, dried over Na₂SO₄, filtered and concentrated. To the residue was added AcOEt, the suspension was filtered and the filtrate was evaporated under HV to afford a mixture of 3,6-dichloro-5-nitropyridin-2(1H)-one and 5,6-dichloro-3-nitropyridin-2(1H)-one. M/z=207/209/211 [M–H]–, Rt=0.57-0.65 min (UPLC Method B2).

c) 3-chloro-5-nitro-6-(1H-pyrazol-1-yl)pyridin-2(1H)-one

To 1H-pyrazole (2.68 g, 39.4 mmol) in dry THF (120 ml) was added portionwise NaH (1.62 g, 40.4 mmol, 60% in mineral oil) at −10° C. and the reaction mixture was stirred at RT overnight. The mixture of 3,6-dichloro-5-nitropyridin-2(1H)-one and 5,6-dichloro-3-nitropyridin-2(1H)-one (2.51 g, 9.85 mmol) was added portionwise, then THF (60 ml) was added. The reaction mixture was stirred at RT for 4 h, quenched carefully with water and the mixture was evaporated to dryness. The residual solid was partitioned between AcOEt and 2N aqueous HCl. The resulting suspension was sonicated and filtered. The organic phase was separated, the aqueous phase was extracted with AcOEt and the combined organic phase was washed with brine, dried over Na₂SO₄, filtered and concentrated. To the residue was added DCM, the suspension was filtered and the filtrate was evaporated under HV to afford a mixture of 3-chloro-5-nitro-6-(1H-pyrazol-1-yl)pyridin-2(1H)-one and 5-chloro-3-nitro-6-(1H-pyrazol-1-yl)pyridin-2(1H)-one. M/z=241/243 [M+H]+, Rt=0.61-0.66 min (UPLC Method B2).

d) 3-chloro-1-methyl-5-nitro-6-(1H-pyrazol-1-yl)pyridin-2(1H)-one

To a mixture of 3-chloro-5-nitro-6-(1H-pyrazol-1-yl)pyridin-2(1H)-one and 5-chloro-3-nitro-6-(1H-pyrazol-1-yl)pyridin-2(1H)-one (3.12 g, 7.0 mmol) in dry DMF 50 ml) were added at RT K₂CO₃ (3.01 g, 21.78 mmol) and at 0° C. dropwise iodomethane (1.02 ml, 16.33 mmol). The reaction mixture was stirred at RT overnight. The mixture was poured onto ice-cold water, the suspension was filtered and the resulting solid was dried under HV at 50° C. The solid was suspended in DCM, triturated, sonicated, the suspension was filtered and the filtrate was concentrated. The residue was purified by two subsequent flash column chromatographies on silica gel (first: hexane/TBME 1/0 to 0/1, second: DCM/TBME 1/0 to 0/1) to afford 3-chloro-1-methyl-5-nitro-6-(1H-pyrazol-1-yl)pyridin-2(1H)-one. M/z=255/257 [M+H]+, Rt=0.96 min (UPLC Method B2). $^1$H NMR (400 MHz, DMSO d₆) δ ppm: 8.83 (s, 1H) 8.59 (m, 1H) 7.95 (m, 1H), 6.67 (m, 1H) 4.10 (s, 3H)

e) 5-amino-3-chloro-1-methyl-6-(1H-pyrazol-1-yl)pyridin-2(1H)-one 3-chloro-1-methyl-5-nitro-6-(1H-pyrazol-1-yl)pyridin-2(1H)-one (682 mg, 2.68 mmol) in EtOH (18 ml) was added aqueous 7M aqueous NH₄Cl (3.83 ml, 26.8 mmol) followed by iron powder (450 mg, 8.04 mmol). The reaction mixture was stirred at reflux for 3.5 h. After cooling at RT, the mixture was filtered through a pad of Celite and the filtrate was concentrated. The resulting solid was treated with Et₂O, triturated, sonicated, the suspension was filtered and the filtrate was evaporated to afford 5-amino-3-chloro-1-methyl-6-(1H-pyrazol-1-yl)pyridin-2(1H)-one. M/z=225/227 [M+H]+, Rt=0.78 min (UPLC Method B2). $^1$H NMR (600 MHz, DMSO d₆) δ ppm: 7.99 (d, 1H), 7.65 (d, 1H), 7.04 (s, 1H), 6.43 (t, 1H), 5.60 (bs, 2H), 3.86 (s, 3H).

E11: 5-chloro-2-((1-methylpyrrolidin-3-yl)oxy)-6-(2H-1,2,3-triazol-2-yl)pyridin-3-amine

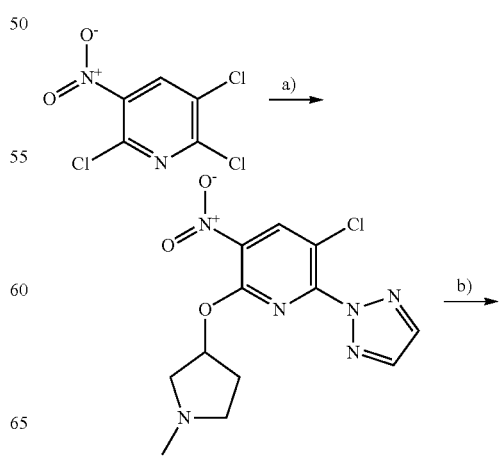

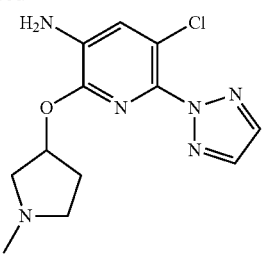

a) 3-chloro-6-((1-methylpyrrolidin-3-yl)oxy)-5-nitro-2-(2H-1,2,3-triazol-2-yl)pyridine To NaH (97 mg, 2.42 mmol; 60% in mineral oil)) in DMF (10 ml) at 0° C. was added 1-methylpyrrolidin-3-ol (229 mg, 2.20 mmol). After 30 min of stirring at RT, 2,3,6-trichloro-5-nitropyridine (500 mg, 2.20 mmol) was added and the reaction mixture was stirred at RT for 2 h. To NaH (97 mg, 2.42 mmol; 60% in mineral oil) in DMF (5 ml) at 0° C. was added 2H-1,2,3-triazole (157 mg, 2.20 mmol) and after 10 min of stirring at RT, the activated 2H-1,2,3-triazole was added at 0° C. in the previous reaction mixture. The obtained reaction mixture was stirred at RT overnight. Water was added and the mixture was extracted with AcOEt. The organic phase was washed with brine, dried over Na₂SO₄ and evaporated. The residue was purified by preparative HPLC (Method A4) to afford 3-chloro-6-((1-methylpyrrolidin-3-yl)oxy)-5-nitro-2-(2H-1,2,3-triazol-2-yl)pyridine. M/z=325-327 [M+H]+, Rt=0.56 min (UPLC Method B2).

b) 5-chloro-2-((1-methylpyrrolidin-3-yl)oxy)-6-(2H-1,2,3-triazol-2-yl)pyridin-3-amine 5-chloro-2-((1-methylpyrrolidin-3-yl)oxy)-6-(2H-1,2,3-triazol-2-yl)pyridin-3-amine was prepared analogously to E10 step e) using 3-chloro-6-((1-methylpyrrolidin-3-yl)oxy)-5-nitro-2-(2H-1,2,3-triazol-2-yl)pyridine instead of 3-chloro-1-methyl-5-nitro-6-(1H-pyrazol-1-yl)pyridin-2(1H)-one. M/z=295-297 [M+H]+, Rt=0.49 min (UPLC Method B2).

E12: 5-amino-2-(3-methyl-1H-1,2,4-triazol-1-yl)benzonitrile

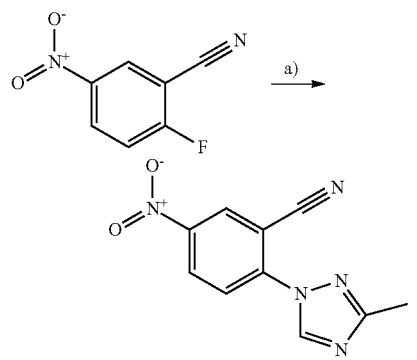

a) 2-(3-methyl-1H-1,2,4-triazol-1-yl)-5-nitrobenzonitrile 2-fluoro-5-nitrobenzonitrile (2.37 g, 14.3 mmol), 3-methyl-1H-1,2,4-triazole (1.18 g, 14.3 mmol) and K₂CO₃ (3.94 g, 28.5 mmol) in DMF (20 ml) were stirred at RT for 18 h. The reaction mixture was quenched with water and extracted with AcOEt. The organic phase was dried over Na₂SO₄, filtered and concentrated. The residue was purified by preparative HPLC (Method A4) to afford 2-(3-methyl-1H-1,2,4-triazol-1-yl)-5-nitrobenzonitrile. M/z=230 [M+H]+, Rt=0.69 min (UPLC Method B5).

b) 5-amino-2-(3-methyl-1H-1,2,4-triazol-1-yl)benzonitrile 2-(3-methyl-1H-1,2,4-triazol-1-yl)-5-nitrobenzonitrile (741 mg, 3.23 mmol) in EtOH (75 ml) was hydrogenated through H-Cube® (Pd/C cartridge, 30° C., 40 bar, 1 ml/min). The resulting solution was evaporated to dryness to afford 5-amino-2-(3-methyl-1H-1,2,4-triazol-1-yl)benzonitrile. M/z=200 [M+H]+, Rt=0.48 min (UPLC Method B6).

E13: 3-chloro-4-(2H-1,2,3-triazol-2-yl)aniline

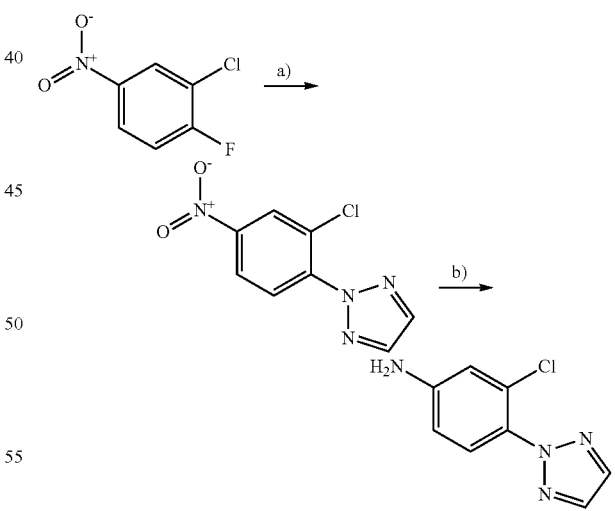

a) 2-(2-chloro-4-nitrophenyl)-2H-1,2,3-triazole

To 2H-1,2,3-triazole (2.0 g, 29 mmol) in DMF (145 mL) was added NaH (1.16 g, 29 mmol, 60% in mineral oil) at RT and the mixture was stirred for 1 h. After cooling to 0° C., 2-chloro-1-fluoro-4-nitrobenzene (4.6 g, 26.1 mmol) was added and the reaction mixture was stirred at 0° C. for 1.5 h, then at RT for 1.5 h. The mixture was quenched with water and extracted with AcOEt. The organic phase was washed with water and brine, dried over Na$_2$SO$_4$, filtered and concentrated. The crude product was purified by silica gel column (heptane/AcOEt: 90/10 to 50/50) to afford 2-(2-chloro-4-nitrophenyl)-2H-1,2,3-triazole. M/z=225-227 [M+H]+, Rt=0.95 min (UPLC Method B3).

b) 3-chloro-4-(2H-1,2,3-triazol-2-yl)aniline

To 2-(2-chloro-4-nitrophenyl)-2H-1,2,3-triazole (2.24 g, 9.97 mmol) in EtOH (130 mL) were added 2N aq. HCl (67 mL) and tin(II) chloride (9.5 g, 50 mmol) at RT. The white suspension was stirred at 85° C. for 45 min. After cooling to RT, the reaction mixture was added to a concentrated aqueous NaOH solution at 0° C. and extracted with TBME/EtOH (9/1). The organic phase was dried over Na$_2$SO$_4$, filtered and concentrated. The residue was purified by silica gel column chromatography (heptane/AcOEt: 90/10 to 25/75) to afford 3-chloro-4-(2H-1,2,3-triazol-2-yl)aniline. M/z=195-197 [M+H]+, Rt=0.88 min (UPLC Method B3).

E14: 3,5-dichloro-4-(2H-1,2,3-triazol-2-yl)aniline

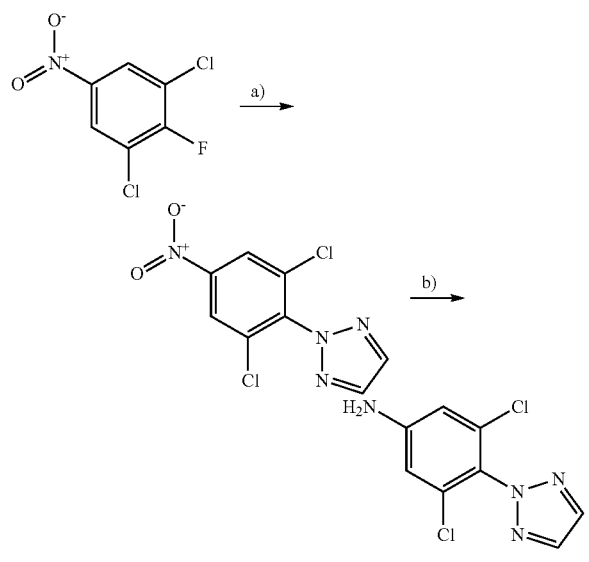

3,5-dichloro-4-(2H-1,2,3-triazol-2-yl)aniline was prepared in analogy to procedure E13 step a) and b) using 1,3-dichloro-2-fluoro-5-nitrobenzene instead of 3-chloro-4-fluoronitro-benzene. Step a) was performed overnight. M/z=229-231 [M+H]+, Rt=0.93 min (UPLC Method B3).

E15: 4-(4-amino-2-chlorophenyl)pyrimidin-2-amine

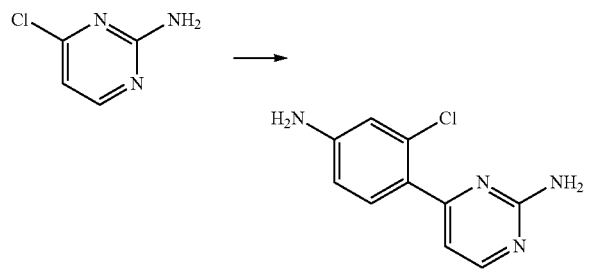

To propanol (8 ml) were added 3-chloro-4-(4,4,5,5-tetramethyl-1,3,2-dioxaborolan-2-yl)aniline (320 mg, 1.26 mmol), 2-amino-4-chloropyrimidine (164 mg, 1.26 mmol) and aqueous 1M Na$_2$CO$_3$ (3.8 ml, 3.8 mmol) After 10 min of stirring, PdCl$_2$(PPh$_3$)$_2$ (44 mg, 0.063 mmol) was added and the reaction mixture was stirred at 80° C. overnight. The mixture was quenched with H$_2$O and extracted with AcOEt. The organic phase was washed with water and brine, dried over Na$_2$SO$_4$, filtered and concentrated. The residue was purified by silica gel column chromatography (heptane/AcOEt) to afford 4-(4-amino-2-chlorophenyl)pyrimidin-2-amine. M/z=221 [M+H]+, Rt=0.54 min (UPLC Method B2).

E16: (1-(4-amino-2-chlorophenyl)-5-methyl-1H-pyrazol-3-yl)methanol

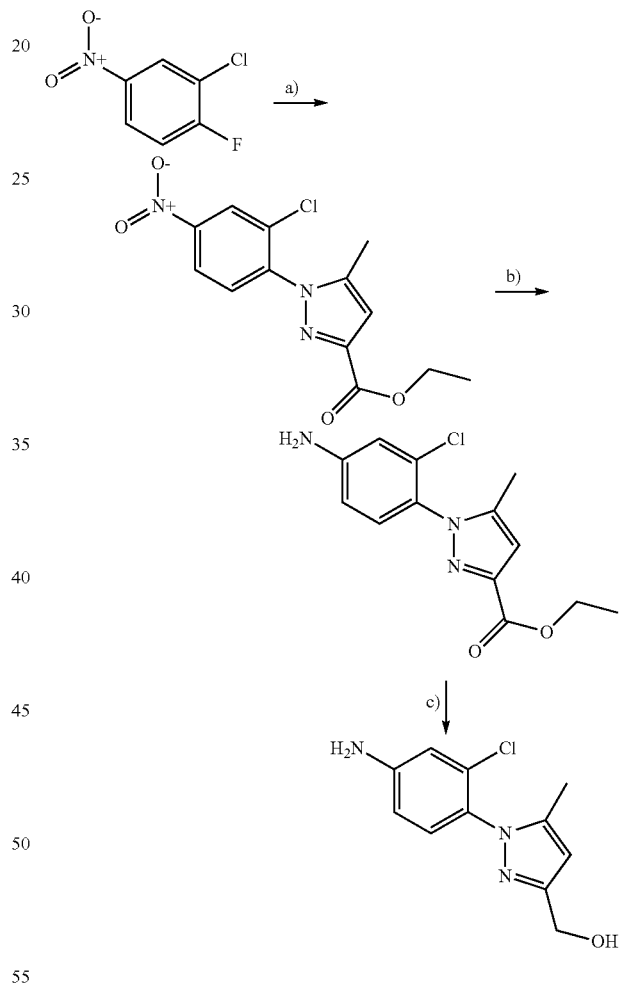

a) ethyl 1-(2-chloro-4-nitrophenyl)-5-methyl-1H-pyrazole-3-carboxylate

2-Chloro-1-fluoro-4-nitrobenzene (1 g, 5.70 mmol), ethyl 3-methylpyrazole-3-carboxylate (0.88 g, 5.70 mmol) and K$_2$CO$_3$ (0.95 g, 6.84 mmol) in DMF (15 ml) were stirred at RT overnight. Water was added, the precipitate was filtered, rinsed with water and dried under HV to afford ethyl 1-(2-chloro-4-nitrophenyl)-5-methyl-1H-pyrazole-3-carboxylate. M/z=310-312 [M+H]+, Rt=1.05 min (UPLC Method B2).

b) ethyl 1-(4-amino-2-chlorophenyl)-5-methyl-1H-pyrazole-3-carboxylate

To ethyl 1-(2-chloro-4-nitrophenyl)-5-methyl-1H-pyrazole-3-carboxylate (1.0 g, 3.23 mmol) in AcOH (50 ml) was added iron powder (1.80 g, 32 mmol)) and the reaction mixture was stirred at RT for 2.5 h. The mixture was evaporated, the residue was treated with DCM and filtered. The organic phase was washed with aqueous saturated NaHCO₃, water and brine, dried over Na₂SO₄, filtered and evaporated to afford ethyl 1-(4-amino-2-chlorophenyl)-5-methyl-1H-pyrazole-3-carboxylate. M/z=280-282 [M+H]+, Rt=0.90 min (UPLC Method B2).

c) (1-(4-amino-2-chlorophenyl)-5-methyl-1H-pyrazol-3-yl)methanol

To ethyl 1-(4-amino-2-chlorophenyl)-5-methyl-1H-pyrazole-3-carboxylate (0.81 g, 2.90 mmol) in THF (15 ml) was added dropwise 2M LiAlH₄ in THF (2.17 ml, 4.35 mmol) and the reaction mixture was stirred at RT for 1.5 h. The reaction mixture was quenched carefully with water and extracted with AcOEt. The organic phase was washed with water and brine, dried over Na₂SO₄, filtered and evaporated to afford (1-(4-amino-2-chlorophenyl)-5-methyl-1H-pyrazol-3-yl)methanol. M/z=238-240 [M+H]+, Rt=0.61 min (UPLC Method B2).

E17: tert-butyl ((1-(4-amino-2-chlorophenyl)-1H-pyrazol-4-yl)methyl)carbamate

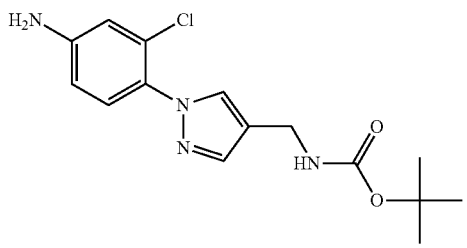

tert-butyl ((1-(4-amino-2-chlorophenyl)-1H-pyrazol-4-yl)methyl)carbamate was prepared analogously to E16 step a) and b) using tert-butyl ((1H-pyrazol-4-yl)methyl)carbamate instead of ethyl 3-methylpyrazole-3-carboxylate. Step b) was performed at RT overnight. M/z=323-325 [M+H]+, Rt=0.90 min (UPLC Method B2).

E18: tert-butyl ((1-(5-amino-3-chloropyridin-2-yl)-1H-pyrazol-4-yl)methyl)carbamate

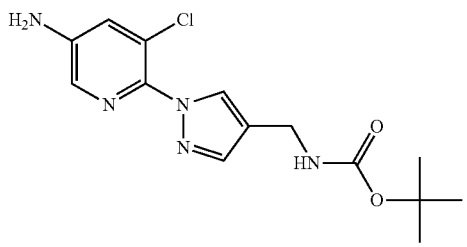 [SMILES: CC(C)(C)OC(=O)NCc1cnn(-c2ncc(N)cc2Cl)c1]

tert-butyl ((1-(5-amino-3-chloropyridin-2-yl)-1H-pyrazol-4-yl)methyl)carbamate was prepared analogously as described for E16 step a) and b) using 2,3-dichloro-5-nitropyridine instead of 2-chloro-1-fluoro-4-nitrobenzene and using tert-butyl ((1H-pyrazol-4-yl)methyl)carbamate instead of ethyl 3-methylpyrazole-3-carboxylate. Step b) was performed at RT overnight. M/z=324-326 [M+H]+, Rt=0.81 min (UPLC Method B2).

E19: (1-(4-amino-2-chlorophenyl)-5-methyl-1H-pyrazol-3-yl)methanol

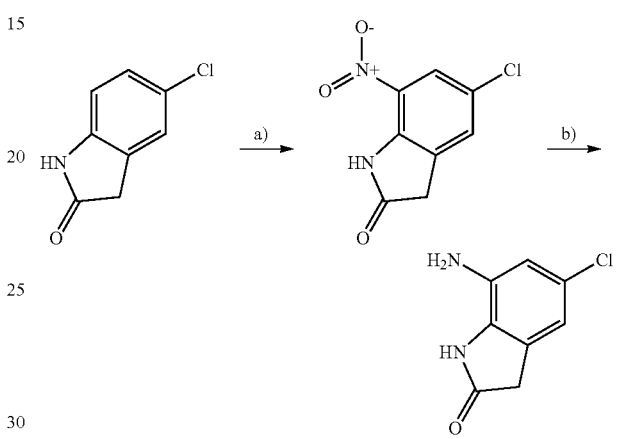

a) 5-chloro-7-nitroindolin-2-one

To 5-chloro oxindole (1.0 g, 5.97 mmol) in H₂SO₄ (20 ml) at 0° C. was added KNO₃ (0.72 g, 7.16 mmol) in H₂SO₄ (20 ml) dropwise. After stirring at 0° C. for 15 min, the reaction mixture was stirred at 90° C. for 45 min. The mixture was cooled to RT and poured onto ice. The suspension was filtered, rinsed with water and dried under HV to afford 5-chloro-7-nitroindolin-2-one. M/z=211 [M−H]−, Rt=0.76 min (UPLC Method B2).

b) 7-amino-5-chloroindolin-2-one

To 5-chloro-7-nitroindolin-2-one (1.2 g, 5.64 mmol) in AcOH (80 ml) was added iron powder (3.15 g, 56.4 mmol)) and the reaction mixture was stirred at RT for 1 h. The mixture was evaporated, the residue was treated with DCM and filtered. The organic phase was washed with aqueous saturated NaHCO₃, water and brine, dried over Na₂SO₄, filtered and evaporated to afford ethyl 7-amino-5-chloroindolin-2-one. M/z=183-185 [M+H]+, Rt=0.62 min (UPLC Method B2).

E20: (1-(4-amino-2-chlorophenyl)-5-methyl-1H-pyrazol-3-yl)methanol

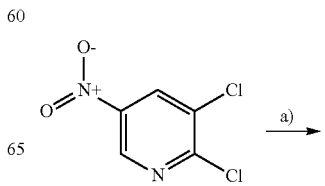

a) 3-chloro-5-nitro-2-(2H-1,2,3-triazol-2-yl)pyridine

To a solution of 2,3-dichloro-5-nitropyridine (1.0 g, 5.18 mmol) and K₂CO₃ (1.43 g, 10.4 mmol) in THF (5 ml) was added 2H-1,2,3-triazole (0.360 ml, 6.22 mmol). The reaction mixture was stirred for overnight at RT. Since the reaction was uncomplete, additional 2H-1,2,3-triazole (0.300 ml, 5.18 mmol) was added and reaction mixture was stirred over 2 days at RT. Water was added and the mixture was extracted with AcOEt. The organic layer was washed with brine, dried over Na₂SO₄, filtered and concentrated under vacuum. The residue taken-up in DCM, the solid was filtered off and the filtrate was evaporated. The residue was purified by flash column chromatography on silica gel (cyclohexane/AcOEt: 1/0 to 7/3) to afford 3-chloro-5-nitro-2-(2H-1,2,3-triazol-2-yl)pyridine. Rt=0.75 min (UPLC Method B1), ¹H NMR (400 MHz, DMSO-d₆) δ ppm: 9.39 (d, 1H), 9.15 (d, 1H), 8.33 (s, 2H).

b) 5-chloro-6-(2H-1,2,3-triazol-2-yl)pyridin-3-amine

To a solution of 3-chloro-5-nitro-2-(2H-1,2,3-triazol-2-yl)pyridine (500 mg, 2.22 mmol) in 1.25M HCl in MeOH (35.5 ml, 44 mmol) at RT was added portionwise tin(II) chloride (2.1 g, 11.1 mmol). The reaction was stirred at RT for 2 h. The mixture was evaporated and residue was diluted with DCM. The mixture was basified with 1N aqueous NaOH and phases were separated. The organic layer was dried over anhydrous Na₂SO₄, filtered and concentrated under vacuum. The residue was purified by flash column chromatography on silica gel (cyclohexane/AcOEt: 1/0 to 0/1) to afford 5-chloro-6-(2H-1,2,3-triazol-2-yl)pyridin-3-amine. M/z=196-198 [M+H]+, Rt=0.50 min (UPLC Method B1), ¹H NMR (400 MHz, DMSO-d₆) δ ppm: 8.05 (s, 2H), 7.81 (s, 1H), 7.20 (s, 1H), 6.20 (d, 2H).

E22: 2-(difluoromethyl)pyridin-4-amine

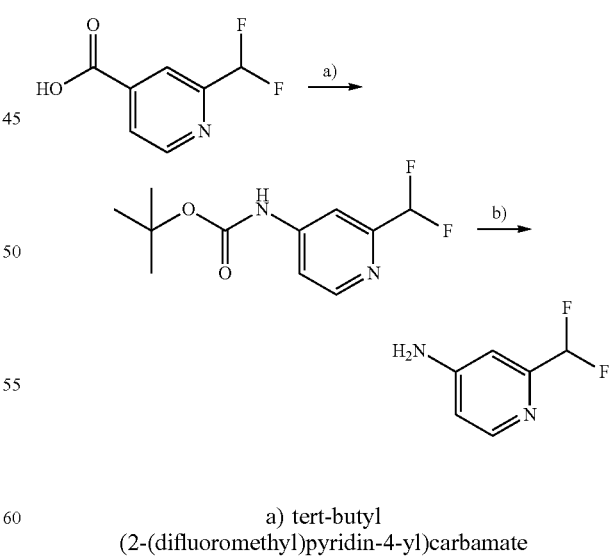

a) tert-butyl (2-(difluoromethyl)pyridin-4-yl)carbamate

To a solution of 2-(difluoromethyl)isonicotinic acid (500 mg, 2.89 mmol) in tBuOH (30 ml) were added DPPA (0.75 ml, 3.47 mmol) followed by Et₃N (1.21 ml, 8.7 mmol). The reaction mixture was stirred at RT for 30 min. Then mixture was stirred at 100° C. for 4 h. The mixture was concentrated,

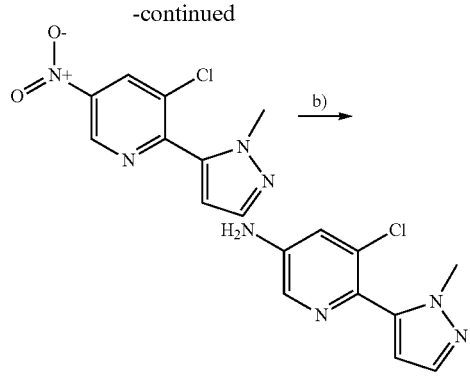

a) 3-chloro-2-(1-methyl-1H-pyrazol-5-yl)-5-nitropyridine

To 2,3-dichloro-5-nitropyridine (0.30 g, 1.56 mmol) in 1,4-dioxane (10.5 ml) were added 1-methyl-1H-pyrazole-5-boronic acid pinacol ester (0.32 g, 1.56 mmol), water (2.4 ml) and K₂CO₃ (1.29 g, 9.3 mmol). Under argon, Pd(PPh₃)₄ (90 mg, 0.078 mmol) was added and the reaction mixture was stirred in microwave at 140° C. for 20 min. Water and AcOEt were added, the organic phase was dried over Na₂SO₄, filtered and evaporated. The crude product was purified by flash chromatography on silica gel (heptane/AcOEt 85/15 to 15/85) to afford 3-chloro-2-(1-methyl-1H-pyrazol-5-yl)-5-nitropyridine. M/z=239-241 [M+H]+, Rt=0.85 min (UPLC Method B2).

b) 5-chloro-6-(1-methyl-1H-pyrazol-5-yl)pyridin-3-amine 5-chloro-6-(1-methyl-1H-pyrazol-5-yl)pyridin-3-amine was prepared analogously as described for G32 step b). M/z=209-211 [M+H]+, Rt=0.60 min (UPLC Method B2).

E21: 5-chloro-6-(2H-1,2,3-triazol-2-yl)pyridin-3-amine

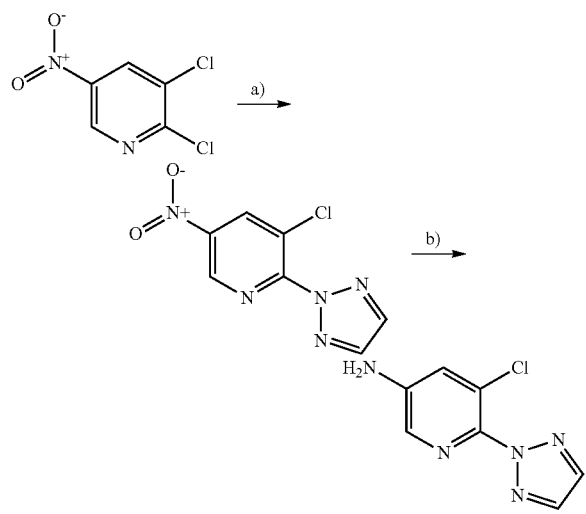

the residue was taken-up in AcOEt and washed with saturated aqueous NaHCO$_3$ solution, dried over Na$_2$SO$_4$, filtered and evaporated. The crude material was purified by flash column chromatography on silica gel (cyclohexane/AcOEt: 1/0 to 1/1) to afford tert-butyl (2-(difluoromethyl)pyridin-4-yl)carbamate. M/z=245 [M+H]+, Rt=0.96 min (UPLC Method B1).

b) 2-(difluoromethyl)pyridin-4-amine

To a solution of tert-butyl (2-(difluoromethyl)pyridin-4-yl)carbamate (125 mg, 0.51 mmol) in MeOH (1 ml) was added 4M HCl in 1,4-dioxane (2.56 ml, 10.2 mmol). The reaction mixture was stirred overnight at RT. The mixture was evaporated and dried on HV to afford 2-(difluoromethyl)pyridin-4-amine. M/z=145 [M+H]+, Rt=0.19 min (UPLC Method B1).

E23: 5-chloro-6-(difluoromethoxy)pyridin-3-amine

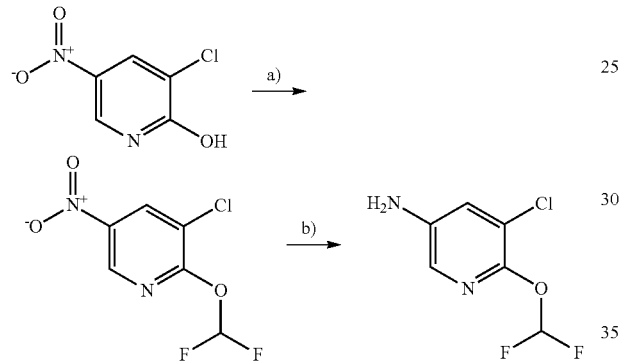

a) 3-chloro-2-(difluoromethoxy)-5-nitropyridine

In a heat-gun dried flask under argon at RT, to a solution of 3-chloro-5-nitropyridin-2-ol (1.0 g, 5.73 mmol) in CH$_3$CN (100 ml) was added portionwise NaH 60% in mineral oil (619 mg, 15.5 mmol). The reaction mixture was stirred at RT for 15 min. Then, 2,2-difluoro-2-(fluorosulfonyl)-acetic acid (1.0 ml, 9.74 mmol) was added dropwise and reaction mixture was stirred at RT for 15 min. Mixture was cooled to 0° C. and quenched by dropwise addition of water (50 ml). Mixture was diluted with AcOEt and phases were separated. The aqueous layer was extracted 3 times with AcOEt. The combined organic layers were washed with water (3 times), brine, dried over Na$_2$SO$_4$, filtered and evaporated. The crude material was purified by flash column chromatography on silica gel (n-hexane/TBME: 1/0 to 8/2) to afford 3-chloro-2-(difluoromethoxy)-5-nitropyridine. Rt=0.99 min (UPLC Method B2), $^1$H NMR (400 MHz, DMSO-d$_6$) δ: 9.11 (d, 1H), 8.97 (d, 1H), 7.84 (t, 1H).

b) 5-chloro-6-(difluoromethoxy)pyridin-3-amine

To a solution of 3-chloro-2-(difluoromethoxy)-5-nitropyridine (454 mg, 2.02 mmol) in AcOH (5 ml) at RT was added iron powder (1.13 g, 20.2 mmol). The reaction mixture was stirred at RT for 1.5 h. The mixture was diluted with toluene and evaporated. The residue was taken-up in DCM and filtered over a Celite pad built in DCM. The filtrate was washed with saturated aqueous NaHCO$_3$ solution and phases were separated. The aqueous layer was extracted twice with DCM. The combined organic layers were washed with water, brine, dried over Na$_2$SO$_4$, filtered and evaporated to afford 5-chloro-6-(difluoromethoxy)pyridin-3-amine. M/z=195-197 [M+H]+, Rt=0.82 min (UPLC Method B2).

E24: 5-chloro-2-(2-(dimethylamino)ethoxy)pyridin-3-amine

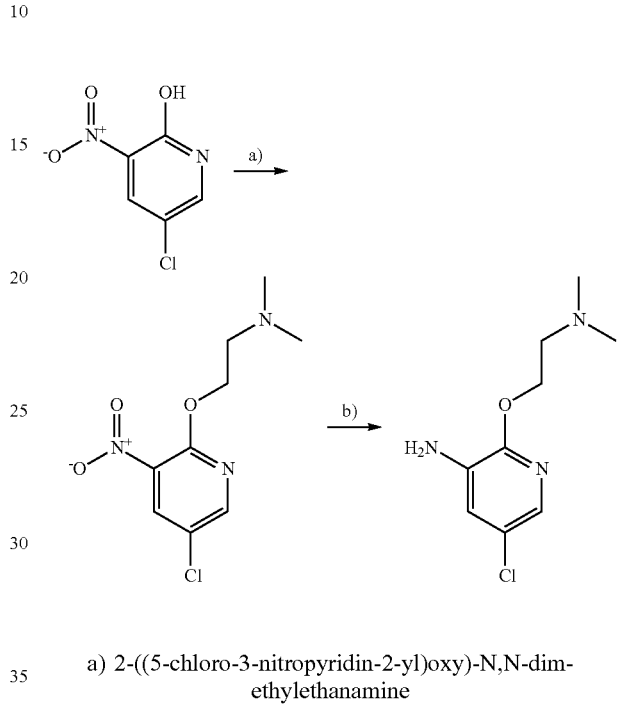

a) 2-((5-chloro-3-nitropyridin-2-yl)oxy)-N,N-dimethylethanamine

To a solution of 5-chloro-3-nitropyridin-2-ol (1.0 g, 5.61 mmol), 2-dimethylamino)ethanol (0.63 ml, 6.18 mmol) and triphenylphosphine (1.79 g, 6.74 mmol) in THF (20 ml) at 0° C. was added DEAD (1.0 ml, 6.18 mmol). The reaction mixture was allowed to warm-up to RT and stirred for 3 h. Then, additional 2-dimethylamino)ethanol (0.63 ml, 6.18 mmol), triphenylphosphine (1.79 g, 6.74 mmol) and DEAD (1.0 ml, 6.18 mmol) were added and the reaction mixture was stirred overnight at RT. Mixture was diluted with water and extracted 3 times with AcOEt. The organic layer was washed with brine, dried over Na$_2$SO$_4$, filtered and evaporated. The crude material was purified by flash column chromatography on silica gel (heptane/AcOEt: 4/6 to 0/1) and then by preparative HPLC (Method A4) to afford 2-((5-chloro-3-nitropyridin-2-yl)oxy)-N,N-dimethylethanamine. M/z=246-248 [M+H]+, Rt=0.47 min (UPLC Method B2).

b) 5-chloro-2-(2-(dimethylamino)ethoxy)pyridin-3-amine

A mixture of 2-((5-chloro-3-nitropyridin-2-yl)oxy)-N,N-dimethylethanamine (235 mg, 0.96 mmol) and iron (534 mg, 9.6 mmol) in EtOH (4 ml) and saturated aqueous NH$_4$Cl (1 ml) was stirred at 100° C. for 2 days. The mixture was filtered over a Celite pad and the filtrate was concentrated. The crude material was purified by flash column chromatography on silica gel (DCM/MeOH+0.1% NH$_3$: 1/0 to 4/6) to afford 5-chloro-2-(2-(dimethylamino)ethoxy)pyridin-3-amine. M/z=216-218 [M+H]+, Rt=0.44 min (UPLC Method B2), ¹H NMR (400 MHz, Methanol-d4) δ: 7.34 (d, 1H), 6.96 (d, 1H), 4.54 (m, 2H), 3.30 (m, 2H), 2.76 (s, 6H).

Part F: Synthesis of Heteroaromatic Acids

F1: 5-(2H-1,2,3-triazol-2-yl)-2-(trifluoromethyl)isonicotinic acid

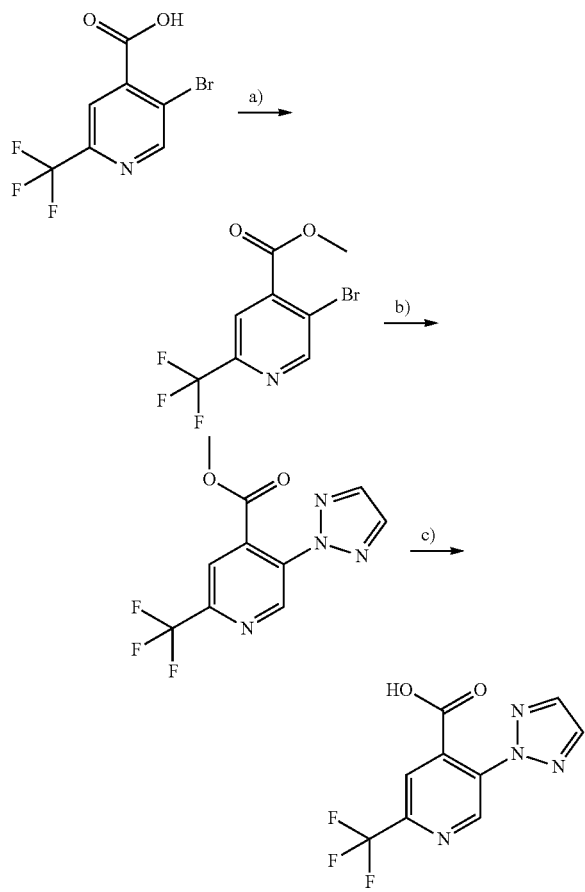

b) methyl 5-bromo-2-(trifluoromethyl)isonicotinate

To a solution of 5-bromo-2-(trifluoromethyl)isonicotinic acid (1.0 g, 3.70 mmol) in THF (5 ml) and MeOH (5 ml) at RT was added trimethylsilyldiazomethane (0.85 g, 7.41 mmol). The reaction mixture was stirred at rt for 1 h. The solvents were evaporated and the residue was purified by flash column chromatography on silica gel (cyclohexane/EtOAc 1/0 to 8/2) to afford methyl 5-bromo-2-(trifluoromethyl)isonicotinate. Rt=1.08 min (UPLC Method B1), ¹H NMR (400 MHz, DMSO-d₆) δ: 9.14 (s, 1H), 8.23 (s, 1H), 3.93 (s, 3H).

b) Methyl 5-(2H-1,2,3-triazol-2-yl)-2-(trifluoromethyl)isonicotinate

A solution of methyl 5-bromo-2-(trifluoromethyl)isonicotinate (200 mg, 0.70 mmol), 1H-1,2,3-triazole (65 mg, 0.92 mmol) and Cs₂CO₃ (252 mg, 0.78 mmol) in DMF (3 ml) was stirred at 60° C. for 1 h. The reaction mixture was quenched with saturated aqueous NaHCO₃ and extracted with AcOEt. The organic phase was dried over Na₂SO₄, filtered and concentrated. The residue was purified by flash column chromatography on silica gel (cyclohexane/EtOAc 1/0 to 1/1) to afford methyl 5-(2H-1,2,3-triazol-2-yl)-2-(trifluoromethyl)isonicotinate. M/z=273 [M+H]+, Rt=1.01 min (UPLC Method B1).

c) 5-(2H-1,2,3-triazol-2-yl)-2-(trifluoromethyl)isonicotinic acid

To a solution of methyl 5-(2H-1,2,3-triazol-2-yl)-2-(trifluoromethyl)isonicotinate (75 mg, 0.276 mmol) in EtOH (3 ml) was added 2M aqueous NaOH (0.15 ml, 0.30 mmol). The mixture was stirred overnight at RT. The reaction mixture was quenched with 1N aqueous HCl to pH 2-3, extracted with AcOEt, dried over Na₂SO₄, filtered and evaporated to afford 5-(2H-1,2,3-triazol-2-yl)-2-(trifluoromethyl)isonicotinic acid. M/z=257 [M−H]−, Rt=0.42 min (UPLC Method B1).

F2: 2-(difluoromethyl)isonicotinic acid

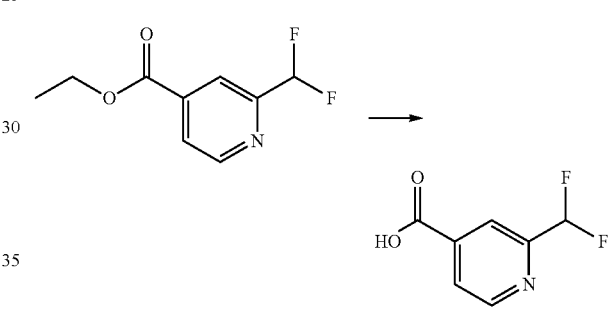

To a stirred solution of ethyl 2-(difluoromethyl)isonicotinate (835 mg, 4.15 mmol) in THF (5 ml) was added LiOH 2M in water (2.59 ml, 5.2 mmol). The reaction mixture was stirred at RT for 2 h. The mixture was evaporated. The residue was taken up in 1N aqueous HCl (pH 4) and the mixture was extracted with DCM (10 times). The combined organic layers were dried over Na₂SO₄, filtered and th solvent was evaporated to afford 2-(difluoromethyl)isonicotinic acid. M/z=174 [M+H]+, Rt=0.42 min (UPLC Method B2).

Example 1

(S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea

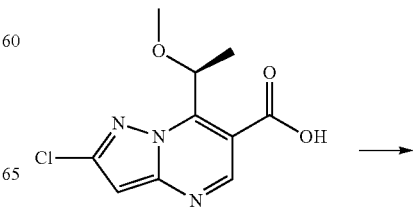

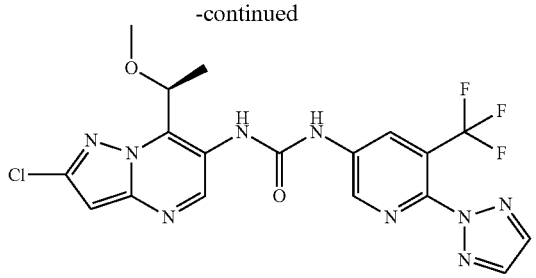

To a solution of (S)-2-chloro-7-(1-methoxyethyl)pyrazolo[1,5-a]pyrimidine-6-carboxylic acid (380 mg, 1.49 mmol) in 1,4-dioxane (5 ml) in a sealed vial were added DPPA (0.38 ml, 1.78 mmol) and Et₃N (0.62 ml, 4.46 mmol). The yellow solution was stirred at RT for 30 min. Then, 6-(2H-1,2,3-triazol-2-yl)-5-(trifluoromethyl)pyridin-3-amine (681 mg, 2.97 mmol) was added and the reaction mixture was stirred for 1 h at 100° C. After cooling to RT, water was added and the mixture was extracted with AcOEt, washed with aqueous saturated NaHCO₃, dried over Na₂SO₄, filtered and concentrated. The crude product was purified by flash column chromatography on silica gel (DCM/MeOH: 100/0 to 80/20), then the product was precipitated in MeOH and filtered to afford (S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea. M/z=482-484 [M+H]+, Rt=4.41 min (HPLC Method C1), ¹H NMR (400 MHz, DMSO-d₆) δ ppm: 10.46 (s, 1H), 8.97 (s, 1H), 8.83 (d, 1H), 8.72 (d, 1H), 8.64 (s, 1H), 8.17 (s, 2H), 6.95 (s, 1H), 5.43 (q, 1H), 1.59 (d, 3H).

Example 2

(S)-1-(2-chloro-7-(1-methoxyethyl)pyrazolo[1,5-a]pyrimidin-6-yl)-3-(2-(trifluoromethyl)pyridin-4-yl)urea

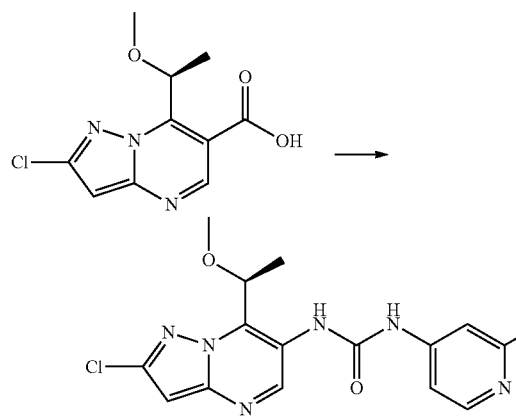

To a solution of (S)-2-chloro-7-(1-methoxyethyl)pyrazolo[1,5-a]pyrimidine-6-carboxylic acid (1.3 g, 4.78 mmol) in 1,4-dioxane (10 ml) were added DPPA (1.24 ml, 5.74 mmol) and Et₃N (3.33 ml, 23.9 mmol). The reaction mixture was stirred at RT for 30 min. Then, 2-(trifluoromethyl)pyridin-4-amine (1.55 g, 9.56 mmol) was added and reaction mixture was stirred at 100° C. for 2 h. The mixture was partitioned between AcOEt and saturated aqueous NaHCO₃ and the phases were separated. The organic layer was dried over Na₂SO₄, filtered and concentrated. The crude material was purified by flash column chromatography on silica gel (cyclohexane/AcOEt: 1/0 to 0/1). The residue was then taken up in MeOH and heated until dissolution. After cooling to RT the precipitate was collected by filtration, washed with MeOH and dried to afford (S)-1-(2-chloro-7-(1-methoxyethyl)pyrazolo[1,5-a]pyrimidin-6-yl)-3-(2-(trifluoromethyl)pyridin-4-yl)urea. M/z=415-417 [M+H]+, Rt=4.18 min (HPLC Method C1), ¹H NMR (400 MHz, DMSO-d₆) δ ppm: 10.38 (s, 1H), 8.92 (s, 1H), 8.57 (s, 1H), 8.56 (s, 1H), 8.06 (d, 1H), 7.61 (dd, 1H), 6.94 (s, 1H), 5.41 (q, 1H), 3.32 (s, 3H), 1.57 (d, 3H).

Example 3

(S)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea

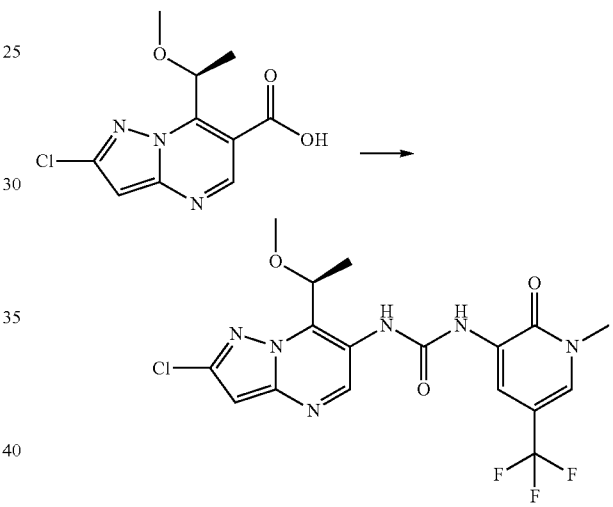

To a solution of (S)-2-chloro-7-(1-methoxyethyl)pyrazolo[1,5-a]pyrimidine-6-carboxylic acid (70 mg, 0.274 mmol) in 1,4-dioxane (5 ml) were added DPPA (0.071 ml, 0.329 mmol) and Et₃N (0.19 ml, 1.37 mmol). The reaction mixture was stirred at RT for 30 min. Then, 3-amino-1-methyl-5-(trifluoromethyl)pyridin-2(1H)-one (52.6 mg, 0.274 mmol) was added and reaction mixture was stirred at 100° C. for 2 h. The mixture was extracted with AcOEt and saturated aqueous NaHCO₃ and phases were separated. The organic layer was dried over Na₂SO₄, filtered and concentrated. The crude material was purified by flash column chromatography on silica gel (cyclohexane/AcOEt: 1/0 to 0/1). The product was then purified again by preparative HPLC (Method A1), fractions were combined, extracted with AcOEt and saturated aqueous NaHCO₃. The organic layer was dried over Na₂SO₄, filtered, evaporated and dried under HV to afford (S)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea. M/z=445-447 [M+H]+, Rt=4.32 min (HPLC Method C1), ¹H NMR (400 MHz, DMSO-d₆) δ ppm: 9.59 (s, 1H), 9.12 (s, 1H), 8.77 (s, 1H), 8.26 (d, 1H), 8.06 (bs, 1H), 6.92 (s, 1H), 5.38 (q, 1H), 3.60 (s, 3H), 3.23 (s, 3H), 1.56 (d, 3H).

Example 4

(R)-1-(6-(2H-1,2,3-triazol-2-yl)-5-(trifluoromethyl)pyridin-3-yl)-3-(2-chloro-7-(1-methoxy-2-methyl-propyl)pyrazolo[1,5-a]pyrimidin-6-yl)urea

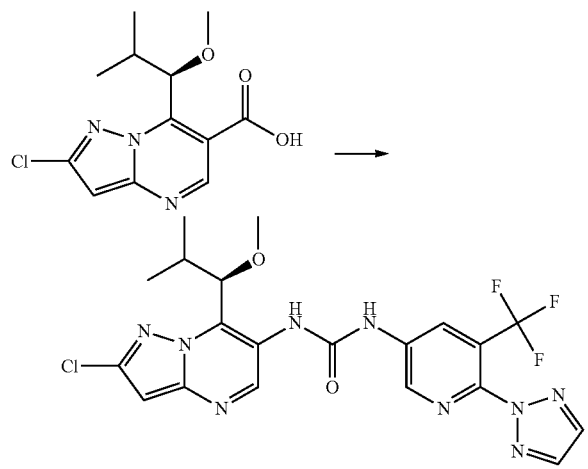

To a solution under argon of (R)-2-chloro-7-(1-methoxy-2-methylpropyl)pyrazolo[1,5-a]pyrimidine-6-carboxylic acid (70 mg, 0.165 mmol) in 1,4-dioxane (8 ml) were added DPPA (0.044 ml, 0.199 mmol) and Et₃N (0.115 ml, 0.827 mmol). The reaction mixture was stirred at RT for 30 min. Then, 6-(2H-1,2,3-triazol-2-yl)-5-(trifluoromethyl)pyridin-3-amine (45.5 mg, 0.199 mmol) was added and reaction mixture was stirred at 100° C. for 16 h. The mixture was cooled to RT, additional diphenyl phosphoryl azide (0.044 ml, 0.199 mmol) and Et₃N (0.115 ml, 0.827 mmol) were added and reaction mixture was stirred at 100° C. for 2.5 h. Aqueous NaHCO₃ was added and the mixture was extracted with AcOEt. The organic layer was washed with water and brine, dried over Na₂SO₄, filtered and concentrated. The crude material was purified by preparative SFC (Method A5) and fractions were lyophilized to afford (R)-1-(6-(2H-1,2,3-triazol-2-yl)-5-(trifluoromethyl)pyridin-3-yl)-3-(2-chloro-7-(1-methoxy-2-methylpropyl)pyrazolo[1,5-a]pyrimidin-6-yl)urea. M/z=510-512 [M+H]+, Rt=5.42 (HPLC Method C1), $^1$H NMR (600 MHz, DMSO-$d_6$) δ ppm: 10.54 (s, 1H), 8.97 (s, 1H), 8.83 (d, 1H), 8.71 (d, 1H), 8.50 (s, 1H), 8.17 (s, 2H), 6.94 (s, 1H), 5.09 (d, 1H), 3.36 (s, 3H), 2.36 (s, 1H), 1.08 (d, 3H), 0.81 (d, 3H).

Example 5

(R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea

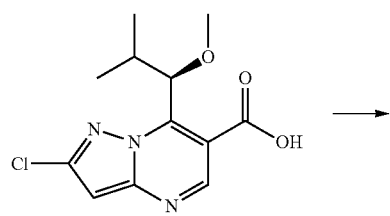

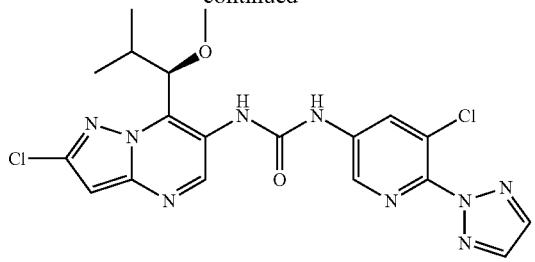

To a solution under argon of (R)-2-chloro-7-(1-methoxy-2-methylpropyl)pyrazolo[1,5-a]pyrimidine-6-carboxylic acid (70 mg, 0.165 mmol) in 1,4-dioxane (8 ml) were added DPPA (0.044 ml, 0.199 mmol) and Et₃N (0.115 ml, 0.827 mmol). The reaction mixture was stirred at RT for 30 min. Then, 5-chloro-6-(2H-1,2,3-triazol-2-yl)pyridin-3-amine (38.8 mg, 0.199 mmol) was added and reaction mixture was stirred at 100° C. for 16 h. The mixture was cooled to RT, diphenyl phosphoryl azide (0.044 ml, 0.199 mmol) and Et₃N (0.115 ml, 0.827 mmol) were added and reaction mixture was stirred at 100° C. for 2.5 h. The mixture was diluted with AcOEt and saturated aqueous NaHCO₃ and phases were separated. The organic layer was washed with water and brine, dried over Na₂SO₄, filtered and concentrated. The crude material was purified by preparative SFC (Method A5) and fractions were lyophilized. The product was purified again by preparative HPLC (Method A2) and fractions were lyophilized to afford (R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea. M/z=476-478 [M+H]+, Rt=4.70 (HPLC Method C1), $^1$H NMR (600 MHz, DMSO-$d_6$) δ ppm: 10.40 (s, 1H), 8.95 (s, 1H), 8.53 (d, 1H), 8.49 (d, 1H), 8.44 (s, 1H), 8.15 (s, 2H), 6.93 (s, 1H), 5.08 (d, 1H), 3.35 (s, 3H), 2.38 (d, 1H), 1.08 (d, 3H), 0.81 (d, 3H).

Example 6

(S)-1-(7-(1-methoxyethyl)-2-methylpyrazolo[1,5-a]pyrimidin-6-yl)-3-(2-(trifluoromethyl)pyridin-4-yl)urea

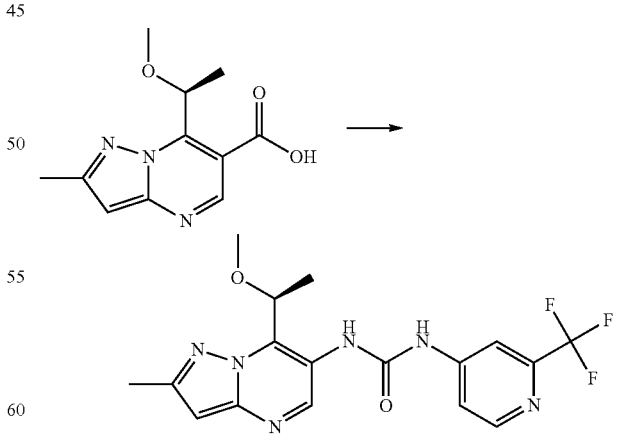

To a solution of (S)-7-(1-methoxyethyl)-2-methylpyrazolo[1,5-a]pyrimidine-6-carboxylic acid (100 mg, 0.425 mmol) in 1,4-dioxane (5 ml) were added DPPA (0.110 ml, 0.510 mmol) and Et₃N (0.296 ml, 2.13 mmol). The reaction mixture was stirred at RT for 30 min. Then, 2-(trifluoromethyl)pyridin-4-amine (138 mg, 0.850 mmol) was added and reaction mixture was stirred overnight at 100° C. AcOEt and saturated aqueous NaHCO₃ was added and the phases were separated. The organic layer was dried over Na₂SO₄, filtered and concentrated. The crude material was purified by flash column chromatography on silica gel (cyclohexane/AcOEt: 1/0 to 0/1). Product was then purified again by preparative HPLC (Method A1), fractions were combined, extracted with AcOEt and saturated aqueous NaHCO₃, the organic layer was dried over Na₂SO₄, filtered, evaporated and dried on HV to afford (S)-1-(7-(1-methoxyethyl)-2-methylpyrazolo[1,5-a]pyrimidin-6-yl)-3-(2-(trifluoromethyl)pyridin-4-yl)urea. M/z=395 [M+H]+, Rt=3.54 min (HPLC Method C1), ¹H NMR (400 MHz, DMSO-d₆) δ ppm: 10.31 (s, 1H), 8.74 (s, 1H), 8.55 (d, 1H), 8.43 (s, 1H), 8.06 (d, 1H), 7.61 (dd, 1H), 6.56 (s, 1H), 5.50 (q, 1H), 3.30 (s, 3H), 2.44 (s, 3H), 1.56 (d, 3H).

Example 7

(S)-1-(2-fluoro-7-(1-methoxyethyl)pyrazolo[1,5-a]pyrimidin-6-yl)-3-(2-(trifluoromethyl)pyridin-4-yl)urea

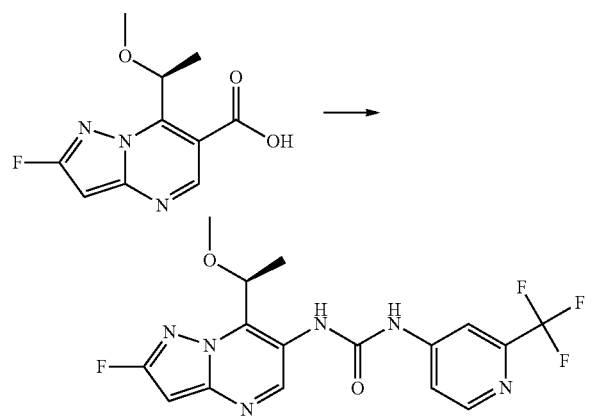

To a solution of (S)-2-fluoro-7-(1-methoxyethyl)pyrazolo[1,5-a]pyrimidine-6-carboxylic acid (140 mg, 0.556 mmol) in 1,4-dioxane (3 ml) under argon were added DPPA (0.144 ml, 0.667 mmol) and Et₃N (0.23 ml, 1.67 mmol). The reaction mixture was stirred at RT for 1 h. Then, 2-(trifluoromethyl)pyridin-4-amine (135 mg, 0.834 mmol) was added and reaction mixture was stirred overnight at 100° C. The mixture was extracted with AcOEt and brine. The organic layer was dried over a phase separator cartridge (IST) and concentrated. The crude material was purified by flash column chromatography on silica gel (cyclohexane/AcOEt: 1/0 to 1/9). Product was dissolved in hot MeOH and after cooling to RT, mixture was centrifuged and the mother liquor was removed to afford a solid. The product was then further purified by preparative HPLC (Method A1), fractions were combined, extracted with DCM and saturated aqueous NaHCO₃, the organic layer was dried over a phase separator cartridge (IST), evaporated and dried on HV to afford (S)-1-(7-(1-methoxyethyl)-2-methylpyrazolo[1,5-a]pyrimidin-6-yl)-3-(2-(trifluoromethyl)pyridin-4-yl)urea. M/z=399 [M+H]+, Rt=3.90 min (HPLC Method C1), ¹H NMR (400 MHz, DMSO-d₆) δ ppm: 10.34 (bs, 1H), 8.87 (s, 1H), 8.56 (d, 1H), 8.53 (bs, 1H), 8.06 (s, 1H), 7.61 (d, 1H), 6.57 (d, 1H), 5.32 (q, 1H), 3.30 (s, 3H), 1.56 (d, 3H).

Example 8

(S)-1-(2-chloro-7-(1-methoxyethyl)pyrazolo[1,5-a]pyrimidin-6-yl)-3-(5-cyanopyridin-3-yl)urea

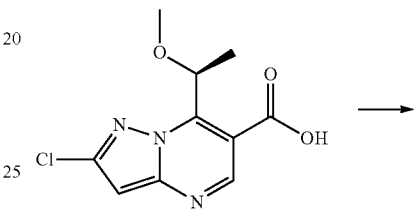

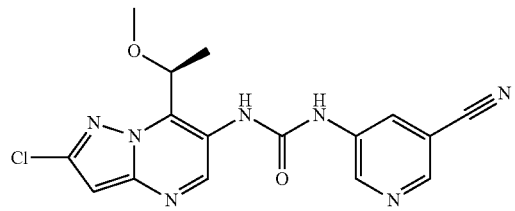

To a solution of (S)-2-chloro-7-(1-methoxyethyl)pyrazolo[1,5-a]pyrimidine-6-carboxylic acid (50 mg, 0.19 mmol) in 1,4-dioxane (0.8 ml) were added DPPA (0.051 ml, 0.228 mmol) and Et₃N (0.079 ml, 0.569 mmol). The reaction mixture was stirred at RT for 30 min. Then, 5-aminonicotinonitrile (67.8 mg, 0.569 mmol) was added and the reaction mixture was stirred at 100° C. for 30 min. The mixture was evaporated and the residue was dissolved in AcOEt. The organic layer was washed with saturated aqueous NaHCO₃, brine, dried over Na₂SO₄, filtered and concentrated. The crude material was purified by flash column chromatography on silica gel (cyclohexane/AcOEt: 1/0 to 0/1) to afford (S)-1-(2-chloro-7-(1-methoxyethyl)pyrazolo[1,5-a]pyrimidin-6-yl)-3-(5-cyanopyridin-3-yl)urea. M/z=372-374 [M+H]+, Rt=3.18 min (HPLC Method C1), ¹H NMR (600 MHz, DMSO-d₆) δ ppm: 10.09 (s, 1H), 8.92 (s, 1H), 8.83 (d, 1H), 8.64 (d, 1H), 8.52 (s, 1H), 8.42 (s, 1H), 6.92 (s, 1H), 5.41 (q, 1H), 3.30 (s, 3H), 1.57 (d, 3H).

In analogy to Example 1 the following examples were prepared:

| Ex | Structure | Name | Analytics |
|---|---|---|---|
| 9 | 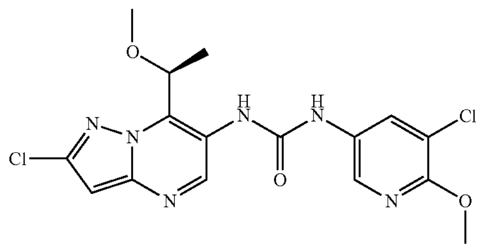 [SMILES: COc1ncc(NC(=O)Nc2cnc3cc(Cl)nn3c2[C@H](C)OC)cc1Cl] | (S)-1-(5-chloro-6-methoxypyridin-3-yl)-3-(2-chloro-7-(1-methoxyethyl)pyrazolo[1,5-a]pyrimidin-6-yl)urea | M/z = 411-413 (M + H)+, Rt = 4.33 min (HPLC Method C1), $^1$H NMR (400 MHz, DMSO-$d_6$) δ ppm: 9.68 (bs, 1H), 8.94 (s, 1H), 8.35 (bs, 1H), 8.15 (d, 1H), 8.12 (d, 1H), 6.91 (s, 1H), 5.41 (q, 1H), 3.91 (s, 3H), 3.31 (s, 3H), 1.57 (d, 3H). |
| 10 | 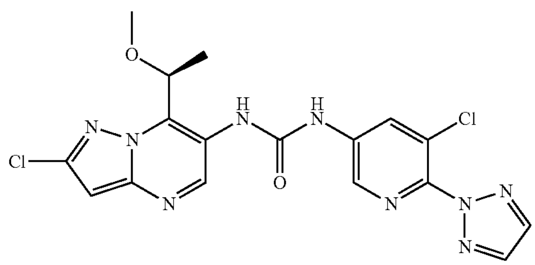 | (S)-1-(5-chloro-6-(2H-1,2,3-triazol-2-yl)pyridin-3-yl)-3-(2-chloro-7-(1-methoxyethyl)pyrazolo[1,5-a]pyrimidin-6-yl)urea | M/z = 448-450 [M + H]+, Rt = 3.99 min (HPLC Method C1), $^1$H NMR (400 MHz, DMSO-$d_6$) δ ppm: 10.33 (bs, 1H), 8.95 (s, 1H), 8.60 (bs, 1H), 8.54 (d, 1H), 8.49 (d, 1H), 8.16 (s, 2H), 6.94 (s, 1H), 5.42 (q, 1H), 3.33 (s, 3H), 1.59 (d, 3H). |
| 11 | 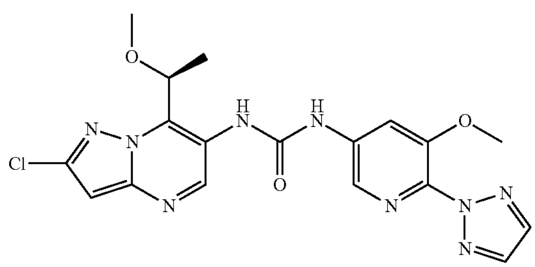 [SMILES: COc1cc(NC(=O)Nc2cnc3cc(Cl)nn3c2[C@H](C)OC)cnc1-n1nccn1] | (S)-1-(2-chloro-7-(1-methoxyethyl)pyrazolo[1,5-a]pyrimidin-6-yl)-3-(5-methoxy-6-(2H-1,2,3-triazol-2-yl)pyridin-3-yl)urea | M/z = 444-446 [M + H]+, Rt = 3.30 min (HPLC Method C1), $^1$H NMR (400 MHz, DMSO-$d_6$) δ ppm: 10.23 (bs, 1H), 8.97 (s, 1H), 8.59 (bs, 1H), 8.19 (s, 1H), 8.04 (s, 2H), 8.03 (s, 1H), 6.94 (s, 1H), 5.44 (q, 1H), 3.80 (s, 3H), 1.59 (d, 3H). |
| 12 | 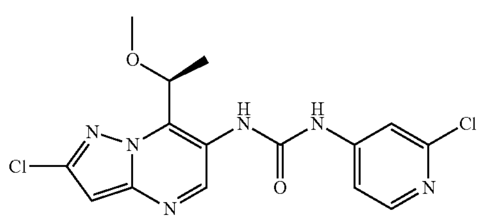 [SMILES: CO[C@@H](C)c1c(NC(=O)Nc2ccnc(Cl)c2)cnc2cc(Cl)nn12] | (S)-1-(2-chloro-7-(1-methoxyethyl)pyrazolo[1,5-a]pyrimidin-6-yl)-3-(2-chloropyridin-4-yl)urea | M/z = 381-383 [M + H]+, Rt = 3.67 min (HPLC Method C1), $^1$H NMR (400 MHz, DMSO-$d_6$) δ ppm: 10.21 (bs, 1H), 8.90 (s, 1H), 8.51 (bs, 1H), 8.21 (d, 1H), 7.69 (d, 1H), 7.33 (dd, 1H), 6.94 (s, 1H), 5.40 (q, 1H), 3.31 (s, 3H), 1.56 (d, 3H). |
| 13 | 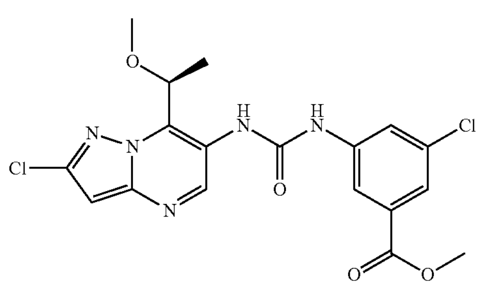 [SMILES: COC(=O)c1cc(Cl)cc(NC(=O)Nc2cnc3cc(Cl)nn3c2[C@H](C)OC)c1] | (S)-methyl 3-chloro-5-(3-(2-chloro-7-(1-methoxyethyl)pyrazolo[1,5-a]pyrimidin-6-yl)ureido)benzoate | M/z = 438-440 [M + H]+, Rt = 2.38 min (HPLC Method C2), $^1$H NMR (400 MHz, DMSO-$d_6$) δ ppm: 10.08 (bs, 1H), 8.94 (s, 1H), 8.42 (bs, 1H), 8.00 (t, 1H), 7.93 (t, 1H), 7.54 (t, 1H), 6.93 (s, 1H), 5.41 (q, 1H), 3.87 (s, 3H), 3.32 (s, 3H), 1.57 (d, 3H). |
| 14 | 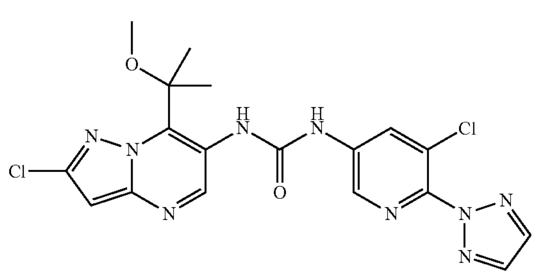 [SMILES: COC(C)(C)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(2-methoxypropan-2-yl)pyrazolo[1,5-a]pyrimidin-6-yl)urea | M/z = 462-464 [M + H]+, Rt = 4.49 min (HPLC Method C1), $^1$H NMR (400 MHz, DMSO-$d_6$) δ ppm: 10.33 (s, 1H), 8.93 (s, 1H), 8.86 (s, 1H), 8.55 (s, 1H), 8.48 (s, 1H), 8.16 (s, 2H), 6.91 (s, 1H), 3.27 (s, 3H), 1.87 (s, 6H). |

| Ex | Structure | Name | Analytics |
|---|---|---|---|
| 15 | 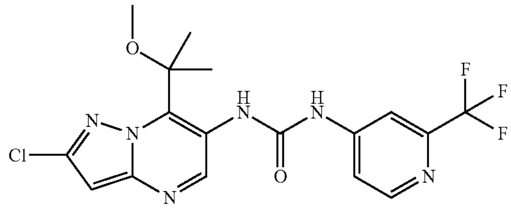 [SMILES: COC(C)(C)c1c(NC(=O)Nc2ccnc(C(F)(F)F)c2)cnc2cc(Cl)nn12] | 1-(2-chloro-7-(2-methoxypropan-2-yl)pyrazolo[1,5-a]pyrimidin-6-yl)-3-(2-(trifluoromethyl)pyridin-4-yl)urea | Mz = 429-431 [M + H]+, Rt = 4.73 min (HPLC Method C1), $^1$H NMR (400 MHz, DMSO-$d_6$) δ ppm: 10.44 (s, 1H), 8.94 (s, 1H), 8.82 (s, 1H), 8.55 (d, 1H), 8.06 (d, 1H), 7.61 (dd, 1H), 6.91 (s, 1H), 3.24 (s, 3H), 1.86 (s, 6H). |
| 16 | 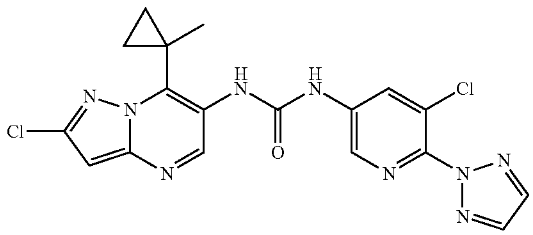 [SMILES: CC1(c2c(NC(=O)Nc3cnc(-n4nccn4)c(Cl)c3)cnc3cc(Cl)nn23)CC1] | 1-(5-chloro-6-(2H-1,2,3-triazol-2-yl)pyridin-3-yl)-3-(2-chloro-7-(1-methylcyclopropyl)pyrazolo[1,5-a]pyrimidin-6-yl)urea | [a], M/z = 444-446 [M + H]+, Rt = 4.13 min (HPLC Method C1), $^1$H NMR (600 MHz, DMSO-$d_6$) δ ppm: 9.85 (bs, 1H), 8.71 (s, 1H), 8.60 (bs, 1H), 8.58 (d, 1H), 8.49 (d, 1H), 8.15 (s, 2H), 6.91 (s, 1H), 1.48 (s, 3H), 1.05 (m, 2H), 0.99 (m, 2H). |
| 17 | 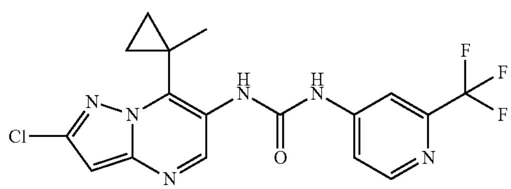 [SMILES: CC1(c2c(NC(=O)Nc3ccnc(C(F)(F)F)c3)cnc3cc(Cl)nn23)CC1] | 1-(2-chloro-7-(1-methylcyclopropyl)pyrazolo[1,5-a]pyrimidin-6-yl)-3-(2-(trifluoromethyl)pyridin-4-yl)urea | [a], M/z = 411-413 [M + H]+, Rt = 4.35 min (HPLC Method C1), $^1$H NMR (600 MHz, DMSO-$d_6$) δ ppm: 9.97 (bs, 1H), 8.68 (s, 1H), 8.58 (bs, 1H), 8.55 (d, 1H), 8.06 (d, 1H), 7.64 (dd, 1H), 6.91 (s, 2H), 1.46 (s, 3H), 1.03 (d, 2H), 0.97 (d, 2H). |
| 18 | 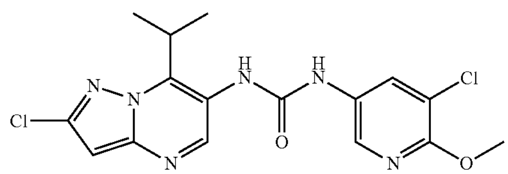 [SMILES: COc1ncc(NC(=O)Nc2cnc3cc(Cl)nn3c2C(C)C)cc1Cl] | 1-(5-chloro-6-methoxypyridin-3-yl)-3-(2-chloro-7-isopropylpyrazolo[1,5-a]pyrimidin-6-yl)urea | M/z = 395-397 [M + H]+, Rt = 4.38 min (HPLC Method C1), $^1$H NMR (400 MHz, DMSO-$d_6$) δ ppm: 9.07 (bs, 1H), 8.52 (s, 2H), 8.14 (d, 1H), 8.09 (d, 1H), 6.90 (s, 1H), 3.89 (s, 3H), 3.78 (m, 1H), 1.47 (d, 6H). |
| 19 | 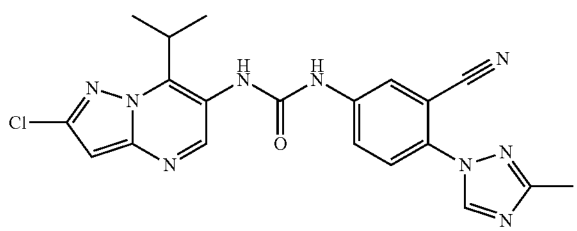 [SMILES: Cc1ncn(-c2ccc(NC(=O)Nc3cnc4cc(Cl)nn4c3C(C)C)cc2C#N)n1] | 1-(2-chloro-7-isopropylpyrazolo[1,5-a]pyrimidin-6-yl)-3-(3-cyano-4-(3-methyl-1H-1,2,4-triazol-1-yl)phenyl)urea | M/z = 436-438 [M + H]+, Rt = 0.93 min (UPLC Method B2), $^1$H NMR (400 MHz, Methanol-$d_4$) δ ppm: 8.85 (s, 1H), 8.45 (s, 1H), 8.12 (d, 1H), 7.86 (dd, 1H), 7.67 (d, 1H), 6.66 (s, 1H), 3.89 (m, 1H), 2.46 (s, 3H), 1.57 (d, 6H). |
| 20 | 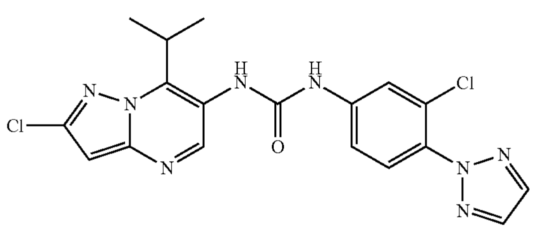 [SMILES: CC(C)c1c(NC(=O)Nc2ccc(-n3nccn3)c(Cl)c2)cnc2cc(Cl)nn12] | 1-(3-chloro-4-(2H-1,2,3-triazol-2-yl)phenyl)-3-(2-chloro-7-isopropylpyrazolo[1,5-a]pyrimidin-6-yl)urea | [a], M/z = 431 [M + H]+, Rt = 4.43 min (HPLC Method C1), $^1$H NMR (400 MHz, DMSO-$d_6$) δ ppm: 9.43 (bs, 1H), 8.55 (s, 1H), 8.51 (s, 1H), 8.11 (s, 2H), 7.92 (d, 1H), 7.56 (m, 2H), 6.91 (s, 1H), 3.80 (m, 1H), 1.49 (d, 6H). |
| 21 | 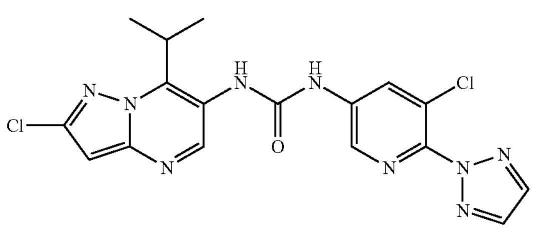 [SMILES: CC(C)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-isopropylpyrazolo[1,5-a]pyrimidin-6-yl)urea | M/z = 432-434 [M + H]+, Rt = 4.31 min (HPLC Method C1), $^1$H NMR (400 MHz, DMSO-$d_6$) δ ppm: 9.71 (bs, 1H), 8.76 (bs, 1H), 8.58 (d, 1H), 8.56 (s, 1H), 8.44 (d, 1H), 8.15 (s, 2H), 6.92 (s, 1H), 3.81 (m, 1H), 1.49 (d, 6H). |

| Ex | Structure | Name | Analytics |
|---|---|---|---|
| 22 | 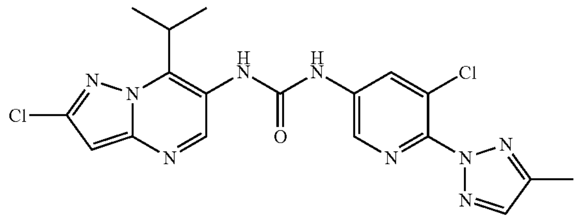 [SMILES: Cc1cnn(-c2ncc(NC(=O)Nc3cnc4cc(Cl)nn4c3C(C)C)cc2Cl)n1] | 1-(5-chloro-6-(4-methyl-2H-1,2,3-triazol-2-yl)pyridin-3-yl)-3-(2-chloro-7-isopropylpyrazolo[1,5-a]pyrimidin-6-yl)urea | M/z = 446 [M + H]+, Rt = 1.08 min (UPLC Method B2), $^1$H NMR (400 MHz, DMSO-$d_6$) δ ppm: 9.67 (bs, 1H), 8.74 (bs, 1H), 8.56 (s, 1H), 8.55 (d, 1H), 8.41 (d, 1H), 7.90 (s, 1H), 6.92 (s, 1H), 3.81 (m, 1H), 2.36 (s, 3H), 1.49 (d, 6H). |
| 23 | 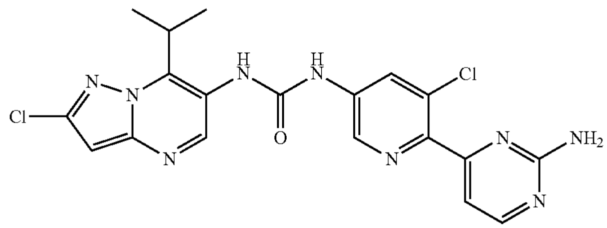 [SMILES: CC(C)c1c(NC(=O)Nc2cnc(-c3ccnc(N)n3)c(Cl)c2)cnc2cc(Cl)nn12] | 1-(4-(2-aminopyrimidin-4-yl)-3-chlorophenyl)-3-(2-chloro-7-isopropylpyrazolo[1,5-a]pyrimidin-6-yl)urea | M/z = 457-459 [M + H]+, Rt = 0.97 min (UPLC Method B2), $^1$H NMR (400 MHz, DMSO-$d_6$) δ ppm: 9.37 (bs, 1H), 8.53 (s, 1H), 8.52 (bs, 1H), 8.28 (d, 1H), 7.80 (d, 1H), 7.53 (d, 1H), 7.45 (dd, 1H), 6.90 (s, 1H), 6.82 (d, 1H), 6.68 (s, 2H), 3.80 (m, 1H), 1.48 (d, 6H). |
| 24 | 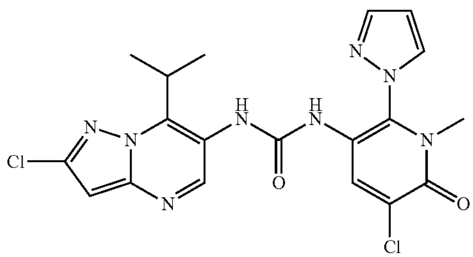 [SMILES: CC(C)c1c(NC(=O)Nc2cc(Cl)c(=O)n(C)c2-n2cccn2)cnc2cc(Cl)nn12] | 1-(5-chloro-1-methyl-6-oxo-2-(1H-pyrazol-1-yl)-1,6-dihydropyridin-3-yl)-3-(2-chloro-7-isopropylpyrazolo[1,5-a]pyrimidin-6-yl)urea | [a], M/z = 461-463 [M + H]+, Rt = 1.22 min (UPLC Method B1), $^1$H NMR (400 MHz, DMSO-$d_6$) δ ppm: 9.00 (bs, 2H), 8.63 (s, 1H), 8.59 (s, 1H), 8.21 (d, 1H), 7.76 (d, 1H), 6.90 (s, 1H), 6.53 (t, 1H), 4.03 (s, 3H), 3.82 (m, 1H), 1.49 (d, 6H). |
| 25 | 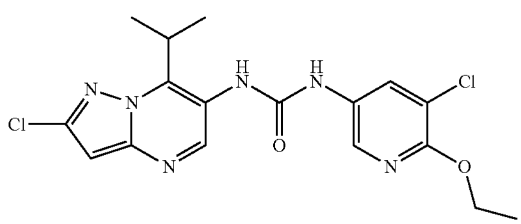 [SMILES: CCOc1ncc(NC(=O)Nc2cnc3cc(Cl)nn3c2C(C)C)cc1Cl] | 1-(5-chloro-6-ethoxypyridin-3-yl)-3-(2-chloro-7-isopropylpyrazolo[1,5-a]pyrimidin-6-yl)urea | [a], M/z = 410-412 [M + H]+, Rt = 4.80 min (HPLC Method C1), $^1$H NMR (400 MHz, DMSO-$d_6$) δ ppm: 8.98 (bs, 1H), 8.52 (s, 1H), 8.44 (bs, 1H), 8.11 (d, 1H), 8.07 (d, 1H), 6.89 (s, 1H), 4.34 (q, 2H), 3.78 (m, 1H), 1.47 (d, 6H), 1.33 (t, 3H). |
| 26 | 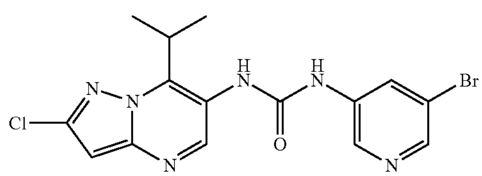 [SMILES: CC(C)c1c(NC(=O)Nc2cncc(Br)c2)cnc2cc(Cl)nn12] | 1-(5-bromopyridin-3-yl)-3-(2-chloro-7-isopropylpyrazolo[1,5-a]pyrimidin-6-yl)urea | [a], M/z = 409-411 [M + H]+, Rt = 3.76 min (HPLC Method C1), $^1$H NMR (400 MHz, DMSO-$d_6$) δ ppm: 9.38 (bs, 1H), 8.62 (bs, 1H), 8.56 (d, 1H), 8.53 (s, 1H), 8.31 (d, 1H), 8.28 (t, 1H), 6.91 (s, 1H), 3.79 (m, 1H), 1.47 (d, 6H). |
| 27 | 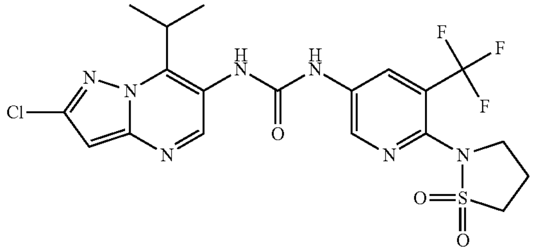 [SMILES: CC(C)c1c(NC(=O)Nc2cnc(N3CCCS3(=O)=O)c(C(F)(F)F)c2)cnc2cc(Cl)nn12] | 1-(2-chloro-7-isopropylpyrazolo[1,5-a]pyrimidin-6-yl)-3-(6-(1,1-dioxidoisothiazolidin-2-yl)-5-(trifluoromethyl)pyridin-3-yl)urea | [a], M/z = 518-520 [M + H]+, Rt = 4.32 min (HPLC Method C1), $^1$H NMR (400 MHz, DMSO-$d_6$) δ ppm: 9.62 (bs, 1H), 8.79 (s, 1H), 8.72 (bs, 1H), 8.54 (d, 1H), 8.42 (s, 1H), 6.92 (s, 1H), 3.80 (m, 4H), 3.27 (m, 3H), 1.49 (d, 6H). |

-continued

| Ex | Structure | Name | Analytics |
|---|---|---|---|
| 28 | 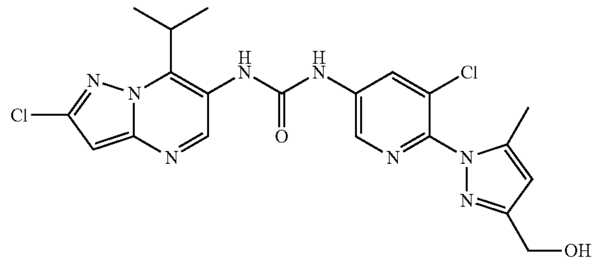 [SMILES: Cc1cc(CO)nn1-c1ncc(NC(=O)Nc2cnc3cc(Cl)nn3c2C(C)C)cc1Cl] | 1-(3-chloro-4-(3-(hydroxymethyl)-5-methyl-1H-pyrazol-1-yl)phenyl)-3-(2-chloro-7-isopropylpyrazolo[1,5-a]pyrimidin-6-yl)urea | M/z = 474-476 [M + H]+, Rt = 0.96 min (HPLC Method B2), $^1$H NMR (600 MHz, DMSO-$d_6$) δ ppm: 9.39 (s, 1H), 8.54 (s, 1H), 8.49 (s, 1H), 7.88 (s, 1H), 7.48 (dd, 1H), 7.37 (d, 1H), 6.90 (s, 1H), 6.18 (s, 1H), 5.05 (bs, 1H), 4.40 (s, 2H), 3.81 (m, 1H), 2.06 (s, 3H), 1.49 (d, 6H). |
| 29 | 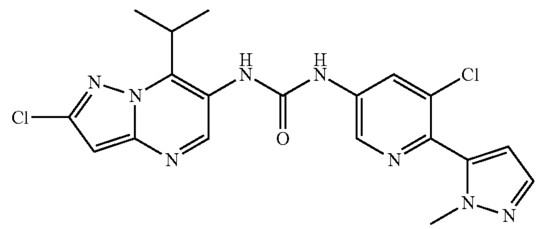 [SMILES: CC(C)c1c(NC(=O)Nc2cnc(-c3ccnn3C)c(Cl)c2)cnc2cc(Cl)nn12] | 1-(5-chloro-6-(1-methyl-1H-pyrazol-5-yl)pyridin-3-yl)-3-(2-chloro-7-isopropylpyrazolo[1,5-a]pyrimidin-6-yl)urea | M/z = 445-447 [M + H]+, Rt = 1.03 min (HPLC Method B2), $^1$H NMR (400 MHz, DMSO-$d_6$) δ ppm: 9.61 (bs, 1H), 8.74 (bs, 1H), 8.68 (d, 1H), 8.54 (s, 1H), 8.30 (d, 1H), 7.51 (d, 1H), 6.91 (s, 1H), 6.57 (d, 1H), 3.81 (m, 4H), 1.48 (d, 6H). |
| 30 | 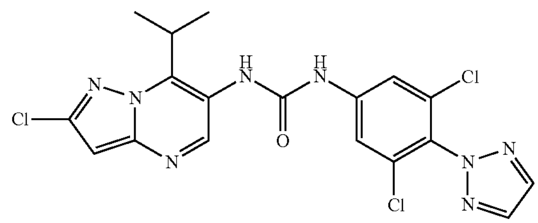 [SMILES: CC(C)c1c(NC(=O)Nc2cc(Cl)c(-n3nccn3)c(Cl)c2)cnc2cc(Cl)nn12] | 1-(2-chloro-7-isopropylpyrazolo[1,5-a]pyrimidin-6-yl)-3-(3,5-dichloro-4-(2H-1,2,3-triazol-2-yl)phenyl)urea | M/z = 465-467 [M + H]+, Rt = 1.16 min (UPLC Method B2), $^1$H NMR (400 MHz, Methanol-$d_4$) δ ppm: 8.45 (s, 1H), 8.01 (s, 2H), 7.78 (s, 2H), 6.67 (s, 1H), 3.89 (hept., 1H), 1.58 (d, 6H). |
| 31 | 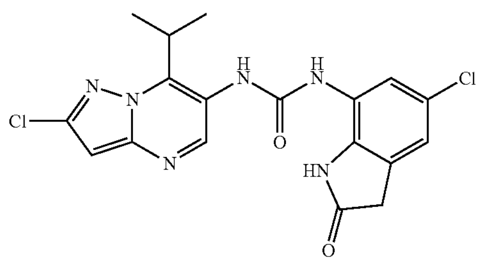 [SMILES: CC(C)c1c(NC(=O)Nc2cc(Cl)cc3c2NC(=O)C3)cnc2cc(Cl)nn12] | 1-(5-chloro-2-oxoindolin-7-yl)-3-(2-chloro-7-isopropylpyrazolo[1,5-a]pyrimidin-6-yl)urea | M/z = 419-421 [M + H]+, Rt = 0.97 min (UPLC Method B2), $^1$H NMR (400 MHz, DMSO-$d_6$) δ ppm: 10.20 (s, 1H), 8.66 (s, 1H), 8.55 (bs, 1H), 7.35 (s, 1H), 7.06 (s, 1H), 6.89 (s, 1H), 3.83 (m, 1H), 3.56 (s, 2H), 1.49 (d, 6H). |
| 32 | 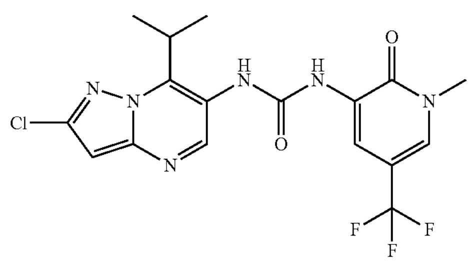 [SMILES: CC(C)c1c(NC(=O)Nc2cc(C(F)(F)F)cn(C)c2=O)cnc2cc(Cl)nn12] | 1-(2-chloro-7-isopropylpyrazolo[1,5-a]pyrimidin-6-yl)-3-(1-methyl-2-oxo-5-(trifluoromethyl)-1,2-dihydropyridin-3-yl)urea | M/z = 429-431 [M + H]+, Rt = 4.54 min (HPLC Method C1), $^1$H NMR (400 MHz, DMSO-$d_6$) δ ppm: 9.17 (s, 1H), 9.15 (s, 1H), 8.58 (s, 1H), 8.20 (d, 1H), 8.05 (d, 1H), 6.89 (s, 1H), 3.81 (m, 1H), 3.60 (s, 3H), 1.47 (d, 6H). |
| 33 | 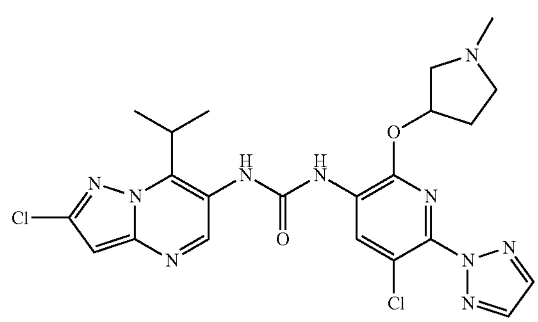 [SMILES: CC(C)c1c(NC(=O)Nc2cc(Cl)c(-n3nccn3)nc2OC2CCN(C)C2)cnc2cc(Cl)nn12] | 1-(5-chloro-2-((1-methylpyrrolidin-3-yl)oxy)-6-(2H-1,2,3-triazol-2-yl)pyridin-3-yl)-3-(2-chloro-7-isopropylpyrazolo[1,5-a]pyrimidin-6-yl)urea | M/z = 531-533 [M + H]+, Rt = 0.85 min (UPLC Method B2), $^1$H NMR (400 MHz, Methanol-d4) δ ppm: 8.70 (s, 1H), 8.43 (s, 1H), 8.00 (bs, 2H), 6.68 (s, 2H), 5.56 (td, 1H), 3.84 (m, 1H), 3.07 (dd, 1H), 2.93 (m, 2H), 2.58 (m, 1H), 2.49 (m, 1H), 2.43 (s, 3H), 2.11 (m, 1H), 1.52 (d, 6H). |

| Ex | Structure | Name | Analytics |
|---|---|---|---|
| 34 | 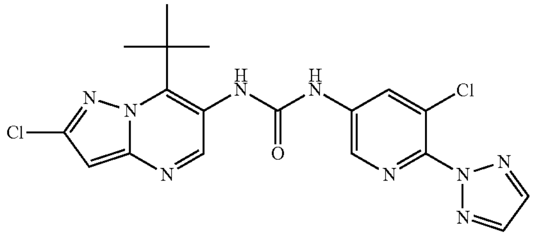 [SMILES: CC(C)(C)c1c(NC(=O)Nc2cnc(-n3nccn3)c(Cl)c2)cnc2cc(Cl)nn12] | 1-(7-(tert-butyl)-2-chloropyrazolo[1,5-a]pyrimidin-6-yl)-3-(5-chloro-6-(2H-1,2,3-triazol-2-yl)pyridin-3-yl)urea | [a], M/z = 446-448 [M + H]+, Rt = 4.71 min (HPLC Method C1), $^1$H NMR (600 MHz, DMSO-$d_6$) δ ppm: 9.88 (bs, 1H), 8.59 (d, 1H), 8.54 (bs, 1H), 8.45 (d, 1H), 8.43 (s, 1H), 8.14 (s, 2H), 6.93 (s, 1H), 1.68 (s, 9H). |
| 35 | 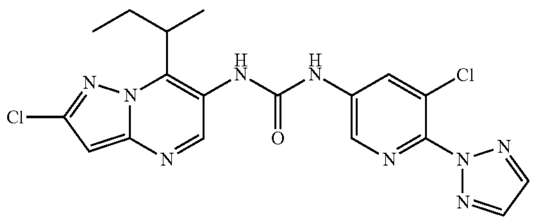 [SMILES: CCC(C)c1c(NC(=O)Nc2cnc(-n3nccn3)c(Cl)c2)cnc2cc(Cl)nn12] | 1-(7-(sec-butyl)-2-chloropyrazolo[1,5-a]pyrimidin-6-yl)-3-(5-chloro-6-(2H-1,2,3-triazol-2-yl)pyridin-3-yl)urea | M/z = 446-448 [M + H]+, Rt = 2.18 min (HPLC Method C2), $^1$H NMR (400 MHz, DMSO-$d_6$) δ ppm: 9.70 (bs, 1H), 8.75 (bs, 1H), 8.58 (d, 1H), 8.45 (d, 1H), 8.15 (s, 2H), 6.92 (s, 1H), 3.58 (m, 1H), 2.12 (m, 1H), 1.88 (m, 1H), 1.47 (d, 3H), 0.78 (t, 3H). |
| 36 | 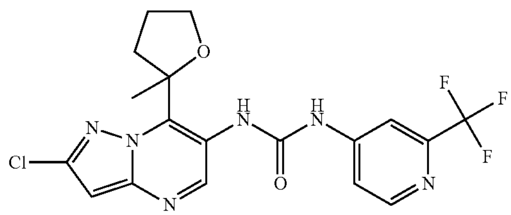 [SMILES: CC1(c2c(NC(=O)Nc3ccnc(C(F)(F)F)c3)cnc3cc(Cl)nn23)CCCO1] | 1-(2-chloro-7-(2-methyltetrahydrofuran-2-yl)pyrazolo[1,5-a]pyrimidin-6-yl)-3-(2-(trifluoromethyl)pyridin-4-yl)urea | [a], M/z = 441-443 [M + H]+, Rt = 5.15 min (HPLC Method C1), $^1$H NMR (600 MHz, DMSO-$d_6$) δ ppm: 10.44 (s, 1H), 9.21 (s, 1H), 8.91 (s, 1H), 8.55 (d, 1H), 8.05 (d, 1H), 7.61 (dd, 1H), 6.89 (s, 1H), 4.09 (td, 1H), 3.79 (td, 1H), 2.52-2.50 (m, 2H), 1.97 (m, 1H), 1.82 (m, 1H), 1.74 (s, 3H). |
| 37 | 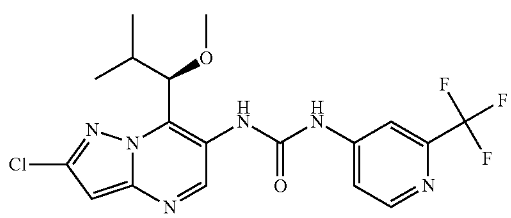 [SMILES: CO[C@@H](c1c(NC(=O)Nc2ccnc(C(F)(F)F)c2)cnc2cc(Cl)nn12)C(C)C] | (R)-1-(2-chloro-7-(1-methoxy-2-methylpropyl)pyrazolo[1,5-a]pyrimidin-6-yl)-3-(2-(trifluoromethyl)pyridin-4-yl)urea | [a], M/z = 443-445 [M + H]+, Rt = 5.30 min (HPLC Method C1), $^1$H NMR (600 MHz, DMSO-$d_6$) δ ppm: 10.46 (s, 1H), 8.92 (s, 1H), 8.57 (d, 1H), 8.43 (s, 1H), 8.06 (d, 1H), 7.61 (dd, 1H), 6.93 (s, 1H), 5.07 (d, 1H), 3.35 (s, 3H), 2.33 (m, 1H), 1.06 (d, 3H), 0.80 (d, 3H). |
| 38 | 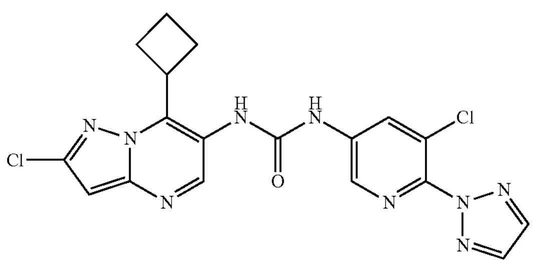 [SMILES: O=C(Nc1cnc(-n2nccn2)c(Cl)c1)Nc1cnc2cc(Cl)nn2c1C1CCC1] | 1-(5-chloro-6-(2H-1,2,3-triazol-2-yl)pyridin-3-yl)-3-(2-chloro-7-cyclobutylpyrazolo[1,5-a]pyrimidin-6-yl)urea | [a], M/z = 444-446 [M + H]+, Rt = 4.37 (HPLC Method C1), $^1$H NMR (600 MHz, DMSO-$d_6$) δ ppm: 9.75 (bs, 1H), 8.72 (s, 1H), 8.58 (d, 1H), 8.52 (s, 1H), 8.44 (d, 1H), 8.14 (s, 2H), 6.90 (s, 1H), 4.12 (m, 1H), 2.66 (m, 2H), 2.42 (m, 2H), 2.06 (m, 1H), 1.86 (q, 1H). |
| 39 | 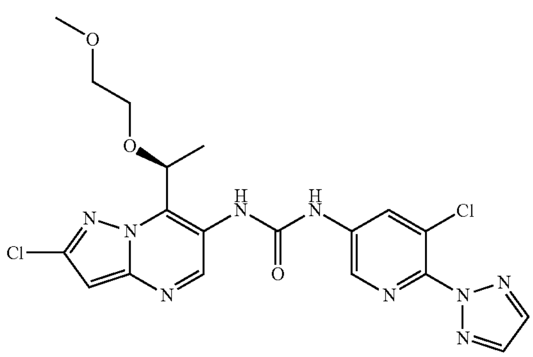 [SMILES: COCCO[C@@H](C)c1c(NC(=O)Nc2cnc(-n3nccn3)c(Cl)c2)cnc2cc(Cl)nn12] | (S)-1-(5-chloro-6-(2H-1,2,3-triazol-2-yl)pyridin-3-yl)-3-(2-chloro-7-(1-(2-methoxyethoxy)ethyl)pyrazolo[1,5-a]pyrimidin-6-yl)urea | M/z = 492-494 [M + H]+, Rt = 4.16 min (HPLC Method C1), $^1$H NMR (400 MHz, DMSO-$d_6$) δ ppm: 10.29 (bs, 1H), 8.97 (s, 1H), 8.61 (bs, 1H), 8.57 (d, 1H), 8.49 (d, 1H), 8.16 (s, 2H), 6.93 (s, 1H), 5.56 (q, 1H), 3.69-3.64 (m, 1H), 3.55-3.50 (m, 1H), 3.48-3.40 (m, 2H), 3.09 (s, 3H), 1.60 (d, 3H). |

| Ex | Structure | Name | Analytics |
|---|---|---|---|
| 40 | 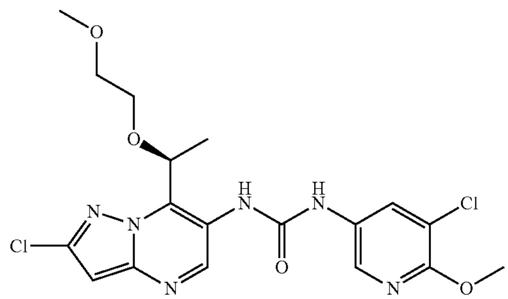 [SMILES: COCCO[C@@H](C)c1c(NC(=O)Nc2cnc(OC)c(Cl)c2)cnc2cc(Cl)nn12] | (S)-1-(5-chloro-6-methoxypyridin-3-yl)-3-(2-chloro-7-(1-(2-methoxyethoxy)ethyl)pyrazolo[1,5-a]pyrimidin-6-yl)urea | M/z = 455-457 [M + H]+, Rt = 4.49 min (HPLC Method C1), $^1$H NMR (400 MHz, DMSO-$d_6$) δ ppm: 9.63 (bs, 1H), 8.95 (s, 1H), 8.34 (bs, 1H), 8.15 (d, 1H), 8.13 (d, 1H), 6.90 (s, 1H), 5.54 (q, 1H), 3.91 (s, 3H), 3.64 (ddd, 1H), 3.52-3.46 (m, 1H), 3.44-3.41 (m, 2H), 3.09 (s, 3H), 1.58 (d, 3H). |
| 41 | 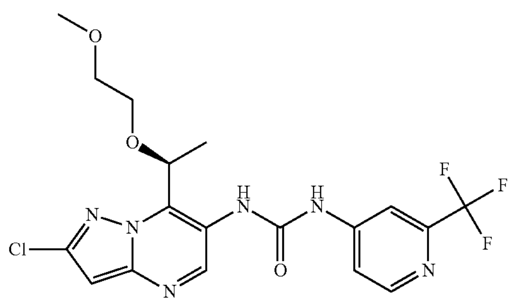 [SMILES: COCCO[C@@H](C)c1c(NC(=O)Nc2ccnc(C(F)(F)F)c2)cnc2cc(Cl)nn12] | (S)-1-(2-chloro-7-(1-(2-methoxyethoxy)ethyl)pyrazolo[1,5-a]pyrimidin-6-yl)-3-(2-(trifluoromethyl)pyridin-4-yl)urea | M/z = 459-461 [M + H]+, Rt = 4.40 min (HPLC Method C1), $^1$H NMR (400 MHz, DMSO-$d_6$) δ ppm: 10.40 (bs, 1H), 8.94 (s, 1H), 8.59 (bs, 1H), 8.56 (d, 1H), 8.08 (d, 1H), 7.63 (dd, 1H), 6.93 (s, 1H), 5.54 (q, 1H), 3.65 (ddd, 1H), 3.51 (ddd, 1H), 3.41 (m, 2H), 3.05 (s, 3H), 1.58 (d, 3H). |
| 42 | 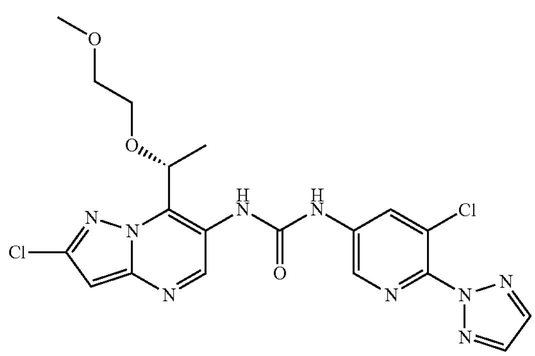 [SMILES: COCCO[C@H](C)c1c(NC(=O)Nc2cnc(-n3nccn3)c(Cl)c2)cnc2cc(Cl)nn12] | (R)-1-(5-chloro-6-(2H-1,2,3-triazol-2-yl)pyridin-3-yl)-3-(2-chloro-7-(1-(2-methoxyethoxy)ethyl)pyrazolo[1,5-a]pyrimidin-6-yl)urea | M/z = 492-494 [M + H]+, Rt = 4.17 min (HPLC Method C1), $^1$H NMR (400 MHz, DMSO-$d_6$) δ ppm: 10.25 (bs, 1H), 8.97 (s, 1H), 8.56 (d, 2H), 8.49 (d, 1H), 8.16 (s, 2H), 6.93 (s, 1H), 5.56 (q, 1H), 3.69-3.64 (ddd, 1H), 3.56-3.51 (ddd, 1H), 3.46-3.42 (m, 2H), 3.09 (s, 3H), 1.60 (d, 3H). |
| 43 | 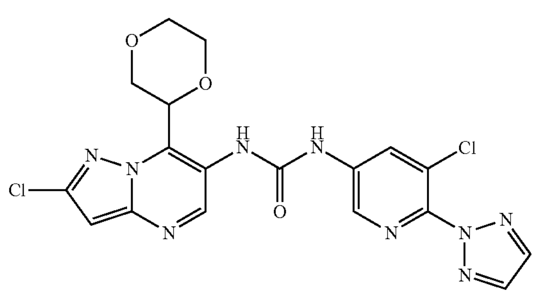 [SMILES: O=C(Nc1cnc(-n2nccn2)c(Cl)c1)Nc1cnc2cc(Cl)nn2c1C1COCCO1] | 1-(5-chloro-6-(2H-1,2,3-triazol-2-yl)pyridin-3-yl)-3-(2-chloro-7-(1,4-dioxan-2-yl)pyrazolo[1,5-a]pyrimidin-6-yl)urea | [a], M/z = 476-478 [M + H]+, Rt = 4.08 min (HPLC Method C1), $^1$H NMR (600 MHz, DMSO-$d_6$) δ ppm: 10.33 (s, 1H), 8.90 (s, 1H), 8.70 (s, 1H), 8.56 (d, 1H), 8.48 (d, 1H), 8.16 (s, 2H), 6.95 (s, 1H), 5.68 (dd, 1H), 4.06 (dd, 1H), 3.98 (dd, 1H), 3.92 (td, 1H), 3.85 (dd, 1H), 3.79-3.75 (m, 2H). |
| 44 | 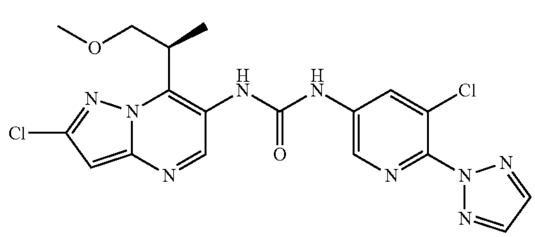 [SMILES: COC[C@@H](C)c1c(NC(=O)Nc2cnc(-n3nccn3)c(Cl)c2)cnc2cc(Cl)nn12] | (S)-1-(5-chloro-6-(2H-1,2,3-triazol-2-yl)pyridin-3-yl)-3-(2-chloro-7-(1-methoxypropan-2-yl)pyrazolo[1,5-a]pyrimidin-6-yl)urea | [b] chiral preparative SFC, Rt = 7.11 min, M/z = 462-464 [M + H]+, Rt = 1.04 min (UPLC Method B1), $^1$H NMR (400 MHz, DMSO-$d_6$) δ ppm: 9.92 (bs, 1H), 8.87 (d, 1H), 8.79 (bs, 1H), 8.69 (d, 1H), 8.61 (s, 1H), 8.17 (s, 2H), 6.94 (s, 1H), 4.07 (t, 1H), 3.99 (q, 1H), 3.73 (dd, 1H), 3.19 (3s, 3H), 1.44 (d, 3H). |

-continued

| Ex | Structure | Name | Analytics |
|---|---|---|---|
| 45 | 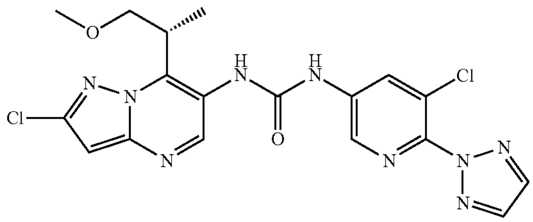 [SMILES: COC[C@H](C)c1c(NC(=O)Nc2cnc(-n3nccn3)c(Cl)c2)cnc2cc(Cl)nn12] | (R)-1-(5-chloro-6-(2H-1,2,3-triazol-2-yl)pyridin-3-yl)-3-(2-chloro-7-(1-methoxypropan-2-yl)pyrazolo[1,5-a]pyrimidin-6-yl)urea | [b] chiral preparative SFC. Rt =13.27 min, M/z = 462-464 [M + H]+, Rt = 1.04 min (HPLC Method B1), $^1$H NMR (400 MHz, DMSO-d$_6$) δ ppm: 9.79 (bs, 1H), 8.73 (s, 1H), 8.60 (s, 1H), 8.58 (d, 1H), 8.45 (d, 1H), 8.15 (s, 2H), 6.93 (s, 1H), 4.07 (t, 1H), 3.98 (q, 1H), 3.73 (dd, 1H), 3.19 (s, 3H), 1.44 (d, 3H). |
| 46 | 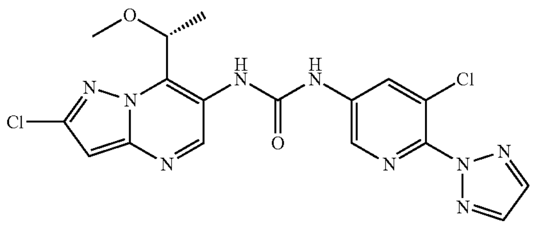 [SMILES: CO[C@H](C)c1c(NC(=O)Nc2cnc(-n3nccn3)c(Cl)c2)cnc2cc(Cl)nn12] | (R)-1-(5-chloro-6-(2H-1,2,3-triazol-2-yl)pyridin-3-yl)-3-(2-chloro-7-(1-methoxyethyl)pyrazolo[1,5-a]pyrimidin-6-yl)urea | M/z = 448-450 [M + H]+, Rt = 4.00 min (HPLC Method C1), $^1$H NMR (400 MHz, DMSO-d$_6$) δ ppm: 10.29 (s, 1H), 8.95 (s, 1H), 8.58 (s, 1H), 8.55 (d, 1H), 8.49 (d, 1H), 8.15 (s, 2H), 6.94 (s, 1H), 5.43 (q, 1H), 3.34 (s, 3H), 1.59 (d, 3H). |
| 47 | 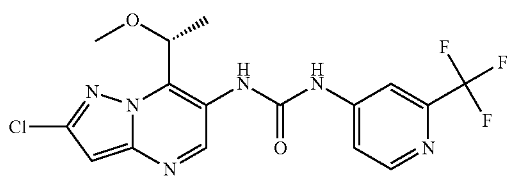 [SMILES: CO[C@H](C)c1c(NC(=O)Nc2ccnc(C(F)(F)F)c2)cnc2cc(Cl)nn12] | (R)-1-(2-chloro-7-(1-methoxyethyl)pyrazolo[1,5-a]pyrimidin-6-yl)-3-(2-(trifluoromethyl)pyridin-4-yl)urea | M/z = 415-417 [M + H]+, Rt = 4.17 min (HPLC Method C1), $^1$H NMR (400 MHz, DMSO-d$_6$) δ ppm: 10.37 (s, 1H), 8.92 (s, 1H), 8.57 (s, 1H), 8.56 (s, 1H), 8.06 (d, 1H), 7.61 (dd, 1H), 6.94 (s, 1H), 5.41 (q, 1H), 3.32 (s, 3H), 1.57 (d, 3H). |
| 48 | 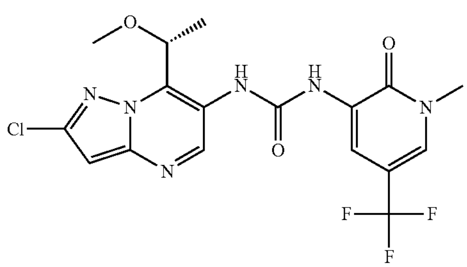 [SMILES: CO[C@H](C)c1c(NC(=O)Nc2cc(C(F)(F)F)cn(C)c2=O)cnc2cc(Cl)nn12] | (R)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea | M/z = 445-447 [M + H]+, Rt = 4.31 min (HPLC Method C1), $^1$H NMR (400 MHz, DMSO-d6) δ pmm: 9.58 (s, 1H), 9.12 (s, 1H), 8.77 (s, 1H), 8.26 (d, 1H), 8.06 (d, 1H), 6.92 (s, 1H), 5.37 (t, 1H), 3.60 (s, 3H), 3.23 (s, 3H), 1.57 (d, 3H). |
| 49 | 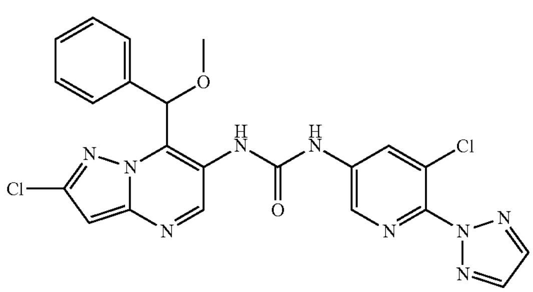 [SMILES: COC(c1ccccc1)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(methoxy(phenyl)methyl)pyrazolo[1,5-a]pyrimidin-6-yl)urea | [a], M/z = 510-512 [M + H]+, Rt = 5.12 min (HPLC Method C1), $^1$H NMR (600 MHz, DMSO-d$_6$) δ 10.38 (s, 1H), 8.97 (s, 1H), 8.66 (s, 1H), 8.51 (d, 1H), 8.42 (d, 1H), 8.16 (s, 2H), 7.50-7.49 (m, 2H), 7.36 (m, 2H), 7.32-7.30 (m, 1H), 6.97 (s, 1H), 6.51 (s, 1H), 3.53 (s, 3H). |
| 50 | 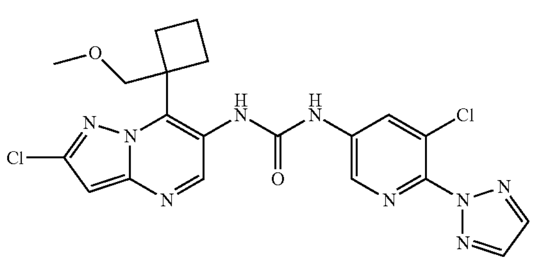 [SMILES: COCC1(c2c(NC(=O)Nc3cnc(-n4nccn4)c(Cl)c3)cnc3cc(Cl)nn23)CCC1] | 1-(5-chloro-6-(2H-1,2,3-triazol-2-yl)pyridin-3-yl)-3-(2-chloro-7-(1-(methoxymethyl)cyclobutyl)pyrazolo[1,5-a]pyrimidin-6-yl)urea | M/z = 488-490 [M + H]+, Rt = 5.07 min (HPLC Method C1), $^1$H NMR (600 MHz, DMSO-d$_6$) δ ppm: 10.35 (bs, 1H), 8.62 (s, 1H), 8.53 (d, 1H), 8.49 (d, 1H), 8.15 (s, 2H), 7.65 (s, 1H), 6.88 (s, 1H), 3.95 (s, 2H), 3.31 (s, 3H), 2.48 (m, 4H), 2.11 (m, 1H), 1.73 (m, 1H). |

| Ex | Structure | Name | Analytics |
|---|---|---|---|
| 51 | 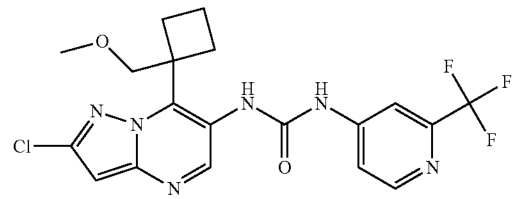 [SMILES: COCC1(c2c(NC(=O)Nc3ccnc(C(F)(F)F)c3)cnc3cc(Cl)nn23)CCC1] | 1-(2-chloro-7-(1-(methoxymethyl)cyclobutyl)pyrazolo[1,5-a]pyrimidin-6-yl)-3-(2-(trifluoromethyl)pyridin-4-yl)urea | [a], M/z = 455-457 [M + H]+, Rt = 5.28 min (HPLC Method C1), $^1$H NMR (600 MHz, DMSO-$d_6$) δ ppm: 10.42 (bs, 1H), 8.59 (s, 1H), 8.56 (d, 1H), 8.06 (d, 1H), 7.63 (s, 1H), 7.61 (dd, 1H), 6.87 (s, 1H), 3.93 (bs, 2H), 3.30 (s, 3H), 2.46 (m, 4H), 2.09 (m, 1H), 1.71 (m, 1H). |
| 52 | 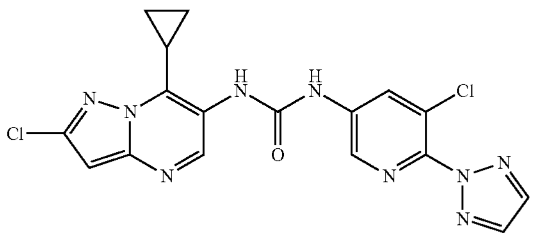 [SMILES: O=C(Nc1cnc(-n2nccn2)c(Cl)c1)Nc1cnc2cc(Cl)nn2c1C1CC1] | 1-(4-chloro-6-(2H-1,2,3-triazol-2-yl)pyridin-3-yl)-3-(2-chloro-7-cyclopropylpyrazolo[1,5-a]pyrimidin-6-yl)urea | [a], M/z = 430-432 [M + H]+, Rt = 3.80 min (HPLC Method C1), $^1$H NMR (600 MHz, DMSO-$d_6$) δ ppm: 9.73 (bs, 1H), 8.73 (s, 1H), 8.58 (d, 1H), 8.54 (s, 1H), 8.45 (d, 1H), 8.14 (s, 2H), 6.88 (s, 1H), 2.40 (tt, 1H), 1.54 (dt, 2H), 1.21 (dt, 2H). |
| 53 | 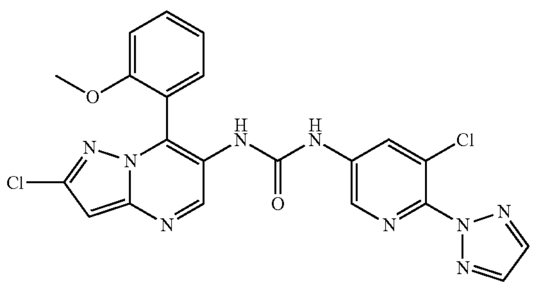 [SMILES: COc1ccccc1-c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(2-methoxyphenyl)pyrazolo[1,5-a]pyrimidin-6-yl)urea | [a], M/z = 496-498 [M + H]+, Rt = 4.26 min (HPLC Method C1), $^1$H NMR (600 MHz, DMSO-$d_6$) δ ppm: 9.63 (bs, 1H), 8.93 (s, 1H), 8.46 (d, 1H), 8.40 (d, 1H), 8.26 (bs, 1H), 8.14 (s, 2H), 7.62 (dt, 1H), 7.51 (dd, 1H), 7.30 (d, 1H), 7.18 (t, 1H), 6.95 (s, 1H), 3.73 (s, 3H). |
| 54 | 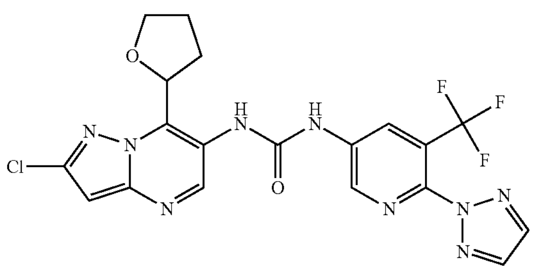 [SMILES: O=C(Nc1cnc(-n2nccn2)c(C(F)(F)F)c1)Nc1cnc2cc(Cl)nn2c1C1CCCO1] | 1-(6-(2H-1,2,3-triazol-2-yl)-5-(trifluoromethyl)pyridin-3-yl)-3-(2-chloro-7-(tetrahydrofuran-2-yl)pyrazolo[1,5-a]pyrimidin-6-yl)urea | [a], M/z = 494-496 [M + H]+, Rt = 4.62 min (HPLC Method C1), $^1$H NMR (600 MHz, DMSO-$d_6$) δ ppm: 10.27 (s, 1H), 8.84 (d, 1H), 8.79 (s, 1H), 8.76 (s, 1H), 8.69 (d, 1H), 8.17 (s, 2H), 6.94 (s, 1H), 5.65 (t, 1H), 4.23 (q, 1H), 3.96 (q, 1H), 2.08 (m, 4H). |
| 55 | 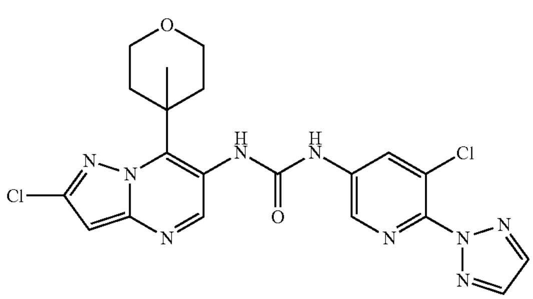 | 1-(5-chloro-6-(2H-1,2,3-triazol-2-yl)pyridin-3-yl)-3-(2-chloro-7-(4-methyltetrahydro-2H-pyran-4-yl)pyrazolo[1,5-a]pyrimidin-6-yl)urea | [a], M/z = 488-490 [M + H]+, Rt = 4.17 min (HPLC Method C1), $^1$H NMR (400 MHz, DMSO-$d_6$) δ ppm: 10.01 (bs, 1H), 8.77 (bs, 1H), 8.58 (d, 1H), 8.47 (s, 1H), 8.45 (d, 1H), 8.14 (s, 2H), 6.95 (s, 1H), 3.71 (t, 2H), 3.55 (s, 2H), 2.29 (m, 4H), 1.71 (s, 3H). |
| 56 | 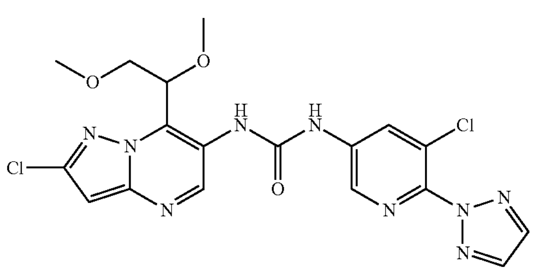 [SMILES: COCC(OC)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea | M/z = 478-480 [M + H]+, Rt = 4.01 min (HPLC Method C1), $^1$H NMR (400 MHz, DMSO-$d_6$) δ ppm: 10.42 (s, 1H), 8.94 (s, 1H), 8.55 (d, 1H), 8.49 (d, 1H), 8.47 (s, 1H), 8.16 (s, 2H), 6.96 (s, 1H), 5.50 (dd, 1H), 3.84 (m, 2H), 3.36 (s, 3H), 3.29 (s, 3H). |

-continued

| Ex | Structure | Name | Analytics |
|---|---|---|---|
| 57 | 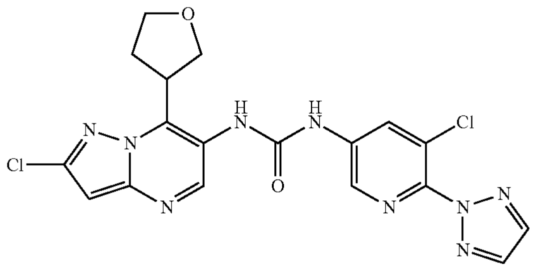 [SMILES: O=C(Nc1cnc(-n2nccn2)c(Cl)c1)Nc1cnc2cc(Cl)nn2c1C1CCOC1] | 1-(5-chloro-6-(2H-1,2,3-triazol-2-yl)pyridin-3-yl)-3-(2-chloro-7-(tetrahydrofuran-3-yl)pyrazolo[1,5-a]pyrimidin-6-yl)urea | [a], M/z = 460-462 [M + H]+, Rt = 3.72 min (HPLC Method C1), $^1$H NMR (400 MHz, DMSO-$d_6$) δ ppm: 9.77 (s, 1H), 8.80 (s, 1H), 8.60 (s, 1H), 8.58 (d, 1H), 8.44 (d, 1H), 8.15 (s, 2H), 6.96 (s, 1H), 4.21 (dd, 1H), 4.16-4.11 (m, 2H), 4.00 (t, 1H), 3.94 (q, 1H), 2.57 (m, 1H), 2.19 (m, 1H) |
| 58 | 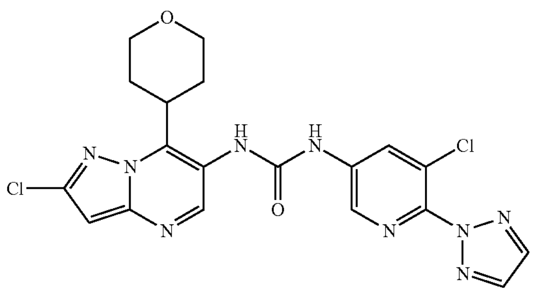 [SMILES: O=C(Nc1cnc(-n2nccn2)c(Cl)c1)Nc1cnc2cc(Cl)nn2c1C1CCOCC1] | 1-(5-chloro-6-(2H-1,2,3-triazol-2-yl)pyridin-3-yl)-3-(2-chloro-7-(tetrahydro-2H-pyran-4-yl)pyrazolo[1,5-a]pyrimidin-6-yl)urea | M/z = 472-474 [M + H]+, Rt = 3.44 min (UPLC Method B7), $^1$H NMR (400 MHz, DMSO-$d_6$) δ ppm: 9.72 (bs, 1H), 8.82 (s, 1H), 8.60 (d, 1H), 8.59 (s, 1H), 8.45 (d, 1H), 8.15 (s, 2H), 6.95 (s, 1H), 4.00 (dd, 2H), 3.76 (ddt, 1H), 3.46 (dd, 2H), 2.69-2.59 (m, 2H), 1.61 (m, 2H). |
| 59 | 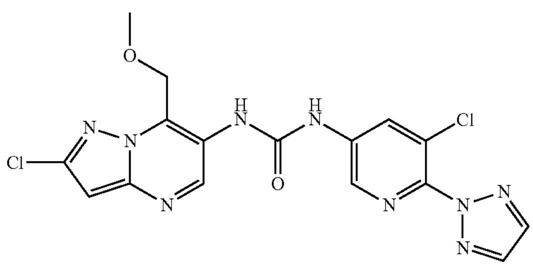 [SMILES: COCc1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(methoxymethyl)pyrazolo[1,5-a]pyrimidin-6-yl)urea | M/z = 434-436 [M + H]+, Rt = 3.66 min (HPLC Method C1), $^1$H NMR (400 MHz, DMSO-$d_6$) δ ppm: 9.97 (bs, 1H), 8.84 (s, 1H), 8.80 (bs, 1H), 8.57 (d, 1H), 8.46 (d, 1H), 8.16 (s, 2H), 6.97 (s, 1H), 4.98 (s, 2H), 3.39 (s, 3H). |
| 60 | 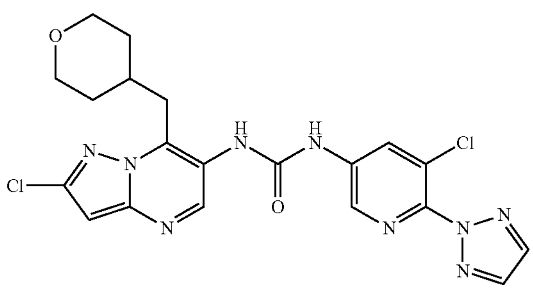 [SMILES: O=C(Nc1cnc(-n2nccn2)c(Cl)c1)Nc1cnc2cc(Cl)nn2c1CC1CCOCC1] | 1-(5-chloro-6-(2H-1,2,3-triazol-2-yl)pyridin-3-yl)-3-(2-chloro-7-((tetrahydro-2H-pyran-4-yl)methyl)pyrazolo[1,5-a]pyrimidin-6-yl)urea | M/z = 488-490 [M + H]+, Rt = 3.87 min (HPLC Method C1), $^1$H NMR (400 MHz, DMSO-$d_6$) δ ppm: 9.75 (bs, 1H), 8.71 (bs, 1H), 8.67 (s, 1H), 8.58 (d, 1H), 8.45 (d, 1H), 8.15 (s, 2H), 6.92 (s, 1H), 3.79 (m, 2H), 3.21 (m, 2H), 3.12 (d, 2H), 2.21 (m, 1H), 1.49 (d, 2H), 1.42-1.36 (m, 2H). |
| 61 | 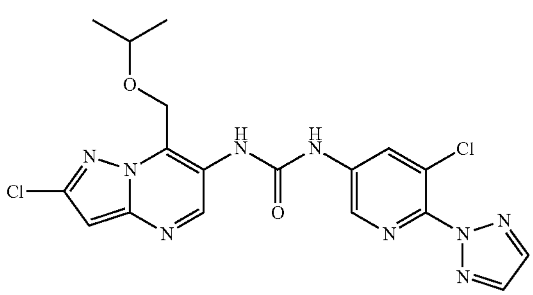 [SMILES: CC(C)OCc1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(isopropoxymethyl)pyraozlo[1,5-a]pyrimidin-6-yl)urea | [a], M/z = 462-464 [M + H]+, Rt = 4.37 min (HPLC Method C1), $^1$H NMR (400 MHz, DMSO-$d_6$) δ ppm: 9.97 (bs, 1H), 8.78 (s, 1H), 8.58 (d, 1H), 8.46 (d, 1H), 8.15 (s, 2H), 6.97 (s, 1H), 5.00 (s, 2H), 3.77 (m, 1H), 1.14 (d, 6H). |
| 62 | 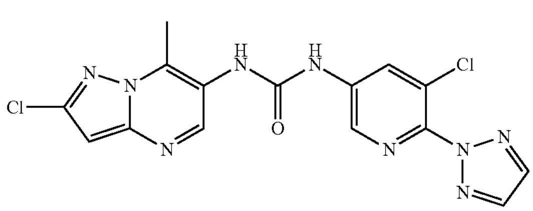 [SMILES: Cc1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-methylpyrazolo[1,5-a]pyrimidin-6-yl)urea | [a], M/z = 404-405 [M + H]+, Rt = 3.39 min (HPLC Method C1), $^1$H NMR (600 MHz, DMSO-$d_6$) δ ppm: 9.72 (bs, 1H), 8.83 (s, 1H), 8.65 (s, 1H), 8.58 (d, 1H), 8.45 (d, 1H), 8.15 (s, 2H), 6.92 (s, 1H), 2.67 (s, 3H). |

| Ex | Structure | Name | Analytics |
|---|---|---|---|
| 63 | 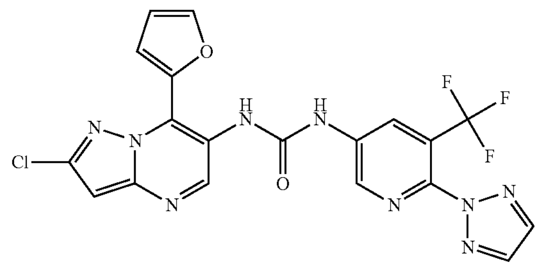 [SMILES: O=C(Nc1cnc(-n2nccn2)c(C(F)(F)F)c1)Nc1cnc2cc(Cl)nn2c1-c1ccco1] | 1-(6-(2H-1,2,3-triazol-2-yl)-5-(trifluoromethyl)pyridin-3-yl)-3-(2-chloro-7-(furan-2-yl)pyrazolo[1,5-a]pyrimidin-6-yl)urea | M/z = 490-492 [M + H]+, Rt = 2.22 min (HPLC Method C2), $^1$H NMR (400 MHz, DMSO-d$_6$) δ ppm: 10.14 (s, 1H), 8.99 (s, 1H), 8.85 (d, 1H), 8.81 (s, 1H), 8.67 (d, 1H), 8.20 (d, 1H), 8.17 (s, 2H), 8.09 (d, 1H), 7.06 (s, 1H), 6.93 (dd, 1H). |
| 64 | 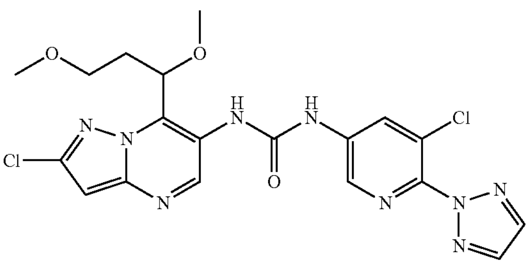 [SMILES: COCCC(OC)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(1,3-dimethoxypropyl)pyrazolo[1,5-a]pyrimidin-6-yl)urea | M/z = 492-494 [M + H]+, Rt = 2.05 min (HPLC Method C2), $^1$H NMR (400 MHz, Methanol-d$_4$) δ ppm: 8.86 (s, 1H), 8.39 (d, 1H), 8.37 (d, 1H), 7.86 (s, 2H), 6.54 s, 1H), 5.45 (dd, 1H), 3.49 (ddd, 1H), 3.39-3.35 (m, 1H), 3.31 (s, 3H), 3.09 (s, 3H), 2.12-2.07 (m, 2H). |
| 65 | 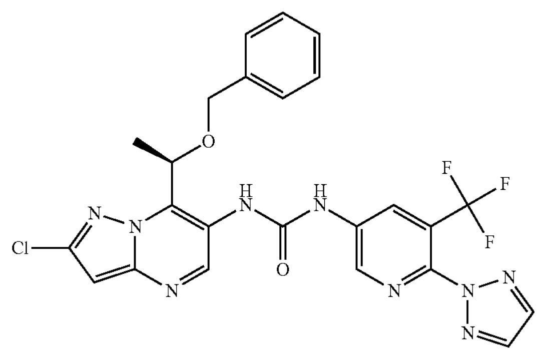 [SMILES: C[C@@H](OCc1ccccc1)c1c(NC(=O)Nc2cnc(-n3nccn3)c(C(F)(F)F)c2)cnc2cc(Cl)nn12] | (R)-1-(6-(2H-1,2,3-triazol-2-yl)-5-(trifluoromethyl)pyridin-3-yl)-3-(7-(1-(benzyloxy)ethyl)-2-chloropyrazolo[1,5-a]pyrimidin-6-yl)urea | M/z = 558-560 [M + H]+, Rt = 1.29 min (UPLC Method B1), $^1$H NMR (400 MHz, DMSO-d$_6$) δ ppm: 10.23 (s, 1H), 8.83 (s, 1H), 8.76 (d, 1H), 8.63 (d, 1H), 8.60 (s, 1H), 8.18 (s, 2H), 7.26 (dd, 2H), 7.13 (dd, 3H), 6.93 (s, 1H), 5.59 (q, 1H), 4.56 (m, 2H), 1.65 (d, 3H). |
| 66 | 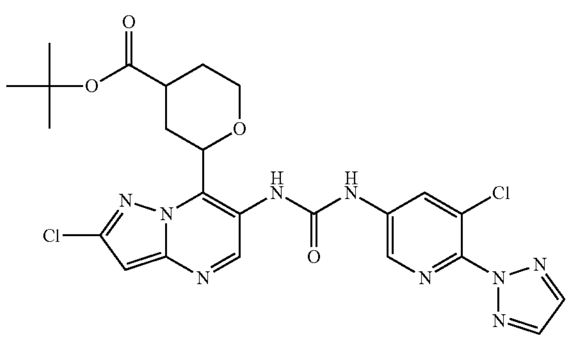 [SMILES: CC(C)(C)OC(=O)C1CCOC(c2c(NC(=O)Nc3cnc(-n4nccn4)c(Cl)c3)cnc3cc(Cl)nn23)C1] | tert-butyl 2-(2-chloro-6-(3-(5-chloro-6-(2H-1,2,3-triazol-2-yl)pyridin-3-yl)ureido)pyrazolo[1,5-a]pyrimidin-7-yl)morpholine-4-carboxylate | M/z = 575-577 [M + H]+, Rt = 2.39 min (HPLC Method C2), $^1$H NMR (400 MHz, DMSO-d$_6$) δ ppm: 8.21 (s, 1H), 7.73 (d, 1H), 7.71 (d, 1H), 7.21 (s, 2H), 5.91 (s, 1H), 4.78 (m, 1H), 3.59 (d, 1H), 3.42 (d, 1H), 3.25 (d, 1H), 2.99 (t, 1H), 2.39 (m, 2H), 0.70 (s, 9H). |
| 67 | 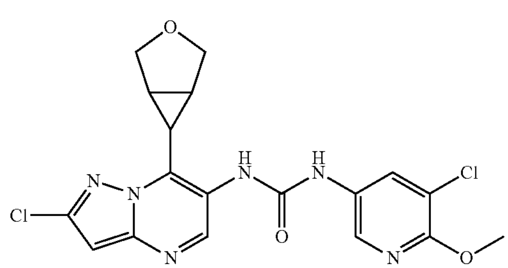 [SMILES: COc1ncc(NC(=O)Nc2cnc3cc(Cl)nn3c2C2C3COCC32)cc1Cl] | 1-(7-(3-oxabicyclo[3.1.0]hexan-6-yl)-2-chloropyrazolo[1,5-a]pyrimidin-6-yl)-3-(5-chloro-6-methoxypyridin-3-yl)urea | [a], M/z = 435-437 [M + H]+, Rt = 3.89 min (HPLC Method C1), $^1$H NMR (400 MHz, DMSO-d$_6$) δ ppm: 9.09 (bs, 1H), 8.55 (s, 1H), 8.51 (s, 1H), 8.15 (d, 1H), 8.09 (d, 1H), 6.88 (s, 1H), 3.93-3.89 (m, 5H), 3.75-3.71 (m, 2H), 2.69 (m, 2H), 2.17 (t, 1H). |

-continued

| Ex | Structure | Name | Analytics |
|---|---|---|---|
| 68 | 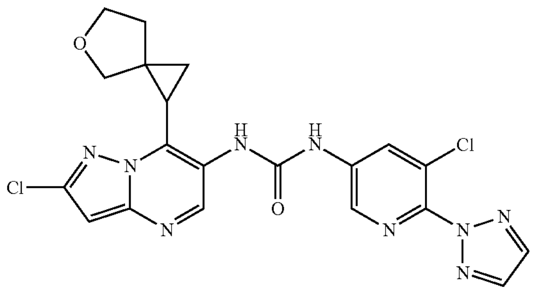 [SMILES: O=C(Nc1cnc(-n2nccn2)c(Cl)c1)Nc1cnc2cc(Cl)nn2c1C1CC12CCOC2] | 1-(5-chloro-6-(2H-1,2,3-triazol-2-yl)pyridin-3-yl)-3-(2-chloro-7-(5-oxaspiro[2.4]heptan-1-yl)pyrazolo[1,5-a]pyrimidin-6-yl)urea | M/z = 486-488 [M + H]+, Rt = 1.83 min (HPLC Method C2), $^1$H NMR (400 MHz, Methanol-d$_4$) δ ppm: diastereoisomeric mixture, 8.57-8.50 (m, 3H), 8.01 (s, 2H), 6.72 (2s, 1H), 4.16-4.10 and 3.85-3.79 (2m, 2H), 3.99-3.85 (m, 2H), 2.59-2.55 and 2.47-2.43 (2m, 1H), 2.36-2.30 and 2.21-2.14 (2m, 1H), 1.72-1.59 (m, 2H), 1.26-1.20 (m, 1H) |
| 69 | 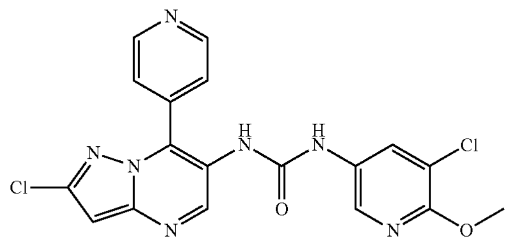 [SMILES: COc1ncc(NC(=O)Nc2cnc3cc(Cl)nn3c2-c2ccncc2)cc1Cl] | 1-(5-chloro-6-methoxypyridin-3-yl)-3-(2-chloro-7-(pyridin-4-yl)pyrazolo[1,5-a]pyrimidin-6-yl)urea | [a], M/z = 430-432 [M + H]+, Rt = 2.81 min (HPLC Method C1), $^1$H NMR (400 MHz, DMSO-d$_6$) δ ppm: 8.95 (bs, 1H), 8.89 (s, 1H), 8.85 (d, 1H), 8.84 (d, 1H), 8.36 (bs, 1H), 8.02 (d, 1H), 7.99 (d, 1H), 7.68 (d, 1H), 7.67 (d, 1H), 7.02 (s, 1H), 3.88 (s, 3H). |
| 70 | 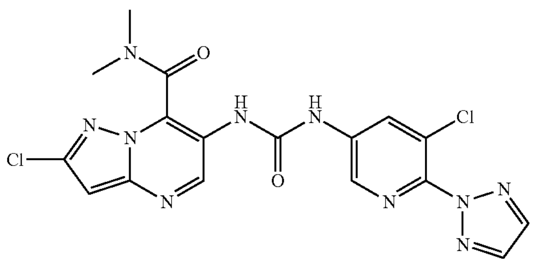 [SMILES: CN(C)C(=O)c1c(NC(=O)Nc2cnc(-n3nccn3)c(Cl)c2)cnc2cc(Cl)nn12] | 2-chloro-6-(3-(5-chloro-6-(2H-1,2,3-triazol-2-yl)pyridin-3-yl)ureido)-N,N-dimethylpyrazolo[1,5-a]pyrimidine-7-carboxamide | M/z = 461-463 [M + H]+, Rt = 1.70 min (HPLC Method C2), $^1$H NMR (400 MHz, Methanol-d$_4$) δ ppm: 8.87 (s, 1H), 8.51 (d, 1H), 8.48 (d, 1H), 8.02 (s, 2H), 6.81 (s, 1H), 3.21 (s, 3H), 2.95 (s, 3H). |
| 71 | 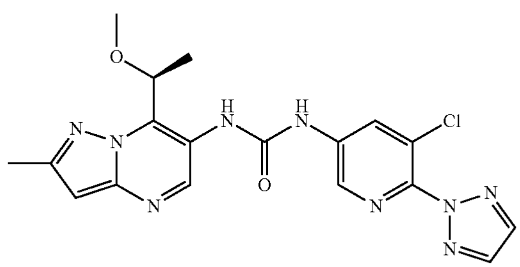 [SMILES: CO[C@@H](C)c1c(NC(=O)Nc2cnc(-n3nccn3)c(Cl)c2)cnc2cc(C)nn12] | (S)-1-(5-chloro-6-(2H-1,2,3-triazol-2-yl)pyridin-3-yl)-3-(7-(1-methoxyethyl)-2-methylpyrazolo[1,5-a]pyrimidin-6-yl)urea | M/z = 428-430 [M + H]+, Rt = 3.25 min (HPLC Method C1), $^1$H NMR (400 MHz, DMSO-d$_6$) δ ppm: 10.25 (s, 1H), 8.77 (s, 1H), 8.54 (d, 1H), 8.49 (d, 1H), 8.47 (s, 1H), 8.15 (s, 2H), 6.57 (s, 1H), 5.51 (q, 1H), 3.32 (s, 3H), 2.44 (s, 3H), 1.58 (d, 3H). |
| 72 | 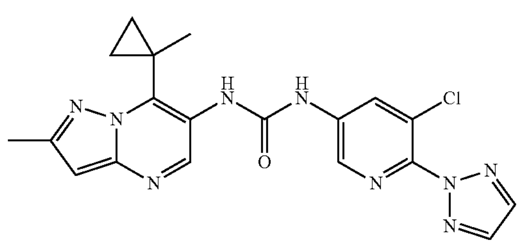 [SMILES: Cc1cc2ncc(NC(=O)Nc3cnc(-n4nccn4)c(Cl)c3)c(C3(C)CC3)n2n1] | 1-(5-chloro-6-(2H-1,2,3-triazol-2-yl)pyridin-3-yl)-3-(2-methyl-7-(1-methylcyclopropyl)pyrazolo[1,5-a]pyrimidin-6-yl)urea | M/z = 424-423 [M + H]+, Rt = 3.41 min (HPLC Method C1), $^1$H NMR (400 MHz, DMSO-d$_6$) δ ppm: 9.81 (bs, 1H), 8.57 (d, 1H), 8.51 (s, 1H), 8.49 (m, 2H), 8.15 (s, 2H), 6.55 (s, 1H), 2.47 (s, 3H), 1.48 (s, 3H), 1.02 (m, 2H), 0.97 (m, 2H). |
| 73 | 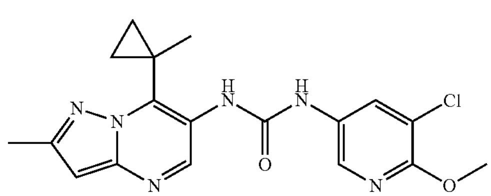 | 1-(5-chloro-6-methoxypyridin-3-yl)-3-(2-methyl-7-(1-methylcyclopropyl)pyrazolo[1,5-a]pyrimidin-6-yl)urea | [a], M/z = 387-388 [M + H]+, Rt = 3.66 min (HPLC Method C1), $^1$H NMR (400 MHz, DMSO-d$_6$) δ ppm: 9.18 (s, 1H), 8.49 (s, 1H), 8.24 (s, 1H), 8.14 (s, 2H), 6.52 (s, 1H), 3.90 (s, 3H), 2.46 (s, 3H), 1.46 (s, 3H), 1.00 (m, 2H), 0.93 (m, 2H). |

| Ex | Structure | Name | Analytics |
|---|---|---|---|
| 74 | 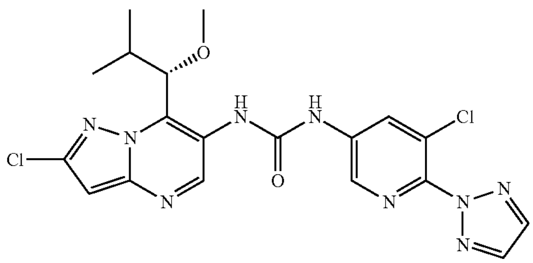 [SMILES: CO[C@H](c1c(NC(=O)Nc2cnc(-n3nccn3)c(Cl)c2)cnc2cc(Cl)nn12)C(C)C] | (S)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea | M/z = 476-478 [M + H]+, Rt = 5.09 min (HPLC Method C1), $^1$H NMR (600 MHz, DMSO-d$_6$) δ ppm: 10.38 (bs, 1H), 8.95 (s, 1H), 8.53 (d, 1H), 8.49 (d, 1H), 8.46 (bs, 1H), 8.15 (s, 2H), 6.93 (s, 1H), 5.08 (d, 1H), 3.36 (s, 3H), 2.36 (m, 1H), 1.08 (d, 3H), 0.81 (d, 3H). |
| 75 | 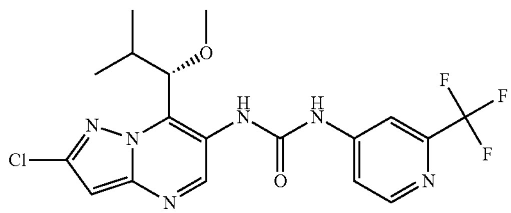 [SMILES: CO[C@H](c1c(NC(=O)Nc2ccnc(C(F)(F)F)c2)cnc2cc(Cl)nn12)C(C)C] | (S)-1-(2-chloro-7-(1-methoxy-2-methylpropyl)pyrazolo[1,5-a]pyrimidin-6-yl)-3-(2-(trifluoromethyl)pyridin-4-yl)urea | M/z = 443-445 [M + H]+, Rt = 5.31 min (HPLC Method C1), $^1$H NMR (600 MHz, DMSO-d$_6$) δ ppm: 10.45 (bs, 1H), 8.92 (s, 1H), 8.56 (d, 1H), 8.42 (bs, 1H), 8.06 (d, 1H), 7.60 (dd, 1H), 6.93 (s, 1H), 5.07 (m, 1H), 3.34 (s, 3H), 2.32 (m, 1H), 1.06 (d, 3H), 0.80 (d, 3H). |
| 76 | 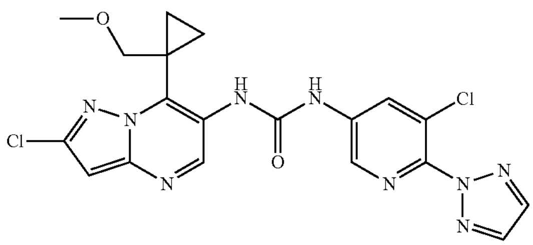 [SMILES: COCC1(c2c(NC(=O)Nc3cnc(-n4nccn4)c(Cl)c3)cnc3cc(Cl)nn23)CC1] | 1-(5-chloro-6-(2H-1,2,3-triazol-2-yl)pyridin-3-yl)-3-(2-chloro-7-(1-(methoxymethyl)cyclopropyl)pyrazolo[1,5-a]pyrimidin-6-yl)urea | M/z = 474-476 [M + H]+, Rt = 4.35 min (HPLC Method C1), $^1$H NMR (400 MHz, DMSO-d$_6$) δ ppm: 10.47 (bs, 1H), 8.81 (s, 1H), 8.55 (d, 1H), 8.49 (d, 1H), 8.26 (bs, 1H), 8.16 (s, 2H), 6.92 (s, 1H), 3.61 (s, 2H), 3.24 (s, 3H), 1.24 (m, 2H), 1.03 (m, 2H). |
| 77 | 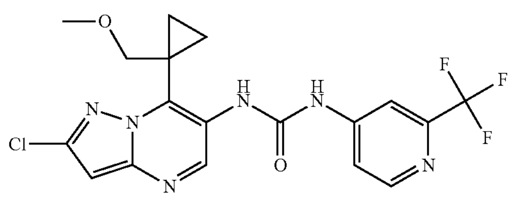 [SMILES: COCC1(c2c(NC(=O)Nc3ccnc(C(F)(F)F)c3)cnc3cc(Cl)nn23)CC1] | 1-(2-chloro-7-(1-(methoxymethyl)cyclopropyl)pyrazolo[1,5-a]pyrimidin-6-yl)-3-(2-(trifluoromethyl)pyridin-4-yl)urea | M/z = 441-443 [M + H]+, Rt = 4.59 min (HPLC Method C1), $^1$H NMR (400 MHz, DMSO-d$_6$) δ ppm: 10.57 (bs, 1H), 8.78 (s, 1H), 8.56 (d, 1H), 8.25 (bs, 1H), 8.07 (d, 1H), 7.62 (d, 1H), 6.92 (s, 1H), 3.60 (s, 2H), 3.23 (s, 3H), 1.24 (m, 2H), 0.99 (m, 2H). |
| 78 | 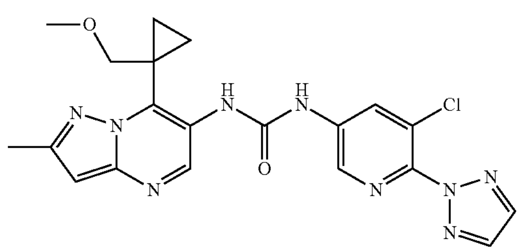 [SMILES: COCC1(c2c(NC(=O)Nc3cnc(-n4nccn4)c(Cl)c3)cnc3cc(C)nn23)CC1] | 1-(5-chloro-6-(2H-1,2,3-triazol-2-yl)pyridin-3-yl)-3-(7-(1-(methoxymethyl)cyclopropyl)-2-methylpyrazolo[1,5-a]pyrimidin-6-yl)urea | M/z = 454-456 [M + H]+, Rt = 3.60 min (HPLC Method C1), $^1$H NMR (400 MHz, DMSO-d$_6$) δ ppm: 10.48 (bs, 1H), 8.61 (s, 1H), 8.55 (s, 1H), 8.49 (s, 1H), 8.29 (bs, 1H), 8.15 (s, 2H), 6.55 (s, 1H), 3.63 (s, 2H), 3.24 (s, 3H), 2.45 (s, 3H), 1.23 (m, 2H), 0.97 (m, 2H). |
| 79 | 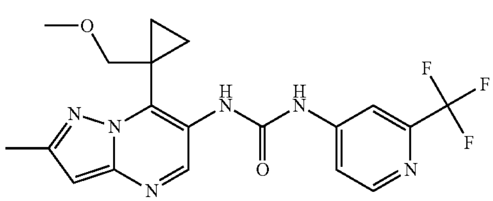 [SMILES: COCC1(c2c(NC(=O)Nc3ccnc(C(F)(F)F)c3)cnc3cc(C)nn23)CC1] | 1-(7-(1-(methoxymethyl)cyclopropyl)-2-methylpyrazolo[1,5-a]pyrimidin-6-yl)-3-(2-(trifluoromethyl)pyridin-4-yl)urea | M/z = 421 [M + H]+, Rt = 3.81 min (HPLC Method C1), $^1$H NMR (400 MHz, DMSO-d$_6$) δ ppm: 10.43 (s, 1H), 8.59 (s, 1H), 8.56 (d, 1H), 8.07 (m, 2H), 7.62 (dd, 1H), 6.55 (s, 1H), 3.61 (bs, 2H), 3.22 (s, 3H), 2.45 (s, 3H), 1.21 (m, 2H), 0.96 (m, 2H). |

| Ex | Structure | Name | Analytics |
|---|---|---|---|
| 80 | 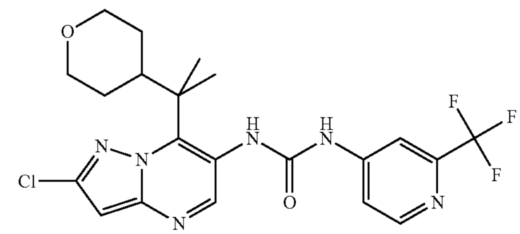 [SMILES: CC(C)(c1c(NC(=O)Nc2ccnc(C(F)(F)F)c2)cnc2cc(Cl)nn12)C1CCOCC1] | 1-(2-chloro-7-(2-(tetrahydro-2H-pyran-4-yl)propan-2-yl)pyrazolo[1,5-a]pyrimidin-6-yl)-3-(2-(trifluoromethyl)pyridin-4-yl)urea | M/z = 483-485 [M + H]+, Rt = 4.74 min (HPLC Method C1), $^1$H NMR (600 MHz, DMSO-$d_6$) δ ppm: 8.53 (m, 2H), 8.39 (s, 1H), 8.06 (s, 1H), 7.64 (s, 1H), 6.91 (s, 1H), 3.82 (m, 2H), 3.16 (m, 3H), 1.60 (s, 6H), 1.42 (m, 2H), 1.25 (m, 2H), one NH not visible. |
| 81 | 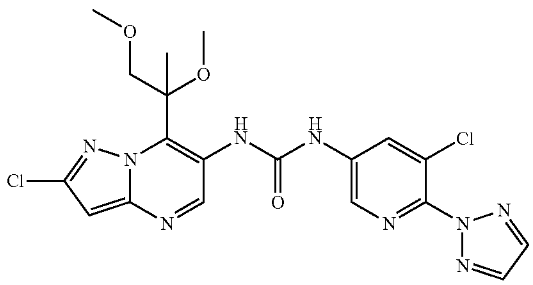 [SMILES: COCC(C)(OC)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(1,2-dimethoxypropan-2-yl)pyrazolo[1,5-a]pyrimidin-6-yl)urea | M/z = 492-494 [M + H]+, Rt = 4.74 min (HPLC Method C1), $^1$H NMR (600 MHz, DMSO-$d_6$) δ ppm: 10.49 (s, 1H), 8.88 (s, 1H), 8.80 (s, 1H), 8.56 (d, 1H), 8.49 (d, 1H), 8.17 (d, 2H), 6.92 (s, 1H), 4.26 (d, 1H), 3.82 (d, 1H), 3.26 (d, 3H), 3.19 (s, 3H), 1.86 (s, 3H). |
| 82 | 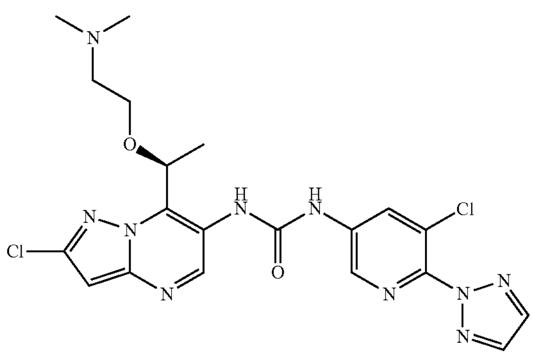 [SMILES: C[C@H](OCCN(C)C)c1c(NC(=O)Nc2cnc(-n3nccn3)c(Cl)c2)cnc2cc(Cl)nn12] | (S)-1-(5-chloro-6-(2H-1,2,3-triazol-2-yl)pyridin-3-yl)-3-(2-chloro-7-(1-(2-(dimethylamino)ethoxy)ethyl)pyrazolo[1,5-a]pyrimidin-6-yl)urea | M/z = 505-507 [M + H]+, Rt = 2.74 min (HPLC Method C1), $^1$H NMR (400 MHz, DMSO-$d_6$) δ ppm: 10.11 (bs, 1H), 8.91 (s, 1H), 8.84 (bs, 1H), 8.58 (d, 1H), 8.48 (d, 1H), 8.16 (s, 2H), 6.95 (s, 1H), 5.54 (q, 1H), 3.65 (m, 1H), 3.50 (m, 1H), 2.13 (bs, 6H), 1.61 (d, 3H). 2 NH signals obscured. |
| 83 | 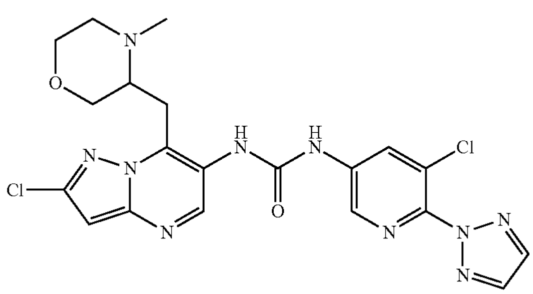 [SMILES: CN1CCOCC1Cc1c(NC(=O)Nc2cnc(-n3nccn3)c(Cl)c2)cnc2cc(Cl)nn12] | 1-(5-chloro-6-(2h-1,2,3-triazol-2-yl)pyridin-3-yl)-3-(2-chloro-7-((4-methylmorpholin-3-yl)methyl)pyrazolo[1,5-a]pyrimidin-6-yl)urea | M/z = 503-505 [M + H]+, Rt = 2.73 min (HPLC Method C1), $^1$H NMR (600 MHz, DMSO-$d_6$) δ ppm: 9.87 (bs, 1H), 8.89 (s, 1H), 8.61 (s, 1H), 8.59 (d, 1H), 8.45 (d, 1H), 8.15 (s, 2H), 6.93 (s, 1H), 3.61 (m, 1H), 3.57-3.50 (m, 2H), 3.40-3.35 (m, 1H), 3.27 (dd, 1H), 3.15 (dd, 1H), 2.77 (m, 1H), 2.71 (dt, 1H), 2.36 (s, 3H), 2.25 (ddd, 1H). |
| 84 | 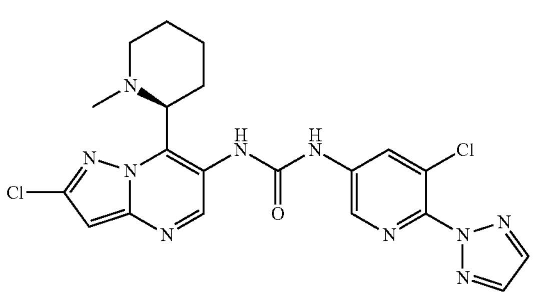 [SMILES: CN1CCCC[C@H]1c1c(NC(=O)Nc2cnc(-n3nccn3)c(Cl)c2)cnc2cc(Cl)nn12] | (S)-1-(5-chloro-6-(2H-1,2,3-triazol-2-yl)pyridin-3-yl)-3-(2-chloro-7-(1-methylpiperidin-2-yl)pyrazolo[1,5-a]pyrimidin-6-yl)urea | M/z = 487-489 [M + H]+, Rt = 1.51 min (HPLC Method C2), $^1$H NMR (400 MHz, DMSO-$d_6$) δ ppm: 10.53 (s, 1H), 10.08 (s, 1H), 9.03 (s, 1H), 8.60 (d, 1H), 8.49 (d, 1H), 8.16 (s, 2H), 6.90 (s, 1H), 4.29 (dd, 1H), 3.14 (d, 1H), 2.20 (m, 1H), 2.16 (s, 3H), 1.84-1.78 (m, 2H), 1.72-1.58 (m, 3H), 1.40 (m, 1H). |

-continued

| Ex | Structure | Name | Analytics |
|---|---|---|---|
| 85 | 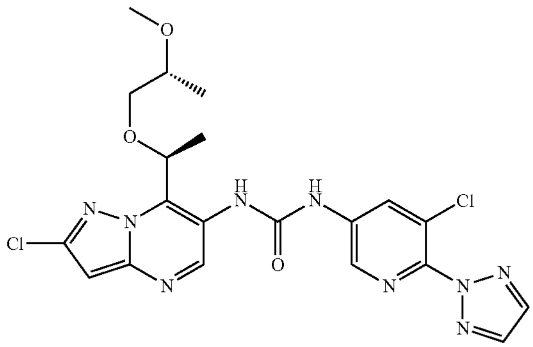 [SMILES: CO[C@H](C)CO[C@@H](C)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-((S)-1-((R)-2-methoxypropoxy)ethyl)pyrazolo[1,5-a]pyrimidin-6-yl)urea | M/z = 506-508 [M + H]+, Rt = 4.46 min (HPLC Method C1), $^1$H NMR (400 MHz, DMSO-$d_6$) δ ppm: 10.21 (s, 1H), 8.98 (s, 1H), 8.59 (s, 1H), 8.56 (d, 1H), 8.49 (d, 1H), 8.16 (s, 2H), 6.94 (s, 1H), 5.56 (q, 1H), 3.52 (dd, 1H), 3.45 (m, 1H), 3.38-3.32 (m, 1H), 3.03 (s, 3H), 1.61 (d, 3H), 0.99 (d, 3H). |
| 86 | 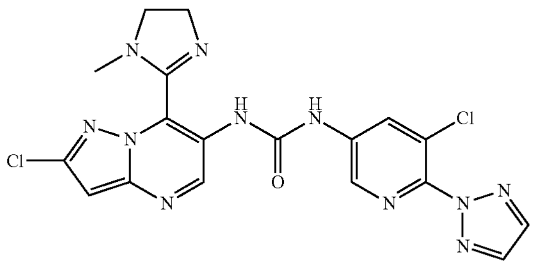 [SMILES: CN1CCN=C1c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-(1-methyl-1H-imidazol-2-yl)pyrazolo[1,5-a]pyrimidin-6-yl)urea | M/z = 470-472 [M + H]+, Rt = 2.64 min (HPLC Method C1), $^1$H NMR (400 MHz, DMSO-$d_6$) δ ppm: 10.22 (bs, 1H), 9.11 (s, 1H), 8.93 (bs, 1H), 8.48 (d, 1H), 8.39 (d, 1H), 8.15 (s, 2H), 7.60 (d, 1H), 7.31 (d, 1H), 7.04 (s, 1H), 3.60 (s, 3H). |
| 87 | 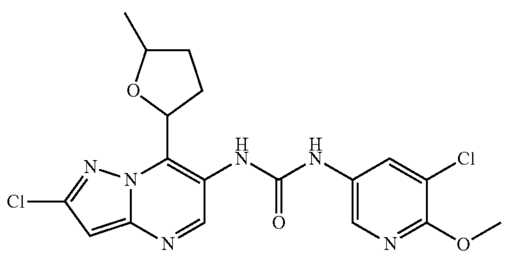 [SMILES: COc1ncc(NC(=O)Nc2cnc3cc(Cl)nn3c2C2CCC(C)O2)cc1Cl] | 1-(5-chloro-6-methoxypyridin-3-yl)-3-(2-chloro-7-(5-methyltetrahydrofuran-2-yl)pyrazolo[1,5-a]pyrimidin-6-yl)urea | M/z = 437-439 [M + H]+, Rt = 4.89 min (HPLC Method C1), $^1$H NMR (600 MHz, DMSO-$d_6$) δ ppm: cis/trans mixture 28:72, major isomer: 9.42 (s, 1H), 8.70 (s, 1H), 8.45 (s, 1H), 8.13 (d, 1H), 8.08 (d, 1H), 6.91 (s, 1H), 5.71 (t, 1H), 4.54 (dt, 1H), 3.90 (s, 3H), 2.53 (m, 1H), 2.23-2.08 (m, 2H), 1.68 (m, 1H), 1.28 (d, 3H). |
| 88 | 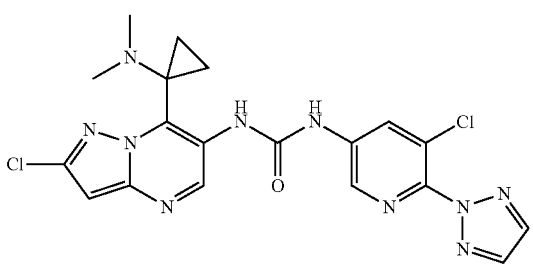 [SMILES: CN(C)C1(c2c(NC(=O)Nc3cnc(-n4nccn4)c(Cl)c3)cnc3cc(Cl)nn23)CC1] | 1-(5-chloro-6-(2H-1,2,3-triazol-2-yl)pyridin-3-yl)-3-(2-chloro-7-(1-(dimethylamino)cyclopropyl)pyrazolo[1,5-a]pyrimidin-6-yl)urea | M/z = 473-475 [M + H]+, Rt = 0.93 min (UPLC Method B2), $^1$H NMR (400 MHz, Methanol-$d_4$) δ ppm: 8.73 (s, 1H), 8.52 (dd, 2H), 8.02 (s, 2H), 6.70 (s, 1H), 2.42 (s, 6H), 1.39 (m, 2H), 1.24 (m, 2H). |
| 89 | 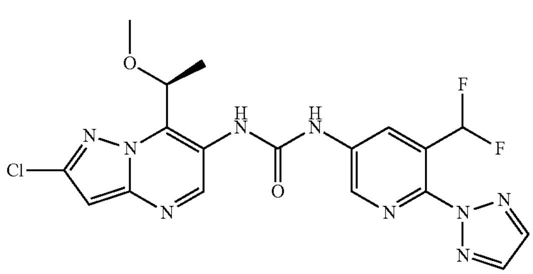 [SMILES: CO[C@@H](C)c1c(NC(=O)Nc2cnc(-n3nccn3)c(C(F)F)c2)cnc2cc(Cl)nn12] | (S)-1-(2-chloro-7-(1-methoxyethyl)pyrazolo[1,5-a]pyrimidin-6-yl)-3-(5-(difluoromethyl)-6-(2H-1,2,3-triazol-2-yl)pyridin-3-yl)urea | M/z = 464-466 [M + H]+, Rt = 1.09 min (HPLC Method C1), $^1$H NMR (400 MHz, DMSO-$d_6$) δ ppm: 10.31 (bs, 1H), 8.98 (s, 1H), 8.73 (d, 1H), 8.60 (d, 1H), 8.56 (bs, 1H), 8.20 (s, 2H), 7.30 (t, 1H), 6.94 (s, 1H), 5.43 (q, 1H), 3.34 (s, 3H), 1.59 (d, 3H). |

-continued

| Ex | Structure | Name | Analytics |
|---|---|---|---|
| 90 | 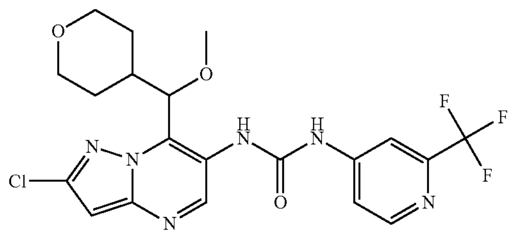 [SMILES: COC(c1c(NC(=O)Nc2ccnc(C(F)(F)F)c2)cnc2cc(Cl)nn12)C1CCOCC1] | 1-(2-chloro-7-(methoxy(tetrahydro-2H-pyran-4-yl)methyl)pyrazolo[1,5-a]pyrimidin-6-yl)-3-(2-(trifluoromethyl)pyridin-4-yl)urea | M/z = 485-487 [M + H]+, Rt = 4.51 min (HPLC Method C1), $^1$H NMR (400 MHz, DMSO-$d_6$) δ ppm: 10.43 (bs, 1H), 8.94 (s, 1H), 8.57 (d, 1H), 8.46 (s, 1H), 8.06 (s, 1H), 7.62 (d, 1H), 6.95 (s, 1H), 5.17 (m, 1H), 3.85 (d, 1H), 3.76 (d, 1H), 3.35 (s, 3H), 3.20 (m, 2H), 2.26 (m, 1H), 1.73 (m, 1H), 1.49 (m, 2H), 1.13 (m, 1H). |
| 91 | 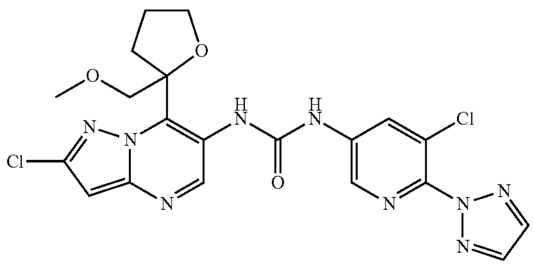 [SMILES: COCC1(c2c(NC(=O)Nc3cnc(-n4nccn4)c(Cl)c3)cnc3cc(Cl)nn23)CCCO1] | 1-(5-chloro-6-(2H-1,2,3-triazol-2-yl)pyridin-3-yl)-3-(2-chloro-7-(2-(methoxymethyl)tetrahydrofuran-2-yl)pyrazolo[1,5-a]pyrimidin-6-yl)urea | M/z = 504-506 [M + H]+, Rt = 4.73 min (HPLC Method C1), $^1$H NMR (400 MHz, DMSO-$d_6$) δ ppm: 10.55 (bs, 1H), 9.19 (s, 1H), 8.98 (d, 1H), 8.54 (m, 1H), 8.47 (m, 1H), 8.16 (m, 2H), 6.90 (s, 1H), 4.35 (dd, 1H), 4.10 (m, 1H), 3.86 (m, 1H), 3.61 (dd, 1H), 3.18 (s, 3H), 2.40 (m, 2H), 1.92 (m, 1H), 1.80 (m, 1H). |
| 92 | 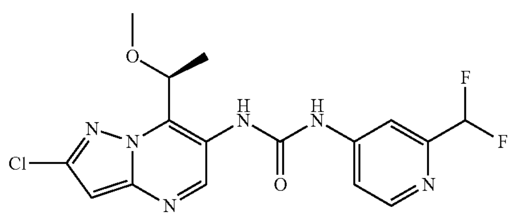 [SMILES: CO[C@@H](C)c1c(NC(=O)Nc2ccnc(C(F)F)c2)cnc2cc(Cl)nn12] | (S)-1-(2-chloro-7-(1-methoxyethyl)pyrazolo[1,5-a]pyrimidin-6-yl)-3-(2-(difluoromethyl)pyridin-4-yl)urea | M/z = 397-399 [M + H]+, Rt = 3.12 min (HPLC Method C1), $^1$H NMR (400 MHz, DMSO-$d_6$) δ ppm: 10.28 (bs, 1H), 8.92 (s, 1H), 8.53 (bs, 1H), 8.48 (d, 1H, 7.88 (s, 1H), 7.52 (d, 1H), 6.94 (s, 1H), 6.89 (t, 1H), 5.41 (m, 1H), 1.57 (d, 3H), OCH3 signal obscured by water. |
| 93 | 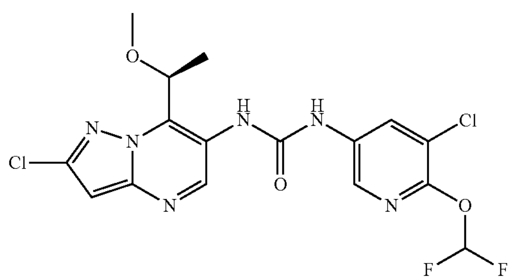 [SMILES: CO[C@@H](C)c1c(NC(=O)Nc2cnc(OC(F)F)c(Cl)c2)cnc2cc(Cl)nn12] | (S)-1-(5-chloro-6-(difluoromethoxy)pyridin-3-yl)-3-(2-chloro-7-(1-methoxyethyl)pyrazolo[1,5-a]pyrimidin-6-yl)urea | M/z = 447-449 [M + H]+, Rt = 4.95 min (HPLC Method C1), $^1$H NMR (400 MHz, DMSO-$d_6$) δ ppm: 9.93 (bs, 1H), 8.92 (s, 1H), 8.46 (bs, 1H), 8.31 (s, 1H), 8.22 (s, 1H), 7.69 (t, 1H), 6.92 (s, 1H), 5.40 (q, 1H), 1.57 (d, 3H), OCH3 signal obscured by water. |
| 94 | 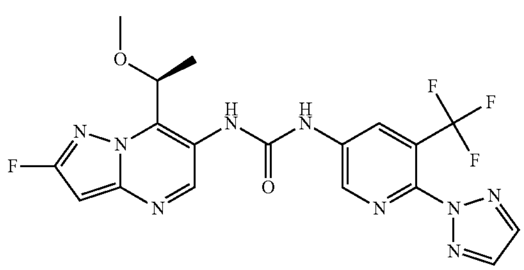 [SMILES: CO[C@@H](C)c1c(NC(=O)Nc2cnc(-n3nccn3)c(C(F)(F)F)c2)cnc2cc(F)nn12] | (S)-1-(6-(2H-1,2,3-triazol-2-yl)-5-(trifluoromethyl)pyridin-3-yl)-3-(2-fluoro-7-(1-methoxyethyl)pyrazolo[1,5-a]pyrimidin-6-yl)urea | [a] M/z = 466 [M + H]+, Rt = 4.09 min (HPLC Method C1), $^1$H NMR (400 MHz, DMSO-$d_6$) δ ppm: 10.41 (bs, 1H), 8.92 (s, 1H), 8.83 (s, 1H), 8.71 (s, 1H), 8.62 (bs, 1H), 8.17 (s, 2H), 6.57 (d, 1H), 5.35 (q, 1H), 3.31 (s, 3H), 1.59 (d, 3H). |
| 95 | 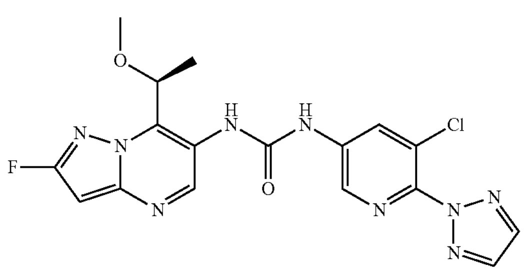 [SMILES: CO[C@@H](C)c1c(NC(=O)Nc2cnc(-n3nccn3)c(Cl)c2)cnc2cc(F)nn12] | (S)-1-(5-chloro-6-(2H-1,2,3-triazol-2-yl)pyridin-3-yl)-3-(2-fluoro-7-(1-methoxyethyl)pyrazolo[1,5-a]pyrimidin-6-yl)urea | [a] M/z = 432-434 [M + H]+, Rt = 3.67 min (HPLC Method C1), $^1$H NMR (400 MHz, DMSO-$d_6$) δ ppm: 10.26 (bs, 1H), 8.90 (s, 1H), 8.60 (bs, 1H), 8.54 (s, 1H), 8.48 (s, 1H), 8.15 (s, 2H), 6.56 (d, 1H), 5.34 (q, 1H), 1.59 (d, 3H), OCH3 signal obscured by water. |

| Ex | Structure | Name | Analytics |
|---|---|---|---|
| 96 | 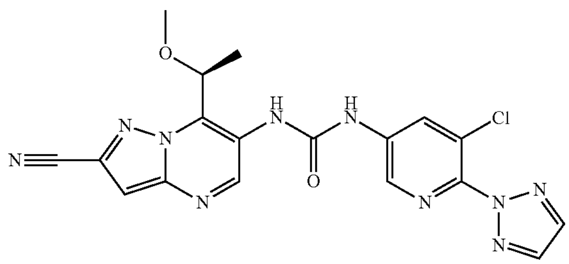 [SMILES: CO[C@@H](C)c1c(NC(=O)Nc2cnc(-n3nccn3)c(Cl)c2)cnc2cc(C#N)nn12] | (S)-1-(5-chloro-6-(2H-1,2,3-tirazol-2-yl)pyridin-3-yl)-3-(2-cyano-7-(1-methoxyethyl)pyrazolo[1,5-a]pyrimidin-6-yl)urea | M/z = 439-441 [M + H]+, Rt = 4.05 min (HPLC Method C1), $^1$H NMR (400 MHz, DMSO-d$_6$) δ ppm: 10.43 (bs, 1H), 9.18 (s, 1H), 8.75 (bs, 1H), 8.55 (s, 1H), 8.49 (s, 1H), 8.16 (s, 2H), 7.60 (s, 1H), 5.49 (q, 1H), 3.36 (s, 3H), 1.61 (d, 3H). |
| 97 | 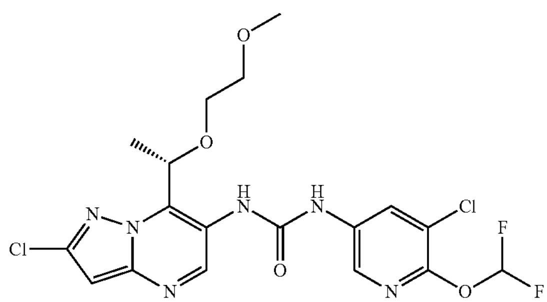 [SMILES: COCCO[C@@H](C)c1c(NC(=O)Nc2cnc(OC(F)F)c(Cl)c2)cnc2cc(Cl)nn12] | (S)-1-(5-chloro-6-(difluoromethoxy)pyridin-3-yl)-3-(2-chloro-7-(1-(2-methoxyethoxy)ethyl)pyrazolo[1,5-a]pyrimidin-6-yl)urea | M/z = 491-493 [M + H]+, Rt = 5.08 min (HPLC Method C1), $^1$H NMR (400 MHz, DMSO-d$_6$) δ ppm: 9.89 (bs, 1H), 8.94 (s, 1H), 8.46 (bs, 1H), 8.32 (s, 1H), 8.23 (s, 1H), 7.66 (t, 1H), 6.91 (s, 1H), 5.54 (q, 1H), 3.64 (m, 1H), 3.51 (m, 1H), 3.42 (m, 2H), 3.09 (s, 3H), 1.58 (d, 3H). |
| 98 | 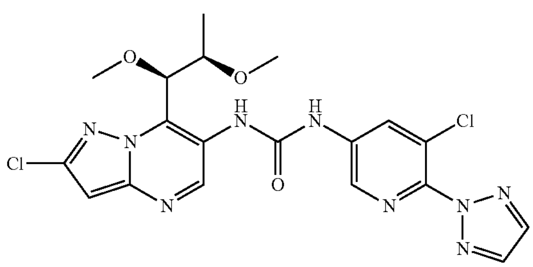 [SMILES: CO[C@H](c1c(NC(=O)Nc2cnc(-n3nccn3)c(Cl)c2)cnc2cc(Cl)nn12)[C@@H](C)OC] | 1-(5-chloro-6-(2H-1,2,3-triazol-2-yl)pyridin-3-yl)-3-(2-chloro-7-((1R,2R)-1,2-dimethoxypropyl)pyrazolo[1,5-a]pyrimidin-6-yl)urea | M/z = 492-494 [M + H]+, Rt = 4.32 min (HPLC Method C1), $^1$H NMR (400 MHz, DMSO-d$_6$) δ ppm: 10.53 (bs, 1H), 8.93 (s, 1H), 8.56 (s, 1H), 8.50 (s, 1H), 8.40 (bs, 1H), 8.15 (s, 2H), 6.96 (s, 1H), 5.28 (s, 1H), 3.87 (m, 1H), 3.22 (s, 3H), 1.24 (d, 3H), one OCH3 signal obscured by water. |
| 99 | 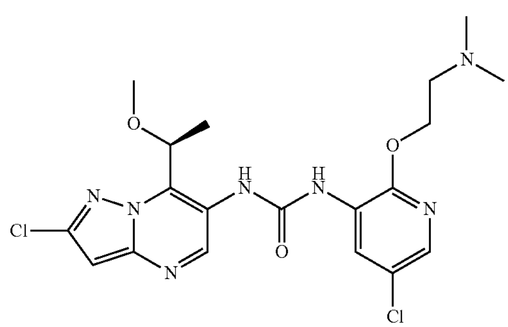 [SMILES: CO[C@@H](C)c1c(NC(=O)Nc2cc(Cl)cnc2OCCN(C)C)cnc2cc(Cl)nn12] | (S)-1-(5-chloro-2-(2-(dimethylamino)ethoxy)pyridin-3-yl)-3-(2-chloro-7-(1-methoxyethyl)pyrazolo[1,5-a]pyrimidin-6-yl)urea | M/z = 468-470 [M + H]+, Rt = 0.83 min (UPLC Method B2), $^1$H NMR (400 MHz, CDCl$_3$) δ ppm: 9.64 (s, 1H), 9.17 (bs, 1H), 8.61 (d, 1H), 8.46 (bs, 1H), 7.67 (d, 1H), 6.62 (s, 1H), 5.62 (q, 1H), 4.45 (m, 2H), 3.41 (s, 3H), 2.93 (bs, 2H), 2.48 (bs, 6H), 1.65 (d, 3H). |
| 100 | 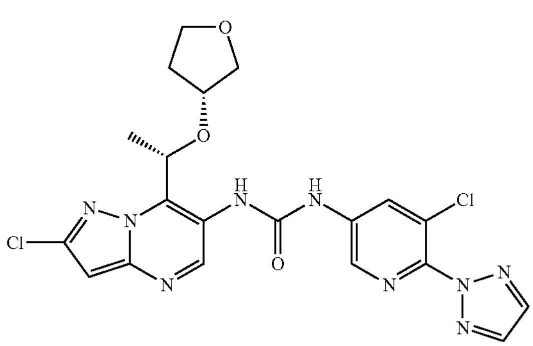 [SMILES: C[C@H](O[C@@H]1CCOC1)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-((S)-1-(((R)-tetrahydrofuran-3-yl)oxy)ethyl)pyrazolo[1,5-a]pyrimidin-6-yl)urea | M/z = 504-506 [M + H]+, Rt = 3.97 min (HPLC Method C1), $^1$H NMR (400 MHz, DMSO-d$_6$) δ ppm: 10.23 (bs, 1H), 8.89 (s, 1H), 8.57 (s, 1H), 8.48 (s, 1H), 8.45 (bs, 1H), 8.15 (s, 2H), 6.95 (s, 1H), 5.58 (q, 1H), 4.10 (m, 1H), 3.78 (q, 1H), 3.68 (m, 2H), 3.53 (dd, 1H), 2.09 (m, 1H), 1.90 (m, 1H), 1.61 (d, 3H). |

| Ex | Structure | Name | Analytics |
|---|---|---|---|
| 101 | 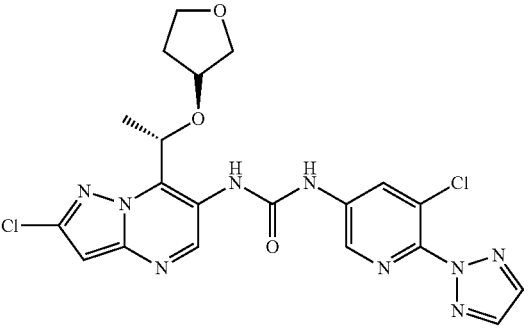 | 1-(5-chloro-6-(2H-1,2,3-triazol-2-yl)pyridin-3-yl)-3-(2-chloro-7-((S)-1-(((S)-tetrahydrofuran-3-yl)oxy)ethyl)pyrazolo[1,5-a]pyrimidin-6-yl)urea | M/z = 504-506 [M + H]+, Rt = 3.90 min (HPLC Method C1), $^1$H NMR (400 MHz, DMSO-d$_6$) δ ppm: 10.25 (bs, 1H), 8.89 (s, 1H), 8.57 (s, 1H), 8.53-8.48 (m, 2H), 8.16 (s, 2H), 6.95 (s, 1H), 5.52 (q, 1H), 4.15 (m, 1H), 3.91 (d, 1H), 3.74 (q, 1H), 3.60-3.54 (m, 2H), 1.91-1.78 (m, 2H), 1.61 (d, 3H). |
| 102 | 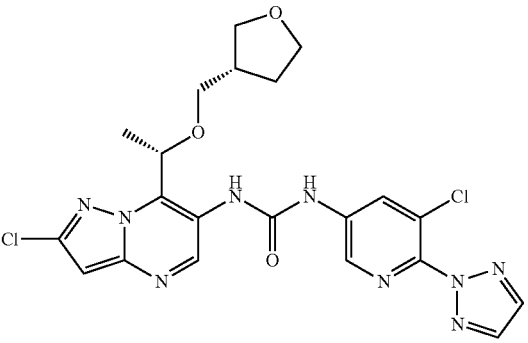 [SMILES: C[C@H](OC[C@H]1CCOC1)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-((S)-1-(((S)-tetrahydrofuran-3-yl)methoxy)ethyl)pyrazolo[1,5-a]pyrimidin-6-yl)urea | M/z = 518-520 [M + H]+, Rt = 4.49 min (HPLC Method C1), $^1$H NMR (400 MHz, DMSO-d$_6$) δ ppm: 10.24 (bs, 1H), 8.90 (s, 1H), 8.56 (m, 2H), 8.48 (s, 1H), 8.15 (s, 2H), 6.93 (s, 1H), 5.57 (q, 1H), 3.95 (m, 1H), 3.59 (dq, 2H), 3.41 (m, 2H), 1.78 (m, 1H), 1.67 (m, 2H), 1.61 (d, 3H), 1.42 (m, 1H). |
| 103 | 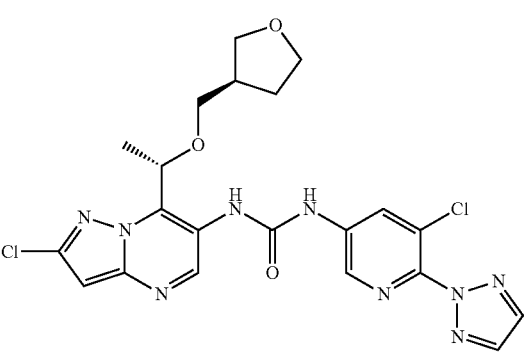 [SMILES: C[C@H](OC[C@@H]1CCOC1)c1c(NC(=O)Nc2cnc(-n3nccn3)c(Cl)c2)cnc2cc(Cl)nn12] | 1-(5-chloro-6-(2H-1,2,3-triazol-2-yl)pyridin-3-yl)-3-(2-chloro-7-((S)-1-(((R)-tetrahydrofuran-3-yl)methoxy)ethyl)pyrazolo[1,5-a]pyrimidin-6-yl)urea | M/z = 518-520 [M + H]+, Rt = 4.62 min (HPLC Method C1), $^1$H NMR (400 MHz, DMSO-d$_6$) δ ppm: 10.18 (bs, 1H), 8.97 (s, 1H), 8.62 (bs, 1H), 8.56 (s, 1H), 8.49 (s, 1H), 8.15 (s, 2H), 6.93 (s, 1H), 5.57 (q, 1H), 4.00 (m, 1H), 3.59-3.48 (m, 3H), 1.83 (m, 1H), 1.72 (m, 2H), 1.60 (d, 3H), 1.45 (s, 1H), one proton obscured by water |
| 104 | 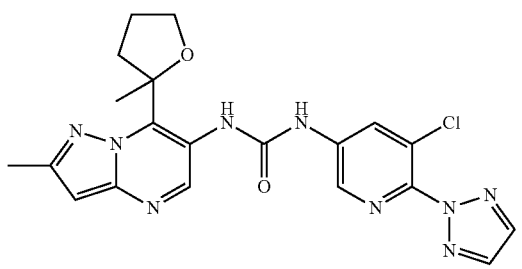 [SMILES: Cc1cc2ncc(NC(=O)Nc3cnc(-n4nccn4)c(Cl)c3)c(C3(C)CCCO3)n2n1] | 1-(5-chloro-6-(2H-1,2,3-triazol-2-yl)pyridin-3-yl)-3-(2-methyl-7-(2-methyltetrahydrofuran-2-yl)pyrazolo[1,5-a]pyrimidin-6-yl)urea | M/z = 454-456 [M + H]+, Rt = 4.41 min (HPLC Method C1), $^1$H NMR (600 MHz, DMSO-d$_6$) δ ppm: 10.30 (s, 1H), 9.11 (s, 1H), 8.75 (s, 1H), 8.54 (d, 1H, 8.47 (d, 1H), 8.15 (s, 2H), 6.51 (s, 1H), 4.09 (m, 1H), 3.82 (q, 1H), 2.55 (t, 1H), 2.43 (s, 3H), 1.98 (m, 1H), 1.81 (m, 1H), 1.78 (s, 3H). |
| 105 | 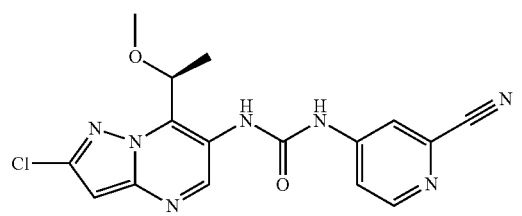 [SMILES: CO[C@@H](C)c1c(NC(=O)Nc2ccnc(C#N)c2)cnc2cc(Cl)nn12] | (S)-1-(2-chloro-7-(1-methoxyethyl)pyrazolo[1,5-a]pyrimidin-6-yl)-3-(2-cyanopyridin-4-yl)urea | M/z = 372-374 [M + H]+, Rt = 3.77 min (HPLC Method C1), $^1$H NMR (600 MHz, DMSO-d$_6$) δ ppm: 10.33 (bs, 1H), 8.90 (s, 1H), 8.59 (bs, 1H), 8.54 (d, 1H), 8.06 (d, 1H), 7.68 (dd, 1H), 6.94 (s, 1H), 5.40 (q, 1H), 3.30 (s, 3H), 1.57 (d, 3H). |

| Ex | Structure | Name | Analytics |
|---|---|---|---|
| 106 | 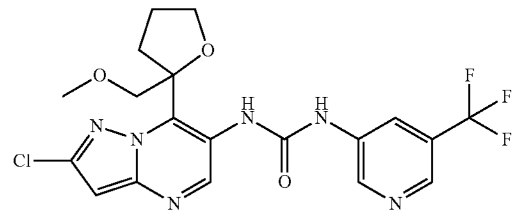 [SMILES: COCC1(c2c(NC(=O)Nc3cncc(C(F)(F)F)c3)cnc3cc(Cl)nn23)CCCO1] | 1-(2-chloro-7-(2-(methoxymethyl)tetrahydrofuran-2-yl)pyrazolo[1,5-a]pyrimidin-6-yl)-3-(5-(trifluoromethyl)pyridin-3-yl)urea | M/z = 471-473 [M + H]+, Rt = 4.94 min (HPLC Method C1), $^1$H NMR (400 MHz, DMSO-d$_6$) δ ppm: 10.59 (s, 1H), 9.16 (s, 1H), 8.94 (s, 1H), 8.55 (d, 1H), 8.05 (s, 1H), 7.61 (d, 1H), 6.89 (s, 1H), 4.33 (d, 1H), 4.09 (m, 1H), 3.82 (q, 1H), 3.61 (dd, 1H), 3.16 (s, 3H), 2.40 (m, 2H), 1.94-1.77 (m, 2H). |
| 107 | 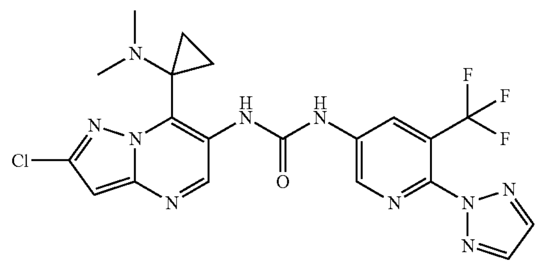 [SMILES: CN(C)C1(c2c(NC(=O)Nc3cnc(-n4nccn4)c(C(F)(F)F)c3)cnc3cc(Cl)nn23)CC1] | 1-(6-(2H-1,2,3-triazol-2-yl)-5-(trifluoromethyl)pyridin-3-yl)-3-(2-chloro-7-(1-(dimethylamino)cyclopropyl)pyrazolo[1,5-a]pyrimidin-6-yl)urea | M/z = 507-509 [M + H]+, Rt = 1.00 min (UPLC Method B2), $^1$H NMR (400 MHz, CDCl$_3$) δ ppm: 9.40 (bs, 1H), 8.82 (m, 1H), 8.70 (m, 2H), 7.93 (s, 3H), 6.66 (s, 1H), 2.50 (s, 6H), 1.54 (m, 2H), 1.20 (m, 2H). |
| 108 | 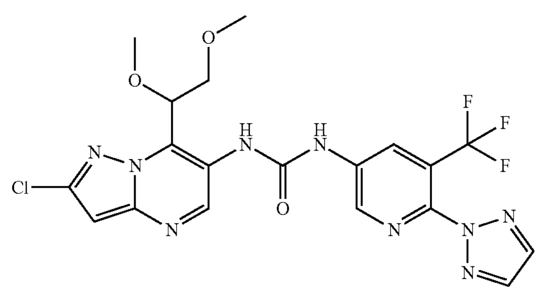 [SMILES: COCC(OC)c1c(NC(=O)Nc2cnc(-n3nccn3)c(C(F)(F)F)c2)cnc2cc(Cl)nn12] | 1-(6-(2H-1,2,3-triazol-2-yl)-5-(trifluoromethyl)pyridin-3-yl)-3-(2-chloro-7-(1,2-dimethoxyethyl)pyrazolo[1,5-a]pyrimidin-6-yl)urea | M/z = 512-514 [M + H]+, Rt = 4.39 min (HPLC Method C1), $^1$H NMR (400 MHz, DMSO-d$_6$) δ ppm: 10.59 (bs, 1H), 8.96 (s, 1H), 8.85 (s, 1H), 8.72 (s, 1H), 8.53 (bs, 1H), 8.17 (s, 2H), 6.96 (s, 1H), 5.52 (m, 1H), 3.85 (m, 2H), 3.37 (s, 3H), 3.29 (s, 3H). |
| 109 | 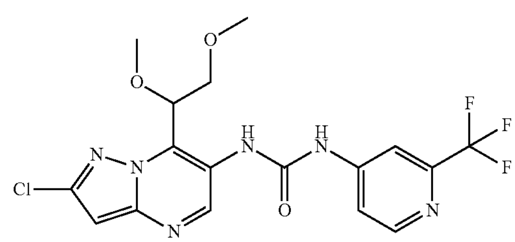 [SMILES: COCC(OC)c1c(NC(=O)Nc2ccnc(C(F)(F)F)c2)cnc2cc(Cl)nn12] | 1-(2-chloro-7-(1,2-dimethoxyethyl)pyrazolo[1,5-a]pyrimidin-6-yl)-3-(2-(trifluoromethyl)pyridin-4-yl)urea | M/z = 445-447 [M + H]+, Rt = 4.22 min (HPLC Method C1), $^1$H NMR (400 MHz, DMSO-d$_6$) δ ppm: 10.48 (bs, 1H), 8.91 (s, 1H), 8.56 (d, 1H), 8.45 (bs, 1H), 8.06 (s, 1H), 7.62 (d, 1H), 6.95 (s, 1H), 5.49 (m, 1H), 3.82 (m, 2H), 3.34 (s, 3H), 3.27 (s, 3H). |
| 110 | 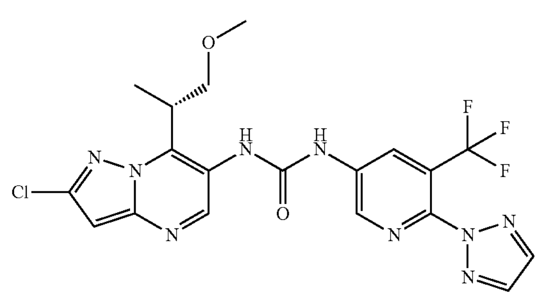 [SMILES: COC[C@@H](C)c1c(NC(=O)Nc2cnc(-n3nccn3)c(C(F)(F)F)c2)cnc2cc(Cl)nn12] | (S)-1-(6-(2H-1,2,3-triazol-2-yl)-5-(trifluoromethyl)pyridin-3-yl)-3-(2-chloro-7-(1-methoxypropan-2-yl)pyrazolo[1,5-a]pyrimidin-6-yl)urea | [c], M/z = 496-498 [M + H]+, Rt = 4.36 min (HPLC Method C1), $^1$H NMR (400 MHz, DMSO-d$_6$) δ ppm: 10.06 (bs, 1H), 8.87 (bs, 2H), 8.68 (s, 1H), 8.61 (s, 1H), 8.16 (s, 2H), 6.93 (s, 1H), 4.10-3.98 (m, 2H), 3.74 (dd, 1H), 3.19 (s, 3H), 1.44 (d, 3H). |

| Ex | Structure | Name | Analytics |
|---|---|---|---|
| 111 | 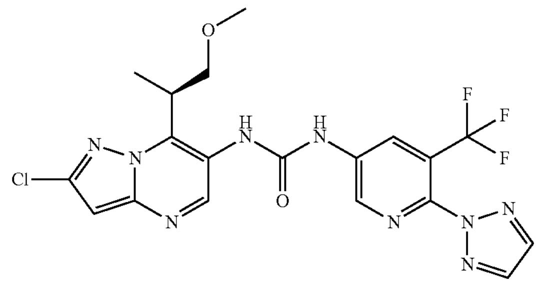 [SMILES: COC[C@H](C)c1c(NC(=O)Nc2cnc(-n3nccn3)c(C(F)(F)F)c2)cnc2cc(Cl)nn12] | (R)-1-(6-(2H-1,2,3-triazol-2-yl)-5-(trifluoromethyl)pyridin-3-yl)-3-(2-chloro-7-(1-methoxypropan-2-yl)pyrazolo[1,5-a]pyrimidin-6-yl)urea | [c], M/z = 496-498 [M + H]+, Rt = 4.42 min (HPLC Method C1), $^1$H NMR (400 MHz, DMSO-$d_6$) δ ppm: 9.94 (bs, 1H), 8.87 (s, 1H), 8.80 (bs, 1H), 8.69 (s, 1H), 8.61 (s, 1H), 8.16 (s, 2H), 6.93 (s, 1H), 4.09-3.97 (m, 2H), 3.74 (dd, 1H), 3.19 (s, 3H), 1.45 (d, 3H). |

[a]: The curtius reaction was performed overnight.

[b]: Product obtained by purification of the mixture of both enantiomers by preparative chiral separation (preparative Thar SFC 200, Chiralpack IA, 30×250 mm, $CO_2$/EtOH 70/30, 120 g/min).

[c] Product obtained by purification of the mixture of both enantiomers by preparative chiral separation (MG II preparative SFC, Chiralpack AD-H, 250×30 mm, 20 μm, $CO_2$/EtOH 6/4, 50 ml/min).

Example 112

1-(5-(2H-1,2,3-triazol-2-yl)-2-(trifluoromethyl)pyridin-4-yl)-3-(2-chloro-7-isopropylpyrazolo[1,5-a]pyrimidin-6-yl)urea

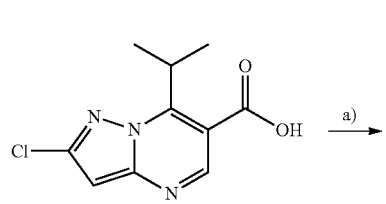

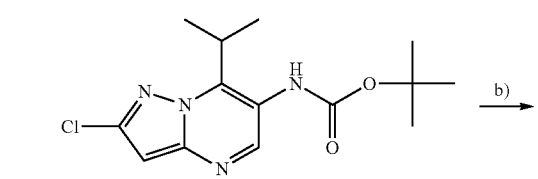

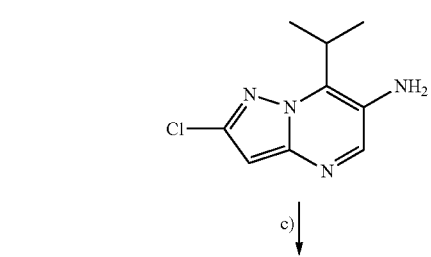

-continued

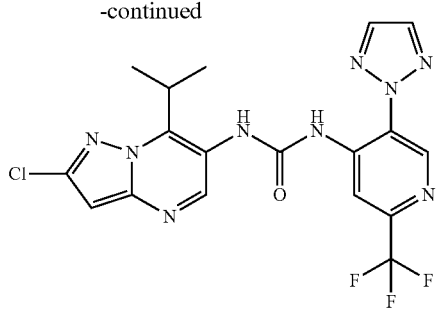

a) tert-butyl (2-chloro-7-isopropylpyrazolo[1,5-a]pyrimidin-6-yl)carbamate

To a solution of 2-chloro-7-isopropylpyrazolo[1,5-a]pyrimidine-6-carboxylic acid (200 mg, 0.835 mmol) in tBuOH (5 ml) were added DPPA (0.198 ml, 0.918 mmol) and $Et_3N$ (0.58 ml, 4.17 mmol). The mixture was stirred at rt for 30 min. Then, the reaction mixture was stirred 3 h at 100° C. The solvent was evaporated and the crude product was purified by flash column chromatography on silica gel (cyclohexane/EtOAc: 1/0 to 1/1) to afford tert-butyl (2-chloro-7-isopropylpyrazolo[1,5-a]pyrimidin-6-yl)carbamate. M/z=311-313 [M+H]+, Rt=1.22 min (UPLC Method B1).

b) 2-chloro-7-isopropylpyrazolo[1,5-a]pyrimidin-6-amine

A solution of tert-butyl (2-chloro-7-isopropylpyrazolo[1,5-a]pyrimidin-6-yl)carbamate (90 mg, 0.290 mmol) and 4N HCl in 1,4-dioxane (0.36 ml, 1.45 mmol) in methanol (3 ml) was stirred overnight at RT. The reaction mixture was concentrated, quenched with saturated aqueous $NaHCO_3$, extracted with AcOEt, and the organic phase was dried over $Na_2SO_4$, filtered and concentrated to afford 2-chloro-7-isopropylpyrazolo[1,5-a]pyrimidin-6-amine. M/z=211-213 [M+H]+, Rt=0.87 min (UPLC Method B1).

c) 1-(5-(2H-1,2,3-triazol-2-yl)-2-(trifluoromethyl)pyridin-4-yl)-3-(2-chloro-7-isopropylpyrazolo[1,5-a]pyrimidin-6-yl)urea To a solution of 5-(2H-1,2,3-triazol-2-yl)-2-(trifluoromethyl)isonicotinic acid (60 mg, 0.232 mmol) in 1,4-dioxane (3 ml) were added DPPA (0.060 ml, 0.279 mmol) and $Et_3N$ (0.065 ml, 0.465 mmol). The mixture was stirred at RT for 30 min. Then, 2-chloro-7-isopropylpyrazolo[1,5-a]pyrimidin-6-amine (58.8 mg, 0.279 mmol) was added and the reaction mixture was stirred for 3 h at 100° C. The reaction mixture was extracted with AcOEt, the organic phase was washed with saturated aqueous NaHCO₃, dried over Na₂SO₄, filtered and concentrated. The residue was purified by flash column chromatography on silica gel (cyclohexane/EtOAc 1/0 to 0/1 then DCM/MeOH 1/0 to 9/1). The obtained residue was purified twice by preparative HPLC (Method A1). The fractions containing the product were extracted with AcOEt/saturated aqueous NaHCO₃. The organic layer was dried over Na₂SO₄, filtered and evaporated to afford 1-(5-(2H-1,2,3-triazol-2-yl)-2-(trifluoromethyl)pyridin-4-yl)-3-(2-chloro-7-isopropylpyrazolo[1,5-a]pyrimidin-6-yl)urea. M/z=466-468 [M+H]+, Rt=2.45 min (HPLC Method C2), ¹H NMR (400 MHz, DMSO-d₆) δ ppm: 10.00 (bs, 1H), 9.16 (s, 1H), 8.97 (s, 1H), 8.57 (s, 1H), 8.41 (s, 1H), 6.94 (s, 1H), 3.79 (hepta, 1H), 1.48 (d, 6H).

Example 113

(R)-1-(6-(2H-1,2,3-triazol-2-yl)-5-(trifluoromethyl)pyridin-3-yl)-3-(2-chloro-7-(1-hydroxyethyl)pyrazolo[1,5-a]pyrimidin-6-yl)urea

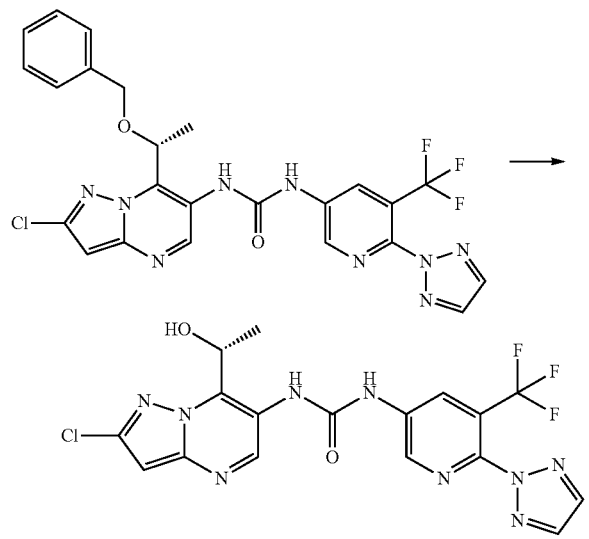

A solution of (R)-1-(6-(2H-1,2,3-triazol-2-yl)-5-(trifluoromethyl)pyridin-3-yl)-3-(7-(1-(benzyloxy)ethyl)-2-chloropyrazolo[1,5-a]pyrimidin-6-yl)urea (20 mg, 0.036 mmol) and palladium Pearlman's catalyst (0.50 mg, 3.58 µmol) in AcOEt (2 ml) was stirred at RT overnight under H₂ atmosphere. The reaction mixture was filtered and concentrated. The residue was purified by preparative HPLC (Method A1) to afford (R)-1-(6-(2H-1,2,3-triazol-2-yl)-5-(trifluoromethyl)pyridin-3-yl)-3-(2-chloro-7-(1-hydroxyethyl)-pyrazolo[1,5-a]pyrimidin-6-yl)urea. M/z=468-470 [M+H]+, Rt=3.90 min (HPLC Method C1), ¹H NMR (400 MHz, DMSO-d₆) δ ppm: 10.68 (s, 1H), 9.04 (s, 1H), 8.85 (d, 1H), 8.74 (d, 1H), 8.18 (d, 2H), 6.93 (s, 1H), 5.79 (q, 1H), 1.56 (d, 3H).

Example 114

(S)-1-(2-chloro-7-(1-hydroxyethyl)pyrazolo[1,5-a]pyrimidin-6-yl)-3-(2-(trifluoromethyl)pyridin-4-yl)urea

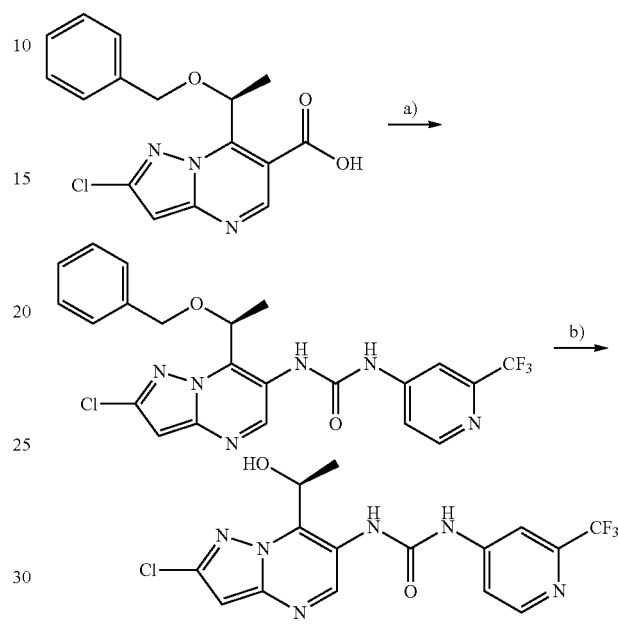

a) (S)-1-(7-(1-(benzyloxy)ethyl)-2-chloropyrazolo[1,5-a]pyrimidin-6-yl)-3-(2-(trifluoro-methyl)pyridin-4-yl)urea To a solution of (S)-7-(1-(benzyloxy)ethyl)-2-chloropyrazolo[1,5-a]pyrimidine-6-carboxylic acid (500 mg, 1.34 mmol) in dioxane (3 ml) were added diphenyl phosphoryl azide (443 mg, 1.61 mmol) and triethylamine (0.56 ml, 4.02 mmol). The mixture was stirred at RT for 30 min. 2-(trifluoromethyl)pyridin-4-amine (435 mg, 2.68 mmol) was then added and the solution was stirred for 1.5 hr at 100° C. After cooling down, the reaction mixture was extracted with EtOAc, washed with sat aqueous NaHCO₃, dried over Na₂SO₄, filtered and concentrated. The residue was purified by flash column chromatography on silica gel (cyclohexane/EtOAc: 100/0 to 0/100) to afford (S)-1-(7-(1-(benzyloxy)ethyl)-2-chloropyrazolo[1,5-a]pyrimidin-6-yl)-3-(2-(trifluoromethyl)pyridin-4-yl)urea. M/z=491-493 [M+H]+, Rt=1.31 min (UPLC Method B1), ¹H NMR (400 MHz, DMSO-d₆) δ ppm: 10.18 (s, 1H), 8.81 (s, 1H), 8.55 (d, 1H), 8.52 (s, 1H), 8.01 (d, 1H), 7.58-7.54 (m, 1H), 7.29-7.20 (m, 2H), 7.15-7.08 (m, 3H), 6.91 (s, 1H), 5.56 (q, 1H), 4.51 (q, 2H), 1.62 (s, 3H).

b) (S)-1-(2-chloro-7-(1-hydroxyethyl)pyrazolo[1,5-a]pyrimidin-6-yl)-3-(2-(trifluoromethyl)pyridin-4-yl)urea A solution of (S)-1-(7-(1-(benzyloxy)ethyl)-2-chloropyrazolo[1,5-a]pyrimidin-6-yl)-3-(2-(trifluoromethyl)pyridin-4-yl)urea (140 mg, 0.285 mmol) and palladium Pearlman's catalyst (4.0 mg, 29 µmol) in THF (5 ml) was stirred at RT overnight under H₂ atmosphere. The reaction mixture was filtered and concentrated. The residue was purified by preparative HPLC (Method A1). EtOAc and aqueous NaHCO3 were added to the fractions containing the product. The organic layer was separated, dried over sodium sulfate, filtered and concentrated. The residue was purified by flash column chromatography on silica gel (DCM/MeOH 1/0 to 8/2) to afford ((S)-1-(2-chloro-7-(1-hydroxyethyl)pyrazolo[1,5-a]pyrimidin-6-yl)-3-(2-(trifluoromethyl)pyridin-4-yl)urea. M/z=401-403 [M+H]+, Rt=0.99 min (UPLC Method B1), $^1$H NMR (400 MHz, DMSO-$d_6$) δ ppm: 10.55 (s, 1H), 8.98 (s, 1H), 8.94 (s, 1H), 8.56 (d, 1H), 8.07 (s, 1H), 7.61 (d, 1H), 6.91 (s, 1H), 6.77-6.61 (m, 1H), 5.76 (q, 1H), 1.52 (d, 3H).

Example 115

1-(5-chloro-6-(2H-1,2,3-triazol-2-yl)pyridin-3-yl)-3-(2-chloro-7-(morpholin-2-yl)pyrazolo[1,5-a]pyrimidin-6-yl)urea

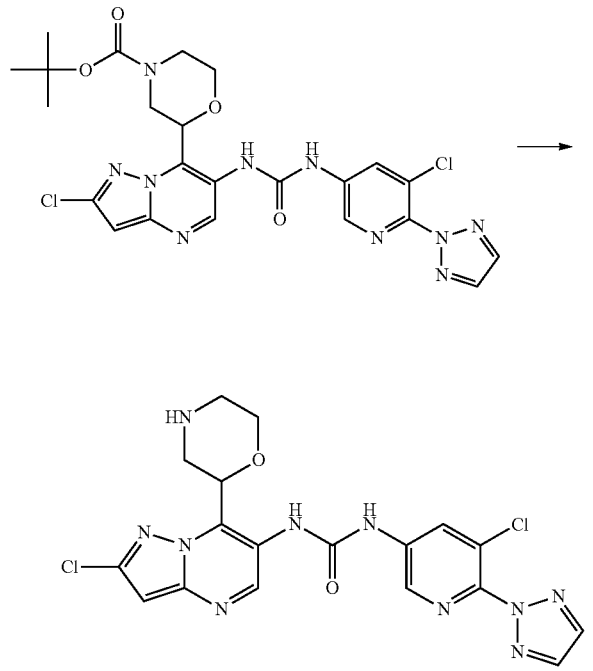

To tert-butyl 2-(2-chloro-6-(3-(5-chloro-6-(2H-1,2,3-triazol-2-yl)pyridin-3-yl)ureido)pyrazolo[1,5-a]pyrimidin-7-yl)morpholine-4-carboxylate (124 mg, 0.082 mmol) dissolved in DCM (0.27 ml) was added TFA (63.1 μl, 0.819 mmol). The reaction mixture was stirred at RT overnight. The reaction mixture was quenched with water, the separated aqueous phase was basified to pH=8-9 with saturated aqueous NaHCO3 and extracted with DCM. The organic phase was washed with brine and dried over a phase separator cartridge (IST) and evaporated. The residue was purified by preparative HPLC (Method A1). The collected fractions were extracted with DCM/saturated aqueous NaHCO3. The organic phase was dried over a phase separator cartridge (IST) and concentrated to afford 1-(5-chloro-6-(2H-1,2,3-triazol-2-yl)pyridin-3-yl)-3-(2-chloro-7-(morpholin-2-yl)pyrazolo[1,5-a]pyrimidin-6-yl)urea. M/z=475-477 [M+H]+, Rt=1.46 min (HPLC Method C2), $^1$H NMR (400 MHz, Methanol-$d_4$) δ ppm: 8.90 (s, 1H), 8.45 (d, 1H), 8.43 (d, 1H), 7.92 (s, 2H), 6.59 (s, 1H), 5.63 (dd, 1H), 4.10 (dd, 1H), 3.76 (td, 1H), 3.07-2.76 (m, 4H).

Example 116

1-(5-chloro-6-(2H-1,2,3-triazol-2-yl)pyridin-3-yl)-3-(2-chloro-7-(4-methylmorpholin-2-yl)pyrazolo[1,5-a]pyrimidin-6-yl)urea

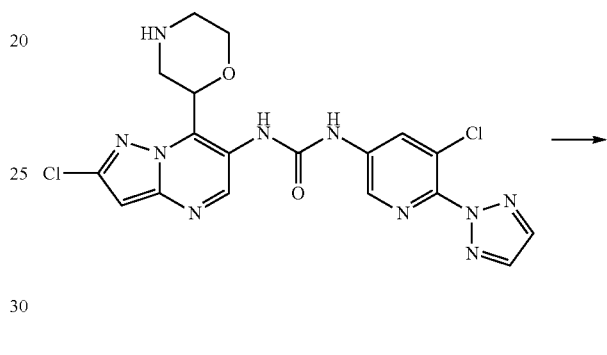

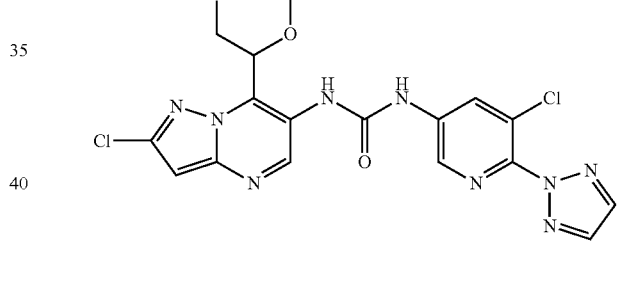

To a solution of 1-(5-chloro-6-(2H-1,2,3-triazol-2-yl)pyridin-3-yl)-3-(2-chloro-7-(morpholin-2-yl)pyrazolo[1,5-a]pyrimidin-6-yl)urea (14 mg, 0.024 mmol) in MeOH (236 μl) was added acetic acid (2.70 μl, 0.047 mmol) and 37% aq. formaldehyde (5.26 μl, 0.071 mmol). After 30 min, NaBH(OAc)$_3$ (15.0 mg, 0.071 mmol) was added at 0° C. and the reaction mixture was stirred at RT during 1 h. Water was added carefully and the solvent was evaporated. The residue was purified by preparative HPLC (Method A1). The collected fractions were extracted with DCM/saturated aqueous NaHCO3. The organic phase was dried over a phase separator cartridge (IST) and concentrated to afford 1-(5-chloro-6-(2H-1,2,3-triazol-2-yl)pyridin-3-yl)-3-(2-chloro-7-(4-methylmorpholin-2-yl)pyrazolo[1,5-a]pyrimidin-6-yl)urea. M/z=489-491 [M+H]+, Rt=1.48 min (HPLC Method C2), $^1$H NMR (400 MHz, Methanol-$d_4$) δ ppm: 8.91 (s, 1H), 8.44 (d, 1H), 8.42 (d, 1H), 7.92 (s, 2H), 6.59 (s, 1H), 5.69 (dd, 1H), 4.13 (ddd, 1H), 3.81 (td, 1H), 3.07 (dt, 1H), 2.76 (ddt, 1H), 2.33 (td, 1H), 2.27 (s, 3H), 2.23 (dd, 1H).

Example 117

1-(4-(4-(aminomethyl)-1H-pyrazol-1-yl)-3-chlorophenyl)-3-(2-chloro-7-isopropylpyrazolo[1,5-a]pyrimidin-6-yl)urea

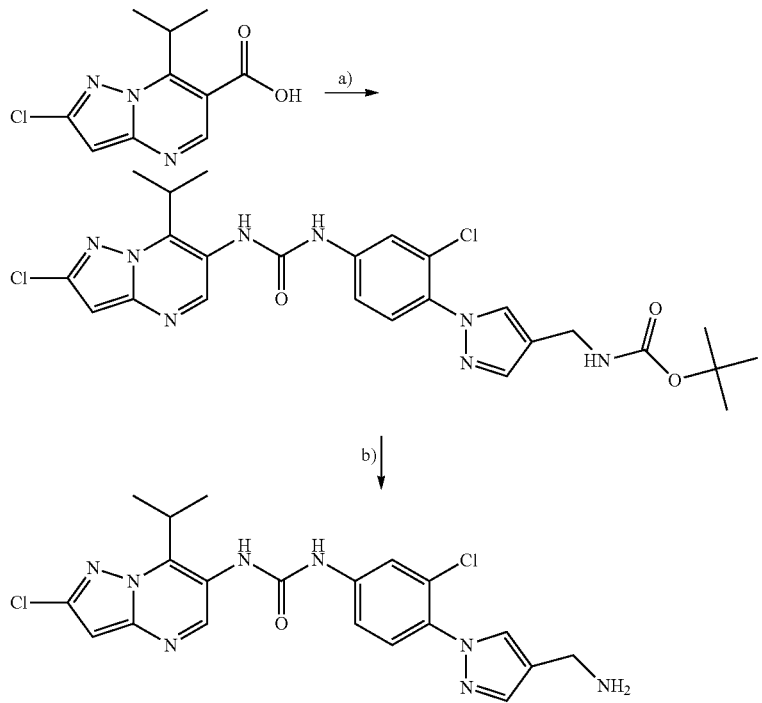

a) tert-butyl ((1-(2-chloro-4-(3-(2-chloro-7-isopropylpyrazolo[1,5-a]pyrimidin-6-yl)ureido)phenyl)-1H-pyrazol-4-yl)methyl)carbamate tert-butyl ((1-(2-chloro-4-(3-(2-chloro-7-isopropylpyrazolo[1,5-a]pyrimidin-6-yl)ureido)phenyl)-1H-pyrazol-4-yl)methyl)carbamate was prepared analogously as described in example 1 using 2-chloro-7-isopropylpyrazolo[1,5-a]pyrimidine-6-carboxylic acid instead of (S)-2-chloro-7-(1-methoxyethyl)pyrazolo[1,5-a]pyrimidine-6-carboxylic acid and using tert-butyl ((1-(4-amino-2-chlorophenyl)-1H-pyrazol-4-yl)methyl)carbamate instead of 6-(2H-1,2,3-triazol-2-yl)-5-(trifluoromethyl)pyridin-3-amine. M/z=559-561 [M+H]+, Rt=1.17 min (UPLC Method B2).

b) 1-(4-(4-(aminomethyl)-1H-pyrazol-1-yl)-3-chlorophenyl)-3-(2-chloro-7-isopropylpyrazolo[1,5-a]pyrimidin-6-yl)urea tert-butyl ((1-(2-chloro-4-(3-(2-chloro-7-isopropylpyrazolo[1,5-a]pyrimidin-6-yl)ureido)phenyl)-1H-pyrazol-4-yl)methyl)carbamate (86 mg, 0.154 mmol) in DCM (2 ml) was added TFA (1 ml, 12.98 mmol). The reaction mixture was stirred for 1 h at RT. The solvent was evaporated and the residue was purified by preparative HPLC (Method A1) to afford 1-(4-(4-(aminomethyl)-1H-pyrazol-1-yl)-3-chlorophenyl)-3-(2-chloro-7-isopropylpyrazolo[1,5-a]pyrimidin-6-yl)urea. M/z=459-461 [M+H]+, Rt=3.09 min (HPLC Method C1), $^1$H NMR (400 MHz, DMSO-d$_6$) δ ppm: 8.55 (s, 1H), 7.88 (d, 2H), 7.64 (s, 1H), 7.49 (dd, 1H), 7.45 (d, 1H), 6.92 (d, 1H), 3.81 (p, 1H), 3.67 (s, 2H), 1.50 (d, 6H).

Example 118

1-(6-(4-(aminomethyl)-1H-pyrazol-1-yl)-5-chloropyridin-3-yl)-3-(2-chloro-7-isopropylpyrazolo[1,5-a]pyrimidin-6-yl)urea

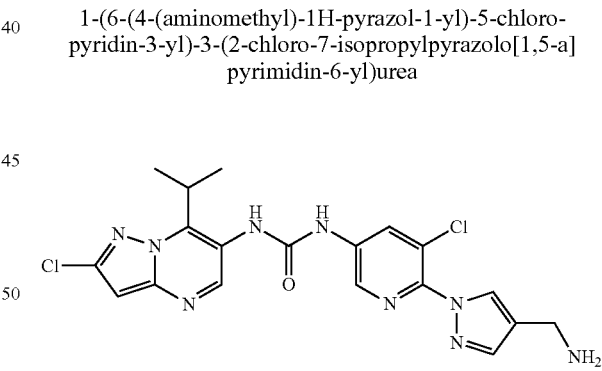

1-(6-(4-(aminomethyl)-1H-pyrazol-1-yl)-5-chloropyridin-3-yl)-3-(2-chloro-7-isopropylpyrazolo[1,5-a]pyrimidin-6-yl)urea was prepared analogously as described for example 117 using tert-butyl ((1-(5-amino-3-chloropyridin-2-yl)-1H-pyrazol-4-yl)methyl)carbamate instead of tert-butyl ((1-(4-amino-2-chlorophenyl)-1H-pyrazol-4-yl)methyl)carbamate. M/z=460-462 [M+H]+, Rt=2.97 min (HPLC Method C1), $^1$H NMR (400 MHz, DMSO-d$_6$) δ ppm: 8.56 (s, 1H), 8.52 (d, 1H), 8.34 (d, 1H), 8.03 (s, 1H), 7.69 (s, 1H), 6.93 (s, 1H), 3.82 (p, 1H), 3.69 (s, 2H), 1.50 (d, 6H).

Example 119

(S)-1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea

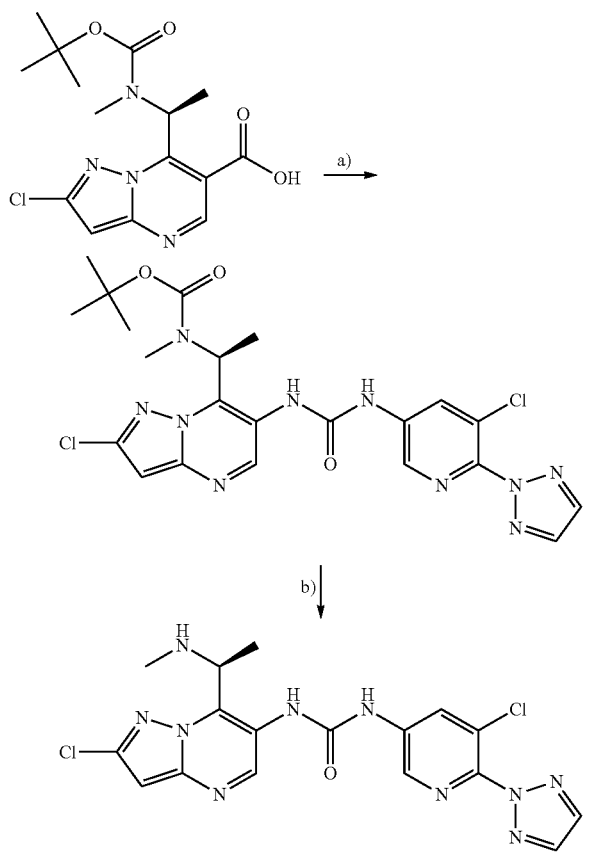

a) (S)-tert-butyl (1-(2-chloro-6-(3-(5-chloro-6-(2H-1,2,3-triazol-2-yl)pyridin-3-yl)ureido)pyrazolo[1,5-a]pyrimidin-7-yl)ethyl)(methyl)carbamate (S)-tert-butyl (1-(2-chloro-6-(3-(5-chloro-6-(2H-1,2,3-triazol-2-yl)pyridin-3-yl)ureido)pyrazolo[1,5-a]pyrimidin-7-yl)ethyl)(methyl)carbamate was prepared analogously as described in example 1 using (S)-7-(1-((tert-butoxycarbonyl)(methyl)amino)ethyl)-2-chloropyrazolo[1,5-a]pyrimidine-6-carboxylic acid instead of (S)-2-chloro-7-(1-methoxyethyl)pyrazolo[1,5-a]pyrimidine-6-carboxylic acid and using 5-chloro-6-(2H-1,2,3-triazol-2-yl)pyridin-3-amine instead of 6-(2H-1,2,3-triazol-2-yl)-5-(trifluoromethyl)pyridin-3-amine. M/z=547-549 [M+H]+, Rt=1.28 min (UPLC Method B1).

b) (S)-1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea To a solution of (S)-tert-butyl (1-(2-chloro-6-(3-(5-chloro-6-(2H-1,2,3-triazol-2-yl)pyridin-3-yl)ureido)pyrazolo[1,5-a]pyrimidin-7-yl)ethyl)(methyl)carbamate (215 mg, 0.393 mmol) in MeOH (3 ml) was added 4N HCl in 1,4-dioxane (0.098 ml, 0.393 mmol). The reaction mixture was stirred at rt overnight. The solvent were evaporated, treated with AcOEt/saturated aqueous NaHCO$_3$, the organic phase was dried over Na$_2$SO$_4$, filtered and concentrated. The crude product was purified by flash column chromatography on silica gel (cyclohexane/AcOEt 1/0 to 0/1 then DCM/MeOH 1/0 to 8/2) to afford 1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea. Chiral analysis indicated that some racemisation occurred during synthesis. The mixture of enantiomers was separated by preparative chiral separation (Chiralpak aD-H, 250×4.6 mm, 5 μm, heptane/EtOH/MeOH 60/20/20, 1 mL/min) to afford (S)-1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea. M/z=447-449 [M+H]+, Rt=2.42 min (HPLC Method C1), $^1$H NMR (400 MHz, DMSO-d$_6$) δ ppm: 10.34 (s, 1H), 9.05 (s, 1H), 8.60 (d, 1H), 8.50 (d, 1H), 8.17 (s, 2H), 6.91 (s, 1H), 4.75 (q, 1H), 2.28 (s, 3H), 1.49 (d, 3H).

Example 120

2-(3-(2-chloro-7-isopropylpyrazolo[1,5-a]pyrimidin-6-yl)ureido)-4-(trifluoromethyl)pyridine 1-oxide

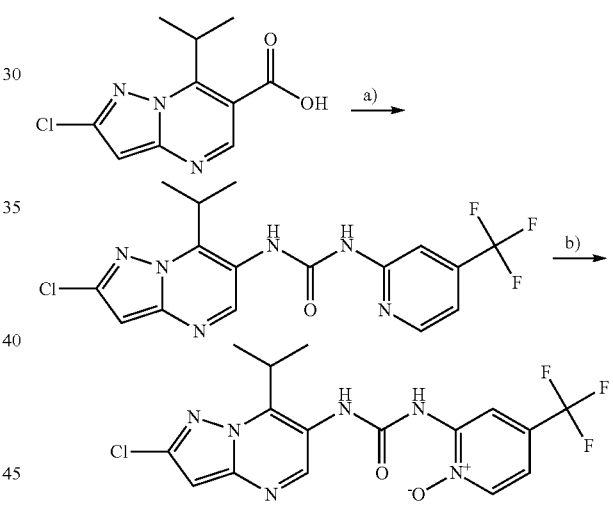

a) 1-(2-chloro-7-isopropylpyrazolo[1,5-a]pyrimidin-6-yl)-3-(4-(trifluoromethyl)pyridin-2-yl)urea 1-(2-chloro-7-isopropylpyrazolo[1,5-a]pyrimidin-6-yl)-3-(4-(trifluoromethyl)pyridin-2-yl)urea was prepared analogously as described in example 1 using 2-chloro-7-isopropylpyrazolo[1,5-a]pyrimidine-6-carboxylic acid instead of (S)-2-chloro-7-(1-methoxyethyl)pyrazolo[1,5-a]pyrimidine-6-carboxylic acid and using 4-(trifluoromethyl)pyridin-2-amine instead of 6-(2H-1,2,3-triazol-2-yl)-5-(trifluoromethyl)pyridin-3-amine. M/z=399-401 [M+H]+, Rt=1.19 min (UPLC Method B2).

b) 2-(3-(2-chloro-7-isopropylpyrazolo[1,5-a]pyrimidin-6-yl)ureido)-4-(trifluoromethyl)pyridine 1-oxide To a stirred solution of 1-(2-chloro-7-isopropylpyrazolo[1,5-a]pyrimidin-6-yl)-3-(4-(trifluoromethyl)pyridin-2-yl)urea (40 mg, 0.100 mmol) in DCM (1 ml) was carefully added mCPBA (17.31 mg, 0.100 mmol) and the reaction mixture was stirred at RT overnight. mCPBA (6.92 mg, 0.040 mmol) was added again and the reaction mixture was stirred for 3 h at RT. The mixture was evaporated to dryness in vacuo and the residue was purified by preparative HPLC (Method A1). The fractions were basified with saturated aqueous NaHCO₃ and extracted with DCM. The organic phase was dried over a phase separator cartridge (IST) and concentrated to afford 2-(3-(2-chloro-7-isopropylpyrazolo[1,5-a]pyrimidin-6-yl)ureido)-4-(trifluoromethyl)pyridine 1-oxide. M/z=413-415 [M+H]+, Rt=2.14 min (HPLC Method C2), $^1$H NMR (400 MHz, DMSO-$d_6$) δ ppm: 10.58 (s, 1H), 9.64 (s, 1H), 8.63 (s, 1H), 8.61 (s, 1H), 8.55 (d, 1H), 7.46 (dd, 1H), 6.93 (s, 1H), 3.85 (p, 1H), 1.49 (d, 6H).

Example 121

(R)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea

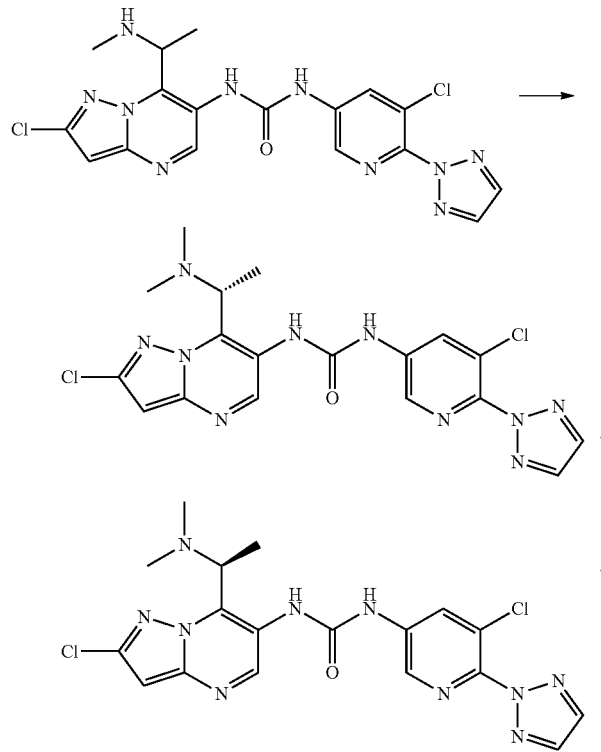

To a solution of 1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea (329 mg, 0.736 mmol) (obtained as described in Example 119) in DMF (6 ml) were added K₂CO₃ (203 mg, 1.471 mmol) and then, dropwise a solution of iodomethane (0.046 ml, 0.736 mmol) in DMF (1 ml). The reaction mixture was stirred at RT for 30 min. Additional iodomethane (0.015 ml, 0.245 mmol) was added and the mixture was stirred for 15 min. The reaction mixture was concentrated, extracted with AcOEt, the organic phase was washed with saturated aqueous NaHCO₃, dried over Na₂SO₄, filtered and concentrated. The residue was purified by flash column chromatography on silica gel (cyclohexane/AcOEt 1/0 to 0/1, then DCM/MeOH 1/0 to 8/2) to afford a mixture of enantiomers. The mixture of both isomers was separated by preparative chiral separation (Chiralpak IC, 250×4.6 mm, 5 μm, heptane/EtOH 60/40+0.05% diethylamine, 1 ml/min) to afford (R)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea. M/z=461-463 [M+H]+, Rt=0.67 min (UPLC Method B1), $^1$H NMR (400 MHz, DMSO-$d_6$) δ ppm: 10.48 (s, 1H), 10.18 (s, 1H), 9.10 (s, 1H), 8.60 (d, 1H), 8.51 (d, 1H), 8.17 (s, 2H), 6.91 (s, 1H), 4.46 (q, 1H), 2.34 (s, 6H), 1.43 (d, 3H).

Example 122

(S)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea

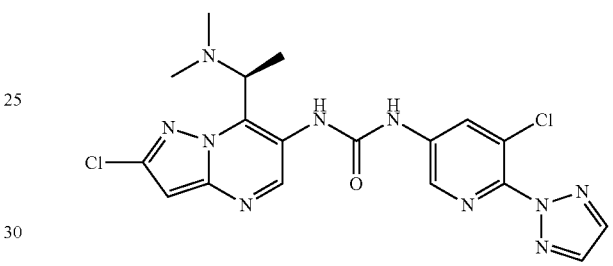

(S)-1-(5-chloro-6-(2H-1,2,3-triazol-2-yl)pyridin-3-yl)-3-(2-chloro-7-(1-(dimethylamino)ethyl)-pyrazolo-[1,5-a]pyrimidin-6-yl)urea was prepared as described in example 121 by purification of the mixture of both isomers by preparative chiral separation (Chiralpak IC, 250×4.6 mm, 5 μm, heptane/EtOH 60/40+0.05% diethylamine, 1 ml/min) to afford (S)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea. M/z=461-463 [M+H]+, Rt=0.68 min (UPLC Method B1), $^1$H NMR (400 MHz, DMSO-$d_6$) δ ppm: 10.49 (s, 1H), 10.18 (s, 1H), 9.10 (s, 1H), 8.60 (d, 1H), 8.51 (d, 1H), 8.17 (s, 2H), 6.91 (s, 1H), 4.46 (q, 1H), 2.34 (s, 6H), 1.43 (d, 3H).

Example 123

1-(5-chloro-6-(2H-1,2,3-triazol-2-yl)pyridin-3-yl)-3-(2-chloro-7-(morpholin-3-yl)pyrazolo[1,5-a]pyrimidin-6-yl)urea

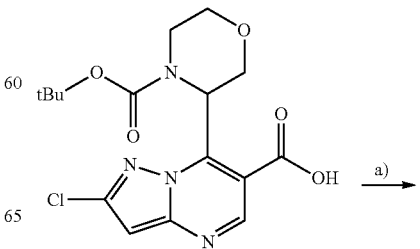

-continued

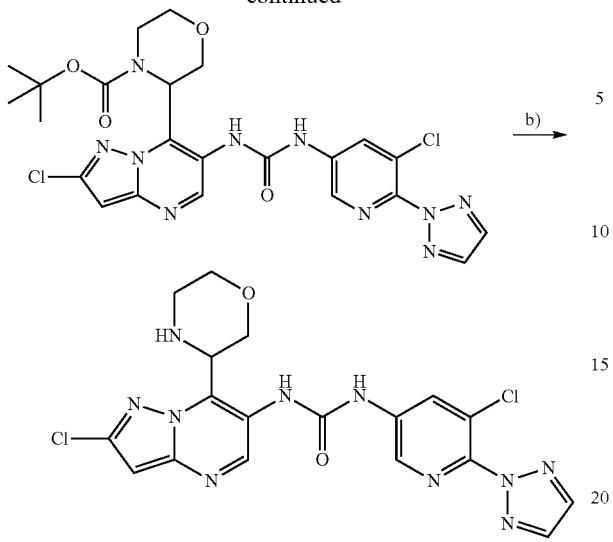

a) tert-butyl 3-(2-chloro-6-(3-(5-chloro-6-(2H-1,2,3-triazol-2-yl)pyridin-3-yl)ureido)pyrazolo[1,5-a]pyrimidin-7-yl)morpholine-4-carboxylate To a mixture of 7-(4-(tert-butoxycarbonyl)morpholin-3-yl)-2-chloropyrazolo[1,5-a]pyrimidine-6-carboxylic acid (289 mg, 0.755 mmol) in 1,4-dioxane (2.5 ml) at RT under argon was added DPPA (0.195 ml, 0.906 mmol) followed by Et$_3$N (0.32 ml, 2.26 mmol). The reaction mixture was stirred at RT for 1 h. Then, 5-chloro-6-(2H-1,2,3-triazol-2-yl)pyridin-3-amine (222 mg, 1.13 mmol) was added and the reaction mixture was stirred at 100° C. for 2 h. The mixture was diluted with AcOEt and organic layer was washed with brine, dried over Na$_2$SO$_4$, filtered and concentrated. The residue was purified by flash column chromatography on silica gel (cyclohexane/AcOEt 1/0 to 0/1) to afford tert-butyl 3-(2-chloro-6-(3-(5-chloro-6-(2H-1,2,3-triazol-2-yl)pyridin-3-yl)ureido)pyrazolo[1,5-a]pyrimidin-7-yl)morpholine-4-carboxylate. M/z=575-577 [M+H]+, Rt=1.11 min (UPLC Method B2).

b) 1-(5-chloro-6-(2H-1,2,3-triazol-2-yl)pyridin-3-yl)-3-(2-chloro-7-(morpholin-3-yl)pyrazolo[1,5-a]pyrimidin-6-yl)urea To a solution of tert-butyl 3-(2-chloro-6-(3-(5-chloro-6-(2H-1,2,3-triazol-2-yl)pyridin-3-yl)ureido)pyrazolo[1,5-a]pyrimidin-7-yl)morpholine-4-carboxylate (163 mg, 0.283 mmol) in 1,4-dioxane (2 ml) at RT was added 4M HCl in 1,4-dioxane (0.71 ml, 2.83 mmol) and the reaction mixture was stirred at RT for 16 h. Mixture was quenched at 0° C. with saturated aqueous NaHCO$_3$ and extracted with AcOEt. The organic layer was dried over Na$_2$SO$_4$, filtered and concentrated. The crude product was purified by flash column chromatography on silica gel (cyclohexane/AcOEt 1/0 to 0/1) and then purified again by preparative HPLC (Method A1). The fractions were combined and extracted with saturated aqueous NaHCO$_3$ and DCM. The organic phase was dried over a phase separator cartridge (IST), evaporated and dried on HV to afford 1-(5-chloro-6-(2H-1,2,3-triazol-2-yl)pyridin-3-yl)-3-(2-chloro-7-(morpholin-3-yl)pyrazolo[1,5-a]pyrimidin-6-yl)urea. M/z=475-477 [M+H]+, Rt=2.53 min (HPLC Method C1), $^1$H NMR (400 MHz, DMSO-d$_6$) δ ppm: 10.54 (bs, 1H), 9.02 (s, 1H), 8.60 (s, 1H), 8.49 (s, 1H), 8.15 (s, 2H), 6.89 (s, 1H), 5.05 (d, 1H), 3.87 (d, 2H), 3.65 (t, 1H), 3.54 (t, 1H), 3.02 (d, 1H), 2.92 (t, 1H), two NH obscured by water peak.

Example 124

(S)-1-(5-chloro-6-(2H-1,2,3-triazol-2-yl)pyridin-3-yl)-3-(2-chloro-7-(2-methyl-1-(methylamino)propyl)pyrazolo[1,5-a]pyrimidin-6-yl)urea

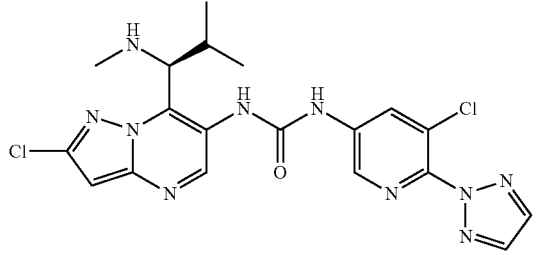 [SMILES: CN[C@H](c1c(NC(=O)Nc2cnc(-n3nccn3)c(Cl)c2)cnc2cc(Cl)nn12)C(C)C]

1-(5-chloro-6-(2H-1,2,3-triazol-2-yl)pyridin-3-yl)-3-(2-chloro-7-(2-methyl-1-(methylamino)propyl)-pyrazolo[1,5-a]pyrimidin-6-yl)urea was prepared analogously as described in example 119 using (S)-7-(1-((tert-butoxycarbonyl)(methyl)amino)-2-methylpropyl)-2-chloropyrazolo[1,5-a]pyrimidine-6-carboxylic acid instead of 7-(4-(tert-butoxycarbonyl)morpholin-3-yl)-2-chloropyrazolo[1,5-a]pyrimidine-6-carboxylic acid in step a). Mixture on step a) was stirred overnight at 100° C. and 2.5 h on step b). M/z=475-477 [M+H]+, Rt=2.77 min (HPLC Method C1), 1H NMR (400 MHz, CDCl$_3$) δ ppm: 11.03 (bs, 1H), 9.23 (s, 1H), 8.59 (s, 1H), 8.37 (s, 1H), 7.94 (s, 2H), 6.87 (bs, 1H), 6.64 (s, 1H), 4.81 (d, 1H), 2.45 (s, 3H), 2.34 (hept., 1H), 1.09 (d, 3H), 0.99 (d, 3H).

Example 125

1-(5-chloro-6-(2H-1,2,3-triazol-2-yl)pyridin-3-yl)-3-(2-chloro-7-(4-methylmorpholin-3-yl)pyrazolo[1,5-a]pyrimidin-6-yl)urea

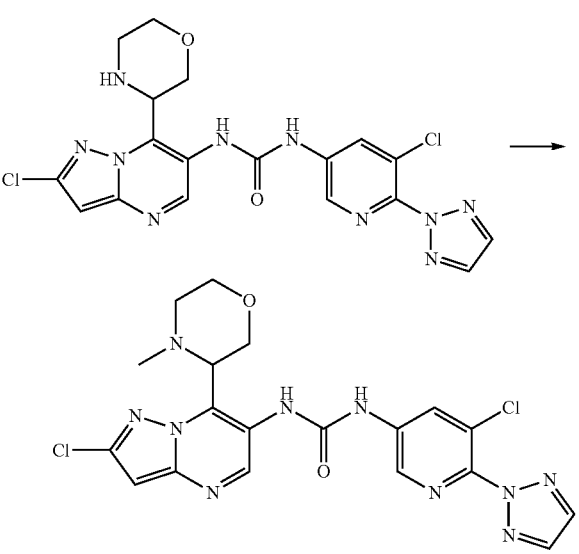

To a solution of 1-(5-chloro-6-(2H-1,2,3-triazol-2-yl)pyridin-3-yl)-3-(2-chloro-7-(morpholin-3-yl)pyrazolo[1,5-a]pyrimidin-6-yl)urea (50 mg, 0.105 mmol) in THF (1.5 ml) were added triphenylphosphine (55.2 mg, 0.21 mmol), diisopropyl azodicarboxylate (0.041 ml, 0.21 mmol) and then methyl iodide (0.013 ml, 0.21 mmol). The reaction mixture was stirred overnight at RT. The mixture was evaporated. The residue was purified by flash column chromatography on silica gel (cyclohexane/AcOEt 1/0 to 35/65). The product was triturated in MeOH, kept at RT for 1 h and centrifuged. The supernatant was removed and the solid product was dried on HV to afford 1-(5-chloro-6-(2H-1,2,3-triazol-2-yl)pyridin-3-yl)-3-(2-chloro-7-(4-methylmorpholin-3-yl)pyrazolo[1,5-a]pyrimidin-6-yl)urea. M/z=489-491 [M+H]+, Rt=2.59 min (HPLC Method C1), $^1$H NMR (400 MHz, DMSO-$d_6$) δ ppm: 10.51 (bs, 1H), 9.95 (bs, 1H), 9.07 (s, 1H), 8.59 (s, 1H), 8.49 (s, 1H), 8.16 (s, 2H), 6.91 (s, 1H), 4.50 (d, 1H), 3.94 (d, 1H), 3.88 (d, 1H), 3.72 (t, 1H), 3.50 (t, 1H), 3.03 (d, 1H), 2.42 (m, 1H), 2.23 (s, 3H).

Example 126

(R)-1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea

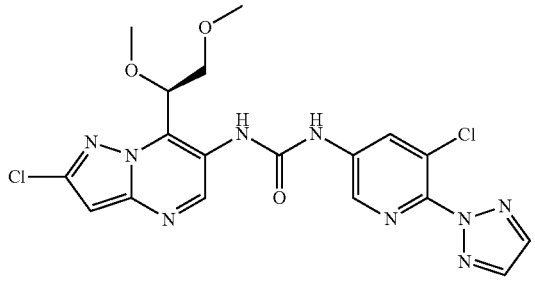 [SMILES: COC[C@H](OC)c1c(NC(=O)Nc2cnc(-n3nccn3)c(Cl)c2)cnc2cc(Cl)nn12]

(R)-1-(5-chloro-6-(2H-1,2,3-triazol-2-yl)pyridin-3-yl)-3-(2-chloro-7-(1,2-dimethoxyethyl)pyrazolo-[1,5-a]pyrimidin-6-yl) urea was obtained by purification of the mixture of both enantiomers by preparative chiral separation (Chiralcel OJ-H, 10×50 cm, 20 μm, n-heptane/(EtOH/MeOH 1/1) from 85/15 to 7/3, 1 ml/min). The product was suspended in cold CH$_3$CN (1.4 ml) and water (0.14 ml) and mixture was heated up to 100° C. until complete dissolution, then cooled down to RT and kept in the fridge over week-end. The solid was filtered and dried on HV to afford pure product. M/z=478-480 [M+H]+, Rt=4.01 min (HPLC Method C1), $^1$H NMR (400 MHz, DMSO-$d_6$) δ ppm: 10.43 (bs, 1H), 8.94 (s, 1H), 8.55 (m, 1H), 8.49 (m, 2H), 8.15 (s, 2H), 6.95 (s, 1H), 5.51 (m, 1H), 3.85 (m, 2H), 3.36 (s, 3H), 3.29 (s, 3H).

Example 127

(S)-1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea

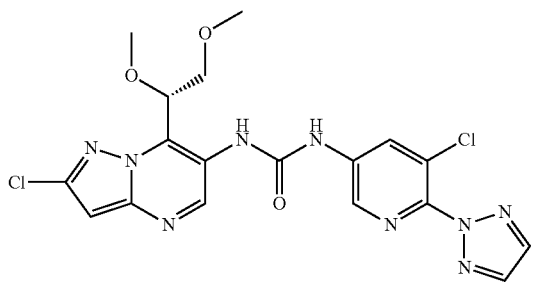 [SMILES: COC[C@@H](OC)c1c(NC(=O)Nc2cnc(-n3nccn3)c(Cl)c2)cnc2cc(Cl)nn12]

(S)-1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea was obtained by purification of the mixture of both isomers by preparative chiral separation (Chiralcel OJ-H, 10×50 cm, 20 μm, n-heptane/(EtOH/MeOH 1/1) from 85/15 to 7/3, 1 ml/min). M/z=478-480 [M+H]+, Rt=4.00 min (HPLC Method C1), $^1$H NMR (400 MHz, DMSO-$d_6$) δ ppm: 10.41 (bs, 1H), 8.95 (s, 1H), 8.55 (m, 1H), 8.49 (m, 1H), 8.47 (bs, 1H), 8.16 (s, 2H), 6.95 (s, 1H), 5.50 (m, 1H), 3.84 (m, 2H), 3.36 (s, 3H), 3.29 (s, 3H).

Biological/Pharmacological Section

The compounds of the invention exhibit valuable pharmacological properties, e.g. properties susceptible to MALT1, for example the inhibition of MALT1 proteolytic and/or autoproteolytic activity e.g. as indicated in the test assays provided infra and are therefore indicated for therapy.

Assays:

MALT1 Biochemical Assay:

IC50 values of test compounds were determined with an enzyme activity assay using the C-domain of MALT1 (amino acids 329-824). The readout parameter is the increase of fluorescence lifetime over time, proportional to enzyme activity.

The assay employs a short peptide substrate labeled with the single fluorophore PT14 as a fluorescence lifetime probe sensitive to the cleavage state of the substrate (PT14: 6-(9-oxo-9H-acridin-10-yl)-hexanoate, AssayMetrics, UK). The peptide substrate has the following sequence: Ac-Trp-Leu-Arg-Ser-Arg^Cys(PT14)-NH$_2$ (Product number BS-9117, Biosyntan, Germany, N-terminus to C-terminus from left to right in three letter code, Ac: acetyl group, Cys(PT14): cysteine residue with the fluorophore PT14 conjugated to the cysteine sulfhydryl group via a maleimide group; C-terminus of the peptide is amidated; within the substrate sequence written above, ^ indicates the scissile bond). The assay buffer consists of 200 mM Tris/HCl at pH 7.5, 0.8 M Na citrate, 100 μM EGTA, 100 μM DTT and 0.05% (w/v) CHAPS. The kinetic characterization of the enzymatic reaction led to the determination of a Michaelis Constant ($K_M$) of 40 μM and a kcat value of 34 s$^{-1}$. The assay was established for the 384-well plate format using black microtiter round well plates (Product number 95040020, Thermo Electron Oy, Finland). Test compounds were dissolved in 100% (v/v) DMSO or a mixture containing 90% (v/v) DMSO and 10% (v/v) H2O at a stock concentration of 100 mM. Serial dilutions of test compounds were prepared using either 100% (v/v) DMSO or a mixture containing 90% (v/v) DMSO and 10% (v/v) H2O.

For the measurement of compound inhibition, 0.25 μl of test compound were mixed with 12.5 μl of enzyme in wells of the 384-well plates, and incubated for 60 minutes at room temperature (22° C.). After that, 12.5 μl of substrate was added, and the enzymatic reaction was allowed to proceed for 60 minutes at room temperature (22° C.). The total assay volume was 25.25 μl, and the final assay concentrations for enzyme and substrate were 2.5 nM and 1 μM, respectively. The increase in assay signal over time is linear for at least 60 minutes at the assay conditions reported, and directly proportional to the concentration of active enzyme up to at least 2.5 nM. The DMSO content was between 0.9 and 1% (v/v). The final assay concentrations of the test compounds ranged typically from 100 μM to 1 nM in a serial dilution series using a dilution factor of 3.16 (i.e. half-logarithmic dilution steps). As controls, reactions were performed in multiple wells either by only adding DMSO instead of test compound, leading to an uninhibited enzymatic reaction (i.e. 0% inhibition), or by adding assay buffer without enzyme mixed with DMSO, which is the equivalent of a fully inhibited reaction (i.e. 100% inhibition). The fluorescence lifetimes were recorded using a microtiter plate reader such as the TECAN Ultra Evolution FLT instrument with fluorescence excitation at 405 nm and emission recording at 450 nm. The fluorescence lifetimes can be transformed to percentage inhibitions using the above mentioned controls as reference (for 0 and 100% inhibition). The IC50 value was calculated from the plot of percentage inhibition versus inhibitor concentration using non-linear regression analysis software (Origin, OriginLab Corporation, USA). The data were fitted using a 4 Parameter Logistic Model, characterized by the following equation:

$$y=A2+(A1-A2)/(1+(x/IC50)^p)$$

where y is the %-inhibition at the inhibitor concentration, x. A1 is the lowest inhibition value, and A2 the maximum inhibition value. The exponent, p, is the Hill coefficient.

cIAP2-MALT1-driven NFkappaB Reporter Gene Assay (RGA) in HEK293

The fusion protein cIAP2-MALT1 is driving constitutive NF-kB activation in the MALT-type of B cell lymphoma. To monitor the activity of MALT1 inhibitors on NF-kB signaling, a mechanistic model was established consisting of a stably transfected HEK293 cell line in which the activated cIAP2-MALT1 fusion protein is constitutively expressed and the firefly luciferase reporter gene is under the control of NF-kB response elements. Inhibition of luciferase gene expression is measured using a luciferase activity detection assay. Briefly, $1.8 \times 10^4$ cells/90 ul/well are seeded in a sterile, white-walled, clear-bottom tissue-culture-treated 96-well mircoplates (Costar, Cat-No 3903). After overnight incubation at 37° C., 10 µL of 10× 3-fold serial compound dilutions prepared initially in DMSO, followed by a 1:100 intermediated dilution in cell culture medium, is added to the cells using liquid handling robotics (Velocity Bravo 11, Agilent). Unless otherwise mentioned, compound start concentration is 10 µM and the final vehicle concentration is 0.1% DMSO in all wells. After 24 h compound incubation, cell viability is assessed in a first step 3 hrs following addition of 10 µl 135 µg/ml resazurin sodium salt (SIGMA Cat-Nr R7017) dissolved in phosphate-buffered saline. Following quantification of reduced resazurin at excitation/emission wavelengths of 540/590 nm on a multipurpose microplate reader (e.g. Infinite M200Pro, TECAN), cells are subjected to quantification of luciferase expression levels following incubation with 70 µL ONEGlow (Promega, Cat-Nr E6120) homogenous assay buffer for 20 min at room temperature. Light emission is recorded on a multipurpose microplate reader (e.g. Infinite M200Pro, TECAN) in luminescence detection mode. Raw data are processed using an Excel analysis template. The effect of a particular test compound concentration on NF-kB activity is expressed as luciferase signal (Relative Light Units) normalized to cell viability by means of division with the reduced resazurin signal (Relative Fluorescence Units). The value obtained for vehicle-treated cells is set as 100%. Absolute (50% reduction relative to vehicle control) and relative (inflection point) IC50 values (µM) are determined using 4-parametric curve-fitting (XLfit, V4.3.2). In addition, % normalized NF-kB signal and % cell viability at the highest compound concentration tested.

Human IL2 Promoter Reporter Gene Assay (RGA) in Jurkat Cells

The transfected Jurkat clone K22 290_H23 was propagated in RPMI 1640 supplemented with 10% heat inactivated fetal calf serum, 50 µM 2-mercaptoethanol and 1 mg/ml Geneticin. The cell concentration should not exceed 1×10e6/ml during culturing. The cells should not exceed passage 30. Prior to the assay the cells were washed and prepared to the concentration of 2×10e6 cells/ml.

Compound dilutions were made as 2×-concentrated solutions then diluted 1/2 by addition to cells. Two hundred and fifty µl of compound dilution and 250 µl of cells were mixed together in wells of a 96-deep well plate. Cells/compounds premix were incubated 30 min at 37° C. and 5% CO2 directly in the deep well plate.

After pre-incubation of cells with compounds, cells were stimulated with anti-CD28 mAb (clone 15E8) at 3 µg/ml+ PMA at 1 µg/ml. Both co-stimulants were diluted in culture medium at a 10×-concentrated solution. 10 µl of co-stimulants were pipetted into the white 96-well plates and 100 µl of cell/compound mix was immediately added in duplicates. The cells were stimulated for 5.5 h at 37° C. and 5% CO2.

After cell stimulation, 50 µl of BriteLitePlus reagent (Perkin Elmer) was added to each well and the bioluminescence was measured with a Wallac EnVision reader (Perkin Elmer).

Using the assays described above the following $IC_{50}$s were determined:

| Example | MALT1 biochemical activity $IC_{50}$ (nM) | NFkappaB reporter gene assay $IC_{50}$ (nM) | IL2 reporter gene assay $IC_{50}$ (nM) |
|---|---|---|---|
| 1 | 0.002 | 0.031 | 0.023 |
| 2 | 0.004 | 0.079 | 0.051 |
| 3 | 0.014 | 0.183 | 0.131 |
| 4 | 0.006 | 0.061 | |
| 5 | 0.005 | 0.112 | |
| 6 | 0.010 | 0.132 | 0.052 |
| 7 | 0.008 | | 0.030 |
| 8 | 0.007 | | 0.033 |
| 9 | 0.002 | 0.044 | 0.109 |
| 10 | 0.002 | 0.044 | 0.019 |
| 11 | 0.019 | 0.164 | |
| 12 | 0.014 | 0.071 | |
| 13 | 0.002 | 0.077 | 0.039 |
| 14 | 0.003 | 0.049 | 0.067 |
| 15 | 0.005 | 0.110 | |
| 16 | 0.002 | 0.035 | |
| 17 | 0.011 | 0.117 | |
| 18 | 0.003 | 0.149 | 0.207 |
| 19 | 0.003 | 0.091 | 0.149 |
| 20 | 0.003 | 0.099 | 0.245 |
| 21 | 0.003 | 0.082 | 0.104 |
| 22 | 0.004 | 0.074 | 0.100 |
| 23 | 0.004 | 0.301 | 0.307 |
| 24 | 0.005 | 0.131 | 0.214 |
| 25 | 0.005 | 0.306 | 0.526 |
| 26 | 0.005 | 0.085 | 0.134 |
| 27 | 0.006 | 0.054 | 0.248 |
| 28 | 0.009 | 0.215 | |
| 29 | 0.370 | | |
| 30 | 0.003 | 0.382 | 0.507 |
| 31 | 0.014 | 0.349 | |
| 32 | 0.019 | 0.214 | 0.221 |
| 33 | 0.030 | 0.408 | |
| 34 | 0.004 | 0.106 | |
| 35 | 0.003 | 0.048 | 0.059 |
| 36 | 0.009 | 0.183 | |
| 37 | 0.011 | 0.221 | |
| 38 | 0.005 | 0.176 | 0.145 |
| 39 | 0.003 | 0.060 | |
| 40 | 0.006 | 0.112 | 0.043 |
| 41 | 0.024 | 0.356 | |
| 42 | 0.021 | 0.378 | |
| 43 | 0.009 | 0.159 | |
| 44 | 0.004 | 0.112 | |
| 45 | 0.003 | 0.157 | |
| 46 | 0.013 | 0.064 | 0.082 |

-continued

| Example | MALT1 biochemical activity IC$_{50}$ (nM) | NFkappaB reporter gene assay IC$_{50}$ (nM) | IL2 reporter gene assay IC$_{50}$ (nM) |
| --- | --- | --- | --- |
| 47 | 0.029 | 0.391 | |
| 48 | 0.042 | 0.341 | |
| 49 | 0.003 | 0.059 | |
| 50 | 0.020 | 0.230 | |
| 51 | 0.006 | 0.195 | |
| 52 | 0.005 | 0.076 | 0.063 |
| 53 | 0.004 | 0.171 | |
| 54 | 0.004 | 0.117 | 0.094 |
| 55 | 0.005 | 0.287 | |
| 56 | 0.005 | 0.131 | 0.095 |
| 57 | 0.019 | 0.284 | |
| 58 | 0.009 | 0.208 | 0.267 |
| 59 | 0.019 | 0.148 | |
| 60 | 0.026 | 0.502 | |
| 61 | 0.019 | 0.370 | |
| 62 | 0.042 | 0.345 | 0.266 |
| 63 | 0.008 | 0.354 | |
| 64 | 0.013 | 0.187 | |
| 65 | 0.009 | 0.405 | |
| 66 | 0.018 | 0.241 | |
| 67 | 0.035 | 0.553 | |
| 68 | 0.039 | 0.586 | |
| 69 | 0.086 | 0.678 | |
| 70 | 0.123 | 0.891 | |
| 71 | 0.005 | 0.079 | 0.014 |
| 72 | 0.003 | 0.179 | 0.140 |
| 73 | 0.012 | 0.163 | 0.091 |
| 74 | 0.002 | 0.030 | 0.032 |
| 75 | 0.005 | 0.100 | 0.072 |
| 76 | 0.006 | 0.084 | 0.028 |
| 77 | 0.006 | 0.241 | |
| 78 | 0.021 | 0.159 | 0.076 |
| 79 | 0.045 | 0.408 | 0.206 |
| 80 | 0.034 | 0.621 | |
| 81 | 0.005 | 0.095 | 0.063 |
| 82 | 0.122 | 0.311 | |
| 83 | 0.055 | 0.829 | |
| 84 | 0.019 | 0.089 | |
| 85 | 0.005 | 0.190 | |
| 86 | 0.080 | 0.569 | |
| 87 | 0.007 | 0.417 | |
| 88 | 0.014 | 0.102 | 0.047 |
| 89 | 0.003 | | 0.046 |
| 90 | 0.097 | 0.696 | 0.927 |
| 91 | 0.002 | 0.105 | 0.089 |
| 92 | 0.009 | | 0.046 |
| 93 | 0.001 | | 0.157 |
| 94 | 0.002 | | 0.016 |
| 95 | 0.002 | | 0.013 |
| 96 | 0.010 | | 0.049 |
| 97 | 0.003 | | 0.068 |
| 98 | 0.005 | | 0.044 |
| 99 | 0.021 | | 0.041 |
| 100 | 0.019 | | 0.084 |
| 101 | 0.005 | | 0.025 |
| 102 | 0.003 | | 0.014 |
| 103 | 0.005 | | 0.050 |
| 104 | 0.002 | | 0.024 |
| 105 | 0.011 | | 0.059 |
| 106 | 0.008 | | 0.484 |
| 107 | 0.013 | | 0.060 |
| 108 | 0.008 | | 0.052 |
| 109 | 0.053 | | 0.218 |
| 110 | 0.009 | | 0.115 |
| 111 | 0.003 | | 0.054 |
| 112 | 0.016 | 0.361 | |
| 113 | 0.011 | | |
| 114 | 0.007 | | |
| 115 | 0.076 | | |
| 116 | 0.071 | 0.687 | |
| 117 | 0.008 | 0.170 | 0.134 |
| 118 | 0.028 | 0.256 | 0.112 |
| 119 | 0.012 | 0.157 | |
| 120 | 0.009 | 0.438 | |
| 121 | 0.020 | 0.218 | |
| 122 | 0.008 | 0.043 | 0.017 |
| 123 | 0.041 | | 0.199 |
| 124 | 0.008 | | 0.041 |
| 125 | 0.009 | | 0.138 |
| 126 | 0.005 | 0.119 | 0.058 |
| 127 | 0.009 | | 0.078 |

Utilities

According to the results obtained in the test assays provided above, it is contemplated that the compounds of the invention may be useful in the treatment of a disease or disorder (an indication) selected from:

Conditions and disorders characterized by disregulated NF-kB activation, in particular autoimmune/immunological and inflammatory disorders, allergic disorders, respiratory disorders and oncological disorders.

Said autoimmune and inflammatory disorders may inter alia be selected from arthritis, ankylosing spondylitis, inflammatory bowel disease, ulcerative colitis, gastritis, pancreatitis, Crohn's disease, celiac disease, multiple sclerosis, systemic lupus erythematosus, rheumatic fever, gout, organ or transplant rejection, acute or chronic graft-versus-host disease, chronic allograft rejection, Behcet's disease, uveitis, psoriasis, dermatitis, atopic dermatitis, dermatomyositis, myasthena gravis, Grave's disease, Hashimoto thyroiditis, Sjögren's syndrome, and blistering disorders (e.g. pemphigus vulgaris), antibody-mediated vasculitis syndromes, including ANCA-associated vasculitides, Hennoch-Schönlein Purpura, and immune-complex vasculitides (either primary or secondary to infection or cancers).

Said oncological disorders may inter alia be selected from carcinoma, sarcoma, lymphoma, leukemia and germ cell tumors, e.g. adenocarcinoma, bladder cancer, clear cell carcinoma, skin cancer, brain cancer, cervical cancer, colon cancer, colorectal cancer, endometrial cancer, bladder cancer, brain tumours, breast cancer, gastric cancer, germ cell tumours, glioblastoma, hepatic adenomas, Hodgkin's lymphoma, liver cancer, kidney cancer, lung cancer, ovarian cancer, dermal tumours, prostate cancer, renal cell carcinoma, stomach cancer, medulloblastoma, non-Hodgkin's lymphoma, diffuse large B-cell lymphoma, mantle cell lymphoma, marginal zone lymphoma, cutaneous T-cell lymphoma, melanoma, mucosa-associated lymphoid tissue (MALT) lymphoma, multiple myeloma, plasma cell neoplasm, lentigo maligna melanomas, and acral lentiginous melanoma.

Said allergic disorder may inter alia be selected from contact dermatitis, celiac disease, asthma, hypersensitivity to house dust mites, pollen and related allergens, Berylliosis Said respiratory disorders may inter alia be selected from asthma, bronchitis, chronic obstructive pulmonary disease (COPD), cystic fibrosis, pulmonary oedema, pulmonary embolism, pneumonia, pulmonary sarcoidosis, silicosis, pulmonary fibrosis, respiratory failure, acute respiratory distress syndrome, primary pulmonary hypertension and emphysema.

In another embodiment the compounds of the invention may be useful in the treatment of rheumatoid arthritis, systemic lupus erythematosus, vasculitic conditions, allergic diseases, asthma, chronic obstructive pulmonary disease (COPD), acute or chronic transplant rejection, graft versus host disease, cancers of hematopoietic origin or solid tumors, chronic myelogenous leukemia, myeloid leukemia, non-Hodgkin lymphoma or other B cell lymphomas.

In another embodiment the compounds of the invention may be useful in the treatment of BENTA disease, berylliosis, rheumatoid arthritis, systemic lupus erythematosus, lupus nephritis, multiple sclerosis, polymyositis, psoriasis, ABC-DLBCL, e.g. with activating mutations in Card11, MALT lymphomas.

Combinations

The compound of the present invention may be administered either simultaneously with, or before or after, one or more other therapeutic agent. The compound of the present invention may be administered separately, by the same or different route of administration, or together in the same pharmaceutical composition as the other agents.

The compounds of the invention may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell antiproliferative agent.

For example, the compounds of the invention may be used in combination with a calcineurin inhibitor, e.g. cyclosporin A or FK 506; a mTOR inhibitor, e.g. rapamycin, 40-O-(2-hydroxyethyl)-rapamycin, biolimus-7 or biolimus-9; an ascomycin having immunosuppressive properties, e.g. ABT-281, ASM981; corticosteroids; cyclophosphamide; azathioprene; methotrexate; leflunomide; mizoribine; mycophenolic acid or salt; mycophenolate mofetil; IL-1beta inhibitor.

In another embodiment compounds of the invention are combined with a co-agent which are PI3Kinase inhibitors.

In another embodiment compounds of the invention are combined with co-agent that influence BTK (Bruton's tyrosine kinase).

For the treatment of oncological diseases compounds of the invention may be used in combination with B-cell modulating agents, e.g. Rituximab, Btk or Syk inhibitors, inhibitors of PKC, PI3 kinases, PDK, PIM, JAK and mTOR and BH3 mimetics.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a co-agent, are both administered to a patient simultaneously in the form of a single entity or dosage. The term "non-fixed combination" means that the active ingredients, e.g. a compound of formula (I) and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by MALT1. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

The invention claimed is:

1. A compound of formula (I) or a pharmaceutically acceptable salt thereof;

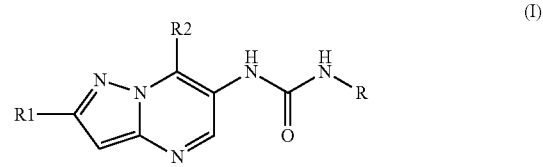

(I)

wherein,
R1 is halogen, cyano, or $C_1$-$C_3$ alkyl optionally substituted by halogen;
R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy wherein said alkoxy again may optionally be substituted by $C_1$-$C_6$ alkoxy, N,N-di-$C_1$-$C_6$ alkyl amino, Rg or phenyl; $C_3$-$C_6$ cycloalkyl optionally substituted by $C_1$-$C_6$ alkyl, N,N-di-$C_1$-$C_6$ alkyl amino or $C_1$-$C_6$ alkoxy-$C_1$-$C_6$ alkyl, or two of said $C_3$-$C_6$ cycloalkyl optional substituents together with the atoms to which they are bound may form an annulated or spirocyclic 4-6 membered saturated heterocyclic ring comprising 1-2 O atoms; phenyl optionally substituted by $C_1$-$C_6$ alkoxy; a 5-6 membered heteroaryl ring having 1 to 3 heteroatoms selected from N and O said ring being optionally substituted by $C_1$-$C_6$ alkyl which may be optionally substituted by amino or hydroxy; Rg; or N,N-di-$C_1$-$C_6$ alkyl amino carbonyl; wherein
Rg is a 5-6 membered heterocyclic ring having 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is phenyl independently substituted two or more times by Ra, 2-pyridyl independently substituted one or more times by Rb, 3-pyridyl independently substituted one or more times by Rc, or 4-pyridyl independently substituted one or more times by Rd; wherein Ra independently from each other is halogen; cyano; —COOC$_1$-C$_6$ alkyl; C$_1$-C$_6$ alkoxy; C$_1$-C$_6$ alkyl optionally substituted by halogen or a 5-6 membered heterocyclyl ring having 1 to 2 heteroatoms selected from N and O which ring is optionally substituted by C$_1$-C$_6$ alkyl; a 5-6 membered heteroaryl ring having 1 to 3 heteroatoms selected from N and O said ring being optionally substituted by amino, C$_1$-C$_6$ alkyl optionally substituted by amino or hydroxy, or by N-mono- or N,N-di-C$_1$-C$_6$ alkylamino carbonyl; or two Ra together with the ring atoms to which they are bound may form a 5 to 6 membered heterocyclic or heteroaromatic ring having 1 to 2 N atoms, any such ring being optionally substituted by C$_1$-C$_6$ alkyl or oxo;

Rb, Rc and Rd independently from each other are halogen; oxo; hydroxyl; cyano; C$_1$-C$_6$ alkoxy optionally substituted by halogen; C$_1$-C$_6$ alkoxy carbonyl; phenyl; N,N-di-C$_1$-C$_6$ alkyl amino; C$_1$-C$_6$ alkyl optionally substituted by halogen or phenyl; a 5-6 membered heteroaryl ring having 1 to 3 N atoms said ring being optionally substituted by C$_1$-C$_6$ alkyl optionally substituted by amino or hydroxy, or by mono- or di-N-C$_1$-C$_6$ alkylamino carbonyl; O—Rh; or Rh; wherein Rh is a 5-6 membered heterocyclyl ring having 1 to 4 heteroatoms selected from N, O and S said ring being optionally substituted by C$_1$-C$_6$ alkyl, hydroxyl or oxo.

2. The compound of claim 1 or a pharmaceutically acceptable salt thereof, wherein R1 is halogen;

R2 is C$_1$-C$_6$ alkyl optionally substituted by one or more times by C$_1$-C$_6$ alkyl, C$_2$-C$_6$ alkenyl, hydroxyl, N,N-di-C$_1$-C$_6$ alkyl amino, N-mono-C$_1$-C$_6$ alkyl amino, O—Rg, Rg, phenyl, or by C$_1$-C$_6$ alkoxy, wherein said alkoxy again may optionally be substituted by C$_1$-C$_6$ alkoxy, N,N-di-C$_1$-C$_6$ alkyl amino, Rg or phenyl; wherein Rg is a 5-6 membered heterocyclic ring containing 1-3 heteroatoms selected from N and O said ring being optionally substituted by C$_1$-C$_6$ alkyl, C$_1$-C$_6$ alkoxy-C$_1$-C$_6$ alkyl, C$_1$-C$_6$ alkoxy-carbonyl;

R is 2-pyridyl independently substituted one or more times by Rb, 3-pyridyl independently substituted one or more times by Rc, or 4-pyridyl independently substituted one or more times by Rd; and Rb, Rc and Rd independently from each other are halogen; oxo; hydroxyl; cyano; C$_1$-C$_6$ alkoxy optionally substituted by halogen; C$_1$-C$_6$ alkoxy carbonyl; phenyl; N,N-di-C$_1$-C$_6$ alkyl amino; C$_1$-C$_6$ alkyl optionally substituted by halogen or phenyl; a 5-6 membered heteroaryl ring having 1 to 3 N atoms said ring being optionally substituted by C$_1$-C$_6$ alkyl optionally substituted by amino or hydroxy, or by mono- or di-N-C$_1$-C$_6$ alkylamino carbonyl; O—Rh; or Rh; wherein Rh is a 5-6 membered heterocyclyl ring having 1 to 4 heteroatoms selected from N, O and S said ring being optionally substituted by C$_1$-C$_6$ alkyl, hydroxyl or oxo.

3. The compound of claim 1, or a pharmaceutically acceptable salt thereof, wherein R1 is chloro.

4. The compound of claim 2, or a pharmaceutically acceptable salt thereof, wherein R1 is chloro;

R is 2-pyridyl independently substituted one or more times by Rb;

or R is 3-pyridyl independently substituted one or more times by Rc;

or R is 4-pyridyl independently substituted one or more times by Rd;

R2 is C$_1$-C$_6$ alkyl optionally substituted one or more times by C$_1$-C$_6$ alkyl, C$_2$-C$_6$ alkenyl, hydroxyl, N,N-di-C$_1$-C$_6$ alkyl amino, N-mono-C$_1$-C$_6$ alkyl amino, O—Rg, Rg, phenyl, or by C$_1$-C$_6$ alkoxy, wherein said alkoxy again may optionally be substituted by C$_1$-C$_6$ alkoxy, N,N-di-C$_1$-C$_6$ alkyl amino, Rg or phenyl; wherein Rg is a 5-6 membered heterocyclic ring containing 1-3 heteroatoms selected from N and O said ring being optionally substituted by C$_1$-C$_6$ alkyl, C$_1$-C$_6$ alkoxy-C$_1$-C$_6$ alkyl, C$_1$-C$_6$ alkoxy-carbonyl;

Rb, Rc and Rd independently from each other are halogen; oxo; hydroxyl; cyano; C$_1$-C$_6$ alkoxy optionally substituted by halogen; C$_1$-C$_6$ alkoxy carbonyl; phenyl; N,N-di-C$_1$-C$_6$ alkyl amino; C$_1$-C$_6$ alkyl optionally substituted by halogen or phenyl; a 5-6 membered heteroaryl ring having 1 to 3 N atoms said ring being optionally substituted by C$_1$-C$_6$ alkyl optionally substituted by amino or hydroxy, or by mono- or di-N-C$_1$-C$_6$ alkylamino carbonyl; O—Rh; or Rh; wherein Rh is a 5-6 membered heterocyclyl ring having 1 to 4 heteroatoms selected from N, O and S said ring being optionally substituted by C$_1$-C$_6$ alkyl, hydroxyl or oxo.

5. The compound of claim 1 or a pharmaceutically acceptable salt thereof, wherein R1 is halogen, cyano, or C$_1$-C$_3$ alkyl optionally substituted by halogen;

R2 is C$_1$-C$_6$ alkyl optionally substituted one or more times by C$_1$-C$_6$ alkyl, C$_2$-C$_6$ alkenyl, hydroxyl, N,N-di-C$_1$-C$_6$ alkyl amino, N-mono-C$_1$-C$_6$ alkyl amino, O—Rg, Rg, phenyl, or by C$_1$-C$_6$ alkoxy wherein said alkoxy again may optionally be substituted by C$_1$-C$_6$ alkoxy, N,N-di-C$_1$-C$_6$ alkyl amino, Rg or phenyl; C$_3$-C$_6$ cycloalkyl optionally substituted by C$_1$-C$_6$ alkyl, N,N-di-C$_1$-C$_6$ alkyl amino or C$_1$-C$_6$ alkoxy-C$_1$-C$_6$ alkyl, or two of said C$_3$-C$_6$ cycloalkyl optional substituents together with the atoms to which they are bound may form an annulated or spirocyclic 4-6 membered saturated heterocyclic ring comprising 1-2 O atoms; phenyl optionally substituted by C$_1$-C$_6$ alkoxy; a 5-6 membered heteroaryl containing 1 to 3 heteroatoms selected from N and O optionally substituted by C$_1$-C$_6$ alkyl which may optionally be substituted by amino or hydroxy; Rg; or N,N-di-C$_1$-C$_6$ alkyl amino carbonyl; wherein Rg is a 5-6 membered heterocyclic ring containing 1-3 heteroatoms selected from N and O said ring being optionally substituted by C$_1$-C$_6$ alkyl, C$_1$-C$_6$ alkoxy-C$_1$-C$_6$ alkyl, C$_1$-C$_6$ alkoxy-carbonyl;

R is phenyl independently substituted two or more times by Ra; wherein

Ra independently from each other is halogen; cyano; —COOC$_1$-C$_6$ alkyl; C$_1$-C$_6$ alkoxy; C$_1$-C$_6$ alkyl optionally substituted by halogen or a 5-6 membered heterocyclic ring containing 1 to 2 N atoms said ring being optionally substituted by C$_1$-C$_6$ alkyl; a 5-6 membered heteroaryl ring containing 1 to 3 N atoms said ring being optionally substituted by amino, $C_1$-$C_6$ alkyl optionally substituted by amino or hydroxy, or by N-mono- or N,N-di-$C_1$-$C_6$ alkylamino carbonyl;

or, two Ra together with the ring atoms to which they are bound form a 5 to 6 membered heterocyclic or heteroaromatic ring containing 1 to 2 N atoms, any such ring being optionally substituted by $C_1$-$C_6$ alkyl or oxo.

6. The compound of claim 1, or a pharmaceutically acceptable salt thereof, wherein R1 is methyl.

7. The compound of claim 1, or a pharmaceutically acceptable salt thereof, wherein R1 is halogen;

R is phenyl independently substituted two or more times by Ra; wherein

Ra independently from each other is halogen; cyano; —COO$C_1$-$C_6$ alkyl; $C_1$-$C_6$ alkoxy; $C_1$-$C_6$ alkyl optionally substituted by fluoro or a 5-6 membered heterocyclic ring containing 1 to 2 N atoms which heterocyclyl is optionally substituted by $C_1$-$C_6$ alkyl; a 5-6 membered heteroaryl ring containing 1 to 3 N atoms said ring being optionally substituted by amino, $C_1$-$C_6$ alkyl optionally substituted by amino or hydroxy, or by N-mono- or N,N-di-$C_1$-$C_6$ alkylamino carbonyl, and R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy wherein said alkoxy again may optionally be substituted by $C_1$-$C_6$ alkoxy, N,N-di-$C_1$-$C_6$ alkyl amino, Rg or phenyl; $C_3$-$C_6$ cycloalkyl optionally substituted by $C_1$-$C_6$ alkyl, N,N-di-$C_1$-$C_6$ alkyl amino or $C_1$-$C_6$ alkoxy-$C_1$-$C_6$ alkyl, or two of said $C_3$-$C_6$ cycloalkyl optional substituents together with the atoms to which they are bound may form an annulated or spirocyclic 4-6 membered saturated heterocyclic ring comprising 1-2 O atoms; phenyl optionally substituted by $C_1$-$C_6$ alkoxy; a 5-6 membered heteroaryl ring having 1 to 3 heteroatoms selected from N and O said ring being optionally substituted by $C_1$-$C_6$ alkyl which may be optionally substituted by amino or hydroxy; Rg; or N,N-di-$C_1$-$C_6$ alkyl amino carbonyl; wherein Rg is a 5-6 membered heterocyclic ring having 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl.

8. The compound of claim 1 or a pharmaceutically acceptable salt thereof, wherein the compound is selected from (S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea;

(S)-1-(2-chloro-7-(1-methoxyethyl)pyrazolo [1,5-a]pyrimidin-6-yl)-3-(2-(trifluoromethyl)pyridin-4-yl)urea;

(S)-1-(2-chloro-7-(1-methoxyethyl)pyrazolo [1,5-a]pyrimidin-6-yl)-3-(1-methyl-2-oxo-5-(trifluoromethyl)-1,2-dihydropyridin-3-yl)urea;

(R)-1-(6-(2H-1,2,3-triazol-2-yl)-5-(trifluoromethyl)pyridin-3-yl)-3-(2-chloro-7-(1-methoxy-2-methylpropyl)pyrazolo[1,5-a]pyrimidin-6-yl)urea;

(R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea;

(S)-1-(7-(1-methoxyethyl)-2-methylpyrazolo[1,5-a]pyrimidin-6-yl)-3-(2-(trifluoromethyl)pyridin-4-yl)urea;

(S)-1-(2-fluoro-7-(1-methoxyethyl)pyrazolo[1,5-a]pyrimidin-6-yl)-3-(2-(trifluoromethyl)pyridin-4-yl)urea;

(S)-1-(2-chloro-7-(1-methoxyethyl)pyrazolo[1,5-a]pyrimidin-6-yl)-3-(5-cyanopyridin-3-yl)urea;

(S)-1-(5-chloro-6-methoxypyridin-3-yl)-3-(2-chloro-7-(1-methoxyethyl)pyrazolo[1,5-a]pyrimidin-6-yl)urea;

(S)-1-(5-chloro-6-(2H-1,2,3-triazol-2-yl)pyridin-3-yl)-3-(2-chloro-7-(1-methoxyethyl)pyrazolo[1,5-a]pyrimidin-6-yl)urea;

(S)-1-(2-chloro-7-(1-methoxyethyl)pyrazolo[1,5-a]pyrimidin-6-yl)-3-(5-methoxy-6-(2H-1,2,3-triazol-2-yl)pyridin-3-yl)urea;

(S)-1-(2-chloro-7-(1-methoxyethyl)pyrazolo[1,5-a]pyrimidin-6-yl)-3-(2-chloropyridin-4-yl)urea;

(S)-methyl 3-chloro-5-(3-(2-chloro-7-(1-methoxyethyl)pyrazolo[1,5-a]pyrimidin-6-yl)ureido)benzoate;

1-(5-chloro-6-(2H-1,2,3-triazol-2-yl)pyridin-3-yl)-3-(2-chloro-7-(2-methoxypropan-2-yl)pyrazolo[1,5-a]pyrimidin-6-yl)urea;

1-(2-chloro-7-(2-methoxypropan-2-yl)pyrazolo[1,5-a]pyrimidin-6-yl)-3-(2-(trifluoromethyl)pyridin-4-yl)urea;

1-(5-chloro-6-(2H-1,2,3-triazol-2-yl)pyridin-3-yl)-3-(2-chloro-7-(1-methylcyclopropyl)pyrazolo[1,5-a]pyrimidin-6-yl)urea;

1-(2-chloro-7-(1-methylcyclopropyl)pyrazolo[1,5-a]pyrimidin-6-yl)-3-(2-(trifluoromethyl)pyridin-4-yl)urea;

1-(5-chloro-6-methoxypyridin-3-yl)-3-(2-chloro-7-isopropylpyrazolo[1,5-a]pyrimidin-6-yl)urea;

1-(2-chloro-7-isopropylpyrazolo[1,5-a]pyrimidin-6-yl)-3-(3-cyano-4-(3-methyl-1H-1,2,4-triazol-1-yl)phenyl)urea;

1-(3-chloro-4-(2H-1,2,3-triazol-2-yl)phenyl)-3-(2-chloro-7-isopropylpyrazolo[1,5-a]pyrimidin-6-yl)urea;

1-(5-chloro-6-(2H-1,2,3-triazol-2-yl)pyridin-3-yl)-3-(2-chloro-7-isopropylpyrazolo[1,5-a]pyrimidin-6-yl)urea;

1-(5-chloro-6-(4-methyl-2H-1,2,3-triazol-2-yl)pyridin-3-yl)-3-(2-chloro-7-isopropylpyrazolo[1,5-a]pyrimidin-6-yl)urea;

1-(4-(2-aminopyrimidin-4-yl)-3-chlorophenyl)-3-(2-chloro-7-isopropylpyrazolo[1,5-a]pyrimidin-6-yl)urea;

1-(5-chloro-l-methyl-6-oxo-2-(1H-pyrazol-1-yl)-1,6-dihydropyridin-3-yl)-3-(2-chloro-7-isopropylpyrazolo[1,5-a]pyrimidin-6-yl)urea;

1-(5-chloro-6-ethoxypyridin-3-yl)-3-(2-chloro-7-isopropylpyrazolo[1,5-a]pyrimidin-6-yl)urea;

1-(5-bromopyridin-3-yl)-3-(2-chloro-7-isopropylpyrazolo[1,5-a]pyrimidin-6-yl)urea;

1-(2-chloro-7-isopropylpyrazolo[1,5-a]pyrimidin-6-yl)-3-(6-(1,1-dioxidoisothiazolidin-2-yl)-5-(trifluoromethyl)pyridin-3-yl)urea;

1-(3-chloro-4-(3-(hydroxymethyl)-5-methyl-1H-pyrazol-1-yl)phenyl)-3-(2-chloro-7-isopropylpyrazolo[1,5-a]pyrimidin-6-yl)urea;

1-(5-chloro-6-(1-methyl-1H-pyrazol-5-yl)pyridin-3-yl)-3-(2-chloro-7-isopropylpyrazolo [1,5-a]pyrimidin-6-yl)urea;

1-(2-chloro-7-isopropylpyrazolo[1,5-a]pyrimidin-6-yl)-3-(3,5-dichloro-4-(2H-1,2,3-triazol-2-yl)phenyl)urea;

1-(5-chloro-2-oxoindolin-7-yl)-3-(2-chloro-7-isopropylpyrazolo[1,5-a]pyrimidin-6-yl)urea;

1-(2-chloro-7-isopropylpyrazolo[1,5-a]pyrimidin-6-yl)-3-(1-methyl-2-oxo-5-(trifluoro-methyl)-1,2-dihydropyridin-3-yl)urea;

1-(5-chloro-2-((1-methylpyrrolidin-3-yl)oxy)-6-(2H-1,2,3-triazol-2-yl)pyridin-3-yl)-3-(2-chloro-7-isopropylpyrazolo[1,5-a]pyrimidin-6-yl)urea;
1-(7-(tert-butyl)-2-chloropyrazolo[1,5-a]pyrimidin-6-yl)-3-(5-chloro-6-(2H-1,2,3-triazol-2-yl)pyridin-3-yl)urea;
1-(7-(sec-butyl)-2-chloropyrazolo[1,5-a]pyrimidin-6-yl)-3-(5-chloro-6-(2H-1,2,3-triazol-2-yl)pyridin-3-yl)urea;
1-(2-chloro-7-(2-methyltetrahydrofuran-2-yl)pyrazolo[1,5-a]pyrimidin-6-yl)-3-(2-(trifluoro-methyl)pyridin-4-yl)urea;
(R)-1-(2-chloro-7-(1-methoxy-2-methylpropyl)pyrazolo[1,5-a]pyrimidin-6-yl)-3-(2-(trifluoro-methyl)pyridin-4-yl)urea;
1-(5-chloro-6-(2H-1,2,3-triazol-2-yl)pyridin-3-yl)-3-(2-chloro-7-cyclobutylpyrazolo[1,5-a]-pyrimidin-6-yl)urea;
(S)-1-(5-chloro-6-(2H-1,2,3-triazol-2-yl)pyridin-3-yl)-3-(2-chloro-7-(1-(2-methoxy-ethoxy)-ethyl)pyrazolo[1,5-a]pyrimidin-6-yl)urea;
(S)-1-(5-chloro-6-methoxypyridin-3-yl)-3-(2-chloro-7-(1-(2-methoxyethoxy)-ethyl)-pyrazolo-[1,5-a]pyrimidin-6-yl)urea;
(S)-1-(2-chloro-7-(1-(2-methoxyethoxy)ethyl)pyrazolo[1,5-a]pyrimidin-6-yl)-3-(2-(trifluoromethyl)-pyridin-4-yl)urea;
(R)-1-(5-chloro-6-(2H-1,2,3-triazol-2-yl)pyridin-3-yl)-3-(2-chloro-7-(1-(2-methoxy-ethoxy)-ethyl)pyrazolo[1,5-a]pyrimidin-6-yl)urea;
1-(5-chloro-6-(2H-1,2,3-triazol-2-yl)pyridin-3-yl)-3-(2-chloro-7-(1,4-dioxan-2-yl)-pyrazolo[1,5-a]pyrimidin-6-yl)urea;
(S)-1-(5-chloro-6-(2H-1,2,3-triazol-2-yl)pyridin-3-yl)-3-(2-chloro-7-(1-methoxypropan-2-yl)-pyrazolo[1,5-a]pyrimidin-6-yl)urea;
(R)-1-(5-chloro-6-(2H-1,2,3-triazol-2-yl)pyridin-3-yl)-3-(2-chloro-7-(1-methoxypropan-2-yl)-pyrazolo[1,5-a]pyrimidin-6-yl)urea;
(R)-1-(5-chloro-6-(2H-1,2,3-triazol-2-yl)pyridin-3-yl)-3-(2-chloro-7-(1-methoxyethyl)-pyrazolo[1,5-a]pyrimidin-6-yl)urea;
(R)-1-(2-chloro-7-(1-methoxyethyl)pyrazolo[1,5-a]pyrimidin-6-yl)-3-(2-(trifluoromethyl)-pyridin-4-yl)urea;
(R)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea;
1-(5-chloro-6-(2H-1,2,3-triazol-2-yl)pyridin-3-yl)-3-(2-chloro-7-(methoxy(phenyl)methyl)-pyrazolo[1,5-a]pyrimidin-6-yl)urea;
1-(5-chloro-6-(2H-1,2,3-triazol-2-yl)pyridin-3-yl)-3-(2-chloro-7-(1-(methoxymethyl)cyclobutyl)pyrazolo[1,5-a]pyrimidin-6-yl)urea;
1-(2-chloro-7-(1-(methoxymethyl)cyclobutyl)pyrazolo[1,5-a]pyrimidin-6-yl)-3-(2-(trifluoromethyl)pyridin-4-yl)urea;
1-(5-chloro-6-(2H-1,2,3-triazol-2-yl)pyridin-3-yl)-3-(2-chloro-7-cyclopropylpyrazolo[1,5-a]pyrimidin-6-yl)urea;
1-(5-chloro-6-(2H-1,2,3-triazol-2-yl)pyridin-3-yl)-3-(2-chloro-7-(2-methoxyphenyl)pyrazolo[1,5-a]pyrimidin-6-yl)urea;
1-(6-(2H-1,2,3-triazol-2-yl)-5-(trifluoromethyl)pyridin-3-yl)-3-(2-chloro-7-(tetrahydrofuran-2-yl)pyrazolo[1,5-a]pyrimidin-6-yl)urea;
1-(5-chloro-6-(2H-1,2,3-triazol-2-yl)pyridin-3-yl)-3-(2-chloro-7-(4-methyltetrahydro-2H-pyran-4-yl)pyrazolo[1,5-a]pyrimidin-6-yl)urea;
1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea;
1-(5-chloro-6-(2H-1,2,3-triazol-2-yl)pyridin-3-yl)-3-(2-chloro-7-(tetrahydrofuran-3-yl)pyrazolo[1,5-a]pyrimidin-6-yl)urea;
1-(5-chloro-6-(2H-1,2,3-triazol-2-yl)pyridin-3-yl)-3-(2-chloro-7-(tetrahydro-2H-pyran-4-yl)pyrazolo[1,5-a]pyrimidin-6-yl)urea;
1-(5-chloro-6-(2H-1,2,3-triazol-2-yl)pyridin-3-yl)-3-(2-chloro-7-(methoxymethyl)pyrazolo[1,5-a]pyrimidin-6-yl)urea;
1-(5-chloro-6-(2H-1,2,3-triazol-2-yl)pyridin-3-yl)-3-(2-chloro-7-((tetrahydro-2H-pyran-4-yl)methyl)pyrazolo[1,5-a]pyrimidin-6-yl)urea;
1-(5-chloro-6-(2H-1,2,3-triazol-2-yl)pyridin-3-yl)-3-(2-chloro-7-(isopropoxymethyl)pyrazolo[1,5-a]pyrimidin-6-yl)urea;
1-(5-chloro-6-(2H-1,2,3-triazol-2-yl)pyridin-3-yl)-3-(2-chloro-7-methylpyrazolo[1,5-a]pyrimidin-6-yl)urea;
1-(6-(2H-1,2,3-triazol-2-yl)-5-(trifluoromethyl)pyridin-3-yl)-3-(2-chloro-7-(furan-2-yl)pyrazolo[1,5-a]pyrimidin-6-yl)urea;
1-(5-chloro-6-(2H-1,2,3-triazol-2-yl)pyridin-3-yl)-3-(2-chloro-7-(1,3-dimethoxypropyl)pyrazolo[1,5-a]pyrimidin-6-yl)urea;
(R)-1-(6-(2H-1,2,3-triazol-2-yl)-5-(trifluoromethyl)pyridin-3-yl)-3-(7-(1-(benzyloxy)ethyl)-2-chloropyrazolo[1,5-a]pyrimidin-6-yl)urea;
tert-butyl 2-(2-chloro-6-(3-(5-chloro-6-(2H-1,2,3-triazol-2-yl)pyridin-3-yl)ureido)pyrazolo[1,5-a]pyrimidin-7-yl)morpholine-4-carboxylate;
1-(7-(3-oxabicyclo[3.1.0]hexan-6-yl)-2-chloropyrazolo[1,5-a]pyrimidin-6-yl)-3-(5-chloro-6-methoxypyridin-3-yl)urea;
1-(5-chloro-6-(2H-1,2,3-triazol-2-yl)pyridin-3-yl)-3-(2-chloro-7-(5-oxaspiro[2.4]heptan-1-yl)pyrazolo[1,5-a]pyrimidin-6-yl)urea;
1-(5-chloro-6-methoxypyridin-3-yl)-3-(2-chloro-7-(pyridin-4-yl)pyrazolo[1,5-a]pyrimidin-6-yl)urea;
2-chloro-6-(3-(5-chloro-6-(2H-1,2,3-triazol-2-yl)pyridin-3-yl)ureido)-N,N-dimethylpyrazolo[1,5-a]pyrimidine-7-carboxamide;
(S)-1-(5-chloro-6-(2H-1,2,3-triazol-2-yl)pyridin-3-yl)-3-(7-(1-methoxyethyl)-2-methyl-pyrazolo[1,5-a]pyrimidin-6-yl)urea;
1-(5-chloro-6-(2H-1,2,3-triazol-2-yl)pyridin-3-yl)-3-(2-methyl-7-(1-methylcyclopropyl)pyrazolo[1,5-a]pyrimidin-6-yl)urea;
1-(5-chloro-6-methoxypyridin-3-yl)-3-(2-methyl-7-(1-methylcyclopropyl)pyrazolo[1,5-a]pyrimidin-6-yl)urea;
(S)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea;
(S)-1-(2-chloro-7-(1-methoxy-2-methylpropyl)pyrazolo[1,5-a]pyrimidin-6-yl)-3-(2-(trifluoromethyl)pyridin-4-yl)urea;
1-(5-chloro-6-(2H-1,2,3-triazol-2-yl)pyridin-3-yl)-3-(2-chloro-7-(1-(methoxymethyl)cyclopropyl)pyrazolo[1,5-a]pyrimidin-6-yl)urea;
1-(2-chloro-7-(1-(methoxymethyl)cyclopropyl)pyrazolo[1,5-a]pyrimidin-6-yl)-3-(2-(trifluoromethyl)pyridin-4-yl)urea;
1-(5-chloro-6-(2H-1,2,3-triazol-2-yl)pyridin-3-yl)-3-(7-(1-(methoxymethyl)cyclopropyl)-2-methylpyrazolo[1,5-a]pyrimidin-6-yl)urea;

1-(7-(1-(methoxymethyl)cyclopropyl)-2-methylpyrazolo[1,5-a]pyrimidin-6-yl)-3-(2-(trifluoromethyl)pyridin-4-yl)urea;
1-(2-chloro-7-(2-(tetrahydro-2H-pyran-4-yl)propan-2-yl)pyrazolo[1,5-a]pyrimidin-6-yl)-3-(2-(trifluoromethyl)pyridin-4-yl)urea;
1-(5-chloro-6-(2H-1,2,3-triazol-2-yl)pyridin-3-yl)-3-(2-chloro-7-(1,2-dimethoxypropan-2-yl)pyrazolo[1,5-a]pyrimidin-6-yl)urea;
(S)-1-(5-chloro-6-(2H-1,2,3-triazol-2-yl)pyridin-3-yl)-3-(2-chloro-7-(1-(2-(dimethylamino)ethoxy)ethyl)pyrazolo[1,5-a]pyrimidin-6-yl)urea;
1-(5-chloro-6-(2H-1,2,3-triazol-2-yl)pyridin-3-yl)-3-(2-chloro-7-((4-methylmorpholin-3-yl)methyl)pyrazolo[1,5-a]pyrimidin-6-yl)urea;
(S)-1-(5-chloro-6-(2H-1,2,3-triazol-2-yl)pyridin-3-yl)-3-(2-chloro-7-(1-methylpiperidin-2-yl)pyrazolo[1,5-a]pyrimidin-6-yl)urea;
1-(5-chloro-6-(2H-1,2,3-triazol-2-yl)pyridin-3-yl)-3-(2-chloro-7-((S)-1-((R)-2-methoxy-propoxy)ethyl)pyrazolo[1,5-a]pyrimidin-6-yl)urea;
1-(5-chloro-6-(2H-1,2,3-triazol-2-yl)pyridin-3-yl)-3-(2-chloro-7-(1-methyl-1H-imidazol-2-yl)pyrazolo[1,5-a]pyrimidin-6-yl)urea;
1-(5-chloro-6-methoxypyridin-3-yl)-3-(2-chloro-7-(5-methyltetrahydrofuran-2-yl)pyrazolo[1,5-a]pyrimidin-6-yl)urea;
1-(5-chloro-6-(2H-1,2,3-triazol-2-yl)pyridin-3-yl)-3-(2-chloro-7-(1-(dimethylamino)cyclopropyl)pyrazolo[1,5-a]pyrimidin-6-yl)urea;
(S)-1-(2-chloro-7-(1-methoxyethyl)pyrazolo[1,5-a]pyrimidin-6-yl)-3-(5-(difluoromethyl)-6-(2H-1,2,3-triazol-2-yl)pyridin-3-yl)urea;
1-(2-chloro-7-(methoxy(tetrahydro-2H-pyran-4-yl)methyl)pyrazolo[1,5-a]pyrimidin-6-yl)-3-(2-(trifluoromethyl)pyridin-4-yl)urea;
1-(5-chloro-6-(2H-1,2,3-triazol-2-yl)pyridin-3-yl)-3-(2-chloro-7-(2-(methoxymethyl)tetrahydrofuran-2-yepyrazolo[1,5-a]pyrimidin-6-yl)urea;
(S)-1-(2-chloro-7-(1-methoxyethyl)pyrazolo[1,5-a]pyrimidin-6-yl)-3-(2-(difluoromethyl)pyridin-4-yl)urea;
(S)-1-(5-chloro-6-(difluoromethoxy)pyridin-3-yl)-3-(2-chloro-7-(1-methoxyethyl)pyrazolo[1,5-a]pyrimidin-6-yl)urea;
(S)-1-(6-(2H-1,2,3-triazol -2-yl)-5-(trifluoromethyl)pyridin-3-yl)-3-(2-fluoro-7-(1-methoxy-ethyl)pyrazolo[1,5-a]pyrimidin-6-yl)urea;
(S)-1-(5-chloro-6-(2H-1,2,3-triazol-2-yl)pyridin-3-yl)-3-(2-fluoro-7-(1-methoxyethyl)pyrazolo[1,5-a]pyrimidin-6-yl)urea;
(S)-1-(5-chloro-6-(2H-1,2,3-triazol-2-yl)pyridin-3-yl)-3-(2-cyano-7-(1-methoxy-ethyl)pyrazolo[1,5-a]pyrimidin-6-yl)urea;
(S)-1-(5-chloro-6-(difluoromethoxy)pyridin-3-yl)-3-(2-chloro-7-(1-(2-methoxyethoxy)ethyl)pyrazolo[1,5-a]pyrimidin-6-yl)urea;
1-(5-chloro-6-(2H-1,2,3-triazol-2-yl)pyridin-3-yl)-3-(2-chloro-7-((1R,2R)-1,2-dimethoxy-propyl)pyrazolo[1,5-a]pyrimidin-6-yl)urea;
(S)-1-(5-chloro-2-(2-(dimethylamino)ethoxy)pyridin-3-yl)-3-(2-chloro-7-(1-methoxyethyl)pyrazolo[1,5-a]pyrimidin-6-yl)urea;
1-(5-chloro-6-(2H-1,2,3-triazol-2-yl)pyridin-3-yl)-3-(2-chloro-7-((S)-1-(((R)-tetrahydro-furan-3-yl)oxy)ethyl)pyrazolo[1,5-a]pyrimidin-6-yl)urea;
1-(5-chloro-6-(2H-1,2,3-triazol-2-yl)pyridin-3-yl)-3-(2-chloro-7-((S)-1-(((S)-tetrahydro-furan-3-yl)oxy)ethyl)pyrazolo[1,5-a]pyrimidin-6-yl)urea;
1-(5-chloro-6-(2H-1,2,3-triazol-2-yl)pyridin-3-yl)-3-(2-chloro-7-((S)-1-(((S)-tetrahydro-furan-3-yl)methoxy)ethyl)pyrazolo[1,5-a]pyrimidin-6-yl)urea;
1-(5-chloro-6-(2H-1,2,3-triazol-2-yl)pyridin-3-yl)-3-(2-chloro-7-((S)-1-(((R)-tetrahydro-furan-3-yl)methoxy)ethyl)pyrazolo[1,5-a]pyrimidin-6-yl)urea;
1-(5-chloro-6-(2H-1,2,3-triazol-2-yl)pyridin-3-yl)-3-(2-methyl-7-(2-methyltetrahydrofuran-2-yl)pyrazolo[1,5-a]pyrimidin-6-yl)urea;
(S)-1-(2-chloro-7-(1-methoxyethyl)pyrazolo[1,5-a]pyrimidin-6-yl)-3-(2-cyanopyridin-4-yl)urea;
1-(2-chloro-7-(2-(methoxymethyl)tetrahydrofuran-2-yl)pyrazolo[1,5-a]pyrimidin-6-yl)-3-(5-(trifluoromethyl)pyridin-3-yl)urea;
1-(6-(2H-1,2,3-triazol-2-yl)-5-(trifluoromethyl)pyridin-3-yl)-3-(2-chloro-7-(1-(dimethyl-amino)cyclopropyl)pyrazolo[1,5-a]pyrimidin-6-yl)urea;
1-(6-(2H-1,2,3-triazol-2-yl)-5-(trifluoromethyl)pyridin-3-yl)-3-(2-chloro-7-(1,2-dimethoxy-ethyl)pyrazolo[1,5-a]pyrimidin-6-yl)urea;
1-(2-chloro-7-(1,2-dimethoxyethyl)pyrazolo[1,5-a]pyrimidin-6-yl)-3-(2-(trifluoromethyl)pyridin-4-yl)urea;
(S)-1-(6-(2H-1,2,3-triazol-2-yl)-5-(trifluoromethyl)pyridin-3-yl)-3-(2-chloro-7-(1-methoxy-propan-2-yl)pyrazolo[1,5-a]pyrimidin-6-yl)urea;
(R)-1-(6-(2H-1,2,3-triazol-2-yl)-5-(trifluoromethyl)pyridin-3-yl)-3-(2-chloro-7-(1-methoxy-propan-2-yl)pyrazolo[1,5-a]pyrimidin-6-yl)urea;
1-(5-(2H-1,2,3-triazol-2-yl)-2-(trifluoromethyl)pyridin-4-yl)-3-(2-chloro-7-isopropylpyrazolo[1,5-a]pyrimidin-6-yl)urea;
(R)-1-(6-(2H-1,2,3-triazol-2-yl)-5-(trifluoromethyl)pyridin-3-yl)-3-(2-chloro-7-(1-hydroxy-ethyl)pyrazolo[1,5-a]pyrimidin-6-yl)urea;
(S)-1-(2-chloro-7-(1-hydroxyethyl)pyrazolo[1,5-a]pyrimidin-6-yl)-3-(2-(trifluoromethyl)pyridin-4-yl)urea;
1-(5-chloro-6-(2H-1,2,3-triazol-2-yl)pyridin-3-yl)-3-(2-chloro-7-(morpholin-2-yl)pyrazolo[1,5-a]pyrimidin-6-yl)urea;
1-(5-chloro-6-(2H-1,2,3-triazol-2-yl)pyridin-3-yl)-3-(2-chloro-7-(4-methylmorpholin-2-yl)pyrazolo[1,5-a]pyrimidin-6-yl)urea;
1-(4-(4-(aminomethyl)-1H-pyrazol-1-yl)-3-chlorophenyl)-3-(2-chloro-7-isopropylpyrazolo[1,5-a]pyrimidin-6-yl)urea;
1-(6-(4-(aminomethyl)-1H-pyrazol-1-yl)-5-chloropyridin-3-yl)-3-(2-chloro-7-isopropylpyrazolo[1,5-a]pyrimidin-6-yl)urea;
(S)-1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea;
2-(3-(2-chloro-7-isopropylpyrazolo[1,5-a]pyrimidin-6-yl)ureido)-4-(trifluoromethyl)pyridine 1-oxide;
(R)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea;
(S)-1-(5-chloro-6-(2H-1,2,3-triazol-2-yl)pyridin-3-yl)-3-(2-chloro-7-(1-(dimethylamino)ethyl)pyrazolo[1,5-a]pyrimidin-6-yl)urea;
1-(5-chloro-6-(2H-1,2,3-triazol-2-yl)pyridin-3-yl)-3-(2-chloro-7-(morpholin-3-yl)pyrazolo[1,5-a]pyrimidin-6-yl)urea;

(S)-1-(5-chloro-6-(2H-1,2,3-triazol-2-yl)pyridin-3-yl)-3-(2-chloro-7-(2-methyl-1-(methyl-amino)propyl)pyrazolo[1,5-a]pyrimidin-6-yl)urea;

1-(5-chloro-6-(2H-1,2,3-triazol-2-yl)pyridin-3-yl)-3-(2-chloro-7-(4-methylmorpholin-3-yl)pyrazolo[1,5-a]pyrimidin-6-yl)urea;

(R)-1-(5-chloro-6-(2H-1,2,3-triazol-2-yl)pyridin-3-yl)-3-(2-chloro-7-(1,2-dimethoxy ethyl)pyrazolo[1,5-a]pyrimidin-6-yl)urea; and (S)-1-(5-chloro-6-(2H-1,2,3-triazol-2-yl)pyridin-3-yl)-3-(2-chloro-7-(1,2-dimethoxyethyl)pyrazolo[1,5-a]pyrimidin-6-yl)urea.

9. The compound of claim 1 or a pharmaceutically acceptable salt thereof, wherein R1 is fluoro;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy or Rg or phenyl; wherein Rg is a 5-6 membered heterocyclic ring having 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 2-pyridyl substituted one or more times by Rb; and

Rb independently from each other is halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring having 1 to 3 N atoms said ring being optionally substituted by $C_1$-$C_6$ alkyl optionally substituted by amino or hydroxy, or by mono- or di-N-$C_1$-$C_6$ alkylamino carbonyl; O—Rh; or Rh; wherein Rh is a 5-6 membered heterocyclyl ring having 1 to 4 heteroatoms selected from N, O and S said ring being optionally substituted by $C_1$-$C_6$ alkyl, hydroxyl or oxo.

10. The compound of claim 1 or a pharmaceutically acceptable salt thereof, wherein R1 is fluoro;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 3-pyridyl substituted one or more times by Rc; and

Rc independently from each other is halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring having 1 to 3 N atoms said ring being optionally substituted by $C_1$-$C_6$ alkyl optionally substituted by amino or hydroxy, or by mono- or di-N-$C_1$-$C_6$ alkylamino carbonyl; O—Rh; or Rh; wherein Rh is a 5-6 membered heterocyclyl having 1 to 4 heteroatoms selected from N, O and S said ring being optionally substituted by $C_1$-$C_6$ alkyl, hydroxyl or oxo.

11. The compound of claim 1 or a pharmaceutically acceptable salt thereof, wherein R1 is fluoro;

R2 is $C_1$-$C_6$ alkyl optionally substituted one or more times by $C_1$-$C_6$ alkyl, $C_2$-$C_6$ alkenyl, hydroxyl, N,N-di-$C_1$-$C_6$ alkyl amino, N-mono-$C_1$-$C_6$ alkyl amino, O—Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkyl amino, Rg or phenyl; wherein Rg is a 5-6 membered heterocyclic ring containing 1-3 heteroatoms selected from N and O said ring being optionally substituted by $C_1$-$C_6$ alkyl, $C_1$-$C_6$ alkoxy-$C_1$-$C_6$ alkyl, $C_1$-$C_6$ alkoxy-carbonyl;

R is 4-pyridyl substituted one or more times by Rd; and

Rd independently from each other is halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring containing 1 to 3 N atoms said ring being optionally substituted by $C_1$-$C_6$ alkyl optionally substituted by amino or hydroxy, or by mono- or di-N-$C_1$-$C_6$ alkylamino carbonyl; O—Rh; or Rh; wherein Rh is a 5-6 membered heterocyclyl containing 1 to 4 heteroatoms selected from N, O and S said ring being optionally substituted by $C_1$-$C_6$ alkyl, hydroxyl or oxo.

12. A pharmaceutical composition comprising a therapeutically effective amount of a compound according to claim 1 and one or more pharmaceutically acceptable carriers.

13. A combination comprising a therapeutically effective amount of a compound according to claim 1 or a pharmaceutically acceptable salt thereof and one or more therapeutically active co-agents.

14. A method of inhibiting MALT1 activity in a subject, wherein the method comprises administering to the subject a therapeutically effective amount of a compound according to claim 1 or a pharmaceutically acceptable salt thereof.

15. A pharmaceutical composition comprising a therapeutically effective amount of a compound according to claim 8 and one or more pharmaceutically acceptable carriers.

16. A combination comprising a therapeutically effective amount of a compound according to claim 8 or a pharmaceutically acceptable salt thereof and one or more therapeutically active co-agents.

17. A method of inhibiting MALT1 activity in a subject, wherein the method comprises administering to the subject a therapeutically effective amount of a compound according to claim 8 or a pharmaceutically acceptable salt thereof.

18. The compound of claim 1 or a pharmaceutically acceptable salt thereof, wherein the compound is selected from:

(S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea;

(S)-1-(2-chloro-7-(1-methoxyethyl)pyrazolo[1,5-a]pyrimidin-6-yl)-3-(2-(trifluoromethyl)pyridin-4-yl)urea;

(R)-1-(6-(2H-1,2,3-triazol-2-yl)-5-(trifluoromethyl)pyridin-3-yl)-3-(2-chloro-7-(1-methoxy-2-methylpropyl)pyrazolo[1,5-a]pyrimidin-6-yl)urea;

(R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea;

(S)-1-(7-(1-methoxyethyl)-2-methylpyrazolo[1,5-a]pyrimidin-6-yl)-3-(2-(trifluoromethyl)pyridin-4-yl)urea, and
(S)-1-(2-fluoro-7-(1-methoxyethyl)pyrazolo[1,5-a]pyrimidin-6-yl)-3-(2-(trifluoromethyl)pyridin-4-yl)urea.

* * * * *